United States Patent
Adams et al.

(10) Patent No.: US 8,058,282 B2
(45) Date of Patent: *Nov. 15, 2011

(54) 2,4,8-TRISUBSTITUTED-8H-PYRIDO[2,3-D]PYRIMIDIN-7-ONE COMPOUNDS AND COMPOSITIONS FOR USE IN THERAPY

(75) Inventors: Jerry L. Adams, King of Prussia, PA (US); Jeffrey C. Boehm, King of Prussia, PA (US); Ralph Hall, King of Prussia, PA (US); Qi Jin, King of Prussia, PA (US); Jiri Kasparec, King of Prussia, PA (US); Domingos J. Silva, King of Prussia, PA (US); John J. Taggart, King of Prussia, PA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/859,645

(22) Filed: Aug. 19, 2010

(65) Prior Publication Data

US 2011/0046109 A1 Feb. 24, 2011

Related U.S. Application Data

(63) Continuation of application No. 11/839,834, filed on Aug. 16, 2007, which is a continuation of application No. 10/399,614, filed as application No. PCT/US01/50493 on Oct. 23, 2001, now Pat. No. 7,323,472.

(60) Provisional application No. 60/242,461, filed on Oct. 23, 2000, provisional application No. 60/310,349, filed on Aug. 6, 2001, provisional application No. 60/326,618, filed on Oct. 2, 2001.

(51) Int. Cl.
*A61P 19/00* (2006.01)
*A61P 31/00* (2006.01)
*A61K 31/505* (2006.01)
*C07D 239/02* (2006.01)
*C07D 471/02* (2006.01)

(52) U.S. Cl. .................. 514/264.1; 514/264.11; 544/279
(58) Field of Classification Search ................ 514/264.1, 514/264.11; 544/279
See application file for complete search history.

(56) References Cited

U.S. PATENT DOCUMENTS

| | | |
|---|---|---|
| 2,833,779 A | 5/1958 | Fields |
| 3,707,475 A | 12/1972 | Lombardino |
| 3,772,441 A | 11/1973 | Lombardino |
| 3,843,663 A | 10/1974 | Williams et al. |
| 3,910,913 A | 10/1975 | Kim et al. |
| 3,929,807 A | 12/1975 | Fitzi |
| 3,940,486 A | 2/1976 | Fitzi |
| 4,058,614 A | 11/1977 | Baldwin |
| 4,199,592 A | 4/1980 | Cherkofsky |
| 4,447,431 A | 5/1984 | Sallmann |
| 4,503,065 A | 3/1985 | Wilkerson |
| 4,560,691 A | 12/1985 | Lesher et al. |
| 4,565,875 A | 1/1986 | Cavender |
| 4,686,231 A | 8/1987 | Bender et al. |
| 4,822,805 A | 4/1989 | Takasugi et al. |
| 4,886,807 A | 12/1989 | Kitamura et al. |
| 4,897,395 A | 1/1990 | Duch et al. |
| 5,304,560 A | 4/1994 | Shimazaki et al. |
| 5,409,930 A | 4/1995 | Spada et al. |
| 5,426,110 A | 6/1995 | Gossett et al. |
| 5,466,692 A | 11/1995 | Ellingboe et al. |
| 5,545,669 A | 8/1996 | Adams et al. |
| 5,547,954 A | 8/1996 | Henrie |
| 5,559,137 A | 9/1996 | Adams et al. |
| 5,591,992 A | 1/1997 | Leach |
| 5,593,991 A | 1/1997 | Adams et al. |
| 5,593,992 A | 1/1997 | Adams et al. |
| 5,597,776 A | 1/1997 | Bratz et al. |
| 5,620,981 A | 4/1997 | Blankley et al. |
| 5,656,644 A | 8/1997 | Adams et al. |
| 5,658,903 A | 8/1997 | Adams et al. |
| 5,663,334 A | 9/1997 | Sheldrake et al. |
| 5,670,527 A | 9/1997 | Adams et al. |
| 5,686,455 A | 11/1997 | Adams et al. |
| 5,716,955 A | 2/1998 | Adams et al. |
| 5,716,972 A | 2/1998 | Adams et al. |
| 5,733,913 A | 3/1998 | Blankley et al. |
| 5,733,914 A | 3/1998 | Blankley et al. |
| 5,739,143 A | 4/1998 | Adams et al. |
| 5,756,499 A | 5/1998 | Adams et al. |
| 5,760,220 A | 6/1998 | Giguere et al. |
| 5,767,097 A | 6/1998 | Tam |
| 5,777,097 A | 7/1998 | Lee et al. |
| 5,783,664 A | 7/1998 | Lee et al. |
| 5,817,670 A | 10/1998 | Takayama et al. |
| 5,864,036 A | 1/1999 | Adams et al. |
| 5,869,043 A | 2/1999 | McDonnell et al. |
| 5,869,660 A | 2/1999 | Adams et al. |
| 5,871,934 A | 2/1999 | Lee et al. |
| 5,916,891 A | 6/1999 | Adams et al. |
| 5,917,043 A | 6/1999 | Sisko |
| 5,929,076 A | 7/1999 | Adams et al. |
| 5,945,422 A | 8/1999 | Doherty et al. |
| 5,955,366 A | 9/1999 | Lee et al. |
| 5,969,184 A | 10/1999 | Adams et al. |
| 5,977,103 A | 11/1999 | Adams et al. |
| 5,977,372 A | 11/1999 | Giguere et al. |
| 5,998,425 A | 12/1999 | Adams et al. |

(Continued)

FOREIGN PATENT DOCUMENTS

EP 0 278 686 8/1988

(Continued)

OTHER PUBLICATIONS

Adams et al., Progress in Medicinal Chemistry, vol. 38, pp. 1-60, 2001.

(Continued)

*Primary Examiner* — Brenda Coleman
(74) *Attorney, Agent, or Firm* — James P. Riek

(57) ABSTRACT

Novel substituted 2,4,8-trisubstituted-8H-pyrido[2,3-d]pyrimidin-7-one compounds and compositions for use in therapy as CSBP/p38 kinase inhibitors.

35 Claims, 1 Drawing Sheet

U.S. PATENT DOCUMENTS

| | | | |
|---|---|---|---|
| 6,008,235 | A | 12/1999 | Adams et al. |
| 6,063,772 | A | 5/2000 | Tam |
| 6,083,948 | A | 7/2000 | Wilde |
| 6,096,739 | A | 8/2000 | Feuerstein |
| 6,150,337 | A | 11/2000 | Tam |
| 6,150,373 | A | 11/2000 | Harris et al. |
| 6,200,977 | B1 | 3/2001 | Cushing et al. |
| 6,235,760 | B1 | 5/2001 | Feuerstein |
| 6,248,225 | B1 | 6/2001 | Palaika et al. |
| 6,277,989 | B1 | 8/2001 | Chakravarty et al. |
| 6,288,062 | B1 | 9/2001 | Adams et al. |
| 6,335,340 | B1 | 1/2002 | Gallagher et al. |
| 6,362,193 | B1 | 3/2002 | Adams et al. |
| 6,399,609 | B1 | 6/2002 | Wilde |
| 6,423,425 | B1 | 7/2002 | Faucher et al. |
| 6,423,695 | B1 | 7/2002 | Tam et al. |
| 6,455,690 | B1 | 9/2002 | Tam et al. |
| 6,476,031 | B1 | 11/2002 | Chakravarty et al. |
| 6,479,463 | B1 | 11/2002 | Wang et al. |
| 6,492,520 | B1 | 12/2002 | Chen |
| 6,498,163 | B1 | 12/2002 | Boschelli et al. |
| 6,509,320 | B1 | 1/2003 | Wang et al. |
| 6,509,363 | B2 | 1/2003 | Salituro et al. |
| 6,528,508 | B2 | 3/2003 | Salituro et al. |
| 6,528,513 | B2 | 3/2003 | Cushing et al. |
| 6,593,333 | B1 | 7/2003 | Cumming |
| 6,800,626 | B2 | 10/2004 | Salituro et al. |
| 6,809,199 | B2 | 10/2004 | Doherty et al. |
| 6,838,559 | B2 | 1/2005 | Vaccaro et al. |
| 6,869,955 | B2 | 3/2005 | Wilde |
| 6,875,769 | B2 | 4/2005 | Chen |
| 7,022,849 | B2 | 4/2006 | Pitts et al. |
| 7,208,629 | B2 | 4/2007 | Angell et al. |
| 7,235,551 | B2 | 6/2007 | Adams et al. |
| 7,314,881 | B2 | 1/2008 | Adams et al. |
| 7,314,934 | B2 | 1/2008 | Adams et al. |
| 7,323,472 | B2 | 1/2008 | Adams et al. |
| 7,423,042 | B2 | 9/2008 | Boehm et al. |
| 2002/0058635 | A1 | 5/2002 | Averett |
| 2002/0132784 | A1 | 9/2002 | Tam et al. |
| 2002/0137696 | A1 | 9/2002 | Tam |
| 2003/0064993 | A1 | 4/2003 | Wilde |
| 2003/0078274 | A1 | 4/2003 | Lipton |
| 2003/0092721 | A1 | 5/2003 | Pitts et al. |
| 2003/0092908 | A1 | 5/2003 | Pitts et al. |
| 2003/0100571 | A1 | 5/2003 | Vaccaro et al. |
| 2003/0100756 | A1 | 5/2003 | Adams et al. |
| 2003/0104974 | A1 | 6/2003 | Pitts et al. |
| 2003/0114671 | A1 | 6/2003 | Chen |
| 2003/0130264 | A1 | 7/2003 | Jaen |
| 2003/0139434 | A1 | 7/2003 | Balkan et al. |
| 2003/0162802 | A1 | 8/2003 | Guo et al. |
| 2003/0191143 | A1 | 10/2003 | Pitts et al. |
| 2003/0207826 | A1 | 11/2003 | Tam et al. |
| 2003/0212015 | A1 | 11/2003 | Tam |
| 2004/0009993 | A1 | 1/2004 | Angiolini et al. |
| 2004/0044012 | A1 | 3/2004 | Dobrusin et al. |
| 2004/0063658 | A1 | 4/2004 | Roberts et al. |
| 2004/0065378 | A1 | 4/2004 | Chini et al. |
| 2004/0077641 | A1 | 4/2004 | Bretschneider et al. |
| 2004/0087600 | A1 | 5/2004 | Cai et al. |
| 2004/0092402 | A1 | 5/2004 | Kuragano et al. |
| 2004/0116697 | A1 | 6/2004 | Adams et al. |
| 2004/0142945 | A1 | 7/2004 | Barbosa et al. |
| 2004/0209901 | A1 | 10/2004 | Adams et al. |
| 2004/0224958 | A1 | 11/2004 | Booth et al. |
| 2004/0235847 | A1 | 11/2004 | Quan et al. |
| 2004/0236084 | A1 | 11/2004 | Biwersi et al. |
| 2004/0242604 | A1 | 12/2004 | Bhattacharya et al. |
| 2005/0187217 | A1 | 8/2005 | Wilson et al. |
| 2005/0203109 | A1 | 9/2005 | Adams et al. |
| 2005/0272728 | A1 | 12/2005 | Altenbach et al. |
| 2006/0116516 | A1 | 6/2006 | Pitts et al. |
| 2006/0217401 | A1 | 9/2006 | Boehm et al. |
| 2006/0235029 | A1 | 10/2006 | Boehm et al. |
| 2006/0235030 | A1 | 10/2006 | Callahan et al. |
| 2006/0258687 | A1 | 11/2006 | Boehm et al. |
| 2007/0167467 | A1 | 7/2007 | Adams et al. |
| 2007/0238743 | A1 | 10/2007 | Adams et al. |
| 2008/0032969 | A1 | 2/2008 | Adams et al. |
| 2008/0033170 | A1 | 2/2008 | Adams et al. |
| 2008/0096905 | A1 | 4/2008 | Callahan et al. |
| 2008/0268044 | A1 | 10/2008 | Appleby et al. |
| 2009/0048442 | A1 | 2/2009 | Adams et al. |
| 2009/0048444 | A1 | 2/2009 | Boehm et al. |
| 2009/0069318 | A1 | 3/2009 | Callahan et al. |
| 2009/0074676 | A1 | 3/2009 | Yang |
| 2009/0149492 | A1 | 6/2009 | Fevig et al. |
| 2009/0156597 | A1 | 6/2009 | Callahan et al. |
| 2009/0170834 | A1 | 7/2009 | Venkat et al. |
| 2009/0176811 | A1 | 7/2009 | Oberborsch |
| 2009/0221600 | A1 | 9/2009 | Verma et al. |
| 2009/0233907 | A1 | 9/2009 | Austin et al. |
| 2009/0270389 | A1 | 10/2009 | Brookfield et al. |
| 2009/0270430 | A1 | 10/2009 | Baik et al. |

FOREIGN PATENT DOCUMENTS

| | | |
|---|---|---|
| EP | 0 530 994 A1 | 10/1993 |
| EP | 0 477 049 B1 | 2/1999 |
| GB | 2 123 830 | 2/1984 |
| JP | 2000 038350 | 9/1999 |
| JP | 1 261 306 | 10/1999 |
| JP | 2003 127542 | 5/2003 |
| JP | 2004 203751 | 7/2004 |
| WO | 91/19497 | 12/1991 |
| WO | 92/10190 | 6/1992 |
| WO | 92/10498 | 6/1992 |
| WO | 92/12154 | 7/1992 |
| WO | 93/14081 | 7/1993 |
| WO | 93/14082 | 7/1993 |
| WO | 94/19350 | 9/1994 |
| WO | 95/02591 | 1/1995 |
| WO | 95/03297 | 2/1995 |
| WO | 95/09847 | 4/1995 |
| WO | 95/09851 | 4/1995 |
| WO | 95/09852 | 4/1995 |
| WO | 95/09853 | 4/1995 |
| WO | 95/13067 | 5/1995 |
| WO | 95/15952 | 6/1995 |
| WO | 95/19774 | 7/1995 |
| WO | 95/31451 | 11/1995 |
| WO | 95/33461 | 12/1995 |
| WO | 95/33750 | 12/1995 |
| WO | 96/21452 | 7/1996 |
| WO | 96/21654 | 7/1996 |
| WO | 96/40143 | 12/1996 |
| WO | 96/40684 | 12/1996 |
| WO | 97/05877 | 2/1997 |
| WO | 97/05878 | 2/1997 |
| WO | 97/12876 | 4/1997 |
| WO | 97/16426 | 5/1997 |
| WO | 97/16441 | 5/1997 |
| WO | 97/16442 | 5/1997 |
| WO | 97/23479 | 7/1997 |
| WO | 97/25045 | 7/1997 |
| WO | 97/25046 | 7/1997 |
| WO | 97/25047 | 7/1997 |
| WO | 97/25048 | 7/1997 |
| WO | 97/32583 | 9/1997 |
| WO | 97/33883 | 9/1997 |
| WO | 97/35855 | 10/1997 |
| WO | 97/35856 | 10/1997 |
| WO | 97/36587 | 10/1997 |
| WO | 97/38992 | 10/1997 |
| WO | 97/47618 | 12/1997 |
| WO | 98/03484 | 1/1998 |
| WO | 98/05661 | 2/1998 |
| WO | 98/06715 | 2/1998 |
| WO | 98/07425 | 2/1998 |
| WO | 98/08846 | 3/1998 |
| WO | 98/16230 | 4/1998 |
| WO | 98/22109 | 5/1998 |
| WO | 98/22457 | 5/1998 |
| WO | 98/24780 | 6/1998 |
| WO | 98/24782 | 6/1998 |
| WO | 98/25619 | 6/1998 |
| WO | 98/27098 | 6/1998 |

| | | |
|---|---|---|
| WO | 98/28292 | 7/1998 |
| WO | 98/30223 | 7/1998 |
| WO | 98/33798 | 8/1998 |
| WO | 98/47892 | 10/1998 |
| WO | 98/48799 | 11/1998 |
| WO | 98/52558 | 11/1998 |
| WO | 98/52937 | 11/1998 |
| WO | 98/52940 | 11/1998 |
| WO | 98/52941 | 11/1998 |
| WO | 98/56377 | 12/1998 |
| WO | 98/56788 | 12/1998 |
| WO | 98/57966 | 12/1998 |
| WO | 99/00357 | 1/1999 |
| WO | 99/01130 | 1/1999 |
| WO | 99/01131 | 1/1999 |
| WO | 99/01136 | 1/1999 |
| WO | 99/01449 | 1/1999 |
| WO | 99/01452 | 1/1999 |
| WO | 99/03837 | 1/1999 |
| WO | 99/17776 | 4/1999 |
| WO | 99/18942 | 4/1999 |
| WO | 99/32110 | 7/1999 |
| WO | 99/32121 | 7/1999 |
| WO | 99/41253 | 8/1999 |
| WO | 99/42592 | 8/1999 |
| WO | 99/57101 | 11/1999 |
| WO | 99/57253 | 11/1999 |
| WO | 99/58128 | 11/1999 |
| WO | 99/58502 | 11/1999 |
| WO | 99/58523 | 11/1999 |
| WO | 99/59959 | 11/1999 |
| WO | 99/59960 | 11/1999 |
| WO | 99/61426 | 12/1999 |
| WO | 99/61437 | 12/1999 |
| WO | 99/61440 | 12/1999 |
| WO | 99/61444 | 12/1999 |
| WO | 99/64400 | 12/1999 |
| WO | 00/01688 | 1/2000 |
| WO | 00/06563 | 2/2000 |
| WO | 00/07980 | 2/2000 |
| WO | 00/07991 | 2/2000 |
| WO | 00/10563 | 3/2000 |
| WO | 00/12074 | 3/2000 |
| WO | 00/12497 | 3/2000 |
| WO | 00/17175 | 3/2000 |
| WO | 00/18738 | 4/2000 |
| WO | 00/19824 | 4/2000 |
| WO | 00/20402 | 4/2000 |
| WO | 00/23072 | 4/2000 |
| WO | 00/23444 | 4/2000 |
| WO | 00/25791 | 5/2000 |
| WO | 00/26209 | 5/2000 |
| WO | 00/31063 | 6/2000 |
| WO | 00/31065 | 6/2000 |
| WO | 00/31072 | 6/2000 |
| WO | 00/35911 | 6/2000 |
| WO | 00/39116 | 7/2000 |
| WO | 00/40243 | 7/2000 |
| WO | 00/41698 | 7/2000 |
| WO | 00/43374 | 7/2000 |
| WO | 00/43384 | 7/2000 |
| WO | 00/59541 | 10/2000 |
| WO | 00/75131 | 12/2000 |
| WO | 01/00229 | 1/2001 |
| WO | 01/19322 | 3/2001 |
| WO | 01/19828 | 3/2001 |
| WO | 01/37835 | 5/2001 |
| WO | 01/38314 | 5/2001 |
| WO | 01/42243 | 6/2001 |
| WO | 01/55147 | 8/2001 |
| WO | 01/55148 | 8/2001 |
| WO | 01/64679 | 9/2001 |
| WO | 01/70741 | 9/2001 |
| WO | 02/07772 | 1/2002 |
| WO | 02/32862 | 4/2002 |
| WO | 02/39954 | 5/2002 |
| WO | 02/060869 | 8/2002 |
| WO | 02/058695 | 9/2002 |
| WO | 02/059083 | 9/2002 |
| WO | 02/102315 | 12/2002 |
| WO | 03/088972 | 10/2003 |
| WO | 03/093290 | 11/2003 |
| WO | 2004/043367 | 5/2004 |
| WO | 2004/065378 | 8/2004 |
| WO | 2005/014558 | 2/2005 |
| WO | 2006/021547 | 3/2006 |
| WO | 2006/104889 | 10/2006 |
| WO | 2006/104917 | 10/2006 |
| WO | 2006/110298 | 10/2006 |
| WO | 2007/144390 | 12/2007 |
| WO | 2007/147103 | 12/2007 |
| WO | 2007/147104 | 12/2007 |
| WO | 2007/147109 | 12/2007 |

OTHER PUBLICATIONS

Agarwal et al., Bioorganic & Medicinal Chemistry Letters, vol. 10(8), pp. 703-706, 2000.
Alves et al., Tetrahedron Letters, vol. 29, pp. 2135-2136, 1988.
Anderson et al., J. Org. Chem., 1977, vol. 42, pp. 993-996.
Armarego, Chem. Soc., Quinazolines, Part IV, (JCSOA9), pp. 561-572, 1962.
Badger et al., Circulatory Shock, vol. 27, pp. 51-61, 1989.
Badger et al., J. Pharm. Exp. Thera., vol. 279(3), pp. 1453-1461, 1996.
Badger et al., Arthritis Rheum., vol. 43, pp. 175-183, 2000.
Baker et al., J. Heterocyclic Chem., vol. 1(5), pp. 263-270, 1964.
Barvian et al., J. Med. Chem., vol. 43, pp. 4606-4616, 2000.
Becker et al., J. Immunol., vol. 147, p. 4307, 1991.
Bedaiwy et al., Human Reproduction, vol. 17, pp. 426-431, 2002.
Boehm et al., J. Med. Chem. vol. 39(20), pp. 3929-3937, 1996.
Boehm et al., Expert Opinion on Therapeutic Patents, vol. 10(1), pp. 25-37, 2000.
Borrell et al., Collect. Czech. Chem. Commun., vol. 61(6), pp. 901-909, 1996.
Boschelli et al., J. Med Chem., vol. 41, pp. 4365-4377, 1998.
Bradlerova et al., Chem. Zvesti, vol. 29(6), pp. 795-802, 1975.
Carboni et al., Gazzetta Chimica Italiana, vol. 97(8), pp. 1262-1273, 1967.
Carboni et al., Gazzetta Chimica Italiana, vol. 98(10), pp. 1174-1188, 1968.
Carter, et al, J. Biological Chem., vol. 274, pp. 30858-30864, 1999.
Cohen et al., Trends in Cell Biology, vol. 7, pp. 353-361, 1997.
Colotta et al., J. Immunol., vol. 132(2), pp. 936-944, 1984.
Courtney et al., Bioorg. Med. Chem. Lett., vol. 14, pp. 3269-3273, 2004.
Damasio et al., Cecil Textbook of Medicine, 20th Edition, vol. 2, pp. 1992-1996, 1996.
De Silva et al., J. Chem. Soc., Perkin Trans. 2, pp. 685-690, 1995.
Dinarello et al., Rev. Infect. Disease, vol. 6(1), pp. 51-95, 1984.
Dinarello et al., J. Clin. Immun., vol. 5(5), pp. 287-297, 1985.
Douglas, Cecil Textbook of Medicine, 20th Edition, vol. 2, pp. 1739-1747, 1996.
Echavarren et al., J. Am. Chem. Soc., vol. 109(18), pp. 5478-5486, 1987.
El-Assiery et al., CAPLUS Abstract 132: 151761, 1999.
El-Reedy et al., CAPLUS Abstract 112: 35791, 1990.
Engel et al., Liebigs Ann. Chem., pp. 1916-1927, 1978.
Ferles et al., Collect. Czech. Chem. Commun., vol. 46, pp. 1167-1172, 1981.
Ferrarini et al., J. Heterocyclic Chem., vol. 21(2), pp. 417-419, 1984.
Ferrarini et al., J. Heterocyclic Chem., vol. 34(5), pp. 1501-1510, 1997.
Fischer et al., Rec. Tray. Chim. Pays. Bas., vol. 84, pp. 439-440, 1965.
Fleisher et al., Advanced Drug Delivery Reviews, vol. 19(2), pp. 115-130, 1996.
Foster et al., Drug News Perspect., vol. 13(8), pp. 488-497, 2000.
Fulmer et al., J. Heterocyclic Chem., vol. 17(4), pp. 799-800, 1980.
Gallagher et al., Bioorg. Med. Chem., vol. 5(1), pp. 49-64, 1997.
Garigipati, Tetrahedron Letters, vol. 31(14), pp. 1969-1972, 1990.
Gartner et al., Pathol. Biol. (Paris), vol. 50(2), pp. 118-126, 2002 (PubMed Abstract).
Gilbert, Synthesis, pp. 30-32, 1972.

Griswold et al., Drugs Exptl. Clin. Res., vol. XIX(6), pp. 243-248, 1993.
Griswold et al., Pharmacol. Comm., vol. 7, pp. 323-329, 1996.
Griswold et al., Arthritis and Rheumatism, vol. 31(11), pp. 1406-1412, 1998.
Grunberg et al., Am. J. Respir. Crit. Care Med., vol. 156, pp. 609-616, 1997.
Han et al., Science, vol. 265, pp. 808-811, 1994.
Hanafusa et al., J. Biol. Chem., vol. 274(38), pp. 27161-27167, 1999.
Hanson, Exp. Opin. Ther. Patents, vol. 7(7), pp. 729-733, 1997.
Hare et al., J. Med. Chem., vol. 47, pp. 4731-4740, 2004.
Henry et al., Bioorg. Med. Chem. Lett., vol. 8, pp. 3335-3340, 1998.
Herlaar et al., Molecular Medicine Today, vol. 5, pp. 439-447, 1999.
Hunt et al., Bioorg. Med. Chem. Lett., vol. 13, pp. 467-470, 2003.
Hunter et al., Methods in Enzymology, vol. 200, pp. 3-37, 1991.
Hurlbert et al., J. Med. Chem., vol. 11, pp. 703-707, 1968.
Irwin et al., Arch. Intern. Med., vol. 157(17), pp. 1981-1987, 1997.
Ishibashi et al., Chem. Pharm. Bull., vol. 37(8), pp. 2214-2216, 1989.
Ishikura et al., Chem. Pharm. Bull., vol. 33(11), pp. 4755-4763, 1985.
Jackson et al., J. Pharmacol. Exp. Ther., vol. 284(2), pp. 687-692, 1998.
Jacobson et al., Tetrahedron, vol. 50(15), pp. 4323-4334, 1994.
Johnson et al., J. Chem. Soc., Perkin Trans. 1, pp. 895-905, 1996.
Jurkowska-Kowalczyk, Roczniki Chemii, vol. 51, pp. 1191-1199, 1977.
Kasparec et al, Tetrahedron Letters, vol. 44(24), pp. 4567-4570, 2003.
Katritzky et al., Synthesis, pp. 45-47, 1993.
Kawasaki et al., J. Biol. Chem., vol. 272(30), pp. 18518-18521, 1997.
Khabar, Journal of Interferon & Cytokine Research, vol. 25, pp. 1-10, 2005.
Kloetzer et al., Monatsh Chem., vol. 96, pp. 1567-1572, 1965.
Kumar et al. Nature Rev. Drug Discovery, vol. 2, pp. 717-726, 2003.
Kyriakis et al., Physiol. Rev., vol. 81(2), pp. 807-809, 2001.
Lamartina et al., Boll. Chim. Farm., vol. 129(12), pp. 314-316, 1990.
Laping et al., Mol. Pharmacol., vol. 62(1), pp. 58-64, 2002.
Layzer, Cecil Textbook of Medicine, 20th Edition, vol. 2, pp. 2050-2057, 1996.
Lee et al., Int. J. Immunopharmac., vol. 10(7), pp. 835-843, 1988.
Lee et al., Annals NY Academy of Sciences, vol. 696, pp. 149-170, 1993.
Lee et al., Nature, vol. 372(22/29), pp. 739-746, 1994.
Lee et al., Pharmacol. Ther., vol. 82(2-3), pp. 389-397, 1999.
Lee et al., Immunopharmacology, vol. 47, pp. 185-201, 2000.
Manhi et al., CAPLUS Abstract 121:83254, 1994.
Marin et al., Blood, vol. 98(3) pp. 667-673, 2001.
Marshall et al., Cell, vol. 80, pp. 179-185, 1995.
Martinez-Teipel et al., J. Comb. Chem., vol. 7(3), pp. 436-448, 2005.
Matyus et al., Heterocycles, vol. 23(8), pp. 2057-2064, 1985.
Mikailu et al., Zh. Obshch. Khim., vol. 56 (7), pp. 1513-1517, 1986.
Minato et al., Tetrahedron Letters, vol. 22(52), pp. 5319-5322, 1981.
Morin et al., Cancer Research, vol. 64, pp. 1893-1898, 2004.
Morton et al., Tetrahedron Letters, pp. 4123-4126, 1982.
Niimi et al., Eur. Respir. J., vol. 11(5), pp. 1064-1069, 1998.
Nishikawa et al., Chem. Pharm. Bull., vol. 24(9), pp. 2057-2077, 1976.
Olivera et al., Circulatory Shock, vol. 37, pp. 301-306, 1992.
Ono et al., Cellular Signalling, vol. 12, pp. 1-13, 2000.
Platanias, Pharmacol. Therap., vol. 98, pp. 129-142, 2003.
Poli et al., Proc. Natl Acad. Sci., vol. 87, pp. 782-785, 1990.
Pridgen, J. Org. Chem., vol. 47, pp. 4319-4323, 1982.
Puig et al., Sleep, vol. 28(10), pp. 1312-1316, 2005.
Protecting Groups in Organic Synthesis, 2nd Edition, Greene TW and Wuts PSM, Wiley Interscience, New York, pp. 10-174 (Hydroxyl and Phenolic), pp. 309-403 (NH protection), 1991.
Ram, CAPLUS Abstract 112:77090, 1990.
Ram, CAPLUS Abstract 113:78321, 1990.
Ram, CAPLUS Abstract 113:97564, 1990.
Ram, CAPLUS Abstract 114:42726, 1991.
Ram et al., CAPLUS Abstract 115:256109, 1991.
Rewcastle et al., J. Med. Chem., vol. 39(6), pp. 1823-1835, 1996.
Ridker, Circulation, pp. 363-369, 2003.
Saccani et al., Nature Immunology vol. 3(1), pp. 69-75, 2002.
Santilli et al., J. Heterocyclic Chem., vol. 8, pp. 445-453, 1971.
Schoffstall et al., J. Org. Chem., 36(16), pp. 2385-2387, 1971.
Simon et al., J. Immunol. Methods, vol. 84, pp. 85-94, 1985.
Solberg et al., Acta Chem. Scand., vol. 43, pp. 62-68, 1989.
Soni, Aust. J. Chem., vol. 35, pp. 1493-1496, 1982.
Still et al., Tetrahedron Letters, vol. 24(41), pp. 4405-4408, 1983.
Strzybny et al., J. Org. Chem., vol. 28, pp. 3381-3383, 1963.
Subauste et al., J. Clin. Invest., vol. 96, pp. 549-557, 1995.
Szucs et al., Chem. Zvesti, vol. 26(4), pp. 354-359, 1972.
Szucs et al., Acta Fac. Pharm. Univ. Commenianae, vol. 30, pp. 127-146, 1977.
Tanji et al., Chem. Pharm. Bull., vol. 35(12) pp. 4972-4976, 1987.
Teren et al., Am. J. Respir. Crit. Care Med., vol. 155, pp. 1362-1366, 1997.
Thompson et al., J. Org. Chem., vol. 49, pp. 5237-5243, 1984.
Tumkevicius, Liebigs Ann., pp. 1703-1705, 1995.
Tumkevicius, Chem. Hetero. Compounds, vol. 36(7), pp. 841-846, 2000.
Turner et al. Clin. Infect. Dis., vol. 26, pp. 840-846, 1998.
Underwood et al., J. Pharmacol. Exp. Ther., vol. 293(1), pp. 281-288, 2000.
Uno et al., Bull. Chem. Soc. Jpn., vol. 69, pp. 1763-1767, 1996.
Upadhyay et al., CAPLUS Abstract 131:18977, 1999.
Upadhyay et al., Indian J. Chemistry, vol. 38B, pp. 173-177, 1999.
VanLeusen et al., J. Org. Chem., vol. 42(7), pp. 1153-1159, 1977.
Vartanyan et al., Arm. Khim. Zh., vol. 40(9), pp. 552-560, 1987.
Victory et al., Heterocycles, vol. 23(5), pp. 1135-1141, 1985.
Victory et al., Heterocycles, vol. 23(8), pp. 1947-1950, 1985.
Victory et al., J. Heterocyclic Chem., vol. 25, pp. 245-247, 1988.
Victory et al., AFINIDAD XLVI, vol. 420, pp. 107-113, 1989.
Votta et al., Int. J. Immunotherapy, vol. VI(1), pp. 1-12, 1990.
Votta et al., Bone, vol. 15(5), pp. 533-538, 1994.
Wadsworth et al., J. Pharmacol. Exp. Ther., vol. 291(2), pp. 680-687, 1999.
Warrior et al., Journal of Biomolecular Screening, vol. 4(3), pp. 129-135, 1999.
Weinstein et al., J. Immunol., vol. 151, pp. 3829-3838, 1993.
Wilson et al., Chemistry & Biology, vol. 4(6), pp. 423-443 1, 1997.
Witz, Fertility and Sterility, vol. 73(2), pp. 212-214, 2000.
Yoo et al., J. Biol. Chem., vol. 278(44), pp. 43001-43007, 2003.
Zavyalov et al., Khim. Farm. Zh., vol. 26(3), p. 88, 1992.
Zhu et al., J. Clin. Invest., vol. 97(2), pp. 421-430, 1996.
U.S. Appl. No. 11/613,517, filed Dec. 20, 2006, Adams, et al.
U.S. Appl. No. 11/613,598, filed Dec. 20, 2006, Adams, et al.
U.S. Appl. No. 11/871,039, filed Oct. 11, 2007, Adams, et al.
U.S. Appl. No. 11/839,830, filed Aug. 16, 2007, Adams, et al.
U.S. Appl. No. 11/839,833, filed Aug. 16,2007, Adams, et al.
U.S. Appl. No. 11/839,834, filed Aug. 16, 2007, Adams, et al.
U.S. Appl. No. 11/908,340, filed Sep. 11, 2007, Boehm, et al.
U.S. Appl. No. 11/908,435, filed Sep. 12,2007, Callahan, et al.
U.S. Appl. No. 11/908,440, filed Sep. 12, 2007, Callahan, et al.
U.S. Appl. No. 11/908,839, filed Sep. 17, 2007, Callahan, et al.
U.S. Appl. No. 11/915,008, filed Jun. 26, 2008, Yang.
U.S. Appl. No. 12/132,793, filed Jun. 4, 2008, Callahan, et al.
U.S. Appl. No. 12/253,327, filed Oct. 17, 2008, Callahan, et al.
U.S. Appl. No. 12/305,067, filed Jun. 15, 2007, Corsi et al.
U.S. Appl. No. 12/305,077, filed Jun. 15, 2007, Corsi et al.
U.S. Appl. No. 12/305,079, filed Jun. 15, 2007, Corsi et al.

2,4,8-TRISUBSTITUTED-8H-PYRIDO[2,3-D]PYRIMIDIN-7-ONE COMPOUNDS AND COMPOSITIONS FOR USE IN THERAPY

CROSS REFERENCE OF PRIOR APPLICATIONS

This application is a continuation of U.S. application Ser. No. 11/839,834 filed 16 Aug. 2007; which is a continuation of U.S. application Ser. No. 10/399,614 filed 18 Apr. 2003, issued as U.S. Pat. No. 7,323,472; which is the national stage entry of PCT/US01/50493, filed 23 Oct. 2001; which claims the benefit of priority of U.S. Provisional Application Nos. 60/242,461 filed 23 Oct. 2000; 60/310,349 filed 6 Aug. 2001; and 60/326,618, filed 2 Oct. 2001.

FIELD OF THE INVENTION

This invention relates to a novel group of 2,4,8-trisubstituted-8H-pyrido[2,3-d]pyrimidin-7-one compounds, processes for the preparation thereof, the use thereof in treating CSBP/p38 kinase mediated diseases and pharmaceutical compositions for use in such therapy.

BACKGROUND OF THE INVENTION

Intracellular signal transduction is the means by which cells respond to extracellular stimuli. Regardless of the nature of the cell surface receptor (e. g. protein tyrosine kinase or seven-transmembrane G-protein coupled), protein kinases and phosphatases along with phopholipases are the essential machinery by which the signal is further transmitted within the cell [Marshall, J. C. *Cell*, 80, 179-278 (1995)]. Protein kinases can be categorized into five classes with the two major classes being, tyrosine kinases and serine/threonine kinases depending upon whether the enzyme phosphorylates its substrate(s) on specific tyrosine(s) or serine/threonine(s) residues [Hunter, T., *Methods in Enzymology (Protein Kinase Classification)* p. 3, Hunter, T.; Sefton, B. M.; eds. vol. 200, Academic Press; San Diego, 1991].

For most biological responses, multiple intracellular kinases are involved and an individual kinase can be involved in more than one signaling event. These kinases are often cytosolic and can translocate to the nucleus or the ribosomes where they can affect transcriptional and translational events, respectively. The involvement of kinases in transcriptional control is presently much better understood than their effect on translation as illustrated by the studies on growth factor induced signal transduction involving MAP/ERK kinase [Marshall, C. J. *Cell*, 80, 179 (1995); Herskowitz, I. *Cell*, 80, 187 (1995); Hunter, T. *Cell*, 80, 225 (1995); Seger, R., and Krebs, E. G. *FASEB J.*, 726-735 (1995)].

While many signaling pathways are part of cell homeostasis, numerous cytokines (e.g., IL-1 and TNF) and certain other mediators of inflammation (e.g., COX-2, and iNOS) are produced only as a response to stress signals such as bacterial lipopolysaccharide (LPS). The first indications suggesting that the signal transduction pathway leading to LPS-induced cytokine biosynthesis involved protein kinases came from studies of Weinstein [Weinstein, et al., *J. Immunol.* 151, 3829 (1993)] but the specific protein kinases involved were not identified. Working from a similar perspective, Han [Han, et al., *Science* 265, 808(1994)] identified murine p38 as a kinase which is tyrosine phosphorylated in response to LPS. Definitive proof of the involvement of the p38 kinase in LPS-stimulated signal transduction pathway leading to the initiation of proinflammatory cytokine biosynthesis was provided by the independent discovery of p38 kinase by Lee [Lee; et al., *Nature,* 372, 739(1994)] as the molecular target for a novel class of anti-inflammatory agents. The discovery of p38 (termed by Lee as CSBP 1 and 2) provided a mechanism of action of a class of anti-inflammatory compounds for which SK&F 86002 was the prototypic example. These compounds inhibited IL-1 and TNF synthesis in human monocytes at concentrations in the low uM range [Lee, et al., *Int. J. Immunopharmac.* 10(7), 835(1988)] and exhibited activity in animal models which are refractory to cyclooxygenase inhibitors [Lee; et al., *Annals N. Y. Acad. Sci.,* 696, 149(1993)].

It is now firmly established that CSBP/p38 is a one of several kinases involved in a stress-response signal transduction pathway which is parallel to and largely independent of the analogous mitogen-activated protein kinase (MAP) kinase cascade. Stress signals, including LPS, pro-inflammatory cytokines, oxidants, UV light and osmotic stress, activate kinases upstream from CSBP/p38 which in turn phosphorylate CSBP/p38 at threonine 180 and tyrosine 182 resulting in CSBP/p38 activation. MAPKAP kinase-2 and MAPKAP kinase-3 have been identified as downstream substrates of CSBP/p38 which in turn phosphorylate heat shock protein Hsp 27 (FIG. 1). Additional downstream substrates known to be phosphorylated by p38 include kinases (Mnk1/2, MSK1/2 and PRAK) and transcription factors (CHOP, MEF2, ATF2 and CREB). While many of the signaling pathways required for cytokine biosynthesis remain unknown it appears clear that many of the substrates for p38 listed above are involved. [Cohen, P. *Trends Cell Biol.,* 353-361(1997) and Lee, J. C. et al, Pharmacol. Ther. vol. 82, nos. 2-3, pp. 389-397, 1999].

What is known, however, is that in addition to inhibiting IL-1 and TNF, CSBP/p38 kinase inhibitors (SK&F 86002 and SB 203580) also decrease the synthesis of a wide variety of pro-inflammatory proteins including, IL-6, IL-8, GM-CSF and COX-2. Inhibitors of CSBP/p38 kinase have also been shown to suppress the TNF-induced expression of VCAM-1 on endothelial cells, the TNF-induced phosphorylation and activation of cytosolic PLA2 and the IL-1-stimulated synthesis of collagenase and stromelysin. These and additional data demonstrate that CSBP/p38 is involved not only cytokine synthesis, but also in cytokine signaling [CSBP/P38 kinase reviewed in Cohen, P. *Trends Cell Biol.,* 353-361(1997)].

Interleukin-1 (IL-1) and Tumor Necrosis Factor (TNF) are biological substances produced by a variety of cells, such as monocytes or macrophages. IL-1 has been demonstrated to mediate a variety of biological activities thought to be important in immunoregulation and other physiological conditions such as inflammation [See, e.g., Dinarello et al., Rev. Infect. Disease, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels.

There are many disease states in which excessive or unregulated IL-1 production is implicated in exacerbating and/or causing the disease. These include rheumatoid arthritis, osteoarthritis, endotoxemia and/or toxic shock syndrome, other acute or chronic inflammatory disease states such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis, and acute synovitis. Evidence also links IL-1 activity to diabetes and pancreatic β cells [review of the biological activities which have been attributed to IL-1 Dinarello, *J. Clinical Immunology,* 5 (5), 287-297 (1985)].

Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, such as influenza, cachexia secondary to infection or malignancy, cachexia, secondary to acquired immune deficiency syndrome (AIDS), AIDS, ARC (AIDS related complex), keloid formation, scar tissue formation, Crohn's disease, ulcerative colitis, or pyresis.

Interleukin-8 (IL-8) is a chemotactic factor produced by several cell types including mononuclear cells, fibroblasts, endothelial cells, and keratinocytes. Its production from endothelial cells is induced by IL-1, TNF, or lipopolysachharide (LPS). IL-8 stimulates a number of functions in vitro. It has been shown to have chemoattractant properties for neutrophils, T-lymphocytes, and basophils. In addition it induces histamine release from basophils from both normal and atopic individuals as well as lysozomal enzyme release and respiratory burst from neutrophils. IL-8 has also been shown to increase the surface expression of Mac-1 (CD11b/CD18) on neutrophils without de novo protein synthesis, this may contribute to increased adhesion of the neutrophils to vascular endothelial cells. Many diseases are characterized by massive neutrophil infiltration. Conditions associated with an increased in IL-8 production (which is responsible for chemotaxis of neutrophil into the inflammatory site) would benefit by compounds which are suppressive of IL-8 production.

IL-1 and TNF affect a wide variety of cells and tissues and these cytokines as well as other leukocyte derived cytokines are important and critical inflammatory mediators of a wide variety of disease states and conditions. The inhibition of these cytokines is of benefit in controlling, reducing and alleviating many of these disease states.

In addition to the involvement of CSBP/p38 signaling in the production of IL-1, TNF, IL-8, IL-6, GM-CSF, COX-2, collagenase and stromelysin, signal transduction via CSBP/p38 is required for the action of several of these same pro-inflammatory proteins plus many others (VEGF, PDGF, NGF) [Ono, K. and Han, J., *Cellular Signaling*, 12 1-13 (2000)]. The involvement of CSBP/p38 in multiple stress-induced signal transduction pathways provides additional rationale for the potential utility of CSBP/p38 in the treatment of diseases resulting from the excessive and destructive activation of the immune system. This expectation is supported by the potent and diverse activities described for CSBP/p38 kinase inhibitors [Badger, et al., *J. Pharm. Exp. Thera.* 279 (3): 1453-1461.(1996); Griswold, et al, *Pharmacol. Comm.* 7, 323-229 (1996); Jackson, et al., J. Pharmacol. Exp. Ther. 284, 687-692 (1998); Underwood, et al., J. Pharmacol. Exp. Ther. 293, 281-288 (2000); Badger, et al., Arthritis Rheum. 43, 175-183 (2000)].

There remains a need for treatment, in this field, for compounds which are cytokine suppressive anti-inflammatory drugs, i.e. compounds which are capable of inhibiting the CSBP/p38/RK kinase.

Other pyrido[2,3-d]pyrimidine containing pharmacophores having varying pharmaceutical, insecticidal, and herbicidal activity may be found in the art, such as in WO 98/33798; WO 98/23613; WO 95/19774, now U.S. Pat. No. 6,265,410; WO 00/23444; WO 01/19828 (published after the filing date of this application); U.S. Pat. Nos. 5,532,370; 5,597,776; JP 2000-38350; WO 00/43374; WO 98/08846; and WO 01/55147 (also published after the filing date of this application).

SUMMARY OF THE INVENTION

Figure 1:
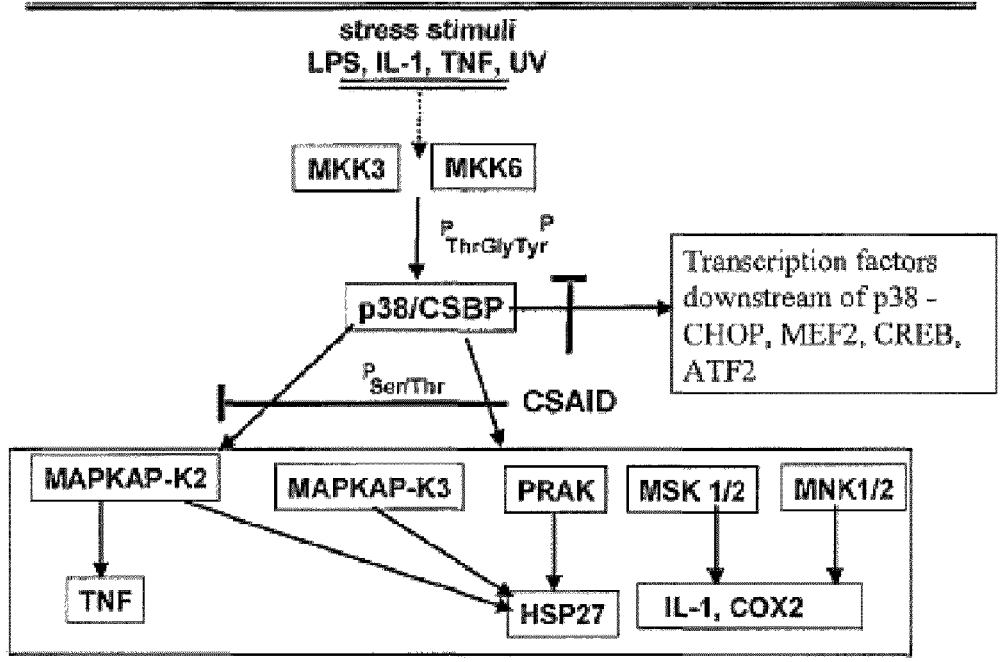
FIG. 1 demonstrates the p38 kinase cascade.

This invention relates to the novel compounds of Formula (I) and (Ia), and Formula (II) and (IIa), and pharmaceutical compositions comprising a compound of Formula (I) and (Ia), and Formula (II) and (IIa), and a pharmaceutically acceptable diluent or carrier.

This invention relates to a method of treating a CSBP/RK/p38 kinase mediated disease in a mammal in need thereof, which comprises administering to said mammal an effective amount of a compound of Formula (I) and (Ia), and Formula (II) and (IIa).

This invention also relates to a method of inhibiting cytokines and the treatment of a cytokine mediated disease, in a mammal in need thereof, which comprises administering to said mammal an effective amount of a compound of Formula (I) and (Ia), and Formula (II) and (IIa).

This invention more specifically relates to a method of inhibiting the production of IL-1 in a mammal in need thereof which comprises administering to said mammal an effective amount of a compound of Formula (I) and (Ia), and Formula (II) and (IIa).

This invention more specifically relates to a method of inhibiting the production of IL-6 in a mammal in need thereof which comprises administering to said mammal an effective amount of a compound of Formula (I) and (Ia), and Formula (II) and (IIa).

This invention more specifically relates to a method of inhibiting the production of IL-8 in a mammal in need thereof which comprises administering to said mammal an effective amount of a compound of Formula (I) and (Ia), and Formula (II) and (IIa).

This invention more specifically relates to a method of inhibiting the production of TNF in a mammal in need thereof which comprises administering to said mammal an effective amount of a compound of Formula (I) and (Ia), and Formula (II) and (IIa).

Accordingly, the present invention provides a compound of Formula (I) and (Ia):

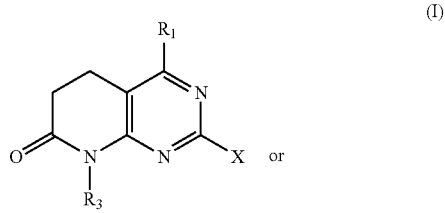

(I)

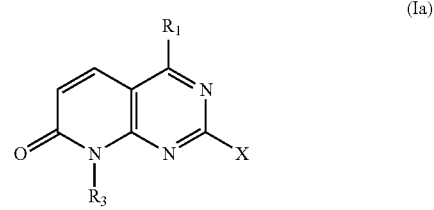

(Ia)

wherein
R$_1$ is an optionally substituted aryl or an optionally substituted heteroaryl ring;
R$_2$ is hydrogen, C$_{1-10}$ alkyl, C$_{3-7}$ cycloalkyl, C$_{3-7}$ cycloalkylalkyl, aryl, arylC$_{1-10}$ alkyl, heteroaryl, heteroarylC$_{1-10}$ alkyl, heterocyclic, or a heterocyclylC$_{1-10}$ alkyl moiety, which moieties are all optionally substituted, or R$_2$ is the moiety X$_1$(CR$_{10}$R$_{20}$)$_q$C(A$_1$)(A$_2$)(A$_3$), or C(A$_1$)(A$_2$)(A$_3$);
A$_1$ is an optionally substituted C$_{1-10}$ alkyl;
A$_2$ is an optionally substituted C$_{1-10}$ alkyl;
A$_3$ is hydrogen or is an optionally substituted C$_{1-10}$ alkyl;
R$_3$ is an C$_{1-10}$ alkyl, C$_{3-7}$ cycloalkyl, C$_{3-7}$ cycloalkylC$_{1-4}$alkyl, aryl, arylC$_{1-10}$ alkyl, heteroaryl, heteroarylC$_{1-10}$ alkyl, heterocyclic, or a heterocyclylC$_{1-10}$ alkyl moiety, which moieties are optionally substituted;
R$_4$ and R$_{14}$ are each independently selected from hydrogen, optionally substituted C$_{1-4}$ alkyl, optionally substituted C$_{3-7}$ cycloalkyl, C$_{3-7}$ cycloalkylC$_{1-4}$alkyl, optionally substituted aryl, or optionally substituted aryl-C$_{1-4}$ alkyl, or R$_4$ and R$_{14}$ together with the nitrogen which they are attached form an optionally substituted heterocyclic ring of 4 to 7 members, which ring optionally contains an additional heteroatom selected from oxygen, sulfur or NR$_9$;
R$_6$ is hydrogen, C$_{1-10}$ alkyl, C$_{3-7}$ cycloalkyl, heterocyclyl, heterocyclyl C$_{1-10}$alkyl, aryl, arylC$_{1-10}$ alkyl, heteroaryl or heteroarylC$_{1-10}$ alkyl, wherein each of these moieties may be optionally substituted;
R$_9$ is hydrogen, C(Z)R$_6$ or optionally substituted C$_{1-10}$ alkyl, optionally substituted aryl or optionally substituted aryl-C$_{1-4}$ alkyl;
R$_{10}$ and R$_{20}$ are independently selected from hydrogen or C$_{1-4}$alkyl;
X is R$_2$, OR$_2$, S(O)$_m$R$_2$, (CH$_2$)$_n$N(R$_{10}$)S(O)$_m$R$_2$, (CH$_2$)$_n$N(R$_{10}$)C(O)R$_2$, (CH$_2$)$_n$NR$_4$R$_{14}$, or (CH$_2$)$_n$N(R$_2$)$_2$;
X$_1$ is N(R$_{10}$), O, S(O)$_m$, or CR$_{10}$R$_{20}$;
n is 0 or an integer having a value of 1 to 10;
m is 0 or an integer having a value of 1 or 2;
q is 0 or an integer having a value of 1 to 10;
Z is oxygen or sulfur;
or a pharmaceutically acceptable salt thereof.

DETAILED DESCRIPTION OF THE INVENTION

Another aspect of the present invention provides for the compound of Formula (II) and (IIa):

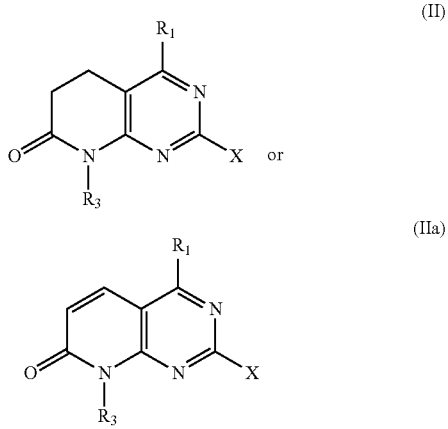

wherein
R$_1$ is the moiety YRa;
R$_2$ is hydrogen, C$_{1-10}$ alkyl, C$_{3-7}$ cycloalkyl, C$_{3-7}$ cycloalkylalkyl, aryl, arylC$_{1-10}$ alkyl, heteroaryl, heteroarylC$_{1-10}$ alkyl, heterocyclic, or a heterocyclylC$_{1-10}$ alkyl moiety, which moieties are all optionally substituted, or R$_2$ is the moiety X$_1$(CR$_{10}$R$_{20}$)$_q$C(A$_1$)(A$_2$)(A$_3$), or C(A$_1$)(A$_2$)(A$_3$);
A$_1$ is an optionally substituted C$_{1-10}$ alkyl;
A$_2$ is an optionally substituted C$_{1-10}$ alkyl;
A$_3$ is hydrogen or is an optionally substituted C$_{1-10}$ alkyl;
R$_3$ is an C$_{1-10}$ alkyl, C$_{3-7}$ cycloalkyl, C$_{3-7}$ cycloalkylC$_{1-4}$alkyl, aryl, arylC$_{1-10}$ alkyl, heteroaryl, heteroarylC$_{1-10}$ alkyl, heterocyclic, or a heterocyclylC$_{1-10}$ alkyl moiety, which moieties are optionally substituted;
R$_4$ and R$_{14}$ are each independently selected from hydrogen, optionally substituted C$_{1-4}$ alkyl, optionally substituted C$_{3-7}$ cycloalkyl, C$_{3-7}$ cycloalkylC$_{1-4}$alkyl, optionally substituted aryl, or optionally substituted aryl-C$_{1-4}$ alkyl, or R$_4$ and R$_{14}$ together with the nitrogen which they are attached form an optionally substituted heterocyclic ring of 4 to 7 members, which ring optionally contains an additional heteroatom selected from oxygen, sulfur or NR$_9$;
R$_6$ is hydrogen, C$_{1-10}$ alkyl, C$_{3-7}$ cycloalkyl, heterocyclyl, heterocyclyl C$_{1-10}$alkyl, aryl, arylC$_{1-10}$ alkyl, heteroaryl or heteroarylC$_{1-10}$ alkyl, wherein each of these moieties may be optionally substituted;
R$_9$ is hydrogen, C(Z)R$_6$ or optionally substituted C$_{1-10}$ alkyl, optionally substituted aryl or optionally substituted aryl-C$_{1-4}$ alkyl;
R$_{10}$ and R$_{20}$ are independently selected from hydrogen or C$_{1-4}$alkyl;
Y is C(R$_b$)(R$_d$), C(O), N(R$_d$), N(R$_d$)C(R$_c$)(R$_d$), oxygen, OC(R$_c$)(R$_d$), S(O)m, or S(O)$_m$C(R$_c$)(R$_d$);
R$_a$ is an aryl or heteroaryl ring, which ring is optionally substituted;
R$_b$ is hydrogen, C$_{1-2}$ alkyl, NR$_c$, hydroxy, thio, C$_{1-2}$ alkoxy, S(O)$_m$C$_{1-2}$ alkyl;
R$_c$ is hydrogen or C$_{1-2}$ alkyl;
R$_d$ is hydrogen or C$_{1-2}$ alkyl;
X is R$_2$, OR$_2$, S(O)$_m$R$_2$, (CH$_2$)$_n$N(R$_{10}$)S(O)$_m$R$_2$, (CH$_2$)$_n$N(R$_{10}$)C(O)R$_2$, (CH$_2$)$_n$NR$_4$R$_{14}$, or (CH$_2$)$_n$N(R$_2$)$_2$;
X$_1$ is N(R$_{10}$), O, S(O)$_m$, or CR$_{10}$R$_{20}$;
n is 0 or an integer having a value of 1 to 10;
m is 0 or an integer having a value of 1 or 2;
q is 0 or an integer having a value of 1 to 10;
Z is oxygen or sulfur;
or a pharmaceutically acceptable salt thereof.

The present invention is directed to novel compounds of Formula (I) and (Ia), and those of Formula (II) and (IIa), or a pharmaceutically acceptable salt thereof. As will be readily recognized, the difference between compounds of Formula (I) and (Ia) and that of Formula (II) and (IIa) lies in the unsaturation of the pyrido-7-one ring. The respective R$_1$, R$_2$, X and R$_3$ terms are the same for both groups within the Formula itself, for instance I and Ia. For purposes herein, everything applicable to Formula (I) is also applicable to Formula (Ia) unless otherwise indicated, and everything applicable to Formula (II) is also applicable to Formula (IIa) unless otherwise indicated.

Suitably, for compounds of Formula (I), and (Ia), R$_1$ is an aryl, or heteroaryl ring, which ring is optionally substituted. The R$_1$ aryl or heteroaryl rings may be substituted one or more times, preferably 1 to 4 times, independently, by substituents selected from halogen, C$_{1-4}$ alkyl, halo-substituted-C$_{1-4}$ alkyl, cyano, nitro, (CR$_{10}$R$_{20}$)$_v$NR$_4$R$_{14}$, (CR$_{10}$R$_{20}$)$_v$C(Z)NR$_4$R$_{14}$, (CR$_{10}$R$_{20}$)$_v$C(Z)OR$_8$, (CR$_{10}$R$_{20}$)$_v$COR$_{a'}$, (CR$_{10}$R$_{20}$)$_v$C(O)H, SR$_5$, S(O)R$_5$, S(O)$_2$R$_5$, (CR$_{10}$R$_{20}$)$_v$OR$_8$, ZC(Z)R$_{11}$, NR$_{10}$C(Z)R$_{11}$, or NR$_{10}$S(O)$_2$R$_7$.

Preferably, $R_1$ is an aryl moiety, more preferably a phenyl ring, optionally substituted one or more times by halogen, $C_{1-4}$ alkyl, or halo-substituted-$C_{1-4}$ alkyl. More preferably, the phenyl ring is substituted in the 2, 4, or 6-position, or di-substituted in the 2,4-position, such as 2-fluoro, 4-fluoro, 2,4-difluoro, or 2-methyl-4-fluoro; or tri-substituted in the 2,4,6-position such as 2,4,6-trifluoro.

Preferably, when $R_1$ is a heteroaryl moiety, the ring is not attached to the pharmacophore via one of the heteroatoms, such as nitrogen to form a charged ring. For instance, a pyridinyl ring would be attached through a carbon atom to yield a 2-, 3- or 4-pyridyl moiety, which is optionally substituted.

Suitably, v is 0 or an integer having a value of 1 or 2.

Suitably, Z is oxygen or sulfur.

Suitably, $R_a$, is $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{5-7}$ cycloalkenyl, aryl, aryl$C_{1-4}$ alkyl, heteroaryl, heteroaryl$C_{1-4}$ alkyl, heterocyclyl, heterocyclyl$C_{1-4}$ alkyl, $(CR_{10}R_{20})_vOR_7$, $(CR_{10}R_{20})_vS(O)_m R_7$, $(CR_{10}R_{20})_vNHS(O)_2R_7$, or $(CR_{10}R_{20})_vNR_4R_{14}$; and wherein the aryl, arylalkyl, heteroaryl, heteroaryl alkyl may be optionally substituted.

Suitably, for compounds of Formula (II), and (IIa), $R_1$ is $Y—R_a$.

Suitably, Y is $C(R_b)(R_d)$, C(O), $N(R_d)$, $N(R_d)C(R_c)(R_d)$, oxygen, $OC(R_c)(R_d)$, $S(O)m$, or $S(O)_mC(R_c)(R_d)$.

Suitably, $R_b$ is hydrogen, $C_{1-2}$ alkyl, $NR_c$, hydroxy, thio, $C_{1-2}$ alkoxy, $S(O)_mC_{1-2}$ alkyl.

Suitably, $R_c$ is hydrogen or $C_{1-2}$ alkyl.

Suitably, $R_d$ is hydrogen or $C_{1-2}$ alkyl.

Suitably, m is 0 or an integer having a value of 1 or 2.

Suitably $R_a$ is an optionally substituted aryl ring or an optionally substituted heteroaryl ring. The optional substitutents for these rings are the same as for the Formula (I) and (Ia) $R_1$ aryl and heteroaryl rings as noted above.

As will be appreciated the difference between compounds of Formula (I) and (II) lies in the $R_1$ substitution. The remaining substituent groups are the same and for purposes herein applicable to all four formulas unless otherwise indicated.

Suitably, $R_4$ and $R_{14}$ are each independently selected from hydrogen, optionally substituted $C_{1-4}$ alkyl, optionally substituted $C_{3-7}$ cycloalkyl, optionally substituted $C_{3-7}$ cycloalkyl$C_{1-4}$ alkyl, optionally substituted aryl or optionally substituted aryl-$C_{1-4}$ alkyl, or $R_4$ and $R_{14}$ together with the nitrogen to which they are attached may form an optionally substituted heterocyclic ring of 4 to 7 members which ring optionally contains an additional heteroatom selected from oxygen, sulfur or $NR_9$.

The $C_{1-4}$ alkyl, $C_{3-7}$ cycloalkyl, $C_{3-7}$ cycloalkyl$C_{1-4}$ alkyl, aryl and aryl-$C_{1-4}$ alkyl moieties may be optionally substituted, one or more times, preferably 1 to 4 times independently by halogen, such as fluorine, chlorine, bromine or iodine; hydroxy; hydroxy substituted $C_{1-10}$alkyl; $C_{1-10}$ alkoxy, such as methoxy or ethoxy; halosubstituted $C_{1-10}$ alkoxy; S(O)m alkyl, such as methyl thio, methylsulfinyl or methyl sulfonyl; aldehydes (—C(O)), or a ketone, such as —C(O)$R_6$, such as C(O)$C_{1-10}$alkyl or C(O)aryl; amides, such as C(O)$NR_4R_{14'}$, or $NR_4C(O)C_{1-10}$alkyl, or $NR_4C(O)$aryl; $NR_4R_{14'}$, wherein $R_4$ and $R_{14'}$ are each independently hydrogen or $C_{1-4}$ alkyl, or wherein the $R_4R_{14'}$ can cyclize together with the nitrogen to which they are attached to form a 5 to 7 membered ring which optionally contains an additional heteroatom selected from O/N/S; cyano, nitro, $C_{1-10}$ alkyl, $C_{3-7}$cycloalkyl, or $C_{3-7}$cycloalkyl $C_{1-10}$ alkyl group, such as methyl, ethyl, propyl, isopropyl, t-butyl, etc, or cyclopropyl methyl; halosubstituted $C_{1-10}$ alkyl, such $CF_2CF_2H$, $CH_2CF_3$, or $CF_3$; an optionally substituted aryl, such as phenyl, or an optionally substituted arylalkyl, such as benzyl or phenethyl, wherein these aryl containing moieties may also be substituted one to two times by halogen; hydroxy; hydroxy substituted alkyl; $C_{1-10}$ alkoxy; $S(O)_m$alkyl; amino, mono & di-substituted $C_{1-4}$ alkyl amino, such as in the $NR_4R_{14'}$ group; $C_{1-4}$ alkyl, or $CF_3$.

When $R_4$ and $R_{14}$ together with the nitrogen cyclize to form a ring, suitably, such rings include, but are not limited to pyrrolidine, piperidine, piperazine, morpholine, and thiomorpholine (including oxidizing the sulfur). The ring may be optional substituted, one or more times, preferably 1 to 4 times, independently by halogen, such as fluorine, chlorine, bromine or iodine; hydroxy; hydroxy substituted $C_{1-10}$alkyl; $C_{1-10}$ alkoxy, such as methoxy or ethoxy; halosubstituted $C_{1-10}$ alkoxy; S(O)m alkyl, such as methyl thio, methylsulfinyl or methyl sulfonyl; a ketone on the cyclized ring (—C(O)), or a ketone or aldehyde off the ring (—C(O)$R_6$), such as C(O)$C_{1-10}$ alkyl or C(O) aryl; $NR_4R_{14'}$, wherein $R_{4'}$ and $R_{14'}$ are each independently hydrogen or $C_{1-4}$ alkyl; $C_{1-10}$ alkyl, $C_{3-7}$cycloalkyl, or $C_{3-7}$cycloalkyl $C_{1-10}$ alkyl group, such as methyl, ethyl, propyl, isopropyl, t-butyl, etc. or cyclopropyl methyl; halosubstituted $C_{1-10}$ alkyl, such $CF_2CF_2H$, $CH_2CF_3$, or $CF_3$; an optionally substituted aryl, such as phenyl, or an optionally substituted arylalkyl, such as benzyl or phenethyl, wherein these aryl containing moieties may also be substituted one to two times by halogen; hydroxy; hydroxy substituted alkyl; $C_{1-10}$ alkoxy; $S(O)_m$alkyl; amino, mono & di-substituted $C_{1-4}$ alkyl amino, such as in the $NR_4R_{14'}$ group; $C_{1-4}$ alkyl, or $CF_3$.

Suitably, $R_5$ is hydrogen, $C_{1-4}$ alkyl, $C_{2-4}$ alkenyl, $C_{2-4}$ alkynyl or $NR_4R_{14}$, excluding the moieties $SR_5$ being $SNR_4R_{14}$, $S(O)_2R_5$ being $SO_2H$ and $S(O)R_5$ being SOH.

Suitably, $R_6$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl, wherein these moieties may be optionally substituted.

Suitably, $R_7$ is $C_{1-6}$alkyl, aryl, aryl$C_{1-6}$alkyl, heterocyclic, heterocyclyl$C_{1-6}$ alkyl, heteroaryl, or heteroaryl$C_{1-6}$alkyl; and wherein each of these moieties may be optionally substituted.

Suitably, $R_8$ is hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{5-7}$ cycloalkenyl, aryl, aryl$C_{1-4}$ alkyl, heteroaryl, heteroaryl$C_{1-4}$ alkyl, heterocyclyl, heterocyclyl$C_{1-4}$ alkyl, $(CR_{10}R_{20})_tOR_7$, $(CR_{10}R_{20})_tS(O)_mR_7$, $(CR_{10}R_{20})_tNHS(O)_2R_7$, or $(CR_{10}R_{20})_t NR_4R_{14}$; and wherein the cycloalkyl, cycloalkenyl, aryl, arylalkyl, heteroaryl, heteroaryl alkyl, heterocyclic and heterocyclic alkyl moieties may be optionally substituted.

Suitably, t is an integer having a value of 1 to 3.

Suitably, $R_9$ is hydrogen, $C(Z)R_6$, optionally substituted $C_{1-10}$ alkyl, optionally substituted aryl or optionally substituted aryl-$C_{1-4}$ alkyl.

Suitably, $R_{10}$ and $R_{20}$ are independently selected from hydrogen or a $C_{1-4}$ alkyl.

Suitably, $R_{11}$ is $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{5-7}$ cycloalkenyl, aryl, aryl$C_{1-4}$ alkyl, heteroaryl, heteroaryl$C_{1-4}$ alkyl, heterocyclyl, heterocyclyl$C_{1-4}$ alkyl, $(CR_{10}R_{20})_tOR_7$, $(CR_{10}R_{20})_tS(O)_mR_7$, $(CR_{10}R_{20})_tNHS(O)_2R_7$, or $(CR_{10}R_{20})_vNR_4R_{14}$; and wherein the aryl, arylalkyl, heteroaryl, heteroaryl alkyl, heterocyclyl, and heterocyclylalkyl moieties may optionally substituted.

Suitably m is 0 or an integer having a value of 1 or 2.

Suitably, $R_3$ is an optionally substituted $C_{1-10}$ alkyl, $C_{3-7}$ cycloalkyl, $C_{3-7}$ cycloalkyl$C_{1-10}$alkyl, aryl, aryl$C_{1-10}$ alkyl, heteroaryl$C_{1-10}$alkyl, or heterocyclyl$C_{1-10}$ alkyl moiety, which moieties are optionally substituted one or more times, preferably 1 to 4 times, independently by $C_{1-10}$ alkyl, halosubstituted $C_{1-10}$ alkyl, $C_{2-10}$ alkenyl, $C_{2-10}$alkynyl, $C_{3-7}$cycloalkyl, $C_{3-7}$cycloalkyl$C_{1-10}$ alkyl, $C_{5-7}$cycloalkenyl, $C_{5-7}$cycloalkenyl$C_{1-10}$ alkyl, halogen, cyano, nitro, $(CR_{10}R_{20})_nOR_6$, $(CR_{10}R_{20})_nSH$, $(CR_{10}R_{20})_nS(O)_mR_7$, $(CR_{10}R_{20})_nNHS(O)_2R_7$, $(CR_{10}R_{20})_nNR_4R_{14}$, $(CR_{10}R_{20})_nCN$, $(CR_{10}R_{20})_nS(O)_2NR_4R_{14}$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_nC(Z)NR_4R_{14}$, $(CR_{10}R_{20})_nNR_{10}C(Z)R_6$, $(CR_{10}R_{20})_nNR_{10}C(=NR_{10})NR_4R_{14}$, $(CR_{10}R_{20})_nOC(Z)NR_4R_{14}$, $(CR_{10}R_{20})_nNR_{10}C(Z)NR_4R_{14}$, or $(CR_{10}R_{20})_nNR_{10}C(Z)OR_7$.

Preferably the optional substituents are independently selected from halogen, alkyl, hydroxy, alkoxy, cyano, nitro, amino, or halosubstituted alkyl. More preferably, halogen, or alkyl.

Preferably, $R_3$ is an optionally substituted $C_{1-10}$ alkyl, $C_{3-7}$cycloalkyl, $C_{3-7}$cycloalkylalkyl, or aryl. More preferably, $R_3$ is an optionally substituted $C_{1-10}$ alkyl, or aryl.

Preferably, when $R_3$ is an aryl moiety, it is a phenyl ring, optionally substituted one or more times by halogen, $C_{1-4}$ alkyl, or halo-substituted-$C_{1-4}$ alkyl. More preferably, the phenyl ring is substituted in the 2, 4, or 6-position, or di-substituted in the 2,4-position, such as 2-fluoro, 4-fluoro, 2,4-difluoro, or 2-methyl-4-fluoro; or tri-substituted in the 2,4,6-position, such as 2,4,6-trifluoro.

Suitably, n is 0, or an integer having a value of 1 to 10.

Suitably, X is $R_2$, $OR_2$, $S(O)_mR_2$, $(CH_2)_nN(R_{10})S(O)mR_2$, $(CH_2)_nN(R_{10})C(O)R_2$, $(CH_2)_nNR_4R_{14}$, or $(CH_2)_nN(R_2)_2$. Preferably X is $R_2$, $OR_2$, $(CH_2)_nNR_4R_{14}$, or $(CH_2)_nN(R_2)_2$. Preferably, when X is $R_2$, then $R_2$ is the moiety $X_1(CR_{10}R_{20})_qC(A_1)(A_2)(A_3)$, or $C(A_1)(A_2)(A_3)$.

Suitably, $R_2$ is independently selected from hydrogen, optionally substituted $C_{1-10}$ alkyl, optionally substituted $C_{3-7}$ cycloalkyl, optionally substituted $C_{3-7}$cycloalkylalkyl, optionally substituted aryl, optionally substituted aryl$C_{1-10}$alkyl, optionally substituted heteroaryl, optionally substituted heteroaryl$C_{1-10}$ alkyl, optionally substituted heterocyclic, optionally substituted heterocyclyl$C_{1-10}$alkyl moiety, or $R_2$ is the moiety $X_1(CR_{10}R_{20})_qC(A_1)(A_2)(A_3)$, or $C(A_1)(A_2)(A_3)$.

The $R_2$ moieties, excluding hydrogen, may be optionally substituted one or more times, preferably 1 to 4 times, independently by $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$alkyl, $C_{5-7}$cycloalkenyl, $C_{5-7}$ cycloalkenyl $C_{1-10}$ alkyl, halogen, —C(O), cyano, nitro, $(CR_{10}R_{20})_nOR_6$, $(CR_{10}R_{20})_n$ SH, $(CR_{10}R_{20})_nS(O)_mR_7$, $(CR_{10}R_{20})_nNHS(O)_2R_7$, $(CR_{10}R_{20})_nNR_4R_{14}$, $(CR_{10}R_{20})_nCN$, $(CR_{10}R_{20})_nS(O)_2NR_4R_{14}$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_nC(Z)NR_4R_{14}$, $(CR_{10}R_{20})_nNR_{10}C(Z)R_6$, $(CR_{10}R_{20})_nNR_{10}C(=NR_{10})NR_4R_{14}$, $(CR_{10}R_{20})_nC(=NOR_6)NR_4R_{14}$, $(CR_{10}R_{20})_nOC(Z)NR_4R_{14}$, $(CR_{10}R_{20})_nNR_{10}C(Z)NR_4R_{14}$, or $(CR_{10}R_{20})_nNR_{10}C(Z)OR_7$.

Suitably $X_1$ is $N(R_{10})$, O, $S(O)_m$, or $CR_{10}R_{20}$. More preferably, $X_1$ is $N(R_{10})$, or O.

Suitably, q is 0 or an integer having a value of 1 to 10.

Suitably, $A_1$ is an optionally substituted $C_{1-10}$ alkyl.

Suitably, $A_2$ is an optionally substituted $C_{1-10}$ alkyl.

Suitably, $A_3$ is hydrogen or is an optionally substituted $C_{1-10}$ alkyl.

The $A_1$, $A_2$, and $A_3$ $C_{1-10}$ alkyl moieties may optionally substituted one or more times, independently, preferably from 1 to 4 times, with halogen, such as chlorine, fluorine, bromine, or iodine; halo-substituted $C_{1-10}$alkyl, such as $CF_3$, or $CHF_2CF_3$; $C_{2-10}$ alkenyl, $C_{2-10}$ alkynyl, $C_{3-7}$ cycloalkyl, $C_{3-7}$cycloalkyl$C_{1-10}$alkyl, $C_{5-7}$cycloalkenyl, $C_{5-7}$ cycloalkenyl$C_{1-10}$alkyl, $(CR_{10}R_{20})_nOR_6$, $(CR_{10}R_{20})_n$SH, $(CR_{10}R_{20})_nS(O)_mR_7$, $(CR_{10}R_{20})_nNHS(O)_2R_7$, $(CR_{10}R_{20})_nNR_4R_{14}$, $(CR_{10}R_{20})_nCN$, $(CR_{10}R_{20})_nS(O)_2NR_4R_{14}$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_nC(Z)NR_4R_{14}$, $(CR_{10}R_{20})_nNR_{10}C(Z)R_6$, $(CR_{10}R_{20})_nNR_{10}C(=NR_{10})NR_4R_{14}$, $(CR_{10}R_{20})_nOC(Z)NR_4R_{14}$, $(CR_{10}R_{20})_nNR_{10}C(Z)NR_4R_{14}$, or $(CR_{10}R_{20})_nNR_{10}C(Z)OR_7$.

Preferably, one or more of $A_1$ to $A_3$ is substituted with $(CR_{10}R_{20})_nOR_6$. More preferably, $R_6$ is hydrogen.

A preferred $C(A_1)(A_2)(A_3)$ grouping is $CH(CH_2OH)_2$, or $C(CH_3)(CH_2OH)_2$, $X_1(CR_{10}R_{20})qCH(CH_2OH)_2$, or $X_1(CR_{10}R_{20})qC(CH_3)(CH_2OH)_2$. $X_1$ is preferably oxygen or nitrogen.

As used herein, "optionally substituted" unless specifically defined shall mean such groups as halogen, such as fluorine, chlorine, bromine or iodine; hydroxy; hydroxy substituted $C_{1-10}$alkyl; $C_{1-10}$ alkoxy, such as methoxy or ethoxy; halo-substituted $C_{1-10}$ alkoxy; S(O)m alkyl, such as methyl thio, methylsulfinyl or methyl sulfonyl; —C(O); $NR_4R_{14'}$, wherein $R_{4'}$ and $R_{14'}$ are each independently hydrogen or $C_{1-4}$ alkyl, such as amino or mono or -disubstituted $C_{1-4}$ alkyl or wherein the $R_4R_{14'}$ can cyclize together with the nitrogen to which they are attached to form a 5 to 7 membered ring which optionally contains an additional heteroatom selected from O/N/S; $C_{1-10}$ alkyl, $C_{3-7}$cycloalkyl, or $C_{3-7}$cycloalkyl $C_{1-10}$ alkyl group, such as methyl, ethyl, propyl, isopropyl, t-butyl, etc. or cyclopropyl methyl; halosubstituted $C_{1-10}$ alkyl, such $CF_2CF_2H$, or $CF_3$; an optionally substituted aryl, such as phenyl, or an optionally substituted arylalkyl, such as benzyl or phenethyl, wherein these aryl containing moieties may also be substituted one to two times by halogen; hydroxy; hydroxy substituted alkyl; $C_{1-10}$ alkoxy; $S(O)_m$alkyl; amino, mono & di-substituted $C_{1-4}$ alkyl amino, such as in the $NR_4R_{14}$ group; $C_{1-4}$ alkyl, or $CF_3$.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid.

In addition, pharmaceutically acceptable salts of compounds of Formula (I) may also be formed with a pharmaceutically acceptable cation, for instance, if a substituent group comprises a carboxy moiety. Suitable pharmaceutically acceptable cations are well known to those skilled in the art and include alkaline, alkaline earth, ammonium and quaternary ammonium cations.

The term "halo" or "halogens" is used herein to mean the halogens, chloro, fluoro, bromo and iodo.

The term "$C_{1-10}$alkyl" or "alkyl" or "alkyl$_{1-10}$" is used herein to mean both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

The term "cycloalkyl" is used herein to mean cyclic radicals, preferably of 3 to 8 carbons, including but not limited to cyclopropyl, cyclopentyl, cyclohexyl, and the like.

The term "cycloalkenyl" is used herein to mean cyclic radicals, preferably of 5 to 8 carbons, which have at least one bond including but not limited to cyclopentenyl, cyclohexenyl, and the like.

The term "alkenyl" is used herein at all occurrences to mean straight or branched chain radical of 2-10 carbon atoms, unless the chain length is limited thereto, including, but not limited to ethenyl, 1-propenyl, 2-propenyl, 2-methyl-1-propenyl, 1-butenyl, 2-butenyl and the like.

The term "aryl" is used herein to mean phenyl and naphthyl.

The term "heteroaryl" (on its own or in any combination, such as "heteroaryloxy", or "heteroaryl alkyl") is used herein to mean a 5-10 membered aromatic ring system in which one or more rings contain one or more heteroatoms selected from the group consisting of N, O or S, such as, but not limited, to pyrrole, pyrazole, furan, pyran, thiophene, quinoline, iso-quinoline, quinazolinyl, pyridine, pyrimidine, pyridazine, pyrazine, uracil, oxadiazole, oxazole, isoxazole, oxathiadiazole, thiazole, isothiazole, thiadiazole, tetrazole, triazole, indazole, imidazole, or benzimidazole.

The term "heterocyclic" (on its own or in any combination, such as "heterocyclylalkyl") is used herein to mean a saturated or partially unsaturated 4-10 membered ring system in which one or more rings contain one or more heteroatoms selected from the group consisting of N, O, S, or S(O)m, and m is 0 or an integer having a value of 1 or 2; such as, but not limited to, the saturated or partially saturated versions of the heteroaryl moieties as defined above, such as tetrahydropyrrole, tetrahydropyran, tetrahydrofuran, tetrahydrothiophene (including oxidized versions of the sulfur moiety), pyrrolidine, piperidine, piperazine, morpholine, thiomorpholine (including oxidized versions of the sulfur moiety), or imidazolidine.

The term "aralkyl" or "heteroarylalkyl" or "heterocyclicalkyl" is used herein to mean $C_{1-4}$ alkyl as defined above attached to an aryl, heteroaryl or heterocyclic moiety as also defined herein unless otherwise indicate.

The term "sulfonyl" is used herein to mean the oxide S(O) of the corresponding sulfide, the term "thio" refers to the sulfide, and the term "sulfonyl" refers to the fully oxidized $S(O)_2$ moiety.

The term "aroyl" is used herein to mean C(O)Ar, wherein Ar is as phenyl, naphthyl, or aryl alkyl derivative such as defined above, such group include but are not limited to benzyl and phenethyl. The term "alkanoyl" is used herein to mean $C(O)C_{1-10}$ alkyl wherein the alkyl is as defined above.

It is recognized that the compounds of the present invention may exist as stereoisomers, regioisomers, or diastereoisomers. These compounds may contain one or more asymmetric carbon atoms and may exist in racemic and optically active forms. All of these individual compounds, isomers, and mixtures thereof are included within the scope of the present invention.

Exemplified compounds of the compounds of this invention include the racemates, or optically active forms of the compounds of the working examples herein, and pharmaceutically acceptable salts thereof.

Methods of Manufacture

The compounds of Formula (I), (Ia), (II) and (IIa) may be obtained by applying synthetic procedures, described herein. The synthesis provided for is applicable to producing compounds of Formula (I), (Ia), (II) and (IIa) having a variety of different $R_1$, $R_2$, Y, X, and $R_3$ groups which are reacted, employing optional substituents which are suitably protected, to achieve compatibility with the reactions outlined herein. Subsequent deprotection, in those cases, then affords compounds of the nature generally disclosed. While a particular formula with particular substituent groups is shown herein, the synthesis is applicable to all formulas and all substituent groups herein.

Once the nucleus has been established, further compounds of Formula (I), (Ia), (II) and (IIa) may be prepared by applying standard techniques for functional group interconversion, well known in the art. For instance: $C(O)NR_4R_{14}$ from $CO_2CH_3$ by heating with $HNR_4R_{14}$ in $CH_3OH$ with or without catalytic or stoichiometric metal cyanide or Aluminum trimethyl, e.g. NaCN; $OC(O)R_3$ from OH with e.g., $ClC(O)R_6$ in bases such as triethylamine and pyridine; $NR_{10}$—C(S) $NR_4R_{14}$ from $NHR_{10}$ with an alkylisothiocyanate, or thiocyanic acid and $ClC(S)NR_4R_{14}$; $NR_{10}C(O)OR_6$ from $NHR_{10}$ with an alkyl or aryl chloroformate; $NR_{10}C(O)NR_4H$ from $NHR_{10}$ by treatment with an isocyanate, e.g. $R_4N$=C=O; $NR_{10}$—$C(O)R_6$ from $NHR_{10}$ by treatment with Cl—$C(O)R_6$ in pyridine; $C(=NR_{10})NR_4R_{14}$ from $C(NR_4R_{14})S$ with $H_3NR_{10}{}^+OAc^-$ by heating in alcohol; $C(NR_4R_{14})SR_6$ from $C(S)NR_4R_{14}$ with $R_6$—I in an inert solvent, e.g. acetone; $NR_{10}SO_2R_7$ from $NHR_{10}$ by treatment with $ClSO_2R_7$ by heating in bases such as pyridine; $NR_{10}C(S)R_6$ from $NR_{10}C(O)R_6$ by treatment with Lawesson's reagent [2,4-bis(4-methoxyphenyl)-1,3,2,4-dithiadiphosphetane-2,4-disulfide]; $NR_{10}SO_2CF_3$ from $NHR_{10}$ with triflic anhydride and base wherein $R_3$, $R_6$, $R_{10}$, $R_4$ and $R_{14}$ are as defined in Formula (I) herein.

Precursors of the groups $R_1$, $R_2$ and $R_3$, can be other $R_1$, $R_2$ and $R_3$, etc. groups that may be interconverted by applying standard techniques for functional group interconversion. For example wherein a moiety is a halo substituted $C_{1-10}$ alkyl can be converted to the corresponding $C_{1-10}$ alkyl$N_3$ derivative by reacting with a suitable azide salt, and thereafter if desired can be reduced to the corresponding $C_{1-10}$alkyl$NH_2$ compound, which in turn can be reacted with $R_7S(O)_2X$ wherein X is halo (e.g., chloro) to yield the corresponding $C_{1-10}$alkylNHS(O)$_2$ $R_7$ compound.

Alternatively wherein the moiety is a halo-substituted $C_{1-10}$-alkyl it can be reacted with an amine $R_4R_{14}NH$ to yield the corresponding $C_{1-10}$-alkyl$NR_4R_{14}$ compound, or can be reacted with an alkali metal salt of $R_7SH$ to yield the corresponding $C_{1-10}$alkyl$SR_7$ compound.

As noted above, it may be desirable during the synthesis of the compounds of this invention, to derivatize reactive functional groups in the molecule undergoing reaction so as to avoid unwanted side reactions. Functional groups such as hydroxy, amino, an acid groups typically are protected with suitable groups that can be readily removed when desired. Suitable common protecting groups for use with hydroxyl groups and nitrogen groups are well known in the art and described in many references, for instance, Protecting Groups in Organic Synthesis, Greene et al., John Wiley & Sons, New York, N.Y., (2nd edition, 1991 or the earlier 1981 version). Suitable examples of hydroxyl protecting groups include ether forming groups such as benzyl, and aryl groups such as tert-butoxycarbonyl (Boc), silyl ethers, such as t-butyldimethyl or t-butyldiphenyl, and alkyl ethers, such as methyl connected by an alkyl chain of variable link, $(CR_{10}R_{20})_n$. Amino protecting groups may include benzyl, aryl such as acetyl and trialkylsilyl groups. Carboxylic acid groups are typically protected by conversion to an ester that can easily be hydrolyzed, for example, trichloethyl, tert-butyl, benzyl and the like.

Pharmaceutically acid addition salts of compounds of Formula (I), (Ia), (II) and (IIa) may be obtained in known manner, for example by treatment thereof with an appropriate amount of acid in the presence of a suitable solvent.

An illustration of the preparation of compounds of the present invention is shown in the scheme below. For purposes herein, the compounds in Schemes I and II are shown with an S-methyl, or $S(O)_2$-methyl group which is deemed representative of the S(O)m-Rg group, as described in the formulas below.

The starting material 1-Scheme I may be obtained from the commercially available 4,6-dihydroxy-2-methylmercapto-pyrimidine by known literature procedures, such as those noted in Santilli et al., *J. Heterocycl. Chem.* (1971), 445-53, wherein POCl$_3$ and DMF are used.

The intermediate 2-Scheme I was produced by two different routes. In the first route, coupling of dichloro aldehyde 1-Scheme I with aryl amines in the presence of NaH in DMSO (Santilli et al., *J. Heterocycl. Chem.* (1971), 445-53) afforded the desired compound 2-Scheme I along with imine 13-Scheme I. The imine was converted to aldehyde 2-Scheme I by treatment with aqueous HCl in THF. Conversion of 1-Scheme I to 2-Scheme I may also be achieved using triethylamine and the desired amine in chloroform at room temperature for 10 minutes. The reaction was very effective for a range of alkyl amines (78-95% yield). For aryl amines, elevated temperatures (reflux) and longer reaction time (24 hours) were necessary for reaction completion. Use of the base could be omitted when 3 or more equivalent of amine were used. Other suitable bases, include but are not limited to pyridine, diisopropyl ethylamine or pyrrolidine, which may also be used in an appropriate organic solvent, including but not limited to THF, diethyl ether or dioxane.

In the second route, the nitrile 9-Scheme I was prepared in three steps from the aldehyde 1-Scheme I (Santilli et al., *J. Heterocycl. Chem.* (1971), 445-53). Coupling of dichloro nitrile 9-Scheme I with aryl amines in the presence of NaH in DMSO afforded the desired compound 10-Scheme I. Other suitable bases such as pyridine, diisopropyl ethylamine, or sodium may also be used in an appropriate organic solvent such as THF, DMF or dioxane. Production and use of the nitrile 9-Scheme-I may also be found in PCT/US01106688, filed Mar. 2, 2001 whose disclosure is incorporated herein by reference in its entirety.

The nitrile 10-Scheme I was easily reduced with DIBAL in dichloromethane at room temperature (Boschelliat et al., *J. Med. Chem.* (1998), 4365-4377) to afford desired 2-Scheme I along with the unsubstituted imine 13-Scheme I (R=H). The latter was hydrolyzed to 2-Scheme I in situ with HCl. Other reduction agents, such as lithium aluminum hydride, Raney Ni, or SnCl$_2$, may be utilized in an appropriate organic solvent such as THF, diethyl ether or dioxane to perform the conversion of 10-Scheme I to 2-Scheme I.

Aldehyde 2-Scheme I was coupled to arylboronic acids under Suzuki coupling conditions, using a palladium catalyst, such as tetrakis(triphenylphosphine)palladium(0), to afford good to excellent yields of 3-Scheme I. Alternatively, the bi-aryl coupling reaction of 2-Scheme I may be performed using aryl or heteroaryl organozinc, organocopper, organotin, or other organometallic reagents known to afford bi-aryl cross-coupling products such as 3-Scheme I [see for example Solberg, J.; Undheim, K. *Acta Chemica Scandinavia* 1989, 62-68]. Displacement of the chlorine in 2-Scheme I may also be achieved with nitrogen nucleophiles [for related aminations see U.S. Pat. Nos. 3,631,045 and 3,910,913], sulphur nucleophiles, [see Tumkevicius, S. *Liebigs Ann.* 1995, 1703-1705], oxygen nucleophiles, or alkyl nucleophiles.

3-Scheme I was then converted to pyridopyrimidinone 5-Scheme I by one of three procedures. The first procedure used the Wittig reaction, as modified by Horner-Emmons, converting 3-Scheme I to 4-Scheme I. In this reaction, the aldehyde 3-Scheme I was treated with a suitable phosphorus ylide, such as triethyl phosphonoacetate or methyl diethylphosphonoacetate, to give the olefin intermediate 4-Scheme I. The reaction was performed under reflux, in a suitable base, such as sodium hydride, sodium methoxide, or sodium hydroxide, and in a suitable organic solvent such as diethyl ether, dioxane or ethanol. The conversion of 3-Scheme I to 4-Scheme I may also be performed using the Peterson olefination reaction, or an aldol-based olefination reaction that utilizes acetic anhydride, malonic acid and its monoalkyl esters, or ethyl acetate.

Heating of 4-Scheme I in toluene at 220° C. in a sealed tube (Matyus et al. *Heterocycles* (1985), 2057-64), followed by solvent removal, afforded the desired product 5-Scheme I. This reaction may be run in the presence of a suitable base, such as DBU or diisopropylethyl amine, pyridine, lithium bi(trimethylsilyl)amide, or LDA and in an appropriate organic solvent such as an organic hydrocarbon, cresol, dioxane, DMF, pyridine, or xylene.

The second procedure used a Horner-Emmons reaction with Still modification (Still et al., *Tetrahedron Lett.* (1983), 4405-8; Jacobsen et al., *Tetrahedron* (1994), 4323-34) to produce a mixture of desired product 5-Scheme I and trans isomer 4-Scheme I. Trans isomer 4-Scheme I was isolated and converted to the desired product 5-Scheme I by heating to 220° C. in toluene in a sealed tube as described above.

The third procedure involved acetylation of 3-Scheme I, followed by the intramolecular aldol condensation, promoted by an acetylating agent (such as acetic anhydride, acetyl chloride, or a ketene) and a suitable base (such as pyridine, diisopropyl ethylamine, or pyrrolidine), to generate 5-Scheme I in a very good yield. The third procedure is optimal when $R_3$ is an optionally substituted aryl, or heteroaryl. When $R_3$ is an arylalkyl, or heteroarylalkyl substituent it is not clear that the reaction will form the key intermediate of Formula (VII), as shown below (3a-Scheme II), which may optionally be isolated, as shown in Scheme II below. Compounds of Formula (VII) are preferably not isolated but further reacted with a base or with heat to cyclize into 5-Scheme-I. The first and second procedures should be utilized for all other $R_3$ moieties.

Oxidation of the sulfide 5-Scheme I to the sulfone 6-Scheme I was performed using meta-chloroperoxybenzoic acid (mCPBA) in high yield and purity. Suitable oxidation methods for use herein include use of one or two equivalents of meta-chloroperoxybenzoic acid (mCPBA) or Oxone® to afford either the sulfoxides or sulfones. Oxidation of the sulfides to sulfoxides or sulfones can also be effected by OsO$_4$ and catalytic tertiary amine N-oxide, hydrogen peroxide, other peracids, oxygen, ozone, organic peroxides, potassium and zinc permanganate, potassium persulfate, and sodium hypochlorite.

Displacements of the sulfones 6-Scheme I to the final products 7-Scheme-I were usually done with an excess of amine in N-methylpyrrolidine (Barvian et al., *J. Med. Chem.* (2000), 4606-4616). A wide range of primary amines underwent this reaction with excellent yields. In some cases (in O-displacement or sulfonamide formation) an anion of the nucleophile was prepared with base (usually sodium hydride) in dimethylformamide and then added to the sulfone. Yields for these reactions were usually lower. Similarly related sulfones and sulfoxides of the compounds herein wherein X is SO-alkyl or SO$_2$-alkyl have been reported in the literature to be displaced by a wide variety of nucleophiles. Thus the analogs of the compounds herein wherein X is an alkyl sulfone or sulfoxide may be displaced by primary and secondary alkylamines without additional base catalysis, preferably in a polar aprotic solvent, such as but not limited to, N-methyl pyrrolidin-2-one (NMP), and at varying temperatures depending upon the nucleophilicity of the amine. For instance displacement of the sulfone of analogs of Formula (I) compounds with ethanolamine, in NMP, occurred in 30 min. at 65° C., while a more hindered amine such as tris(hydroxymethyl)-aminomethane may require elevated temperatures and extended reaction times (80° C. over a 24 hour reaction time). The sulfone may also be displaced with a substituted arylamine, or heteroarylamine at elevated temperatures, sometimes requiring formation of the aryl or heteroarylamine anion with sodium hydride, or other suitable base, in DMSO. In addition, the sulfoxide analogs of Formula (I) compounds may be readily displaced with aluminum salts of aryl or heteroaryl amines as previously described in the patent literature (WO 99/32121). Likewise, sulfone and sulfoxide analogs of Formula (I) and (Ia) may be displaced with aryl or heteroaryl or alkyl thiols or alkyl or aryl or heteroaryl alcohols. For instance analogs of (I) containing sulfones as the X substituents may be displaced with sodium alkoxide in the alcohol, or alternatively reactive alkoxide or phenoxide nucleophiles may be generated from the alcohol or phenol with a suitable base such as sodium, NaH or sodium bistrimethylsilyl amide in a polar aprotic solvent such as DMSO, or run as a neat reaction. Similarly sulfones related to Formula (I) and (Ia), for instance, may be displaced with carbon nucleophiles such as aryl or alkyl Grignard reagents or related organometallics such as organo lithium, zinc, tin or boron. These reactions may, in some cases, require transition metal catalysis such as with Pd or Ni catalysts. Displacement of related 2-pyrimidine sulfones with cyanide, malonate anions, unactivated enolates, or heterocyclic C nucleophiles such as 1-methylimidazole anion, by the generation of the anion with NaH or other suitable base in THF also has precedent (see for example, Chem Pharm Bull. 1987, 4972-4976.). For example, analogs of Formula (I) and (Ia) compounds wherein X is an alkyl sulfone may be displaced with the anion of 1-methyl imidazole, generated by treatment of 1-methyl imidazole with n-butyl lithium in a solvent such as THF at temperatures of about −70°, to afford the C-alkylated product substituted on the imidazole C-2.

For the purposes herein, compounds of Formulas (I), (Ia), (II) and (IIa) wherein X is $R_2$ or $NHS(O)mR_2$ may be obtained from compounds of 6-Scheme I by displacement of the sulfone using the appropriate "X" functionality as defined in Formula (I) and (Ia). To obtain compounds of Formulas (I), (Ia), (II) and (IIa) wherein X is $S(O)_mR_2$ and $R_2$ is other than methyl, displacement of the sulfone on the corresponding compound 6-Scheme I by thiol ($R_2SH$) and then followed by oxidation, if desired, with an appropriate oxidating agent, such as MCPBA, or $KMnO_4$. Suitable oxidation methods for use herein include use of an oxidant such as one or two equivalents of meta-chloroperoxybenzoic acid or Oxone® to afford either the sulfoxides or sulfones. Oxidation of the sulfides to sulfones may also be effected by $OsO_4$ and catalytic tertiary amine N-oxide. Other methods for sulfide oxidation include the use of hydrogen peroxide, other peracids, oxygen, ozone, organic peroxides, potassium and zinc permanganate, potassium persulfate, and sodium hypochlorite.

8-Scheme I can be also prepared by heating the trans ester 4-Scheme I in alcohol in the presence of the corresponding sodium alkoxide. The yield of this reaction was very high for primary alcohols, but longer reaction times were required for secondary alcohols. Sodium alkoxides may be easily prepared from corresponding alcohol and base, such as sodium or sodium hydride.

Reduction of trans ester 4-Scheme I with $SmI_2$ gives the reduced analogue 11-Scheme I. This reduction can be also done in the presence of other reducing agents such as hydrogen gas, lithium in liquid ammonia, magnesium or sodium borohydride in the appropriate organic solvent such as THF, ethanol or diethyl ether.

Cyclization of the ester 11-Scheme I can be done utilizing sodium methoxide in methanol to give reduced analogue 12-Scheme I. Other organic bases, such as sodium, sodium ethoxide or TEA can be used in an appropriate organic solvent such as methanol, ethanol or dioxane. The product 12-Scheme I can be also obtained by heating ester 11-Scheme I to 150° C. in an appropriate organic solvent, such as toluene, xylene or isopropanol.

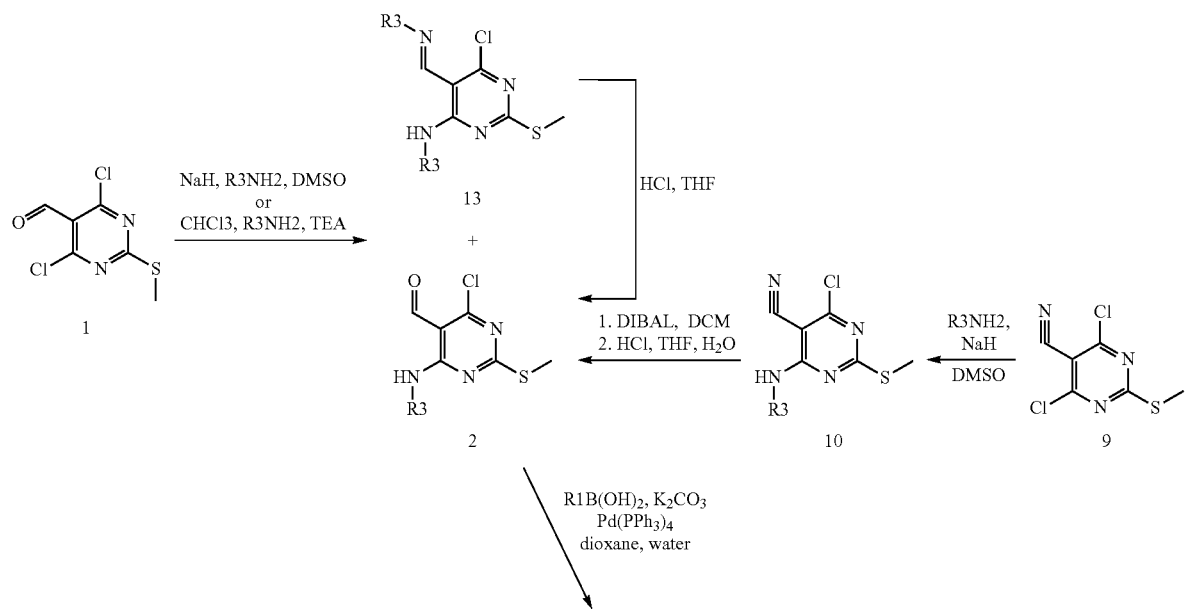

Scheme I

-continued
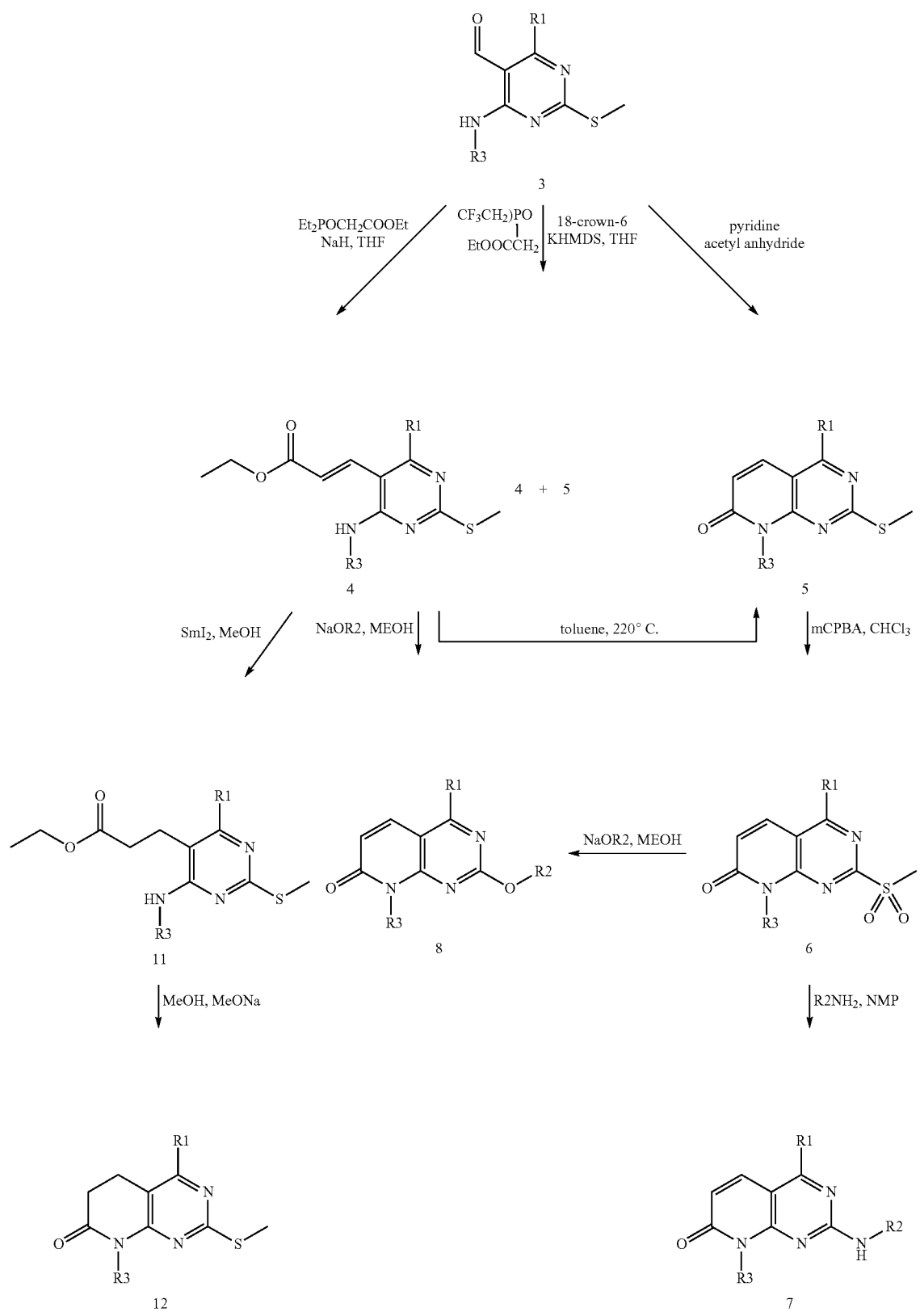

Additional procedures for producing similar intermediates to those herein, which the skilled artisan may find may be found in WO 99/41253, now U.S. Pat. Nos. 6,200,977; 6,153,619; 6,268,310; 5,468,751; 5,474,996; and EP 1 040 831.

An illustration of an alternative preparation of compounds of Formula (VII) the present invention is shown in Scheme II below, and described above.

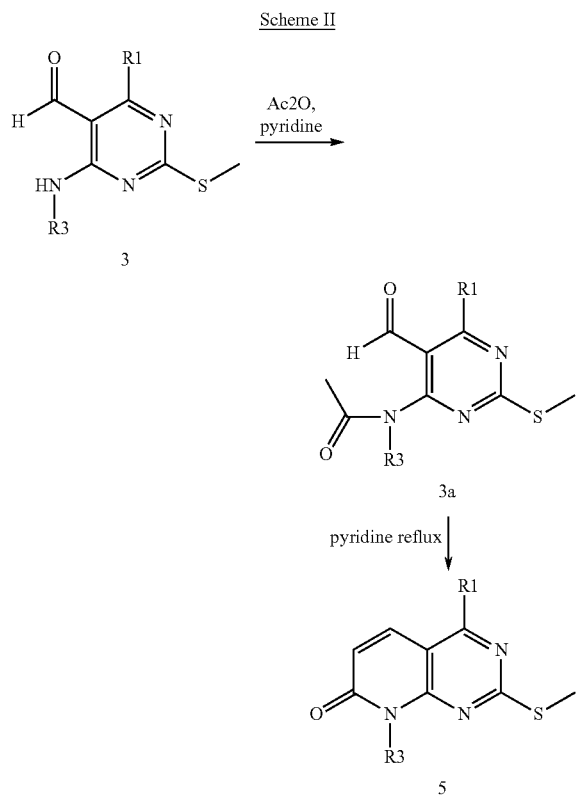

Another aspect of the present invention are novel intermediates of the formula (III)

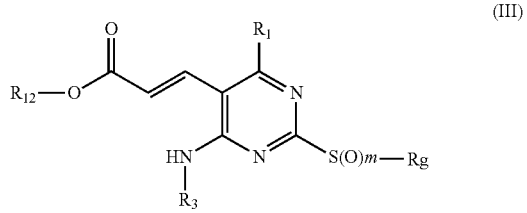

wherein
R$_1$ is an aryl or heteroaryl ring, which ring is optionally substituted;
R$_3$ is an C$_{1-10}$ alkyl, C$_{3-7}$ cycloalkyl, C$_{3-7}$ cycloalkylalkyl, aryl, arylC$_{1-10}$ alkyl, heteroaryl, heteroarylC$_{1-10}$ alkyl, heterocyclic, or a heterocyclylC$_{1-10}$ alkyl moiety, which moieties are optionally substituted;
R$_{12}$ is a C$_{1-10}$ alkyl, aryl, heteroaryl, or arylalkyl;
m is 0 or an integer having a value of 1 or 2; and
Rg is a C$_{1-4}$ alkyl.
Preferably, Rg is a C$_{1-4}$ alkyl, and more preferably methyl.

Preferably, m is 0 or an integer having a value of 1 or 2. More preferably m is 0 or 2.

Preferably, R$_1$ is an aryl moiety, more preferably a phenyl ring, optionally substituted one or more times by halogen, C$_{1-4}$ alkyl, or halo-substituted-C$_{1-4}$ alkyl. More preferably, the phenyl ring is substituted in the 2, 4, or 6-positions, or di-substituted in the 2,4-positions, such as 2-fluoro, 4-fluoro, 2,4-difluoro, 2,4,6-trifluoro, or 2-methyl-4-fluoro.

Another aspect of the present invention are novel intermediates of the formula (IIIa)

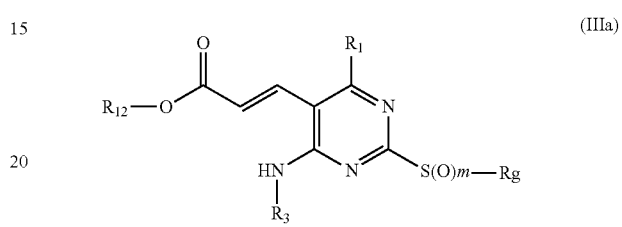

wherein
R$_1$ is the moiety YRa;
Y is C(R$_b$)(R$_d$), C(O), N(R$_d$), N(R$_d$)C(R$_c$)(R$_d$), oxygen, OC(R$_c$)(R$_d$), S(O)m, or S(O)$_m$C(R$_c$)(R$_d$);
R$_a$ is an aryl or heteroaryl ring, which ring is optionally substituted;
R$_b$ is hydrogen, C$_{1-2}$ alkyl, NR$_c$, hydroxy, thio, C$_{1-2}$ alkoxy, S(O)$_m$C$_{1-2}$ alkyl;
R$_c$ is hydrogen or C$_{1-2}$ alkyl;
R$_d$ is hydrogen or C$_{1-2}$ alkyl;
m is 0 or an integer having a value of 1 or 2; and
R$_3$ is an C$_{1-10}$ alkyl, C$_{3-7}$ cycloalkyl, C$_{3-7}$ cycloalkylalkyl, aryl, arylC$_{1-10}$ alkyl, heteroaryl, heteroarylC$_{1-10}$ alkyl, heterocyclic, or a heterocyclylC$_{1-10}$ alkyl moiety, which moieties are optionally substituted;
R$_{12}$ is a C$_{1-10}$ alkyl, aryl, heteroaryl, or arylalkyl;
m is 0 or an integer having a value of 1 or 2; and
Rg is a C$_{1-4}$ alkyl.

The substituents of compounds of Formula (III) and (IIIa), and (IV) and (IVa) below follow those preferences of the final compounds of Formula (I) or (II) herein, respectively.

Another aspect of the present invention are novel intermediates of the formula (IV)

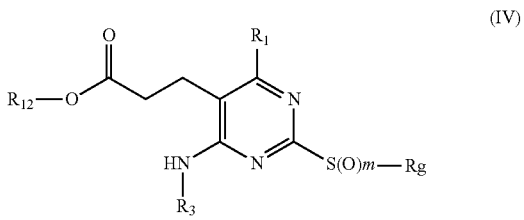

wherein R$_1$, R$_3$, R$_{12}$, m and R$_g$ are as defined for Formula (III) above.

Another aspect of the present invention are novel intermediates of the formula (IVa)

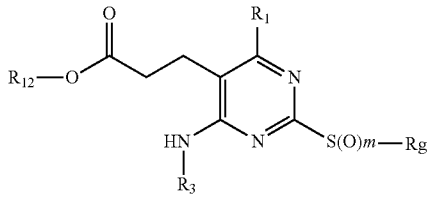

(IVa)

wherein $R_1$, $R_3$, $R_{12}$, m and $R_g$ are as defined for Formula (IIIa) above.

Another aspect of the present invention are novel intermediates of the formula (IV)

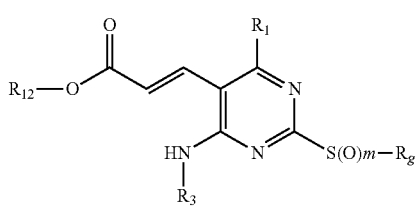

(V)

wherein $R_1$, $R_3$, $R_{12}$, m and $R_g$ are as defined for Formula (III) above.

Another aspect of the present invention are novel intermediates of the formula (IVa)

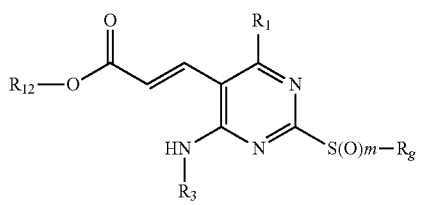

(Va)

wherein $R_1$, $R_3$, $R_{12}$, Rg and m are as defined for Formula (IIIa) above.

Another aspect of the present invention are novel intermediates of the formula

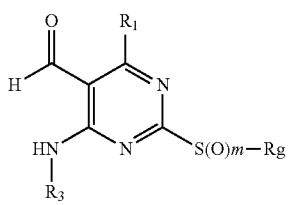

(VI)

wherein
$R_1$ is a halogen, an optionally substituted aryl or an optionally substituted heteroaryl ring;
$R_3$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, which moieties are optionally substituted; provided that when $R_3$ is hydrogen, then $R_1$ is other than chlorine;
m is 0 or an integer having a value of 1 or 2; and
Rg is a $C_{1-4}$ alkyl.

Preferably, $R_1$ is a halogen, more preferably chlorine, or an aryl moiety, more preferably a phenyl ring, optionally substituted one or more times by halogen, $C_{1-4}$ alkyl, or halo-substituted-$C_{1-4}$ alkyl. More preferably, the phenyl ring is substituted in the 2, 4, or 6-positions, or di-substituted in the 2,4-positions, such as 2-fluoro, 4-fluoro, 2,4-difluoro, 2,4,6-trifluoro, or 2-methyl-4-fluoro.

Preferably, $R_3$ is an optionally substituted $C_{1-10}$ alkyl, $C_{3-7}$ cycloalkyl, $C_{3-7}$ cycloalkylalkyl, or aryl.

Preferably, the $R_3$ optional substituents are independently selected from $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$ cycloalkenyl $C_{1-10}$ alkyl, halogen, $(CR_{10}R_{20})_nOR_6$, $(CR_{10}R_{20})_nSH$, $(CR_{10}R_{20})_nS(O)_mR_7$, $(CR_{10}R_{20})_nNHS(O)_2R_7$, $(CR_{10}R_{20})_nNR_4R_{14}$, $(CR_{10}R_{20})_n$ CN, $(CR_{10}R_{20})_nS(O)_2NR_4R_{14}$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_nC(Z)NR_4R_{14}$, $(CR_{10}R_{20})_nNR_{10}C(Z)R_6$, $(CR_{10}R_{20})_nNR_{10}C(=NR_{10})NR_4R_{14}$, $(CR_{10}R_{20})_nOC(Z)NR_4R_{14}$, $(CR_{10}R_{20})_nNR_{10}C(Z)NR_4R_{14}$, or $(CR_{10}R_{20})_nNR_{10}C(Z)OR_7$.

More preferably, the optional substituents are independently selected from halogen, alkyl, hydroxy, alkoxy, amino, or halosubstituted alkyl.

Exemplified compounds of Formula (VI) include, but are not limited to:
4-Chloro-2-methylsulfanyl-6-phenylamino-pyrimidine-5-carbaldehyde;
4-Chloro-6-(2,6-difluoro-phenylamino)-2-methylsulfanyl-pyrimidine-5-carbaldehyde;
4-Chloro-6-(2-chloro-phenylamino)-2-methylsulfanyl-pyrimidine-5-carbaldehyde;
4-Chloro-6-(2-fluoro-phenylamino)-2-methylsulfanyl-pyrimidine-5-carbaldehyde;
4-Chloro-6-(1-ethyl-propylamino)-2-methylsulfanyl-pyrimidine-5-carbaldehyde;
4-Chloro-6-isopropylamino-2-methylsulfanyl-pyrimidine-5-carbaldehyde;
4-Chloro-6-cyclopropylamino-2-methylsulfanyl-pyrimidine-5-carbaldehyde;
4-Chloro-6-(cyclopropylmethyl-amino)-2-methylsulfanyl-pyrimidine-5-carbaldehyde;
2-Methylsulfanyl-4-phenyl-6-phenylamino-pyrimidine-5-carbaldehyde;
4-(2-Chlorophenyl)-6-(1-ethyl-propylamino)-2-methylsulfanyl-pyrimidine-5-carbaldehyde;
4-(2-Chlorophenyl)-6-(2-chloro-phenylamino)-2-methylsulfanyl-pyrimidine-5-carbaldehyde;
4-(2-Fluorophenyl)-6-(2-chloro-phenylamino)-2-methylsulfanyl-pyrimidine-5-carbaldehyde;
4-(2-Fluoro-phenyl)-6-isopropylamino-2-methylsulfanyl-pyrimidine-5-carbaldehyde;
4-Chloro-2-methylsulfanyl-6-cyclohexylaminopyrimidine-5-carboxaldehyde;
2-Methylsulfanyl-4-(2-methyl-4-fluorophenyl)-6-cyclohexylaminopyrimidine-5-carbaldehyde;
4-Amino-6-(2-fluoro-phenyl)-2-methylsulfanyl-pyrimidine-5-carbaldehyde;
4-Cyclopropylamino-6-(2-fluoro-phenyl)-2-methylsulfanyl-pyrimidine-5-carbaldehyde;
4-(Cyclopropylmethyl-amino)-6-(2-fluoro-phenyl)-2-methylsulfanyl-pyrimidine-5-carbaldehyde;
4-(2,6-Difluoro-phenylamino)-6-(2-fluoro-phenyl)-2-methylsulfanyl-pyrimidine-5-carbaldehyde;

4-(2-Fluorophenyl)-6-(2-fluoro-phenylamino)-2-methylsulfanyl-pyrimidine-5-carbaldehyde;
4-sec-Butylamino-6-(2-fluoro-phenyl)-2-methylsulfanyl-pyrimidine-5-carbaldehyde;
4-(4-Fluoro-2-methyl-phenyl)-6-isopropylamino-2-methylsulfanyl-pyrimidine-5-carbaldehyde;
4-Cyclopropylamino-6-(4-fluoro-2-methyl-phenyl)-2-methylsulfanyl-pyrimidine-5-carbaldehyde;
4-(Cyclopropylmethyl-amino)-6-(4-fluoro-2-methyl-phenyl)-2-methylsulfanyl-pyrimidine-5-carbaldehyde;
4-(4-Fluoro-2-methyl-phenyl)-6-(2-fluoro-phenylamino)-2-methylsulfanyl-pyrimidine-5-carbaldehyde;
4-sec-Butylamino-6-(4-fluoro-2-methyl-phenyl)-2-methylsulfanyl-pyrimidine-5-carbaldehyde;
4-Amino-6-(2-fluoro-phenyl)-2-methylsulfanyl-pyrimidine-5-carbaldehyde;
4-Amino-6-chloro-2-methylsulfanyl-pyrimidine-5-carbaldehyde;
4-sec-Butylamino-6-chloro-2-methylsulfanyl-pyrimidine-5-carbaldehyde;
4-(2,6-Difluoro-phenylamino)-6-(4-fluoro-2-methyl-phenyl)-2-methylsulfanyl-pyrimidine-5-carbaldehyde;
4-(1-Ethylpropylamino)-6-(4-fluoro-2-methyl-phenyl)-2-methylsulfanyl-pyrimidine-5-carbaldehyde;
2-Methylsulfanyl-4-(2-methyl-4-fluorophenyl)-6-cyclohexylaminopyrimidine-5-carbaldehyde; and
4-Chloro-2-methylsulfanyl-6-cyclohexylaminopyrimidine-5-carboxaldehyde.

Another aspect of the present invention are novel intermediates of the formula

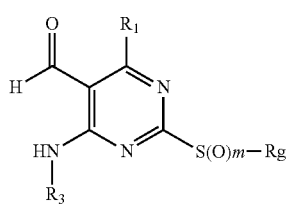

(VIa)

wherein
$R_1$ is YRa;
Y is $C(R_b)(R_d)$, $C(O)$, $N(R_d)$, $N(R_d)C(R_c)(R_d)$, oxygen, $OC(R_c)(R_d)$, $S(O)m$, or $S(O)_mC(R_c)(R_d)$;
$R_a$ is an aryl or heteroaryl ring, which ring is optionally substituted;
$R_b$ is hydrogen, $C_{1-2}$ alkyl, $NR_c$, hydroxy, thio, $C_{1-2}$ alkoxy, $S(O)_mC_{1-2}$ alkyl;
$R_c$ is hydrogen or $C_{1-2}$ alkyl;
$R_d$ is hydrogen or $C_{1-2}$ alkyl;
m is 0 or an integer having a value of 1 or 2; and
$R_3$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, which moieties are optionally substituted;
m is 0 or an integer having a value of 1 or 2; and
Rg is a $C_{1-4}$ alkyl.

Preferably, as noted above, the substituents of compounds of Formula (VI) and (VIa) follow those of the final compounds of Formula (I), and (II) herein.

Exemplified compounds of Formula (VI) include, but are not limited to, 4-(2-Chloro-phenylamino)-2-methylsulfanyl-6-phenoxy-pyrimidine-5-carbaldehyde.

Another aspect of this invention are novel intermediates of Formula (VII)

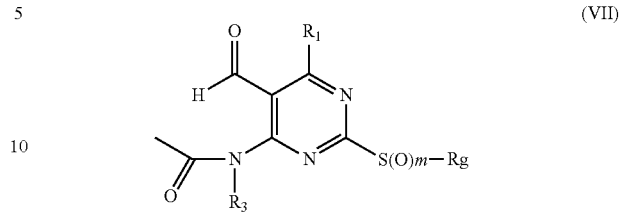

(VII)

wherein
$R_1$ is as defined above for Formula (I) compounds, and $R_3$, Rg, and m is an optionally substituted aryl or heteroaryl moiety, as defined for Formula (III) compounds.

Another aspect of this invention are novel intermediates of Formula (VIIa)

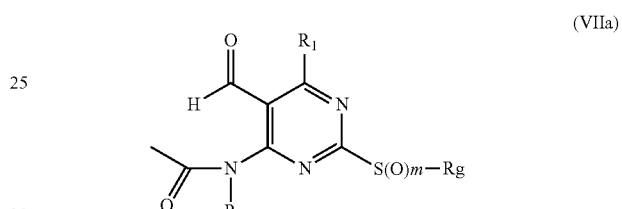

(VIIa)

wherein
$R_1$ is defined above for Formula (II) compounds, and $R_3$, Rg, and m is an optionally substituted aryl or heteroaryl moiety, as defined for Formula (IIIa) compounds.

Another aspect of the present invention are novel intermediates of the formula

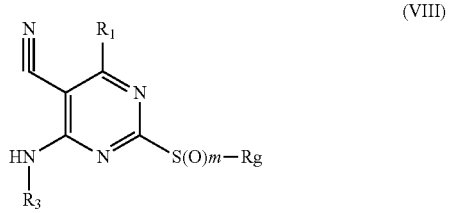

(VIII)

wherein
$R_1$ is a halogen;
$R_3$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, which moieties are optionally substituted; provided that when $R_3$ is hydrogen, then $R_1$ is other than chlorine;
m is 0 or an integer having a value of 1 or 2; and
Rg is a $C_{1-4}$ alkyl.

Preferably $R_1$ is a halogen, more preferably chlorine.
Suitably, the $R_3$ substituents are the same as those for compounds of Formulas (I) and (II) herein.

Methods of Treatment

The compounds of Formula (I) and (Ia) or a pharmaceutically acceptable salt thereof can be used in the manufacture of a medicament for the prophylactic or therapeutic treatment of any disease state in a human, or other mammal, which is exacerbated or caused by excessive or unregulated cytokine production by such mammal's cell, such as but not limited to monocytes and/or macrophages.

For purposes herein, compounds of Formula (I) and (Ia) will all be referred to as compounds of Formula (I) unless otherwise indicated.

Compounds of Formula (I) are capable of inhibiting proinflammatory cytokines, such as IL-1, IL-6, IL-8, and TNF and are therefore of use in therapy. IL-1, IL-6, IL-8 and TNF affect a wide variety of cells and tissues and these cytokines, as well as other leukocyte-derived cytokines, are important and critical inflammatory mediators of a wide variety of disease states and conditions. The inhibition of these pro-inflammatory cytokines is of benefit in controlling, reducing and alleviating many of these disease states.

Accordingly, the present invention provides a method of treating a cytokine-mediated disease which comprises administering an effective cytokine-interfering amount of a compound of Formula (I) or a pharmaceutically acceptable salt thereof.

Compounds of Formula (I) are capable of inhibiting inducible proinflammatory proteins, such as COX-2, also referred to by many other names such as prostaglandin endoperoxide synthase-2 (PGHS-2) and are therefore of use in therapy. These proinflammatory lipid mediators of the cyclooxygenase (CO) pathway are produced by the inducible COX-2 enzyme. Regulation, therefore of COX-2 which is responsible for the these products derived from arachidonic acid, such as prostaglandins affect a wide variety of cells and tissues are important and critical inflammatory mediators of a wide variety of disease states and conditions. Expression of COX-1 is not effected by compounds of Formula (I). This selective inhibition of COX-2 may alleviate or spare ulcerogenic liability associated with inhibition of COX-1 thereby inhibiting prostoglandins essential for cytoprotective effects. Thus inhibition of these pro-inflammatory mediators is of benefit in controlling, reducing and alleviating many of these disease states. Most notably these inflammatory mediators, in particular prostaglandins, have been implicated in pain, such as in the sensitization of pain receptors, or edema. This aspect of pain management therefore includes treatment of neuromuscular pain, headache, cancer pain, and arthritis pain. Compounds of Formula (I) or a pharmaceutically acceptable salt thereof, are of use in the prophylaxis or therapy in a human, or other mammal, by inhibition of the synthesis of the COX-2 enzyme.

Accordingly, the present invention provides a method of inhibiting the synthesis of COX-2 which comprises administering an effective amount of a compound of Formula (I) or a pharmaceutically acceptable salt thereof. The present invention also provides for a method of prophylaxis treatment in a human, or other mammal, by inhibition of the synthesis of the COX-2 enzyme.

In particular, compounds of Formula (I) or a pharmaceutically acceptable salt thereof are of use in the prophylaxis or therapy of any disease state in a human, or other mammal, which is exacerbated by or caused by excessive or unregulated IL-1, IL-6, IL-8 or TNF production by such mammal's cell, such as, but not limited to, monocytes and/or macrophages.

Accordingly, in another aspect, this invention relates to a method of inhibiting the production of IL-1 in a mammal in need thereof which comprises administering to said mammal an effective amount of a compound of Formula (I) or a pharmaceutically acceptable salt thereof.

There are many disease states in which excessive or unregulated IL-1 production is implicated in exacerbating and/or causing the disease. These include rheumatoid arthritis, osteoarthritis, meningitis, ischemic and hemorrhagic stroke, neurotrauma/closed head injury, stroke, endotoxemia and/or toxic shock syndrome, other acute or chronic inflammatory disease states such as the inflammatory reaction induced by endotoxin or inflammatory bowel disease, tuberculosis, atherosclerosis, muscle degeneration, multiple sclerosis, cachexia, bone resorption, psoriatic arthritis, Reiter's syndrome, gout, traumatic arthritis, rubella arthritis and acute synovitis. Recent evidence also links IL-1 activity to diabetes, pancreatic β cell diseases and Alzheimer's disease.

Use of a CSAID inhibitor compound for the treatment of CSBP mediated disease states, can include, but not be limited to neurodegenerative diseases, such as Alzheimer's disease (as noted above), Parkinson's disease and multiple sclerosis, etc.

In a further aspect, this invention relates to a method of inhibiting the production of TNF in a mammal in need thereof which comprises administering to said mammal an effective amount of a compound of Formula (I) or a pharmaceutically acceptable salt thereof.

Excessive or unregulated TNF production has been implicated in mediating or exacerbating a number of diseases including rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, chronic pulmonary inflammatory disease and chronic obstructive pulmonary disease, silicosis, pulmonary sarcoisosis, bone resorption diseases, such as osteoporosis, cardiac, brain and renal reperfusion injury, graft vs. host reaction, allograft rejections, fever and myalgias due to infection, such as influenza, brain infections including encephalitis (including HIV-induced forms), cerebral malaria, meningitis, ischemic and hemorrhagic stroke, cachexia secondary to infection or malignancy, cachexia secondary to acquired immune deficiency syndrome (AIDS), AIDS, ARC (AIDS related complex), keloid formation, scar tissue formation, inflammatory bowel disease, Crohn's disease, ulcerative colitis and pyresis.

Compounds of Formula (I) are also useful in the treatment of viral infections, where such viruses are sensitive to upregulation by TNF or will elicit TNF production in vivo. The viruses contemplated for treatment herein are those that produce TNF as a result of infection, or those which are sensitive to inhibition, such as by decreased replication, directly or indirectly, by the TNF inhibiting-compounds of Formula (1). Such viruses include, but are not limited to HIV-1, HIV-2 and HIV-3, Cytomegalovirus (CMV), Influenza, adenovirus and the Herpes group of viruses, such as but not limited to, Herpes Zoster and Herpes Simplex. Accordingly, in a further aspect, this invention relates to a method of treating a mammal afflicted with a human immunodeficiency virus (HIV) which comprises administering to such mammal an effective TNF inhibiting amount of a compound of Formula (I) or a pharmaceutically acceptable salt thereof.

It is also recognized that both IL-6 and IL-8 are produced during rhinovirus (HRV) infections and contribute to the pathogenesis of common cold and exacerbation of asthma associated with HRV infection (Turner et al. (1998), Clin. Infec. Dis., Vol 26, p 840; Teren et al. (1997), Am J Respir Crit Care Med vol 155, p 1362; Grunberg et al. (1997), Am J Respir Crit Care Med 156:609 and Zhu et al, J Clin Invest (1996), 97:421). It has also been demonstrated in vitro that infection of pulmonary epithelial cells with HRV results in production of IL-6 and IL-8 (Subauste et al., J. Clin. Invest. 1995, 96:549.) Epithelial cells represent the primary site of infection of HRV. Therefore another aspect of the present invention is a method of treatment to reduce inflammation associated with a rhinovirus infection, not necessarily a direct effect on virus itself.

Compounds of Formula (I) may also be used in association with the veterinary treatment of mammals, other than in humans, in need of inhibition of TNF production. TNF mediated diseases for treatment, therapeutically or prophylactically, in animals include disease states such as those noted above, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine immunodeficiency virus or other retroviral infections.

The compounds of Formula (I) may also be used topically in the treatment or prophylaxis of topical disease states mediated by or exacerbated by excessive cytokine production, such as by IL-1 or TNF respectively, such as inflamed joints, eczema, psoriasis and other inflammatory skin conditions such as sunburn; inflammatory eye conditions including conjunctivitis; pyresis, pain and other conditions associated with inflammation. Periodontal disease has also been implemented in cytokine production, both topically and systemically. Hence use of compounds of Formula (I) to control the inflammation associated with cytokine production in such peroral diseases such as gingivitis and periodontitis is another aspect of the present invention.

Compounds of Formula (I) have also been shown to inhibit the production of IL-8 (Interleukin-8, NAP). Accordingly, in a further aspect, this invention relates to a method of inhibiting the production of IL-8 in a mammal in need thereof which comprises administering to said mammal an effective amount of a compound of Formula (I) or a pharmaceutically acceptable salt thereof.

There are many disease states in which excessive or unregulated IL-8 production is implicated in exacerbating and/or causing the disease. These diseases are characterized by massive neutrophil infiltration such as, psoriasis, inflammatory bowel disease, asthma, cardiac, brain and renal reperfusion injury, adult respiratory distress syndrome, thrombosis and glomerulonephritis. All of these diseases are associated with increased IL-8 production which is responsible for the chemotaxis of neutrophils into the inflammatory site. In contrast to other inflammatory cytokines (IL-1, TNF, and IL-6), IL-8 has the unique property of promoting neutrophil chemotaxis and activation. Therefore, the inhibition of IL-8 production would lead to a direct reduction in the neutrophil infiltration.

The compounds of Formula (I) are administered in an amount sufficient to inhibit cytokine, in particular IL-1, IL-6, IL-8 or TNF, production such that it is regulated down to normal levels, or in some case to subnormal levels, so as to ameliorate or prevent the disease state. Abnormal levels of IL-1, IL-6, IL-8 or TNF, for instance in the context of the present invention, constitute: (i) levels of free (not cell bound) IL-1, IL-6, IL-8 or TNF greater than or equal to 1 picogram per ml; (ii) any cell associated IL-1, IL-6, IL-8 or TNF; or (iii) the presence of IL-1, IL-6, IL-8 or TNF mRNA above basal levels in cells or tissues in which IL-1, IL-6, IL-8 or TNF, respectively, is produced.

The discovery that the compounds of Formula (I) are inhibitors of cytokines, specifically IL-1, IL-6, IL-8 and TNF is based upon the effects of the compounds of Formulas (I) on the production of the IL-1, IL-8 and TNF in in vitro assays which are described herein.

As used herein, the term "inhibiting the production of IL-1 (IL-6, IL-8 or TNF)" refers to:
a) a decrease of excessive in vivo levels of the cytokine (IL-1, IL-6, IL-8 or TNF) in a human to normal or sub-normal levels by inhibition of the in release of the cytokine by all cells, including but not limited to monocytes or macrophages;
b) a down regulation, at the genomic level, of excessive in vivo levels of the cytokine (IL-1, IL-6, IL-8 or TNF) in a human to normal or sub-normal levels;
c) a down regulation, by inhibition of the direct synthesis of the cytokine (IL-1, IL-6, IL-8 or TNF) as a postranslational event; or
d) a down regulation, at the translational level, of excessive in vivo levels of the cytokine (IL-1, IL-6, IL-8 or TNF) in a human to normal or sub-normal levels.

As used herein, the term "TNF mediated disease or disease state" refers to any and all disease states in which TNF plays a role, either by production of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disease stated mediated by TNF.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-a) and Tumor Necrosis Factor beta (TNF-$\beta$).

As used herein, the term "cytokine interfering" or "cytokine suppressive amount" refers to an effective amount of a compound of Formula (I) which will cause a decrease in the in vivo levels of the cytokine to normal or sub-normal levels, when given to a patient for the prophylaxis or treatment of a disease state which is exacerbated by, or caused by, excessive or unregulated cytokine production.

As used herein, the cytokine referred to in the phrase "inhibition of a cytokine, for use in the treatment of a HIV-infected human" is a cytokine which is implicated in (a) the initiation and/or maintenance of T cell activation and/or activated T cell-mediated HIV gene expression and/or replication and/or (b) any cytokine-mediated disease associated problem such as cachexia or muscle degeneration.

As TNF-$\beta$ (also known as lymphotoxin) has close structural homology with TNF-$\alpha$ (also known as cachectin) and since each induces similar biologic responses and binds to the same cellular receptor, both TNF-$\alpha$ and TNF-$\beta$ are inhibited by the compounds of the present invention and thus are herein referred to collectively as "TNF" unless specifically delineated otherwise.

A member of the MAP kinase family, alternatively termed CSBP, p38, or RK, has been identified independently by several laboratories. Activation of this novel protein kinase via dual phosphorylation has been observed in different cell systems upon stimulation by a wide spectrum of stimuli, such as physicochemical stress and treatment with lipopolysaccharide or proinflammatory cytokines such as interleukin-1 and tumor necrosis factor. The cytokine biosynthesis inhibitors, of the present invention, compounds of Formula (I) have been determined to be potent and selective inhibitors of CSBP/p38/RK kinase activity. These inhibitors are of aid in determining the signaling pathways involvement in inflammatory responses. In particular, for the first time a definitive signal transduction pathway can be prescribed to the action of lipopolysaccharide in cytokine production in macrophages. In addition to those diseases already noted, treatment of stroke, neurotrauma, cardiac and renal reperfusion injury, congestive heart failure, coronary arterial bypass grafting (CABG) surgery, chronic renal failure, angiogenesis & related processes, such as cancer, thrombosis, glomerulonephritis, diabetes and pancreatic β cells, multiple sclerosis, muscle degeneration, eczema, psoriasis, sunburn, and conjunctivitis are also included.

The CSBP inhibitors were subsequently tested in a number of animal models for anti-inflammatory activity. Model systems were chosen that were relatively insensitive to cyclooxygenase inhibitors in order to reveal the unique activities of cytokine suppressive agents. The inhibitors exhibited significant activity in many such in vivo studies. Most notable are its effectiveness in the collagen-induced arthritis model and inhibition of TNF production in the endotoxic shock model. In the latter study, the reduction in plasma level of TNF correlated with survival and protection from endotoxic shock related mortality. Also of great importance are the compounds effectiveness in inhibiting bone resorption in a rat fetal long bone organ culture system. Griswold et al., (1988) *Arthritis Rheum.* 31:1406-1412; Badger, et al., (1989) *Circ. Shock* 27, 51-61; Votta et al., (1994) *in vitro. Bone* 15, 533-538; Lee et al., (1993). B *Ann. N. Y. Acad. Sci.* 696, 149-170.

Chronic diseases which have an inappropriate angiogenic component are various ocular neovascularizations, such as diabetic retinopathy and macular degeneration. Other chronic diseases which have an excessive or increased proliferation of vasculature are tumor growth and metastasis, atherosclerosis, and certain arthritic conditions. Therefore CSBP kinase inhibitors will be of utility in the blocking of the angiogenic component of these disease states.

The term "excessive or increased proliferation of vasculature inappropriate angiogenesis" as used herein includes, but is not limited to, diseases which are characterized by hemangiomas and ocular diseases.

The term "inappropriate angiogenesis" as used herein includes, but is not limited to, diseases which are characterized by vesicle proliferation with accompanying tissue proliferation, such as occurs in cancer, metastasis, arthritis and atherosclerosis.

Accordingly, the present invention provides a method of treating a CSBP kinase mediated disease in a mammal in need thereof, preferably a human, which comprises administering to said mammal, an effective amount of a compound of Formula (I) or a pharmaceutically acceptable salt thereof.

In order to use a compound of Formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of Formula (I) and a pharmaceutically acceptable carrier or diluent.

Compounds of Formula (I), pharmaceutically acceptable salts thereof and pharmaceutical compositions incorporating such may conveniently be administered by any of the routes conventionally used for drug administration, for instance, orally, topically, parenterally or by inhalation. The compounds of Formula (I) may be administered in conventional dosage forms prepared by combining a compound of Formula (I) with standard pharmaceutical carriers according to conventional procedures. The compounds of Formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of Formula (I) may be administered topically, that is by non-systemic administration. This includes the application of a compound of Formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of Formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of Formula (I) may also be administered by inhalation, that is by intranasal and oral inhalation administration. Appropriate dosage forms for such administration, such as an aerosol formulation or a metered dose inhaler, may be prepared by conventional techniques.

For all methods of use disclosed herein for the compounds of Formula (I), the daily oral dosage regimen will preferably be from about 0.1 to about 80 mg/kg of total body weight, preferably from about 0.2 to 30 mg/kg, more preferably from about 0.5 mg to 15mg. The daily parenteral dosage regimen about 0.1 to about 80 mg/kg of total body weight, preferably from about 0.2 to about 30 mg/kg, and more preferably from about 0.5 mg to 15 mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

The novel compounds of Formula (I) may also be used in association with the veterinary treatment of mammals, other than humans, in need of inhibition of CSBP/p38 or cytokine inhibition or production. In particular, CSBP/p38 mediated diseases for treatment, therapeutically or prophylactically, in animals include disease states such as those noted herein in the Methods of Treatment section, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine immunodeficiency virus or other retroviral infections.

Another aspect of the present invention is a method of treating the common cold or respiratory viral infection caused by human rhinovirus (HRV), other enteroviruses, coronavirus, influenza virus, parainfluenza virus, respiratory syncytial virus, or adenovirus in a human in need thereof which method comprises administering to said human an effective amount of a CBSP/p38 inhibitor.

Another aspect of the present invention is a method of treating, including prophylaxis of influenza induced pneumonia in a human in need thereof which method comprises administering to said human an effective amount of a CBSP/p38 inhibitor The present invention also relates to the use of the CSBP/p38 kinase inhibitor for the treatment, including prophylaxis, of inflammation associated with a viral infection of a human rhinovirus (HRV), other enteroviruses, coronavirus, influenza virus, parainfluenza virus, respiratory syncytial virus, or adenovirus.

In particular, the present invention is directed to the treatment of a viral infection in a human, which is caused by the human rhinovirus (HRV), other enterovirus, coronavirus, influenza virus, parainfluenza virus, respiratory syncytial virus, or an adenovirus. In particular the invention is directed to respiratory viral infections that exacerbate asthma (induced by such infections), chronic bronchitis, chronic obstructive pulmonary disease, otitis media, and sinusitis. While inhibiting IL-8 or other cytokines may be beneficial in treating a rhinovirus may be known, the use of an inhibitor of the p38 kinase for treating HRV or other respiratory viral infections causing the common cold is believed novel.

It should be noted that the respiratory viral infection treated herein may also be associated with a secondary bacterial infection, such as otitis media, sinusitis, or pneumonia.

For use herein treatment may include prophylaxis for use in a treatment group susceptible to such infections. It may also include reducing the symptoms of, ameliorating the symptoms of, reducing the severity of, reducing the incidence of, or any other change in the condition of the patient, which improves the therapeutic outcome.

It should be noted that the treatment herein is not directed to the elimination or treatment of the viral organism itself but is directed to treatment of the respiratory viral infection that exacerbates other diseases or symptoms of disease, such as asthma (induced by such infections), chronic bronchitis, chronic obstructive pulmonary disease, otitis media, and sinusitis.

A preferred virus for treatment herein is the human rhinovirus infection (HRV) or respiratory syncytial virus (RSV).

The invention will now be described by reference to the following biological examples which are merely illustrative and are not to be construed as a limitation of the scope of the present invention.

Biological Examples

The cytokine-inhibiting effects of compounds of the present invention may be determined by the following in vitro assays:

Assays for Interleukin-1 (IL-1), Interleukin-8 (IL-8), and Tumour Necrosis Factor (TNF) are well known in the art, and may be found in a number of publications, and patents. Representative suitable assays for use herein are described in Adams et al., U.S. Pat. No. 5,593,992, whose disclosure is incorporated by reference in its entirety.

Interleukin-1 (IL-1)

Human peripheral blood monocytes are isolated and purified from either fresh blood preparations from volunteer donors, or from blood bank buffy coats, according to the procedure of Colotta et al, J Immunol, 132, 936 (1984). These monocytes ($1 \times 10^6$) are plated in 24-well plates at a concentration of 1-2 million/ml per well. The cells are allowed to adhere for 2 hours, after which time non-adherent cells are removed by gentle washing. Test compounds are then added to the cells for 1 h before the addition of lipopolysaccharide (50 ng/ml), and the cultures are incubated at 37° C. for an additional 24 h. At the end of this period, culture supernatants are removed and clarified of cells and all debris. Culture supernatants are then immediately assayed for IL-1 biological activity, either by the method of Simon et al., J. Immunol. Methods, 84, 85, (1985) (based on ability of IL-1 to stimulate a Interleukin 2 producing cell line (EL-4) to secrete IL-2, in concert with A23187 ionophore) or the method of Lee et al., J. ImmunoTherapy, 6 (1), 1-12 (1990) (ELISA assay).

In Vivo TNF Assay:

(1) Griswold et al., *Drugs Under Exp. and Clinical Res.*, XIX (6), 243-248 (1993); or (2) Boehm, et al., *Journal Of Medicinal Chemistry* 39, 3929-3937 (1996) whose disclosures are incorporated by reference herein in their entirety.

LPS-Induced TNFα Production in Mice and Rats

In order to evaluate in vivo inhibition of LPS-induced TNFα production in rodents, both mice and rats are injected with LPS.

Mouse Method

Male Balb/c mice from Charles River Laboratories are pretreated (30 minutes) with compound or vehicle. After the 30 min. pretreat time, the mice are given LPS (lipopolysaccharide from *Escherichia coli* Serotype 055-85, Sigma Chemical Co., St Louis, Mo.) 25 ug/mouse in 25 ul phosphate buffered saline (pH 7.0) intraperitoneally. Two hours later the mice are killed by $CO_2$ inhalation and blood samples are collected by exsanguination into heparinized blood collection tubes and stored on ice. The blood samples are centrifuged and the plasma collected and stored at −20° C. until assayed for TNFα by ELISA.

Rat Method

Male Lewis rats from Charles River Laboratories are pretreated at various times with compound or vehicle. After a determined pretreat time, the rats are given LPS (lipopolysaccharide from *Escherichia coli* Serotype 055-85, Sigma Chemical Co., St Louis, Mo.) 3.0 mg/kg intraperitoneally. The rats are killed by $CO_2$ inhalation and heparinized whole blood is collected from each rat by cardiac puncture 90 minutes after the LPS injection. The blood samples are centrifuged and the plasma collected for analysis by ELISA for TNFα levels.

ELISA Method

TNFα levels were measured using a sandwich ELISA, as described in Olivera et al., Circ. Shock, 37, 301-306, (1992), whose disclosure is incorporated by reference in its entirety herein, using a hamster monoclonal antimurine TNFα (Genzyme, Boston, Mass.) as the capture antibody and a polyclonal rabbit antimurine TNFa (Genzyme) as the second antibody. For detection, a peroxidase-conjugated goat antirabbit antibody (Pierce, Rockford, Ill.) was added, followed by a substrate for peroxidase (1 mg/ml orthophenylenediamine with 1% urea peroxide). TNFα levels in the plasma samples from each animal were calculated from a standard curve generated with recombinant murine TNFα (Genzyme).

LPS-Stimulated Cytokine Production in Human Whole Blood

Assay: Test compound concentrations were prepared at 10× concentrations and LPS prepared at 1 ug/ml (final conc. of 50 ng/ml LPS) and added in 50 uL volumes to 1.5 mL eppendorf tubes. Heparinized human whole blood was obtained from healthy volunteers and was dispensed into eppendorf tubes containing compounds and LPS in 0.4 mL volumes and the tubes incubated at 37 C. Following a 4 hour incubation, the tubes were centrifuged at 5000 rpm for 5 minutes in a TOMY microfuge, plasma was withdrawn and frozen at −80 C.

Cytokine measurement: IL-I and/or TNF were quantified using a standardized ELISA technology. An in-house ELISA kit was used to detect human IL-1 and TNF. Concentrations of IL-1 or TNF were determined from standard curves of the appropriate cytokine and IC50 values for test compound (concentration that inhibited 50% of LPS-stimulated cytokine production) were calculated by linear regression analysis.

CSBP/p38 Kinase Assay:

This assay measures the CSBP/p38-catalyzed transfer of $^{32}P$ from [a-$^{32}P$]ATP to threonine residue in an epidermal growth factor receptor (EGFR)-derived peptide (T669) with the following sequence: KRELVEPLTPSGEAPNQALLR (SEQ ID No. 1) (residues 661-681). (See Gallagher et al., "Regulation of Stress Induced Cytokine Production by Pyridinyl Imidazoles: Inhibition of CSBP Kinase", BioOrganic & Medicinal Chemistry, 1997, 5, 49-64).

Reactions were carried in round bottom 96 well plate (from Corning) in a 30 ml volume. Reactions contained (in final concentration): 25 mM Hepes, pH 7.5; 8 mM $MgCl_2$; 0.17 mM ATP (the $Km_{[ATP]}$ of p38 (see Lee et al., Nature 300, n72 pg. 639-746 (December 1994)); 2.5 uCi of [g-32P]ATP; 0.2 mM sodium orthovanadate; 1 mM DTT; 0.1% BSA; 10% glycerol; 0.67 mM T669 peptide; and 2-4 nM of yeast-expressed, activated and purified p38. Reactions were initiated by the addition of [gamma-32P]Mg/ATP, and incubated for 25 min. at 37° C. Inhibitors (dissolved in DMSO) were incubated with the reaction mixture on ice for 30 minutes prior to adding the 32P-ATP. Final DMSO concentration was 0.16%. Reactions were terminated by adding 10 ul of 0.3 M phosphoric acid, and phosphorylated peptide was isolated from the reactions by capturing it on p81 phosphocellulose filters. Filters were washed with 75 mM phosphoric acids, and incorporated 32P was quantified using beta scintillation counter. Under these conditions, the specific activity of p38 was 400-450 pmol/pmol enzyme, and the activity was linear for up to 2 hours of incubation. The kinase activity values were obtained after subtracting values generated in the absence of substrate which were 10-15% of total values.

Representative final compounds of Formula (I) and (Ia) which have been tested, Examples 29, 31 to 35, 37 to 41, 43, 45 to 47, 60 to 65, 67 to 105, 107 to 109, 112 to 186, 188 to 193, 195 to 231, 233 to 239, 241 to 243 have all demonstrated positive inhibitory activity in this binding assay, having an $IC_{50}$ of <10 uM.

Representative final compounds of Formula (II) and (IIa) which have been tested. Example 111 has demonstrated positive inhibitory activity in this binding assay, having an $IC_{50}$ of <10 uM.

TNF-α in Traumatic Brain Injury Assay

This assay provides for examination of the expression of tumor necrosis factor mRNA in specific brain regions which follow experimentally induced lateral fluid-percussion traumatic brain injury (TBI) in rats. Since TNF-α is able to induce nerve growth factor (NGF) and stimulate the release of other cytokines from activated astrocytes, this post-traumatic alteration in gene expression of TNF-α plays an important role in both the acute and regenerative response to CNS trauma. A suitable assay may be found in WO 97/35856 whose disclosure is incorporated herein by reference.

CNS Injury Model for IL-b mRNA

This assay characterizes the regional expression of interleukin-1β (IL-1β) mRNA in specific brain regions following experimental lateral fluid-percussion traumatic brain injury (TBI) in rats. Results from these assays indicate that following TBI, the temporal expression of IL-1β mRNA is regionally stimulated in specific brain regions. These regional changes in cytokines, such as IL-1β play a role in the post-traumatic pathologic or regenerative sequelae of brain injury. A suitable assay may be found in WO 97/35856 whose disclosure is incorporated herein by reference.

Angiogenesis Assay:

Described in WO 97/32583, whose disclosure is incorporated herein by reference, is an assay for determination of inflammatory angiogenesis which may be used to show that cytokine inhibition will stop the tissue destruction of excessive or inappropriate proliferation of blood vessels.

Rhinovirus/Influenza Assay:

Cell lines, rhinovirus serotype 39, and influenza virus A/PR/8/34 were purchased from American Type Culture Collection (ATCC). BEAS-2B cells were cultured according to instructions provided by ATCC using BEGM (bronchial epithelial growth media) purchased from Clonetics Corp. HELA cell cultures, used for detection and titration of virus, were maintained in Eagle's minimum essential media containing 10% fetal calf serum, 2 mM 1-glutamine, and 10 mM HEPES buffer (MEM).

A modification of the method reported by Subauste et al., Supra, for in vitro infection of human bronchial epithelial cells with rhinovirus was used in these studies. BEAS-2B cells ($2 \times 10^5$/well) were cultured in collagen-coated wells for 24 hours prior to infection with rhinovirus. Rhinovirus serotype 39 was added to cell cultures for one hour incubation at 34° C. after which inoculum was replaced with fresh media and cultures were incubated for an additional 72 hours at 34° C. Supernatants collected at 72 hours post-infection were assayed for cytokine protein concentration by ELISA using commercially available kits (R&D Systems). Virus yield was also determined from culture supernatants using a microtitration assay in HELA cell cultures (Subauste et al., supra 1995). In cultures treated with p38 kinase inhibitors, drug was added 30 minutes prior to infection. Stocks of compounds were prepared in DMSO (10 mM drug) and stored at −20° C.

For detection of p38 kinase, cultures were incubated in basal media without growth factors and additives to reduce endogenous levels of activated p38 kinase. Cells were harvested at various timepoints after addition of rhinovirus. Detection of tyrosine phosphorylated p38 kinase by immunoblot was analyzed by a commercially available kit and was performed according to the manufacturer's instructions (PhosphoPlus p38 MAPK Antibody Kit: New England BioLabs Inc.).

In some experiments, BEAS-2B cells were infected with influenza virus (strain A/PR/8/34) in place of rhinovirus. Culture supernatant was harvested 48 and 72 hour post-infection and tested by ELISA for cytokine as described above.

Cells and Virus: Influenza A/PR/8/34 sub type H1N1 (VR-95 American Type Culture Collection, Rockville, Md.) was grown in the allantoic cavity of 10 day old chicken eggs. Following incubation at 37° C., and refrigeration for 2½ hours at 4° C., allantoic fluid was harvested, pooled, and centrifuged (1,000 rcf; 15 min; 4° C.) to remove cells. Supernatent was aliquoted and stored at −70° C. The titer of the stock culture of virus was $1.0 \times 10^{10}$ Tissue Culture Infective Dose/ml ($TCID_{50}$)

Inoculation procedure: Four-six week old female Balb/cAnNcrlBr mice were obtained from Charles River, Raleigh, N.C. Animals were infected intranasally. Mice were anesthetized by intraperitioneal injection of Ketamine (40 mg/kg; Fort Dodge Labs, Fort Dodge, Iowa) and Xylazine (5 mg/kg; Miles, Shawnee Mission, Kans.) and then inoculated with 100 TCID50 of PR8 diluted in PBS in 20 ul. Animals were observed daily for signs of infection. All animal studies were approved by SmithKline Beecham Pharmaceuticals Institutional Animal Care and Use Committee.

Virus titration: At various times post infection, animals were sacrificed and lungs were aseptically harvested. Tissues were homogenized, in vials containing 1 micron glass beads (Biospec Products, Bartlesville, Okla.) and 1 ml. of Eagles minimal essential medium. Cell debris was cleared by centrifugation at 1,000 rcf for 15 minutes at 4° C., and supernatants were serially diluted on Madin-Darby canine kidney (MDCK) cells. After 5 days of incubation at 37° C. (5% $CO_2$), 50 µl of 0.5% chick red blood cells were added per well, and agglutination was read after 1 hour at room temperature. The virus titer is expressed as 50% tissue culture infective dose ($TCID_{50}$) calculated by logistic regression.

ELISA: Cytokine levels were measured by quantitative ELISA using commercially available kits. Ear samples were homogenized using a tissue minser in PBS. Cell debris was cleared by centrifugation at 14,000 rpm for 5 minutes. The cytokine concentrations and thresholds were determined as described by the manufacturer; IL-6, IFN-γ, and KC (R&D Systems, Minneapolis, Minn.).

Myeloperoxidase Assay: Myeloperoxidase (MPO) activity was determined kinetically as described by Bradley et al. (1982). Briefly, rabbit cornea were homogenized in Hexadecyl Trimethyl-Ammonium Bromide (HTAB) (Sigma Chemical Co. St. Louis, Mo.) which was dissolved in 0.5 m Potassium phosphate buffer (J.T. Baker Scientific, Phillipsburg, N.J.). Following homogenization, the samples were subjected to freeze-thaw-sonication (Cole-Parmer 8853, Cole-Parmer, Vernon Hills, Ill.) 3 times. Suspensions were then cleared by centrifugation at 12,500 for 15 minutes at 4° C. MPO enzymatic activity was determined by colormetric change in absorbance during a reaction of O-Dianisidine dihydrochloride (ODI) 0.175 mg/ml (Sigma Chemical Co. St. Louis, Mo.) with 0.0002% Hydrogen peroxide (Sigma Chemical Co. St. Louis, Mo.). Measurements were performed by using a Beckman Du 640 Spectrophotometer (Fullerton, Calif.) fitted with a temperature control device. 50 ul of material to be assayed was added to 950 ul of ODI and change in absorbance was measured at a wave length of 460 nm for 2 minutes at 25° C.

Whole Body Plethysomography: Influenza virus infected mice were placed into a whole body plethysomograph box with an internal volume of approximately 350-ml. A bias airflow of one l/min was applied to the box and flow changes were measured and recorded with a Buxco XA data acquisition and respiratory analysis system (Buxco Electronics, Sharon, Conn.). Animals were allowed to acclimate to the plethysmograph box for 2 min. before airflow data was recorded. Airway measurements were calculated as Penh (enhanced pause). Penh has previously been shown as an index of airway obstruction and correlates with increased intrapleural pressure. The algorithm for Penh calculation is as follows: Penh=[(expiratory time/relaxation time)−1]×(peak expiratory flow/peak inspiratory flow) where relaxation time is the amount of time required for 70% of the tidal volume to be expired.

Determination of arterial oxygen saturation. A Nonin veterinary hand held pulse oximeter 8500V with lingual sensor (Nonin Medical, Inc., Plymouth Minn.) was used to determine daily arterial oxygen saturation % SpO2 as described (Sidwell et al. 1992 Antimicrobial Agents and Chemotherapy 36:473-476).

Additional data and assay modifications may be found in PCT/US00/25386, (WO 01/19322) filed 15 Sep. 2000, whose disclosure is incorporated herein by reference in its entirety.

Synthetic Examples

The invention will now be described by reference to the following examples which are merely illustrative and are not to be construed as a limitation of the scope of the present invention. All temperatures are given in degrees centigrade, all solvents are highest available purity and all reactions run under anhyd conditions in an Ar atmosphere where necessary.

Mass spectra were run on an open access LC-MS system using electrospray ionization. LC conditions: 4.5% to 90% CH$_3$CN (0.02% TFA) in 3.2 min with a 0.4 min hold and 1.4 min re-equilibration; detection by MS, UV at 214 nm, and a light scattering detector (ELS). Column: 1×40 mm Aquasil (C18) $^1$H-NMR (hereinafter "NMR") spectra were recorded at 400 MHz using a Bruker AM 400 spectrometer or a Bruker AVANCE 400. Multiplicities indicated are: s=singlet, d=doublet, t=triplet, q=quartet, m=multiplet and br indicates a broad signal. For preparative (prep) hplc; ca 50 mg of the final products were injected in 500 uL of DMSO onto a 50×20 mm I. D. YMC CombiPrep ODS-A column at 20 mL/min with a 10 min gradient from 10% CH$_3$CN (0.1% TFA) to 90% CH$_3$CN (0.1% TFA) in H$_2$O (0.1% TFA) and a 2 min hold (unless otherwise stated). Flash chromatography was run over Merck Silica gel 60 (230-400 mesh) in solvent mixtures containing varying relative concentrations of dichloromethane and methanol, or EtOAc, and hexane, unless otherwise stated. Chromatotron chromatography as has been previously described (Desai, H K; Joshi, B S; Panu, A M; Pelletier, S W *J. Chromatogr.* 1985 223-227.) was run on chromatotron plates available from Analtech, Wilmington Del., USA.

satd=saturated; aq=aqueous; NMP=1-methyl-2-pyrrolidinone; other abbreviations are as described in the ACS Style Guide (American Chemical Society, Washington, D.C., 1986).

Example 1

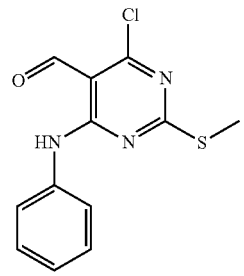

4-Chloro-2-methylsulfanyl-6-phenylamino-pyrimidine-5-carbaldehyde

To a solution of aniline (550 microliter (hereinafter "μL" or "uL"), 6 millimoles (hereinafter "mmol"), 1.2 equivalents (hereinafter "eq")) in dry DMSO (100 mL) was added NaH as a 60% suspension in mineral oil (240 milligrams (hereinafter "mg"), 6 mmol, 1.2 eq) and the reaction mixture was stirred for 1 hour (hereinafter "h"). To the red solution was then added 4,6-dichloro-2-methylsulfanyl-pyrimidine-5-carbaldehyde (1.11 grams (hereinafter "g"), 5 mmol) [Santilli, et al., *J. Heterocycl. Chem.* 1971, 8, 445-45] dissolved in anhydrous DMSO (20 milliliters (hereinafter "mL")). The reaction mixture turned yellow and was stirred 2 h at 23°, H$_2$O (250 mL) was added followed by EtOAc (500 mL) The layers were separated; the organic layer was washed with saturated (hereinafter sat'd) aq. NaCl, dried (MgSO$_4$) and filtered. The organic layer was evaporated and the crude residue was dissolved in isopropanol (50 mL) and heated to 60°, H$_2$O (50 mL) was added and the solution was cooled slowly to 23°. The product was isolated by filtration and dried in vacuo to afford 1.06 g (76% yield) of pure 4-chloro-2-methylsulfanyl-6-phenylamino-pyrimidine-5-carbaldehyde. $^1$H-NMR δ 2.59 (s, 3H), 7.21 (m, 1H), 7.44 (m, 2H), 7.68 (m, 2H), 10.37 (s, 1H), 11.38 (br s, 1H). LC MS (m/e)=280 (MH+).

Example 2

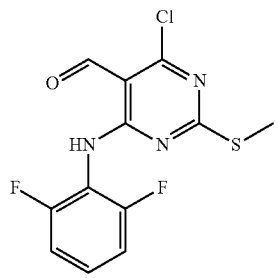

4-Chloro-6-(2,6-difluoro-phenylamino)-2-methylsulfanyl-pyrimidine-5-carbaldehyde To a solution of 4,6-dichloro-2-methylsulfanyl-pyrimidine-5-carbaldehyde (11.1 g, 50 mmol) in CHCl$_3$ (100 mL)

was added 2,6-difluoroaniline (8.07 mL, 75 mmol, 1.5 eq) followed by Et₃N (10.43 mL, 75 mmol, 1.5 eq). The reaction mixture turned yellow and was heated to reflux for 24 h, H₂O (50 mL) was added and the layers were separated. The organic layer was evaporated and the crude product was recrystallized from 200 mL of a methanol:H₂O mixture (2:1) to give 12.03 g (76%) of pure 4-chloro-6-(2,6-difluoro-phenylamino)-2-methylsulfanyl-pyrimidine-5-carbaldehyde. ¹H-NMR: δ 2.21 (s, 3H), 6.91 (m, 2H), 7.24 (m, 1H), 10.29 (s, 1H), 10.35 (br s, 1H). LC MS (m/e)=316 (MH+).

Example 3

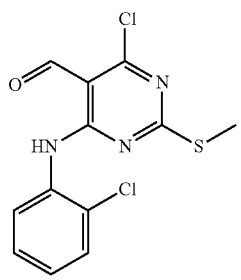

4-Chloro-6-(2-chloro-phenylamino)-2-methylsulfanyl-pyrimidine-5-carbaldehyde

Prepared as described above in Example 1 starting from 4,6-dichloro-2-methylsulfanyl-pyrimidine-5-carbaldehyde and 2-chloroaniline to give the title compound 4-chloro-6-(2-chloro-phenylamino)-2-methylsulfanyl-pyrimidine-5-carbaldehyde. ¹H-NMR: δ 2.55 (s, 3H), 7.17 (m, 1H), 7.29 (m, 2H), 7.44 (m, 1H), 10.37 (s, 1H), 11.49 (br s, 1H). LC MS (m/e)=315 (MH+).

Example 4

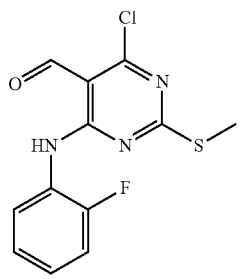

4-Chloro-6-(2-fluoro-phenylamino)-2-methylsulfanyl-pyrimidine-5-carbaldehyde

Prepared as described above in Example 2 starting from 4,6-dichloro-2-methylsulfanyl-pyrimidine-5-carbaldehyde and 2-fluoroaniline to give the title compound 4-chloro-6-(2-fluoro-phenylamino)-2-methylsulfanyl-pyrimidine-5-carbaldehyde. ¹H-NMR: δ 2.53 (s, 3H), 7.15 (m, 3H), 8.25 (m, 1H), 7.44 (m, 1H), 10.31 (s, 1H), 11.35 (br s, 1H). LC MS (m/e)=298 (MH+).

Example 5

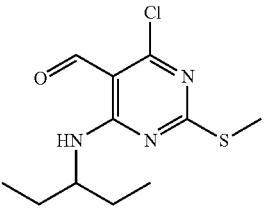

4-Chloro-6-(1-ethyl-propylamino)-2-methylsulfanyl-pyrimidine-5-carbaldehyde

Prepared as described above in Example 2 starting from 4,6-dichloro-2-methylsulfanyl-pyrimidine-5-carbaldehyde and 3-pentylamine to give the title compound 4-chloro-6-(1-ethyl-propylamino)-2-methylsulfanyl-pyrimidine-5-carbaldehyde. ¹H-NMR: δ 0.92 (t, 6H, J=7.3 Hz), 1.50-1.74 (m, 4H), 2.52 (s, 3H), 4.22 (m, 1H), 9.21 (br s, 1H), 10.33 (s, 1H). LC MS (m/e)=274 (MH+).

Example 6

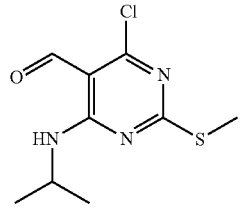

4-Chloro-6-isopropylamino-2-methylsulfanyl-pyrimidine-5-carbaldehyde

Prepared as described above in Example 2 starting from 4,6-dichloro-2-methylsulfanyl-pyrimidine-5-carbaldehyde and isopropylamine to give the title compound 4-chloro-6-isopropylamino-2-methylsulfanyl-pyrimidine-5-carbaldehyde. ¹H-NMR: δ 1.31 (d, 6H, J=5.7 Hz), 2.60 (s, 3H), 4.47 (m, 1H), 9.16 (br s, 1H), 10.25 (s, 1H). LC MS (m/e)=246 (MH+).

Example 7

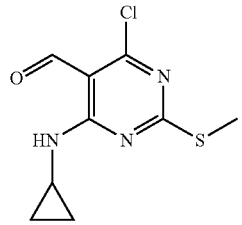

4-Chloro-6-cyclopropylamino-2-methylsulfanyl-pyrimidine-5-carbaldehyde

Prepared as described above in Example 2 starting from 4,6-dichloro-2-methylsulfanyl-pyrimidine-5-carbaldehyde and cyclopropylamine to give the title compound 4-chloro-6-cyclopropylamino-2-methylsulfanyl-pyrimidine-5-carbaldehyde. ¹H-NMR: δ 0.68 (m, 2H), 0.90 (m, 2H), 2.58 (s, 3H), 3.07 (m, 1H), 9.20 (br s, 1H), 10.28 (s, 1H). LC MS (m/e)=244 (MH+).

Example 8

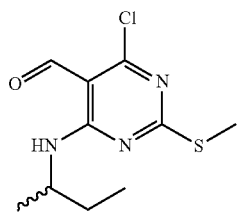

4-sec-Butylamino-6-chloro-2-methylsulfanyl-pyrimidine-5-carbaldehyde

Prepared as described above in Example 2 starting from 4,6-dichloro-2-methylsulfanyl-pyrimidine-5-carbaldehyde and 2-butylamine to give the title compound 4-sec-butylamino-6-chloro-2-methylsulfanyl-pyrimidine-5-carbaldehyde. ¹H-NMR: δ 0.87 (m, 3H), 1.18 (m, 3H), 1.20 (m, 2H), 2.51 (s, 3H), 4.24 (m, 1H), 9.12 (br s, 1H), 10.18 (s, 1H). LC MS (m/e)=260 (MH+).

Example 9

4-Chloro-6-(cyclopropylmethyl-amino)-2-methylsulfanyl-pyrimidine-5-carbaldehyde

Prepared as described above in Example 2 starting from 4,6-dichloro-2-methylsulfanyl-pyrimidine-5-carbaldehyde and (aminomethyl)cyclopropane to give the title compound 4-chloro-6-(cyclopropylmethyl-amino)-2-methylsulfanyl-pyrimidine-5-carbaldehyde. ¹H-NMR: δ 0.32 (m, 2H), 0.59 (m, 2H), 1.12 (m, 1H), 2.55 (s, 3H), 3.46 (m, 2H), 9.35 (br s, 1H), 10.28 (s, 1H). LC MS (m/e)=258 (MH+).

Example 10

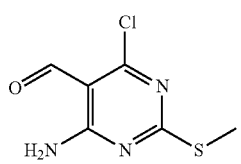

4-Amino-6-chloro-2-methylsulfanyl-pyrimidine-5-carbaldehyde

To the solution of 4,6-dichloro-2-methylsulfanyl-pyrimidine-5-carbaldehyde (2 g, 7.36 mmol) in benzene (20 mL) was introduced NH₃ gas for 30 minutes (hereinafter "min"). The formed solid was then filtered and recrystallized from EtOAc (15 mL) to give 1.18 g (80%) of pure 4-amino-6-chloro-2-methylsulfanyl-pyrimidine-5-carbaldehyde. ¹H-NMR: δ 2.50 (s, 3H), 7.28 (t, 3H, J=45 Hz, D₂O exchangeable), 8.65 (d, 3H, J=41 Hz, D₂O exchangeable), 10.11 (s, 1H).

Example 11

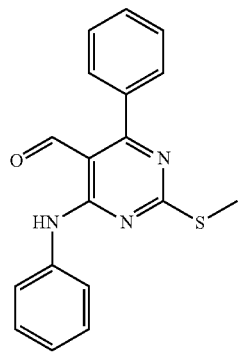

2-Methylsulfanyl-4-phenyl-6-phenylamino-pyrimidine-5-carbaldehyde

To a solution of 4-chloro-2-methylsulfanyl-6-phenylamino-pyrimidine-5-carbaldehyde (300 mg, 1.07 mmol) in dioxane (21 mL) and H₂O (7 mL) was added anhyd K₂CO₃ (443 mg, 3.21 mmol, 3 eq) followed by phenylboronic acid (196 mg, 1.6 mmol, 1.5 eq). The reaction mixture was degassed and tetrakis(triphenylphosphine)-palladium (61 mg, 0.053 mmol, 0.05 eq) was added. The reaction mixture was then heated under reflux for 24 h and cooled 23°, the layers were separated, EtOAc (50 mL), followed by H₂O (10 mL), was added, the organic layer was separated, washed with satd aq NaCl, dried (MgSO₄) and filtered. The yellow solution was then evaporated. Product was purified by column chromatography or by crystallization from 10 mL of isopropanol:H₂O (2:1) to give 240 mg (70% yield) of pure 2-methylsulfanyl-4-phenyl-6-phenylamino-pyrimidine-5-carbaldehyde. ¹H-NMR δ 2.60 (s, 3H), 7.22 (m, 1H), 7.35-7.81 (m, 9H), 9.89 (s, 1H), 11.31 (br s, 1H), LC MS (m/e)=322 (MH+).

Example 12

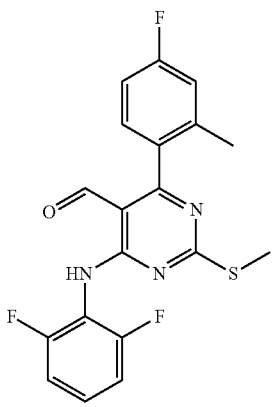

4-(2,6-Difluoro-phenylamino)-6-(4-fluoro-2-methyl-phenyl)-2-methylsulfanyl-pyrimidine-5-carbaldehyde Prepared as described above in Example 11 starting from 4-chloro-6-(2,6-difluoro-phenylamino)-2-methylsulfanyl-pyrimidine-5-carbaldehyde and 4-fluoro-2-methyl-phenyl-boronic acid to give the title compound 4-(2,6-difluoro-phenylamino)-6-(4-fluoro-2-methyl-phenyl)-2-methylsulfanyl-pyrimidine-5-carbaldehyde. $^1$H-NMR: δ 2.21 (s, 3H), 2.25 (s, 3H), 6.95 (m, 4H), 7.18 (m, 4H), 9.54 (s, 1H), 10.29 (br s, 1H). LC MS (m/e)=390 (MH+).

Example 13

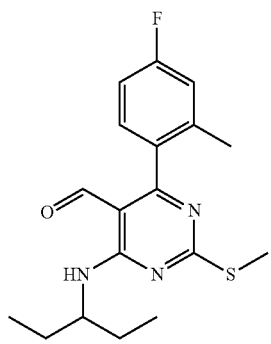

4-(1-Ethyl-propylamino)-6-(4-fluoro-2-methyl-phenyl)-2-methylsulfanyl-pyrimidine-5-carbaldehyde Prepared as described above in Example 11 starting from 4-chloro-6-(1-ethyl-propylamino)-2-methylsulfanyl-pyrimidine-5-carbaldehyde and 4-fluoro-2-methyl-phenylboronic acid to give the title compound 4-(1-ethyl-propylamino)-6-(4-fluoro-2-methyl-phenyl)-2-methylsulfanyl-pyrimidine-5-carbaldehyde. $^1$H-NMR: δ 0.92 (m, 6H), 1.54-1.71 (m, 4H), 2.21 (s, 3H), 2.53 (s, 3H), 4.28 (m, 1H), 6.63-7.05 (m, 2H), 7.21 (m, 1H), 9.05 (br s, 1H), 10.50 (s, 1H). LC MS (m/e)= 348 (MH+).

Example 14

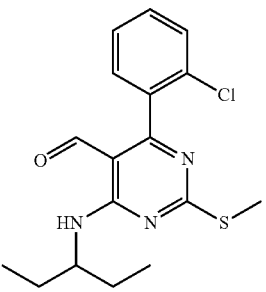

4-(2-Chloro-phenyl)-6-(1-ethyl-propylamino)-2-methylsulfanyl-pyrimidine-5-carbaldehyde Prepared as described above in Example 11 starting from 4-chloro-6-(1-ethyl-propylamino)-2-methylsulfanyl-pyrimidine-5-carbaldehyde and 2-chlorophenylboronic acid to give the title compound 4-(2-chloro-phenyl)-6-(1-ethyl-propylamino)-2-methylsulfanyl-pyrimidine-5-carbaldehyde. $^1$H-NMR: δ 0.91 (m, 6H), 1.42-1.60 (m, 4H), 2.45 (s, 3H), 4.21 (m, 1H), 7.32 (m, 4H), 8.96 (br s, 1H), 9.44 (s, 1H). LC MS (m/e)=350 (MH+).

Example 15

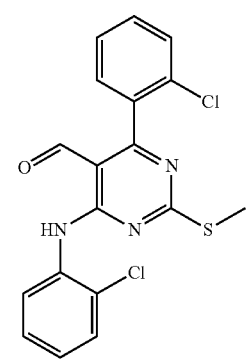

4-(2-Chloro-phenyl)-6-(2-chloro-phenylamino)-2-methylsulfanyl-pyrimidine-5-carbaldehyde Prepared as described above in Example 11 starting from 4-chloro-6-(2-chloro-phenylamino)-2-methylsulfanyl-pyrimidine-5-carbaldehyde and 2-chlorophenylboronic acid to give the title compound 4-(2-chloro-phenyl)-6-(2-chloro-phenylamino)-2-methylsulfanyl-pyrimidine-5-carbaldehyde. $^1$H-NMR: δ 2.58 (s, 3H), 7.01-7.59 (m, 7H), 8.61 (d, 1H, J=4.7 Hz), 9.65 (s, 1H), 11.48 (br s, 1H). LC MS (m/e)= 390 (MH+).

Example 16

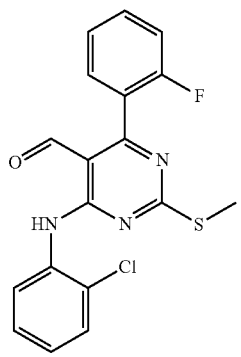

4-(2-Fluoro-phenyl)-6-(2-chloro-phenylamino)-2-methylsulfanyl-pyrimidine-5-carbaldehyde Prepared as described above in Example 11 starting from 4-chloro-6-(2-chloro-phenylamino)-2-methylsulfanyl-pyrimidine-5-carbaldehyde and 2-fluorophenylboronic acid to give the title compound 4-(2-fluoro-phenyl)-6-(2-chloro-phenylamino)-2-methylsulfanyl-pyrimidine-5-carbaldehyde. $^1$H-NMR: δ 2.60 (s, 3H), 6.99-7.68 (m, 7H), 8.47 (d, 1H, J=4.7 Hz), 9.78 (s, 1H), 11.59 (br s, 1H). LC MS (m/e)=374 (MH+).

Example 17

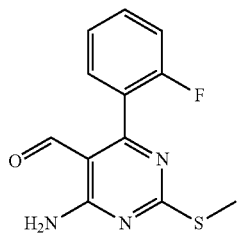

4-Amino-6-(2-fluoro-phenyl)-2-methylsulfanyl-pyrimidine-5-carbaldehyde

Prepared as described above in Example 11 starting from 4-amino-6-chloro-2-methylsulfanyl-pyrimidine-5-carbaldehyde and 2-fluorophenylboronic acid to give the title compound 4-amino-6-(2-fluoro-phenyl)-2-methylsulfanyl-pyrimidine-5-carbaldehyde. $^1$H-NMR: δ 2.59 (s, 3H), 5.78 (br s, 1H), 7.11-7.32 (m, 2H), 7.42-7.58 (m, 2H), 8.65 (br s, 1H), 9.71 (s, 1H). LC MS (m/e)=264 (MH+).

Example 18

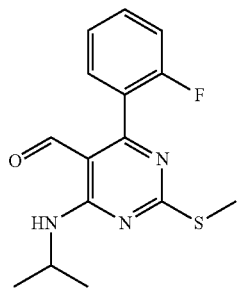

4-(2-Fluoro-phenyl)-6-isopropylamino-2-methylsulfanyl-pyrimidine-5-carbaldehyde Prepared as described above in Example 11 starting from 4-chloro-6-isopropylamino-2-methylsulfanyl-pyrimidine-5-carbaldehyde and 2-fluorophenylboronic acid to give the title compound 4-(2-fluoro-phenyl)-6-isopropylamino-2-methylsulfanyl-pyrimidine-5-carbaldehyde. $^1$H-NMR: δ 1.31 (d, 6H, J=5.7 Hz), 2.56 (s, 3H), 4.51 (m, 1H), 7.05-7.31 (m, 2H), 7.41-7.55 (m, 2H), 9.02 (br s, 1H), 9.64 (s, 1H). LC MS (m/e)=306 (MH+).

Example 19

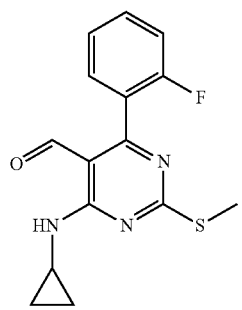

4-Cyclopropylamino-6-(2-fluoro-phenyl)-2-methylsulfanyl-pyrimidine-5-carbaldehyde Prepared as described above in Example 11 starting from 4-chloro-6-cyclopropylamino-2-methylsulfanyl-pyrimidine-5-carbaldehyde and 2-fluorophenylboronic acid to give the title compound 4-cyclopropylamino-6-(2-fluoro-phenyl)-2-methylsulfanyl-pyrimidine-5-carbaldehyde. $^1$H-NMR: δ 0.66 (m, 2H), 0.92 (m, 2H) 2.60 (s, 3H), 3.11 (m, 1H), 7.10-7.30 (m, 2H), 7.41-7.57 (m, 2H), 9.10 (br s, 1H), 9.66 (s, 1H). LC MS (m/e)=304 (MH+).

Example 20

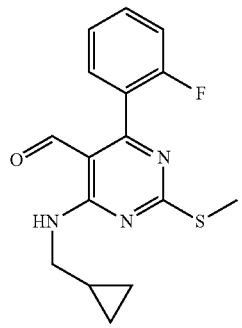

4-(Cyclopropylmethyl-amino)-6-(2-fluoro-phenyl)-2-methylsulfanyl-pyrimidine-5-carbaldehyde Prepared as described above in Example 11 starting from 4-chloro-6-cyclopropylmethyl-amino-2-methylsulfanyl-pyrimidine-5-carbaldehyde and 2-fluorophenylboronic acid to give the title compound 4-(cyclopropylmethyl-amino)-6-(2-fluoro-phenyl)-2-methylsulfanyl-pyrimidine-5-carbaldehyde. $^1$H-NMR: δ 0.34 (m, 2H), 0.61 (m, 2H), 1.19 (m, 1H), 2.56 (s, 3H), 3.51 (m, 2H), 7.11-7.27 (m, 2H), 7.31-7.52 (m, 2H), 9.22 (br s, 1H), 9.69 (s, 1H). LC MS (m/e)=318 (MH+).

Example 21

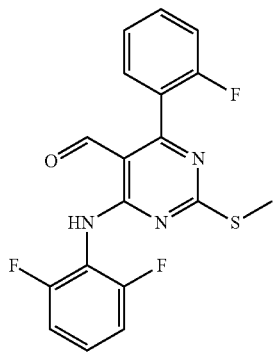

4-(2,6-Difluoro-phenylamino)-6-(2-fluoro-phenyl)-2-methylsulfanyl-pyrimidine-5-carbaldehyde Prepared as described above in Example 11 starting from 4-chloro-6-(2,6-difluoro-phenylamino)-2-methylsulfanyl-pyrimidine-5-carbaldehyde and 2-fluorophenylboronic acid to give the title compound 4-(2,6-difluoro-phenylamino)-6-(2-fluoro-phenyl)-2-methylsulfanyl-pyrimidine-5-carbaldehyde. $^1$H-NMR: δ0.31 (s, 3H), 6.98-7.20 (m, 3H), 7.26 (m, 2H), 7.38-7.42 (m, 2H), 9.79 (s, 1H), 10.39 (br s, 1H). LC MS (m/e)=376 (MH+).

Example 22

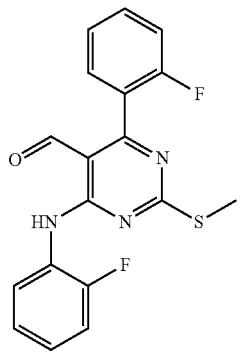

4-(2-Fluoro-phenyl)-6-(2-fluoro-phenylamino)-2-methylsulfanyl-pyrimidine-5-carbaldehyde Prepared as described above in Example 11 starting from 4-chloro-6-(2-fluoro-phenylamino)-2-methylsulfanyl-pyrimidine-5-carbaldehyde and 2-fluorophenylboronic acid to give the title compound 4-(2-fluoro-phenyl)-6-(2-fluoro-phenylamino)-2-methylsulfanyl-pyrimidine-5-carbaldehyde. $^1$H-NMR: δ0.61 (s, 3H), 7.11-7.23 (m, 4H), 7.26 (m, 1H), 7.45-7.62 (m, 2H), 8.38 (m, 1H), 9.80 (s, 1H), 11.33 (br s, 1H). LC MS (m/e)=358 (MH+).

Example 23

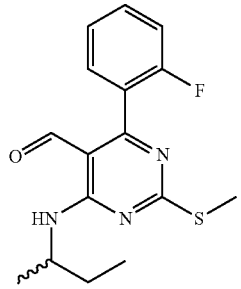

4-sec-Butylamino-6-(2-fluoro-phenyl)-2-methylsulfanyl-pyrimidine-5-carbaldehyde

Prepared as described above in Example 11 starting from 4-sec-butylamino-6-chloro-2-methylsulfanyl-pyrimidine-5-carbaldehyde and 2-fluorophenylboronic acid to give the title compound 4-sec-butylamino-6-(2-fluoro-phenyl)-2-methylsulfanyl-pyrimidine-5-carbaldehyde. $^1$H-NMR: δ 0.96 (m, 3H), 1.30 (m, 3H), 1.67 (m, 2H), 2.58 (s, 3H), 4.38 (m, 1H), 7.11-7.31 (m, 2H), 7.42-7.58 (m, 2H), 9.07 (br s, 1H), 9.63 (s, 1H). LC MS (m/e)=306 (MH+).

Example 24

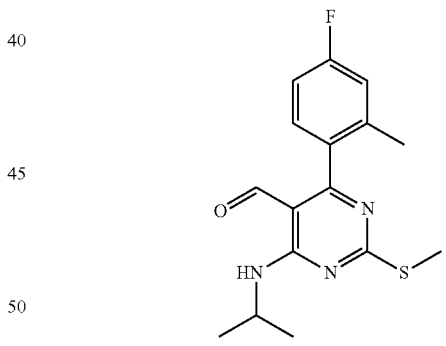

4-(4-Fluoro-2-methyl-phenyl)-6-isopropylamino-2-methylsulfanyl-pyrimidine-5-carbaldehyde Prepared as described above in Example 11 starting from 4-chloro-6-isopropylamino-2-methylsulfanyl-pyrimidine-5-carbaldehyde and 4-fluoro-2-methylphenylboronic acid to give the title compound 4-(4-fluoro-2-methyl-phenyl)-6-isopropylamino-2-methylsulfanyl-pyrimidine-5-carbaldehyde. $^1$H-NMR: δ 1.31 (d, 6H, J=5.7 Hz), 2.21 (s, 3H), 2.59 (s, 3H), 4.52 (m, 1H), 7.90-7.15 (m, 2H), 7.18-7.25 (m, 1H), 9.06 (br s, 1H), 9.50 (s, 1H). LC MS (m/e)=320 (MH+).

Example 25

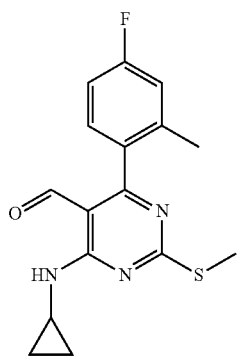

4-Cyclopropylamino-6-(4-fluoro-2-methyl-phenyl)-
2-methylsulfanyl-pyrimidine-5-carbaldehyde Prepared as described above in Example 11 starting from 4-chloro-6-cyclopropylamino-2-methylsulfanyl-pyrimidine-5-carbaldehyde and 4-fluoro-2-methylphenylboronic acid to give the title compound 4-cyclopropylamino-6-(4-fluoro-2-methyl-phenyl)-2-methylsulfanyl-pyrimidine-5-carbaldehyde. $^1$H-NMR: δ 0.69 (m, 2H), 0.94 (m, 2H), 2.23 (s, 3H), 2.62 (s, 3H), 3.14 (m, 1H), 6.98 (m, 2H), 7.20 (m, 1H), 9.09 (br s, 1H), 9.49 (s, 1H). LC MS (m/e)=318 (MH+).

Example 26

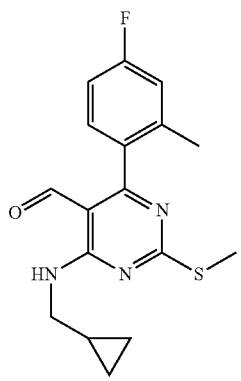

4-(Cyclopropylmethyl-amino)-6-(4-fluoro-2-methyl-
phenyl)-2-methylsulfanyl-pyrimidine-5-carbaldehyde Prepared as described above in Example 11 starting from 4-chloro-6-cyclopropylmethyl-amino-2-methylsulfanyl-pyrimidine-5-carbaldehyde and 4-fluoro-2-methylphenylboronic acid to give the title compound 4-(cyclopropylmethyl-amino)-6-(4-fluoro-2-methyl-phenyl)-2-methylsulfanyl-pyrimidine-5-carbaldehyde. $^1$H-NMR: δ 0.30 (m, 2H), 0.60 (m, 2H), 1.18 (m, 1H), 2.24 (s, 3H), 2.55 (s, 3H), 3.50 (m, 2H), 6.98 (m, 2H), 7.18 (m, 1H), 9.21 (br s, 1H), 9.50 (s, 1H). LC MS (m/e)=332 (MH+).

Example 27

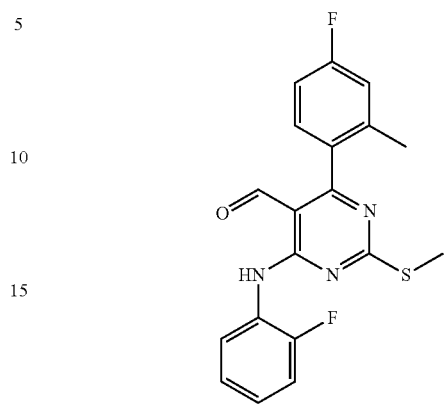

4-(4-Fluoro-2-methyl-phenyl)-6-(2-fluoro-phenylamino)-2-methylsulfanyl-pyrimidine-5-carbaldehyde Prepared as described above in Example 11 starting from 4-chloro-6-(2-fluoro-phenylamino)-2-methylsulfanyl-pyrimidine-5-carbaldehyde and 4-fluoro-2-methylphenylboronic acid to give the title compound 4-(4-fluoro-2-methyl-phenyl)-6-(2-fluoro-phenylamino)-2-methylsulfanyl-pyrimidine-5-carbaldehyde. $^1$H-NMR: δ 2.28 (s, 3H).59 (s, 3H), 7.01 (m, 2H), 7.18 (m, 3H), 7.24 (m, 1H), 8.42 (m, 1H), 9.63 (s, 1H), 11.30 (br s, 1H). LC MS (m/e)=372 (MH+).

Example 28

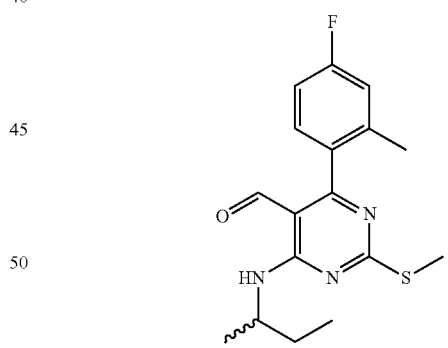

4-sec-Butylamino-6-(4-fluoro-2-methyl-phenyl)-2-methylsulfanyl-pyrimidine-5-carbaldehyde Prepared as described above in Example 11 starting from 4-sec-butylamino-6-chloro-2-methylsulfanyl-pyrimidine-5-carbaldehyde and 4-fluoro-2-methylphenylboronic acid to give the title compound 4-sec-butylamino-6-(4-fluoro-2-methyl-phenyl)-2-methylsulfanyl-pyrimidine-5-carbaldehyde. $^1$H-NMR: δ 1.02 (in, 3H), 1.30 (m, 3H), 1.70 (m, 2H), 2.28 (m, 3H), 2.59 (s, 3H), 4.37 (m, 1H), 6.98 (m, 2H), 7.20 (m, 1H), 9.04 (br s, 1H), 9.50 (s, 1H). LC MS (m/e)=334 (MH+).

Example 29

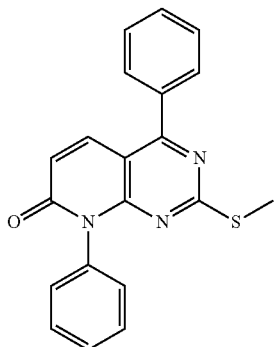

2-Methylsulfanyl-4,8-diphenyl-8H-pyrido[2,3-d]pyrimidin-7-one

A solution of 18-crown-6 (422 mg, 1.6 mmol, 5 eq) and bis(2,2,2-trifluoroethyl)(methoxycarbonylmethyl)phosphonate (81 µL, 0.38 mmol, 1.2 eq) in anhydrous THF (20 mL) was cooled to −78°. To this solution was added potassium bis(trimethylsilyl)amide (0.96 mL, 0.48 mmol, 1.5 eq) as a 0.5 mol solution in toluene. This solution was stirred for additional 30 min at −78° and 2-methylsulfanyl-4-phenyl-6-phenylamino-pyrimidine-5-carbaldehyde (102 mg, 0.32 mmol) in dry THF (1 mL) was added dropwise. The reaction mixture was then stirred for 8 h at −78° and warmed to 23° and stirred 16 h. Sat'd aq. NH$_4$Cl (5 mL), followed by diethyl ether (20 mL), was added. The layers were separated. The organic layer was washed with satd aq NaCl, dried (MgSO$_4$), filtered and solvent was evaporated. The yellow residue was then purified by flash chromatography to afford 100 mg (91% yield) of pure 2-methylsulfanyl-4,8-diphenyl-8H-pyrido[2,3-d]pyrimidin-7-one. $^1$H-NMR δ 2.19 (s, 3H), 6.70 (d, 1H, J=9.9 Hz), 7.26 (m, 2H), 7.42-7.83 (m, 8H), 7.88 (d, 1H, J=9.9 Hz), LC MS (m/e)=346 (MH+).

Example 30

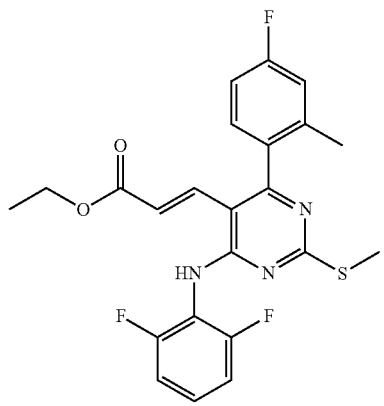

(E)-3-[4-(2,6-Difluoro-phenylamino)-6-(4-fluoro-2-methyl-phenyl)-2-methylsulfanyl-pyrimidin-5-yl]-acrylic acid ethyl ester To a solution of triethyl phosphonoacetate (8.18 mL, 41.3 mmol, 2 eq) in 120 mL of anhyd THF was added NaH (2.05 g, 60% dispersion in mineral oil, 51.4 mmol, 2.5 eq) and the reaction mixture was stirred for 30 min at 23°. To this solution was added 4-(2,6-difluoro-phenylamino)-6-(4-fluoro-2-methyl-phenyl)-2-methylsulfanyl-pyrimidine-5-carbaldehyde (8 g, 20.65 mmol) as a solution in 10 mL of anhyd THF and the reaction mixture was heated under reflux for 3 h while being monitored by HPLC. After completion, 20 mL of satd aq NH$_4$Cl was added and the layers were separated. The aq layer was washed with Et$_2$O (100 mL) and the organic layers were combined. The organic layer was washed with H$_2$O, and satd aq NaCl, dried (MgSO$_4$), filtered and solvent was evaporated. The crude product was recrystalized from 100 mL of methanol: H$_2$O (1:1) to afford 8.1 g (88%) of pure (E)-3-[4-(2,6-difluoro-phenylamino)-6-(4-fluoro-2-methyl-phenyl)-2-methylsulfanyl-pyrimidin-5-yl]-acrylic acid ethyl ester. LC MS (m/e)=460 (MH+). Rt=2.49 min

Example 31

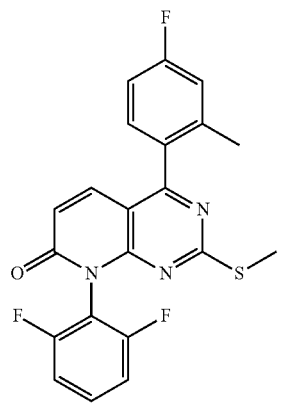

8-(2,6-Difluoro-phenyl)-4-(4-fluoro-2-methyl-phenyl)-2-methylsulfanyl-8H-pyrido[2,3-d]pyrimidin-7-one (E)-3-[4-(2,6-difluoro-phenylamino)-6-(4-fluoro-2-methyl-phenyl)-2-methylsulfanyl-pyrimidin-5-yl]-acrylic acid ethyl ester (8.1 g, 17.6 mmol) was dissolved in 50 mL of anhydrous toluene. Reaction mixture was heated in a sealed tube at 220° C. for 48 h, toluene was evaporated and the yellow residue purified by Flash chromatography to give 7.1 g (96%) of 8-(2,6-difluoro-phenyl)-4-(4-fluoro-2-methyl-phenyl)-2-methylsulfanyl-8H-pyrido[2,3-d]pyrimidin-7-one. $^1$H-NMR (CDCl$_3$) δ 2.24 (s, 3H), 2.29 (s, 3H), 6.63 (d, 1H, J=9.6 Hz), 7.03-7.20 (m, 4H), 7.25 (m, 1H), 7.51 (m, 2H); LC MS (m/e)=414 (M:H+).

Example 32

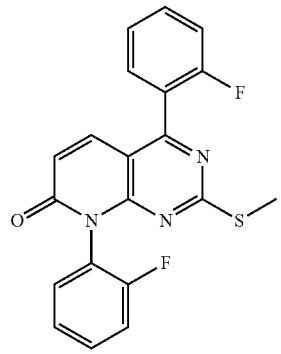

4,8-Bis-(2-fluoro-phenyl)-2-methylsulfanyl-8H-pyrido[2,3-d]pyrimidin-7-one

To a solution of 4-(2-fluoro-phenyl)-6-(2-fluoro-phenylamino)-2-methylsulfanyl-pyrimidine-5-carbaldehyde, as described in Example 22, (400 mg, 1.1 mmol) in pyridine (2 mL) was added Ac$_2$O (2 mL) and the reaction mixture was heated under reflux for 48 h, solvent was evaporated and the residue was dissolved in EtOAc (40 mL), washed with 1 M aq Na$_2$CO$_3$, and H$_2$O and satd aq NaCl, dried (MgSO$_4$), filtered and solvent was evaporated. The yellow residue was purified by Flash chromatography to afford pure 4,8-bis-(2-fluoro-phenyl)-2-methylsulfanyl-8H-pyrido[2,3-d]pyrimidin-7-one (320 mg, 76% yield). $^1$H-NMR (CDCl$_3$) δ 2.21 (s, 3H), 6.76 (d, 1H, J=9.6 Hz), 7.22-7.42 (m, 4H), 7.45-7.67 (m, 5H). LC MS (m/e)=382 (MH+).

Example 33

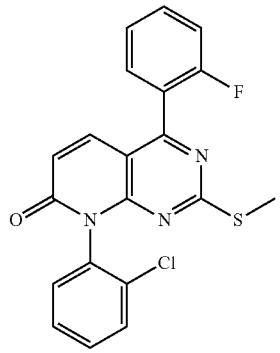

8-(2-Chloro-phenyl)-4-(2-fluoro-phenyl)-2-methylsulfanyl-8H-pyrido[2,3-d]pyrimidin-7-one Prepared as described above in Example 29 starting from 4-(2-fluoro-phenyl)-6-(2-chloro-phenylamino)-2-methylsulfanyl-pyrimidine-5-carbaldehyde to give the title compound 8-(2-chloro-phenyl)-4-(2-fluoro-phenyl)-2-methylsulfanyl-8H-pyrido[2,3-d]pyrimidin-7-one. $^1$H-NMR: δ 2.08 (s, 3H), 6.61 (d, 1H, J=9.7 Hz), 7.11-7.51 (m, 9H). LC MS (m/e)=399 (MH+)

Example 34

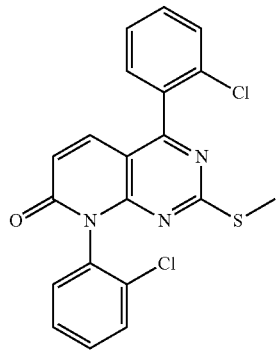

4,8-Bis-(2-chloro-phenyl)-2-methylsulfanyl-8H-pyrido[2,3-d]pyrimidin-7-one

Prepared as described above in Example 29 starting from 4-(2-chloro-phenyl)-6-(2-chloro-phenylamino)-2-methylsulfanyl-pyrimidine-5-carbaldehyde to give the title compound 4,8-bis-(2-chloro-phenyl)-2-methylsulfanyl-8H-pyrido[2,3-d]pyrimidin-7-one. $^1$H-NMR: δ 1.99 (s, 3H), 6.50 (d, 1H, J=9.7 Hz), 7.11-7.48 (m, 9H). LC MS (m/e)=414 (MH+)

Example 35

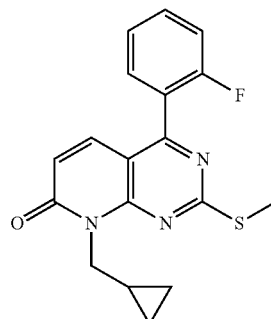

8-Cyclopropylmethyl-4-(2-fluoro-phenyl)-2-methylsulfanyl-8H-pyrido[2,3-d]pyrimidin-7-one Prepared as described above in Example 29 starting from 4-(cyclopropylmethyl-amino)-6-(2-fluoro-phenyl)-2-methylsulfanyl-pyrimidine-5-carbaldehyde to give the title compound 8-cyclopropylmethyl-4-(2-fluoro-phenyl)-2-methylsulfanyl-8H-pyrido[2,3-d]pyrimidin-7-one. $^1$H-NMR: δ 0.56 (m, 4H), 1.48 (m, 1 H), 2.65 (s, 3H), 3.79 (s, 2H), 6.62 (d, 1H, J=9.7 Hz), 7.19-7.39 (m, 3H), 7.42-7.60 (m, 2H). LC MS (m/e)=342 (MH+)

Example 36

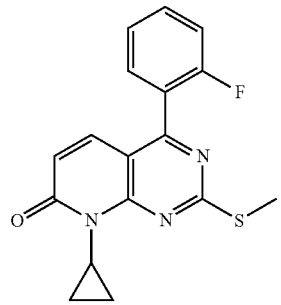

8-Cyclopropyl-4-(2-fluoro-phenyl)-2-methylsulfanyl-8H-pyrido[2,3-d]pyrimidin-7-one Prepared as described above in Example 29 starting from 4-cyclopropylamino-6-(2-fluoro-phenyl)-2-methylsulfanyl-pyrimidine-5-carbaldehyde to give the title compound 8-cyclopropyl-4-(2-fluoro-phenyl)-2-methylsulfanyl-8H-pyrido[2,3-d]pyrimidin-7-one. $^1$H-NMR: δ 0.98 (m, 2H), 1.35 (m, 2H) 2.69 (s, 3H), 3.02 (m, 1H), 6.55 (d, 1H, J=9.6 Hz), 7.12-7.36 (m, 2H), 7.42-7.60 (m, 3H). LC MS (m/e)=328 (MH+).

Example 37

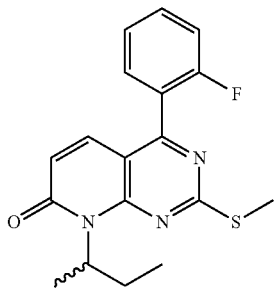

8-sec-Butyl-4-(2-fluoro-phenyl)-2-methylsulfanyl-8H-pyrido[2,3-d]pyrimidin-7-one Prepared as described above in Example 29 starting from 4-sec-butylamino-6-(2-fluoro-phenyl)-2-methylsulfanyl-pyrimidine-5-carbaldehyde to give the title compound 8-sec-butyl-4-(2-fluoro-phenyl)-2-methylsulfanyl-8H-pyrido[2,3-d]pyrimidin-7-one. $^1$H-NMR: δ 0.91 (m, 3H), 1.67 (m, 3H), 2.00-2.42 (m, 2H), 2.69 (s, 3H), 5.85 (m, 1H), 6.79 (d, 1H, J=9.7 Hz), 7.24-7.44 (m, 1H), 7.50-7.75 (m, 4H). LC MS (m/e)=328 (MH+)

Example 38

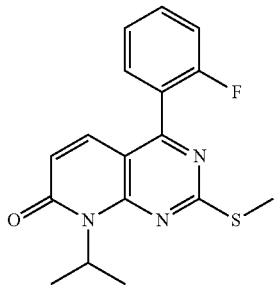

4-(2-Fluoro-phenyl)-8-isopropyl-2-methylsulfanyl-8H-pyrido[2,3-d]pyrimidin-7-one Prepared as described above in Example 29 starting from 4-(2-fluoro-phenyl)-6-isopropylamino-2-methylsulfanyl-pyrimidine-5-carbaldehyde to give the title compound 4-(2-fluoro-phenyl)-8-isopropyl-2-methylsulfanyl-8H-pyrido[2,3-d]pyrimidin-7-one. $^1$H-NMR: δ 1.69 (m, 6H), 2.60 (s, 3H), 5.91 (m, 1H), 6.52 (d, 1H, J=9.6 Hz), 7.16-7.49 (m, 5H). LC MS (m/e)=330 (MH+).

Example 39

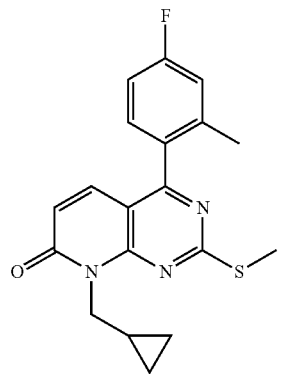

8-Cyclopropylmethyl-4-(4-fluoro-2-methyl-phenyl)-2-methylsulfanyl-8H-pyrido[2,3-d]pyrimidin-7-one Prepared as described above in Example 29 starting from 4-(cyclopropylmethyl-amino)-6-(4-fluoro-2-methyl-phenyl)-2-methylsulfanyl-pyrimidine-5-carbaldehyde to give the title compound 8-cyclopropylmethyl-4-(4-fluoro-2-methyl-phenyl)-2-methylsulfanyl-8H-pyrido[2,3-d]pyrimidin-7-one. $^1$H-NMR: δ 0.55 (m, 4H), 1.56 (m, 1H), 2.23 (s, 3H), 2.67 (s, 3H), 4.40 (m, 2H), 6.60 (d, 1H, J=9.6 Hz), 7.05 (m, 2H), 7.22 (m, 1H), 7.39 (d, 1H, J=9.6 Hz). LC MS (m/e)=356 (MH+).

Example 40

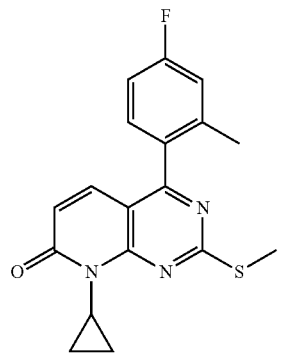

8-Cyclopropyl-4-(4-fluoro-2-methyl-phenyl)-2-methylsulfanyl-8H-pyrido[2,3-d]pyrimidin-7-one Prepared as described above in Example 29 starting from 4-cyclopropylamino-6-(4-fluoro-2-methyl-phenyl)-2-methylsulfanyl-pyrimidine-5-carbaldehyde to give the title compound 8-cyclopropyl-4-(4-fluoro-2-methyl-phenyl)-2-methylsulfanyl-8H-pyrido[2,3-d]pyrimidin-7-one. $^1$H-NMR: δ 0.99 (m, 2H), 1.40 (m, 2H), 2.21 (s, 3H), 2.71 (s, 3H), 3.06 (m, 1H), 6.61 (d, 1H, J=9.6 Hz), 7.02 (m, 2H), 7.24 (m, 1H), 7.34 (d, 1H, J=9.6 Hz), LC MS (m/e)=342 (MH+).

Example 41

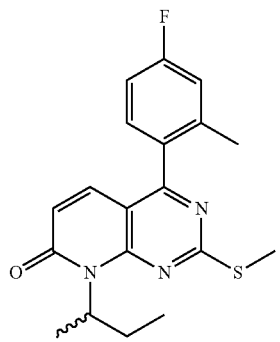

8-sec-Butyl-4-(4-fluoro-2-methyl-phenyl)-2-methyl-
sulfanyl-8H-pyrido[2,3-d]pyrimidin-7-one Prepared as described above in Example 29 starting from 4-sec-butylamino-6-(4-fluoro-2-methyl-phenyl)-2-methyl-sulfanyl-pyrimidine-5-carbaldehyde to give the title compound 8-sec-butyl-4-(4-fluoro-2-methyl-phenyl)-2-methyl-sulfanyl-8H-pyrido[2,3-d]pyrimidin-7-one. $^1$H-NMR: δ 0.89 (m, 3H), 1.70 (m, 3H), 2.06-2.42 (m, 2H), 2.21 (s, 3H), 2.65 (s, 3H), 5.80 (m, 1H), 6.61 (d, 1H, J=9.7 Hz), 7.03 (m, 2H), 7.24 (m, 1H), 7.39 (d, 1H, J=9.7 Hz). LC MS (m/e)=328 (MH+).

Example 42

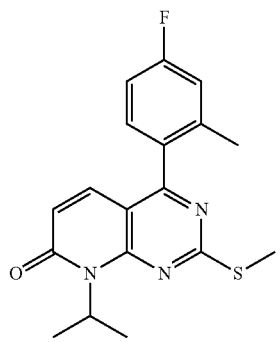

4-(4-Fluoro-2-methyl-phenyl)-8-isopropyl-2-methyl-
sulfanyl-8H-pyrido[2,3-d]pyrimidin-7-one Prepared as described above in Example 29 starting from 4-(4-fluoro-2-methylphenyl)-6-isopropylamino-2-methyl-sulfanyl-pyrimidine-5-carbaldehyde to give the title compound 4-(4-fluoro-2-methyl-phenyl)-8-isopropyl-2-methyl-sulfanyl-8H-pyrido[2,3-d]pyrimidin-7-one. $^1$H-NMR: δ 1.68 (m, 6H), 2.21 (s, 3H), 2.70 (s, 3H), 5.95 (m, 1H), 6.60 (d, 1H, J=9.6 Hz), 6.95-7.11 (m, 2H), 7.18-7.32 (m, 2H). LC MS (m/e)=344 (MH+).

Example 43

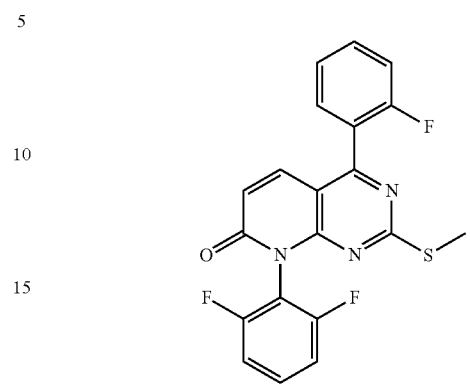

8-(2,6-Difluoro-phenyl)-4-(2-fluoro-phenyl)-2-meth-
ylsulfanyl-8H-pyrido[2,3-d]pyrimidin-7-one Prepared as described above in Example 29 starting from 4-(2,6-difluoro-phenylamino)-6-(2-fluoro-phenyl)-2-meth-ylsulfanyl-pyrimidine-5-carbaldehyde to give the title compound 8-(2,6-Difluoro-phenyl)-4-(2-fluoro-phenyl)-2-meth-ylsulfanyl-8H-pyrido[2,3-d]pyrimidin-7-one. LC MS (m/e)=400 (MH+). Rt=2.42 min.

Example 44

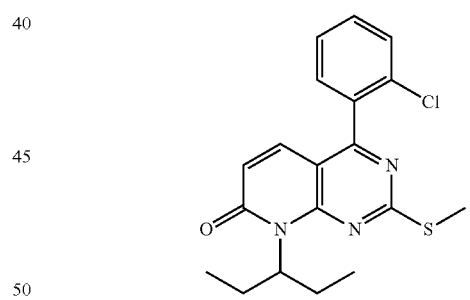

4-(2-Chloro-phenyl)-8-(1-ethyl-propyl)-2-methylsul-
fanyl-8H-pyrido[2,3-d]pyrimidin-7-one Prepared as described above in Example 29 starting from 4-(2-chloro-phenyl)-6-(1-ethyl-propylamino)-2-methylsul-fanyl-pyrimidine-5-carbaldehyde to give the title compound 4-(2-chloro-phenyl)-8-(1-ethyl-propyl)-2-methylsulfanyl-8H-pyrido[2,3-d]pyrimidin-7-one. $^1$H-NMR: δ 0.85 (m, 6H), 2.01 (m, 4H), 2.26-2.44 (m, 2H), 2.63 (s, 3H), 5.39 (m, 0.5H), 5.75 (m, 0.5H), 6.62 (br d, 1H, J=9.6), 7.31-7.60 (m, 5H). LC MS (m/e)=482 (MH+).

Example 45

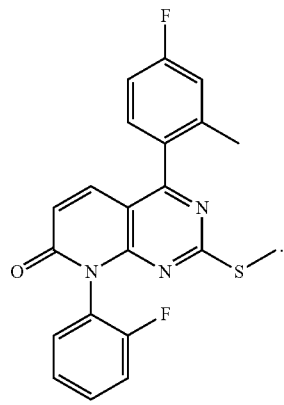

4-(4-Fluoro-2-methyl-phenyl)-8-(2-fluoro-phenyl)-2-methylsulfanyl-8H-pyrido[2,3-d]pyrimidin-7-one Prepared as described above in Example 29 starting from 4-(4-fluoro-2-methyl-phenyl)-6-(2-fluoro-phenylamino)-2-methylsulfanyl-pyrimidine-5-carbaldehyde to give the title compound 4-(4-fluoro-2-methyl-phenyl)-8-(2-fluoro-phenyl)-2-methylsulfanyl-8H-pyrido[2,3-d]pyrimidin-7-one. $^1$H-NMR (CDCl$_3$) δ 2.19 (s, 3H), 2.28 (s, 3H), 6.76 (d, 1H, J=9.6 Hz), 7.05 (m, 2H), 7.24-7.40 (m, 4H), 7.51 (m, 2H); LC MS (m/e)=396 (MH+).

Example 46

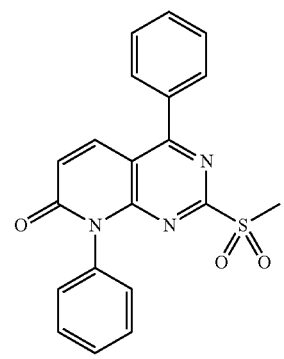

2-Methanesulfonyl-4,8-diphenyl-8H-pyrido[2,3-d]pyrimidin-7-one

To a solution of 2-methylsulfanyl-4,8-diphenyl-8H-pyrido[2,3-d]pyrimidin-7-one (70 mg, 0.2 mmol) in dichloromethane (5 mL) was added 3-chloroperoxybenzoic acid (109 mg, 0.6 mmol, 3 eq) and the reaction mixture was stirred 2 h at 23°, solvent was evaporated and the yellow residue purified by Flash chromatography to afford 2-methanesulfonyl-4,8-diphenyl-8H-pyrido[2,3-d]pyrimidin-7-one (55 mg, 71% yield). $^1$H-NMR (CDCl$_3$) δ 2.96 (s, 3H), 6.89 (d, 1H, J=9.8 Hz), 7.26 (m, 2H), 7.40-7.81 (m, 8H), 8.01 (d, 1H, J=9.8 Hz), LC MS (m/e)=378 (MH+).

Example 47

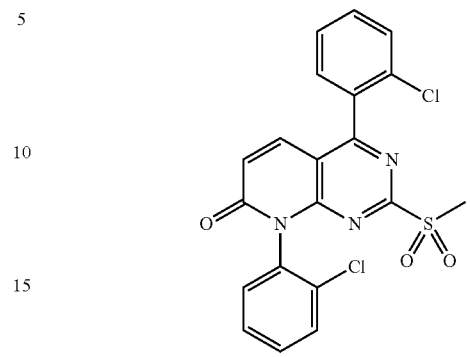

4,8-Bis-(2-chloro-phenyl)-2-methanesulfonyl-8H-pyrido[2,3-d]pyrimidin-7-one

To a solution of 4,8-bis-(2-chloro-phenyl)-2-methylsulfanyl-8H-pyrido[2,3-d]pyrimidin-7-one (414 mg, 1 mmol) in CHCl$_3$ (15 mL) was added 3-chloro-peroxybenzoic acid (549 mg, 3 mmol, 3 eq) and the reaction mixture was stirred 5 h at 23°, then 1 M aq Na$_2$CO$_3$ (10 mL) was added, the layers were separated, and the organic layer was washed with H$_2$O, dried (MgSO$_4$) and the solvent was evaporated to afford 4,8-bis-(2-chloro-phenyl)-2-methanesulfonyl-8H-pyrido[2,3-d]pyrimidin-7-one (550 mg, 89% yield). $^1$H-NMR (CDCl$_3$) δ 3.15 (s, 3H), 6.96 (d, 1H, J=9.8 Hz), 7.26 (m, 2H), 7.51-7.80 (m, 9H). LC MS (m/e)=446 (MH+).

Example 48

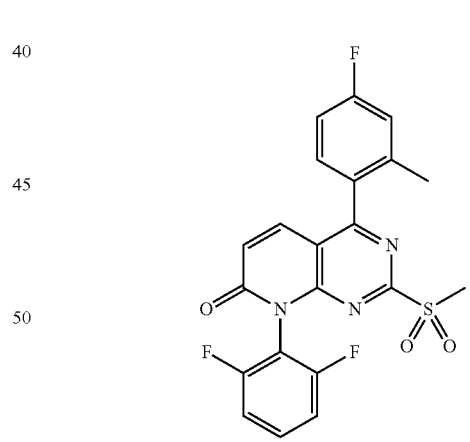

8-(2,6-Difluoro-phenyl)-4-(4-fluoro-2-methyl-phenyl)-2-methanesulfonyl-8H-pyrido[2,3-d]pyrimidin-7-one Prepared as described above in Example 47 starting from 8-(2,6-difluoro-phenyl)-4-(4-fluoro-2-methyl-phenyl)-2-methylsulfanyl-8H-pyrido[2,3-d]pyrimidin-7-one to give the title compound 8-(2,6-difluoro-phenyl)-4-(4-fluoro-2-methyl-phenyl)-2-methane-sulfonyl-8H-pyrido[2,3-d]pyrimidin-7-one. LC MS (m/e)=446 (MH+). Rt=2.13 min.

Example 49

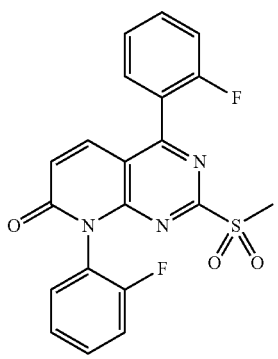

4,8-Bis-(2-fluoro-phenyl)-2-methanesulfonyl-8H-pyrido[2,3-d]pyrimidin-7-one

Prepared as described above in Example 47 starting from 4,8-bis-(2-fluoro-phenyl)-2-methylsulfanyl-8H-pyrido[2,3-d]pyrimidin-7-one to give the title compound 4,8-bis-(2-fluoro-phenyl)-2-methanesulfonyl-8H-pyrido[2,3-d]pyrimidin-7-one. LC MS (m/e)=414 (MH+). Rt=1.96 min.

Example 50

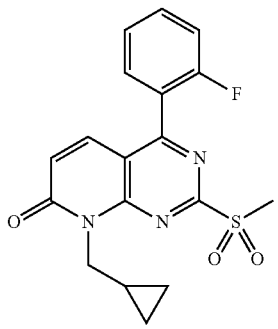

8-Cyclopropylmethyl-4-(2-fluoro-phenyl)-2-methanesulfonyl-8H-pyrido[2,3-d]pyrimidin-7-one Prepared as described above in Example 47 starting from 8-cyclopropylmethyl-4-(2-fluoro-phenyl)-2-methylsulfanyl-8H-pyrido[2,3-d]pyrimidin-7-one to give the title compound 8-cyclopropylmethyl-4-(2-fluoro-phenyl)-2-methanesulfonyl-8H-pyrido[2,3-d]pyrimidin-7-one. LC MS (m/e)=374 (MH+). Rt=1.90 min

Example 51

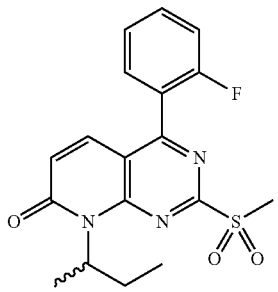

8-sec-Butyl-4-(2-fluoro-phenyl)-2-methanesulfonyl-8H-pyrido[2,3-d]pyrimidin-7-one Prepared as described above in Example 47 starting from 8-sec-butyl-4-(2-fluoro-phenyl)-2-methylsulfanyl-8H-pyrido[2,3-d]pyrimidin-7-one to give the title compound 8-sec-butyl-4-(2-fluoro-phenyl)-2-methanesulfonyl-8H-pyrido[2,3-d]pyrimidin-7-one. LC MS (m/e)=376 (MH+). Rt=1.95 min

Example 52

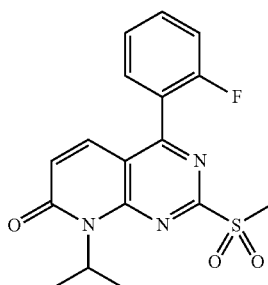

4-(2-Fluoro-phenyl)-8-isopropyl-2-methanesulfonyl-8H-pyrido[2,3-d]pyrimidin-7-one Prepared as described above in Example 47 starting from 4-(2-fluoro-phenyl)-8-isopropyl-2-methylsulfanyl-8H-pyrido[2,3-d]pyrimidin-7-one to give the title compound 4-(2-fluoro-phenyl)-8-isopropyl-2-methanesulfonyl-8H-pyrido[2,3-d]pyrimidin-7-one. LC MS (m/e)=362 (MH+). Rt=1.85 min.

Example 53

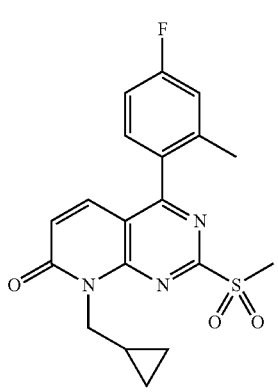

8-Cyclopropylmethyl-4-(4-fluoro-2-methyl-phenyl)-2-methanesulfonyl-8H-pyrido[2,3-d]pyrimidin-7-one Prepared as described above in Example 47 starting from 8-cyclopropylmethyl-4-(4-fluoro-2-methyl-phenyl)-2-methylsulfanyl-8H-pyrido[2,3-d]pyrimidin-7-one to give the title compound 8-cyclopropylmethyl-4-(4-fluoro-2-methyl-phenyl)-2-methanesulfonyl-8H-pyrido[2,3-d]pyrimidin-7-one. LC MS (m/e)=388 (MH+). Rt=2.13 min.

Example 54

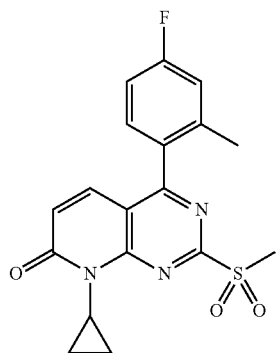

8-Cyclopropyl-4-(4-fluoro-2-methyl-phenyl)-2-methanesulfonyl-8H-pyrido[2,3-d]pyrimidin-7-one Prepared as described above in Example 47 starting from 8-cyclopropyl-4-(4-fluoro-2-methyl-phenyl)-2-methylsulfanyl-8H-pyrido[2,3-d]pyrimidin-7-one to give the title compound 8-cyclopropyl-4-(4-fluoro-2-methyl-phenyl)-2-methanesulfonyl-8H-pyrido[2,3-d]pyrimidin-7-one. LC MS (m/e)=374 (MH+). Rt=1.79 min.

Example 55

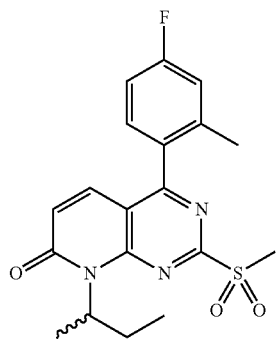

8-sec-Butyl-4-(4-fluoro-2-methyl-phenyl)-2-methanesulfonyl-8H-pyrido[2,3-d]pyrimidin-7-one Prepared as described above in Example 47 starting from 8-sec-butyl-4-(4-fluoro-2-methyl-phenyl)-2-methylsulfanyl-8H-pyrido[2,3-d]pyrimidin-7-one to give the title compound 8-sec-butyl-4-(4-fluoro-2-methyl-phenyl)-2-methanesulfonyl-8H-pyrido[2,3-d]pyrimidin-7-one. LC MS (m/e)=390 (MH+). Rt=2.05 min.

Example 56

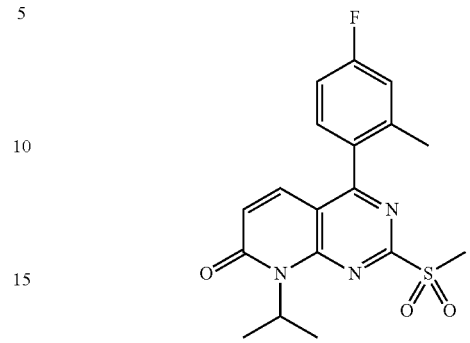

4-(4-Fluoro-2-methyl-phenyl)-8-isopropyl-2-methanesulfonyl-8H-pyrido[2,3-d]pyrimidin-7-one Prepared as described above in Example 47 starting from 4-(4-fluoro-2-methyl-phenyl)-8-isopropyl-2-methylsulfanyl-8H-pyrido[2,3-d]pyrimidin-7-one to give the title compound 4-(4-fluoro-2-methyl-phenyl)-8-isopropyl-2-methanesulfonyl-8H-pyrido[2,3-d]pyrimidin-7-one. LC MS (m/e)=376 (MH+). Rt=2.00 min.

Example 57

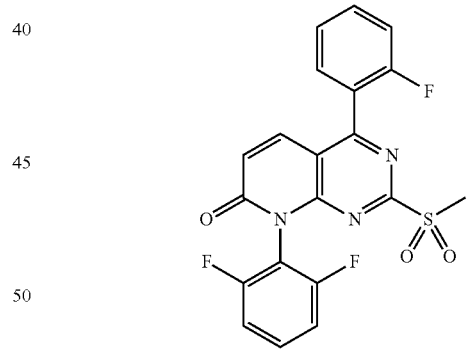

8-(2,6-Difluoro-phenyl)-4-(2-fluoro-phenyl)-2-methanesulfonyl-8H-pyrido[2,3-d]pyrimidin-7-one Prepared as described above in Example 47 starting from 8-(2,6-difluoro-phenyl)-4-(2-fluoro-phenyl)-2-methylsulfanyl-8H-pyrido[2,3-d]pyrimidin-7-one to give the title compound 8-(2,6-difluoro-phenyl)-4-(2-fluoro-phenyl)-2-methanesulfonyl-8H-pyrido[2,3-d]pyrimidin-7-one. LC MS (m/e)=432 (MH+). Rt=2.04 min.

Example 58

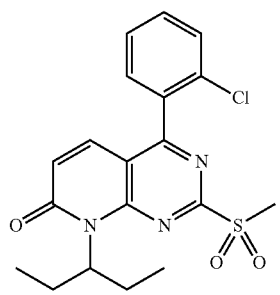

4-(2-Chloro-phenyl)-8-(1-ethyl-propyl)-2-methane-sulfonyl-8H-pyrido[2,3-d]pyrimidin-7-one Prepared as described above in Example 47 starting from 4-(2-chloro-phenyl)-8-(1-ethyl-propyl)-2-methylsulfanyl-8H-pyrido[2,3-d]pyrimidin-7-one to give the title compound 4-(2-chloro-phenyl)-8-(1-ethyl-propyl)-2-methanesulfonyl-8H-pyrido[2,3-d]pyrimidin-7-one. LC MS (m/e)=406 (MH+). Rt=2.15 min.

Example 59

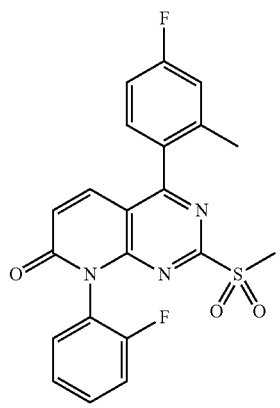

4-(4-Fluoro-2-methyl-phenyl)-8-(2-fluoro-phenyl)-2-methanesulfonyl-8H-pyrido[2,3-d]pyrimidin-7-one Prepared as described above in Example 47 starting from 4-(4-fluoro-2-methyl-phenyl)-8-(2-fluoro-phenyl)-2-methylsulfanyl-8H-pyrido[2,3-d]pyrimidin-7-one to give the title compound 4-(4-fluoro-2-methyl-phenyl)-8-(2-fluoro-phenyl)-2-methanesulfonyl-8H-pyrido[2,3-d]pyrimidin-7-one; LC MS (m/e)=428 (MH+). Rt=2.04 min.

Example 60

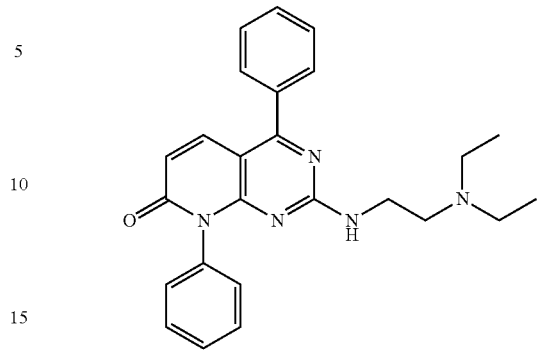

2-(2-Diethylamino-ethylamino)-4,8-diphenyl-8H-pyrido[2,3-d]pyrimidin-7-one

A solution of the product of Example 46 (18.8 mg, 0.05 mmol), NMP (5 mL) and N,N-diethylethylenediamine (28 mg, 0.25 mmol, 5 eq) was heated to 50°. After 1 h, H$_2$O (20 mL) was added and then EtOAc (20 mL). The layers were separated. The organic layer was washed with satd aq NaCl, dried (MgSO$_4$) filtered and the solvent was evaporated in vacuo. The yellow residue was purified by Flash chromatography to afford 2-(2-diethylamino-ethylamino)-4,8-diphenyl-8H-pyrido[2,3-d]pyrimidin-7-one (21 mg, 89% yield). $^1$H-NMR (CDCl$_3$) δ 0.74-0.98 (m, 6H), 2.28-2.56 (m, 8H), 2.98 (br s, 1H), 6.32 (d, 1H, J=9.8 Hz), 7.26 (m, 2H), 7.09-7.88 (m, 11H), LC MS (m/e)=414 (MH+).

Example 61

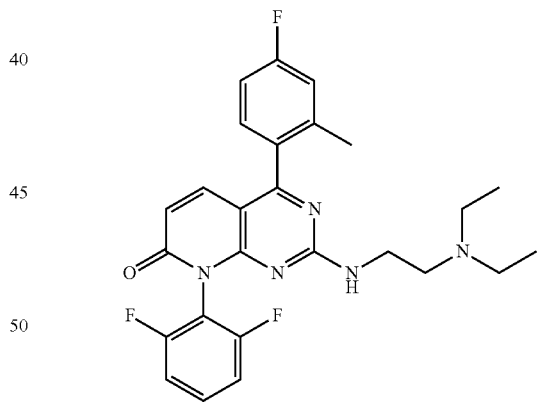

2-(2-Diethylamino-ethylamino)-8-(2,6-difluoro-phenyl)-4-(4-fluoro-2-methyl-phenyl)-8H-pyrido[2,3-d]pyrimidin-7-one The product of Example 48, and N,N-diethylenediamine were reacted by the procedure of Example 60 to afford the title compound 2-(2-diethylamino-ethylamino)-8-(2,6-difluoro-phenyl)-4-(4-fluoro-2-methyl-phenyl)-8H-pyrido[2,3-d]pyrimidin-7-one. $^1$H-NMR (CDCl$_3$) δ 0.96 (m, 6H), 2.24 (s, 3H), 2.50 (m, 6H), 3.14 (m, 2H), 6.02 (br s, 1H), 6.36 (d, 1H, J=9.6 Hz), 7.08 (m, 4H), 7.24 (m, 2H), 7.49 (m, 1H). LC MS (m/e)=482 (MH+).

Example 62

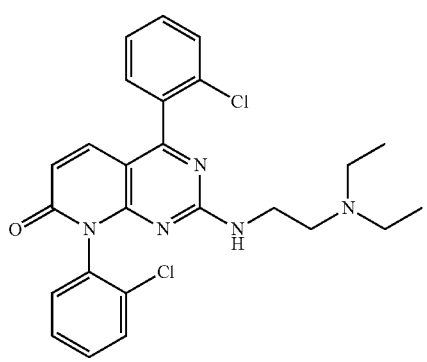

4,8-Bis-(2-chloro-phenyl)-2-(2-diethylamino-ethylamino)-8H-pyrido[2,3-d]pyrimidin-7-one The product of Example 47, and N,N-diethylenediamine were reacted by the procedure of Example 60 to afford the title compound 4,8-bis-(2-chloro-phenyl)-2-(2-diethylamino-ethylamino)-8H-pyrido[2,3-d]pyrimidin-7-one. $^1$H-NMR (CDCl$_3$) δ 0.97 (m, 6H), 2.49 (s, 6H), 3.12 (m, 2H), 6.00 (br s, 1H), 7.18-7.63 (m, 9H). LC MS (m/e)=482 (MH+).

Example 63

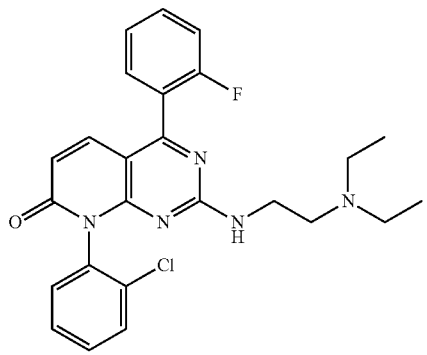

8-(2-Chloro-phenyl)-2-(2-diethylamino-ethylamino)-4-(2-fluoro-phenyl)-8H-pyrido[2,3-d]pyrimidin-7-one a) 8-(2-Chlorophenyl)-4-(2-fluorophenyl)-2-methanesulfonyl-8-H-pyrido[2,3d]-pyrimidine-7-one Prepared as described above in Example 47 starting from the product of Example 33 to afford the title compound.

b) 8-(2-Chloro-phenyl)-2-(2-diethylamino-ethylamino)-4-(2-fluoro-phenyl)-8H-pyrido[2,3-d]pyrimidin-7-one Prepared as described above in Example 60 starting from the product of Example 63(a) to afford the title compound 8-(2-choro-phenyl)-2-(2-diethylamino-ethylamino)-4-(2-fluoro-phenyl)-8H-pyrido[2,3-d]pyrimidin-7-one. $^1$H-NMR (CDCl$_3$) δ 0.99 (m, 6H), 2.49 (s, 6H), 3.16 (m, 2H), 6.03 (br s, 1H), 7.13-7.63 (m, 914). LC MS (m/e)=466 (MH+).

Example 64

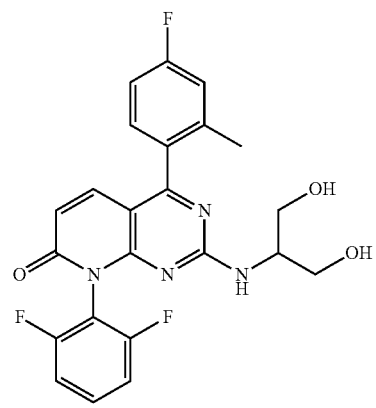

8-(2,6-Difluoro-phenyl)-4-(4-fluoro-2-methyl-phenyl)-2-(2-hydroxy-1-hydroxymethyl-ethylamino)-8H-pyrido[2,3-d]pyrimidin-7-one To a solution of 8-(2,6-difluoro-phenyl)-4-(4-fluoro-2-methyl-phenyl)-2-methanesulfonyl-8H-pyrido[2,3-d]pyrimidin-7-one (800 mg, 1.8 mmol) in 1-methyl-2-pyrrolidinone (8 mL) was added serinol (819 mg, 9 mmol, 5 eq) and the reaction mixture was heated to 50°. After 1 h, H$_2$O (20 mL) was added, followed by Et$_2$O (20 mL) and EtOAc (20 mL). The layers were separated. The organic layer was washed with satd aq NaCl, dried (MgSO$_4$), filtered and the solvent was evaporated. The yellow residue was then purified by Flash chromatography to afford 8-(2,6-difluoro-phenyl)-4-(4-fluoro-2-methyl-phenyl)-2-(2-hydroxy-1-hydroxymethyl-ethylamino)-8H-pyrido[2,3-d]pyrimidin-7-one (750 mg, 92% yield). $^1$H-NMR (CDCl$_3$) δ 2.30 (s, 3H), 3.67 (m, 1H), 3.88 (m, 4H), 6.30 (br s, 1H), 6.41 (d, 1H, J=9.6 Hz), 7.08 (m, 4H), 7.24 (m, 1H), 7.31 (d, 1H, J=9.6 Hz), 7.49 (m, 1H). LC MS (m/e)=457 (MH+).

Example 65

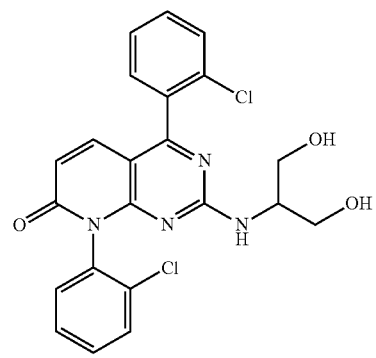

4,8-Bis-(2-chloro-phenyl)-2-(2-hydroxy-1-hydroxymethyl-ethylamino)-8H-pyrido[2,3-d]pyrimidin-7-one The product of Example 47, and serinol were reacted by the procedure of Example 60 to afford the title compound 4,8-bis-(2-chloro-phenyl)-2-(2-hydroxy-1-hydroxymethyl-ethylamino)-8H-pyrido[2,3-d]pyrimidin-7-one. $^1$H-NMR (CDCl$_3$) δ 3.44 (m, 1H), 3.68 (m, 4H), 6.30 (br s, 1H), 6.48 (d, 1H, J=9.7 Hz), 7.24-7.65 (m, 9H). LC MS (m/e)=457 (MH+).

Example 66

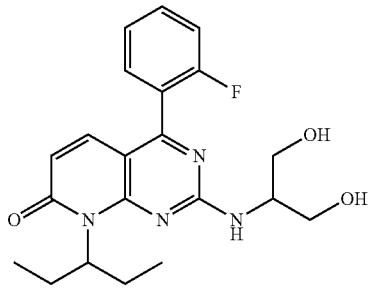

4-(2-Fluoro-phenyl)-8-(1-ethyl-propyl)-2-(2-hydroxy-1-hydroxymethyl-ethylamino)-8H-pyrido[2,3-d]pyrimidin-7-one 4-(2-Fluorophenyl)-8-(1-ethylpropyl)-2-methanesulfonyl-8H-pyrido[2,3-d]pyrimidin-7-one, and serinol were reacted by the procedure of Example 60 to afford the title compound 4-(2-fluoro-phenyl)-8-(1-ethyl-propyl)-2-(2-hydroxy-1-hydroxymethyl-ethylamino)-8H-pyrido[2,3-d]pyrimidin-7-one. $^1$H-NMR: δ 0.82 (m, 6H), 1.32 (m, 4H), 1.90 (m, 2H), 2.32 (m, 2H), 3.71 (m, 2H), 4.24 (m, 1H), 5.38 (m, 0.5H), 5.69 (m, 0.5H), 5.71 (br s, 1H), 6.30 (br d, 1H, J=9.6), 7.13 (d, 1H, J=9.6 Hz), 7.30-7.55 (m, 4H). LC MS (m/e)=401 (MH+)

Example 67

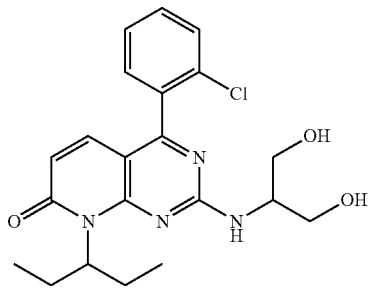

4-(2-Chloro-phenyl)-8-(1-ethyl-propyl)-2-(2-hydroxy-1-hydroxymethyl-ethylamino)-8H-pyrido[2,3-d]pyrimidin-7-one The product of Example 58, and serinol were reacted by the procedure of Example 60 to afford the title compound 4-(2-chloro-phenyl)-8-(1-ethyl-propyl)-2-(2-hydroxy-1-hydroxymethyl-ethylamino)-8H-pyrido[2,3-d]pyrimidin-7-one. $^1$H-NMR: δ 0.84 (m, 6H), 1.91 (m, 2H), 2.32 (m, 2H), 3.02 (m, 2H), 3.95 (m, 4H), 4.14 (m, 1H), 5.30 (m, 0.5H), 5.52 (m, 0.5H), 6.28 (br d, 1H, J=9.6), 6.40 (br s, 1H), 7.12 (d, 1H, J=9.6 Hz), 7.30-7.58 (m, 4H). LC MS (m/e)=417 (MH+).

Example 68

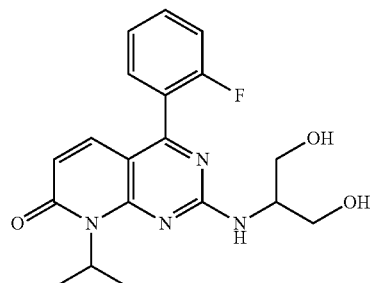

4-(2-Fluoro-phenyl)-2-(2-hydroxy-1-hydroxymethyl-ethylamino)-8-isopropyl-8H-pyrido[2,3-d]pyrimidin-7-one The product of Example 52, and serinol were reacted by the procedure of Example 60 to afford the title compound 4-(2-fluoro-phenyl)-2-(2-hydroxy-1-hydroxymethyl-ethylamino)-8-isopropyl-8H-pyrido[2,3-d]pyrimidin-7-one. $^1$H-NMR: δ 1.54 (m, 6H), 3.80 (m, 4H), 4.11 (m, 1H), 5.75 (m, 1H), 6.19 (d, 1H, J=9.8), 6.38 (br s, 1H), 7.01-7.21 (m, 2H), 7.30-7.49 (m, 3H). LC MS (m/e)=373 (MH+).

Example 69

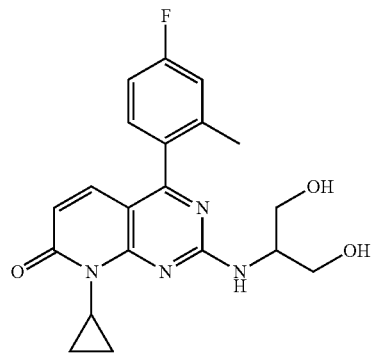

8-Cyclopropyl-4-(4-fluoro-2-methyl-phenyl)-2-(2-hydroxy-1-hydroxymethyl-ethylamino)-8H-pyrido[2,3-d]pyrimidin-7-one The product of Example 54, and serinol were reacted by the procedure of Example 60 to afford the title compound 8-cyclopropyl-4-(4-fluoro-2-methyl-phenyl)-2-(2-hydroxy-1-hydroxymethyl-ethylamino)-8H-pyrido[2,3-d]pyrimidin-7-one. $^1$H-NMR: δ 0.85 (m, 2H), 1.28 (m, 2H), 2.11 (m, 3H), 2.79 (m, 1H), 3.89 (m, 4H), 4.16 (m, 1H), 6.18 (d, 1H, J=9.8), 6.31 (br s, 1H), 6.85-7.14 (m, 4H). LC MS (m/e)=385 (MH+).

Example 70

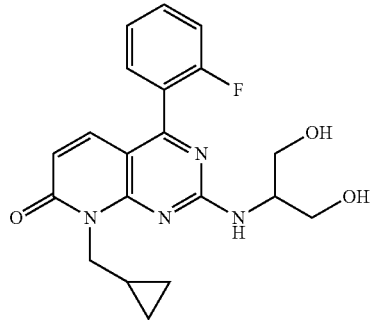

8-Cyclopropylmethyl-4-(2-fluoro-phenyl)-2-(2-hydroxy-1-hydroxymethyl-ethylamino)-8H-pyrido[2,3-d]pyrimidin-7-one The product of Example 50, and serinol were reacted by the procedure of Example 60 to afford the title compound 8-cyclopropylmethyl-4-(2-fluoro-phenyl)-2-(2-hydroxy-1-hydroxymethyl-ethylamino)-8H-pyrido[2,3-d]pyrimidin-7-one. $^1$H-NMR: δ 0.40 (m, 4H), 1.25 (m, 1H), 3.89 (m, 4H), 4.13 (m, 3H), 5.75 (m, 1H), 6.30 (d, 1H, J=9.8 Hz), 6.59 (br s, 1H), 7.08-7.48 (m, 5H). LC MS (m/e)=385 (MH+).

Example 71

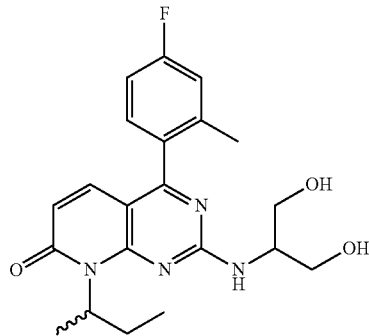

8-sec-Butyl-4-(4-fluoro-2-methyl-phenyl)-2-(2-hydroxy-1-hydroxymethyl-ethylamino)-8H-pyrido[2,3-d]pyrimidin-7-one The product of Example 55, and serinol were reacted by the procedure of Example 60 to afford the title compound 8-sec-butyl-4-(4-fluoro-2-methyl-phenyl)-2-(2-hydroxy-1-hydroxymethyl ethylamino)-8H-pyrido[2,3-d]pyrimidin-7-one. $^1$H-NMR: δ 0.80 (m, 3H), 1.37 (m, 3H), 2.21 (m, 3H), 2.73 (m, 2H), 3.96 (m, 4H), 4.20 (m, 1H), 5.52 (m, 1H), 6.29 (m, 1H), 6.59 (br s, 1H), 6.91-7.40 (m, 4H). LC MS (m/e)= 401 (MH+).

Example 72

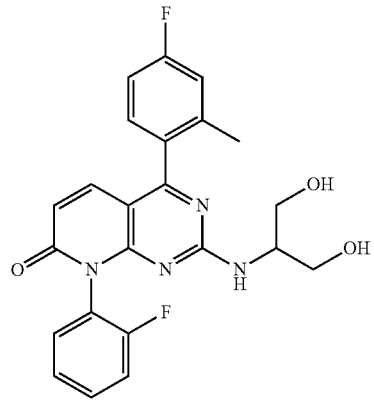

4-(4-Fluoro-2-methyl-phenyl)-8-(2-fluoro-phenyl)-2-(2-hydroxy-1-hydroxymethyl-ethylamino)-8H-pyrido[2,3-d]pyrimidin-7-one The product of Example 59, and serinol were reacted by the procedure of Example 60 to afford the title compound 4-(4-fluoro-2-methyl-phenyl)-8-(2-fluoro-phenyl)-2-(2-hydroxy-1-hydroxymethyl-ethylamino)-8H-pyrido[2,3-d]pyrimidin-7-one. $^1$H-NMR: δ 2.24 (s, 3H), 2.68 (br s, 2H), 3.42 (m, 1H), 3.61 (m, 4H), 6.30 (br s, 1H), 6.38 (d, 1H, J=9.7 Hz), 7.02 (m, 2H), 7.27 (m, 5H), 7.46 (m, 1H). LC MS (m/e)=439 (MH+).

Example 73

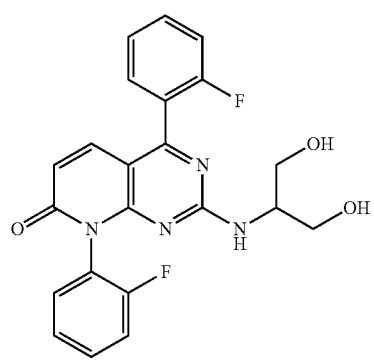

4,8-Bis-(2-fluoro-phenyl)-2-(2-hydroxy-1-hydroxymethyl-ethylamino)-8H-pyrido[2,3-d]pyrimidin-7-one The product of Example 49, and serinol were reacted by the procedure of Example 60 to afford the title compound 4,8-bis-(2-fluoro-phenyl)-2-(2-hydroxy-1-hydroxymethyl-ethylamino)-8H-pyrido[2,3-d]pyrimidin-7-one. $^1$H-NMR: δ 2.91 (br s, 2H), 3.39 (m, 1H), 3.55 (m, 4H), 6.05 (br s, 1H), 6.33 (d, 1H, J=9.7 Hz), 6.21 (m, 5H), 7.39 (m, 4H). LC MS (m/e)=425 (MH+).

Example 74

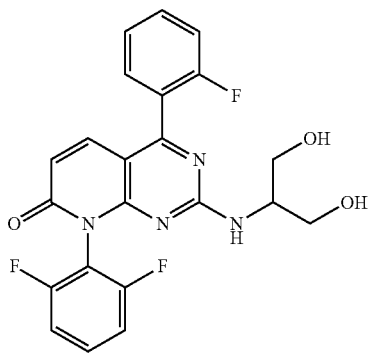

8-(2,6-Difluoro-phenyl)-4-(2-fluoro-phenyl)-2-(2-hydroxy-1-hydroxymethyl-ethylamino)-8H-pyrido[2,3-d]pyrimidin-7-one The product of Example 57, and serinol were reacted by the procedure of Example 60 to afford the title compound, 8-(2,6-difluoro-phenyl)-4-(2-fluoro-phenyl)-2-(2-hydroxy-1-hydroxymethyl-ethylamino)-8H-pyrido[2,3-d]pyrimidin-7-one. $^1$H-NMR: δ 2.52 (br s, 2H), 3.45 (m, 1H), 3.60 (m, 4H), 6.28 (br s, 1H), 6.34 (d, 1H, J=9.7 Hz), 6.98 (m, 2H), 7.19 (m, 3H), 7.42 (m, 3H). LC MS (m/e)=443 (MH+).

Example 75

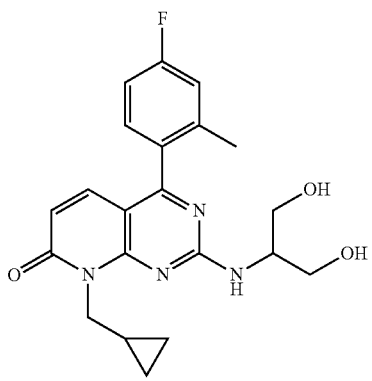

8-Cyclopropylmethyl-4-(4-fluoro-2-methyl-phenyl)-2-(2-hydroxy-1-hydroxymethyl-ethylamino)-8H-pyrido[2,3-d]pyrimidin-7-one The product of Example 53, and serinol were reacted by the procedure of Example 60 to afford the title compound 8-cyclopropylmethyl-4-(2-fluoro-phenyl)-2-(2-hydroxy-1-hydroxymethyl-ethylamino)-8H-pyrido[2,3-d]pyrimidin-7-one. $^1$H-NMR: δ 0.46 (m, 4H), 1.32 (m, 1H), 2.18 (s, 3H), 3.31 (br s, 2H), 3.89 (m, 4H), 4.15 (m, 3H), 6.30 (d, 1H, J=9.8 Hz), 6.59 (br s, 1H), 6.97 (m, 2H), 7.19 (m, 2H). LC MS (m/e)=399 (MH+).

Example 76

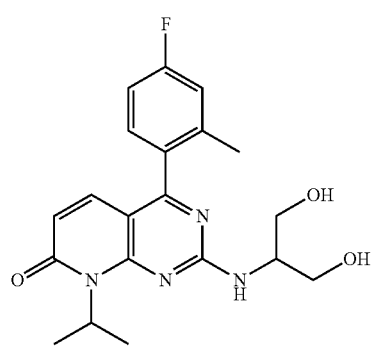

4-(4-Fluoro-2-methyl-phenyl)-2-(2-hydroxy-1-hydroxymethyl-ethylamino)-8-isopropyl-8H-pyrido[2,3-d]pyrimidin-7-one The product of Example 56, and serinol were reacted by the procedure of Example 60 to afford the title compound 4-(4-fluoro-2-methyl-phenyl)-2-(2-hydroxy-1-hydroxymethyl-ethylamino)-8-isopropyl-8H-pyrido[2,3-d]pyrimidin-7-one $^1$H-NMR: δ 1.61 (m, 6H), 2.15 (m, 3H), 3.45 (br s, 2H), 3.85 (m, 5H), 5.74 (m, 1H), 6.21 (d, 1H, J=9.8Hz), 6.36 (br s, 1H), 6.91-7.20 (m, 4H). LC MS (m/e)=387 (MH+).

Example 77

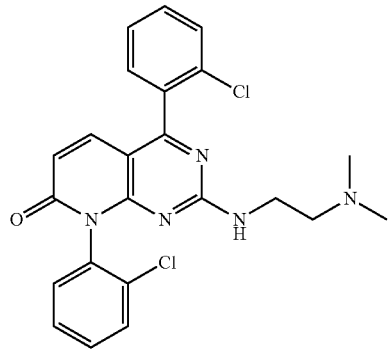

4,8-Bis-(2-chloro-phenyl)-2-(2-dimethylamino-ethylamino)-8H-pyrido[2,3-d]pyrimidin-7-one The product of Example 47, and N,N-dimethylethylenediamine were reacted by the procedure of Example 60 to afford the title compound 4,8-bis-(2-chloro-phenyl)-2-(2-dimethylamino-ethylamino)-8H-pyrido[2,3-d]pyrimidin-7-one (396 mg, 84% yield). $^1$H-NMR (CDCl$_3$) δ 2.02-2.34 (m, 8H), 3.05 (m, 2H), 6.02 (br s, 1H), 6.39 (d, 1H, J=9.8 Hz), 7.24-7.62 (m, 9H). LC MS (m/e)=455 (MH+).

Example 78

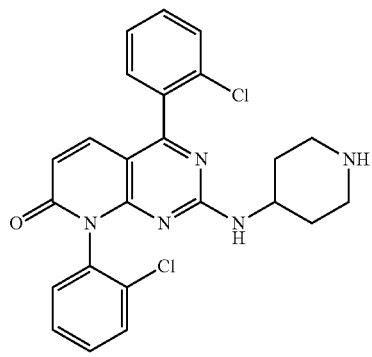

4,8-Bis-(2-chloro-phenyl)-2-(piperidin-4-ylamino)-8H-pyrido pyrimidin-7-one

The product of Example 47, and piperidin-4-ylamine were reacted by the procedure of Example 60 to afford the title compound 4,8-bis-(2-chloro-phenyl)-2-(piperidin-4-ylamino)-8H-pyrido[2,3-d]pyrimidin-7-one. $^1$H-NMR (CDCl$_3$) δ 1.21 (m, 2H), 1.84 (m, 2H), 2.38 (m, 2H), 3.01 (m, 2H), 3.30 (m, 1H), 5.36 (s, 1H), 6.40 (d, 1H, J=9.8 Hz), 7.20-7.62 (m, 9H). LC MS (m/e)=466 (MH+).

Example 79

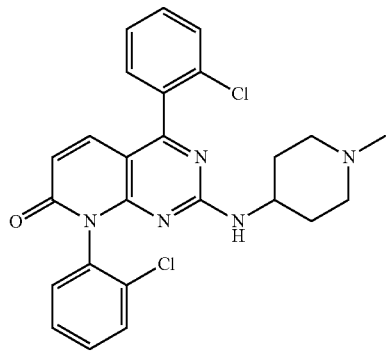

4,8-Bis-(2-chloro-phenyl)-2-(1-methyl-piperidin-4-ylamino)-8H-pyrido[2,3-d]pyrimidin-7-one The product of Example 47, and 1-methylpiperidin-4-ylamine were reacted by the procedure of Example 60 to afford the title compound 4,8-bis-(2-chloro-phenyl)-2-(1-methyl-piperidin-4-ylamino)-8H-pyrido[2,3-d]pyrimidin-7-one. $^1$H-NMR (CDCl$_3$) δ 1.42 (m, 2H), 1.79 (m, 4H), 2.25 (s, 3H), 2.75 (m, 2H), 3.15 (m, 1H), 5.33 (s, 1H), 6.39 (d, 1H, J=9.8 Hz), 7.24-7.59 (m, 9H). LC MS (m/e)=480 (MH+).

Example 80

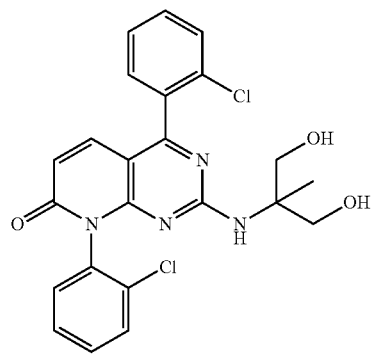

4,8-Bis-(2-chloro-phenyl)-2-(2-hydroxy-1-hydroxymethyl-1-methyl-ethylamino)-8H-pyrido[2,3-d]pyrimidin-7-one The product of Example 47, and 2-amino-2-methylpropane 1,3-diol were reacted by the procedure of Example 60 to afford the title compound 4,8-bis-(2-chloro-phenyl)-2-(2-hydroxy-1-hydroxymethyl-1-methyl-ethylamino)-8H-pyrido[2,3-d]pyrimidin-7-one. $^1$H-NMR (CDCl$_3$) δ 1.01 (s, 3H), 3.43 (m, 2H), 3.62 (m, 2H), 6.03 (br s, 1H), 6.41 (d, 1H, J=9.6 Hz), 7.27-7.65 (m, 9H). LC MS (m/e)=471 (MH+).

Example 81

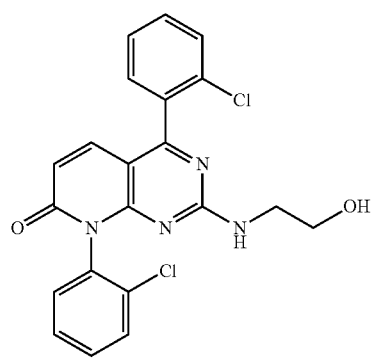

4,8-Bis-(2-chloro-phenyl)-2-(2-hydroxy-ethylamino)-8H-pyrido[2,3-d]pyrimidin-7-one The product of Example 47, and 2-aminoethanol were reacted by the procedure of Example 60 to afford the title compound 4,8-bis-(2-chloro-phenyl)-2-(2-hydroxy-ethylamino)-8H-pyrido[2,3-d]pyrimidin-7-one. $^1$H-NMR (CDCl$_3$) δ 3.17 (m, 2H), 3.48 (m, 2H), 6.08 (br s, 1H), 6.45 (d, 1H, J=9.6 Hz), 7.26-7.67 (m, 9H). LC MS (m/e)=427 (MH+).

Example 82

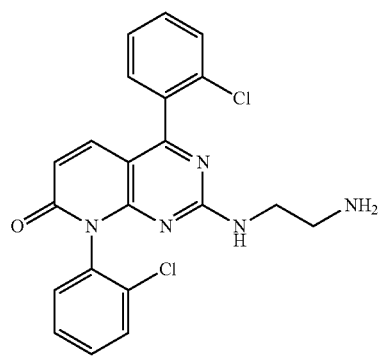

2-(2-Amino-ethylamino)-4,8-bis-(2-chloro-phenyl)-8H-pyrido[2,3-d]pyrimidin-7-one The product of Example 47, and 1,2-diaminoethane were reacted by the procedure of Example 60 to afford the title compound 2-(2-amino-ethylamino)-4,8-bis-(2-chloro-phenyl)-8H-pyrido[2,3-d]pyrimidin-7-one. $^1$H-NMR (CDCl$_3$) δ 2.59 (m, 2H), 3.11 (m, 2H), 5.91 (br s, 1H), 6.40 (d, 1H, J=9.6 Hz), 7.25-7.61 (m, 9H). LC MS (m/e)=426 (MH+).

Example 83

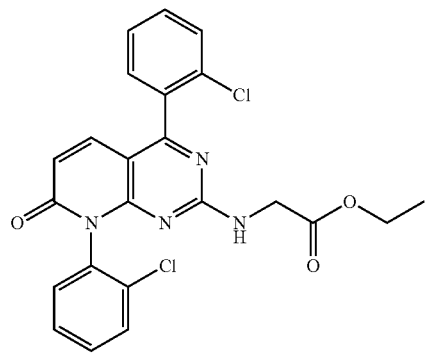

[4,8-Bis-(2-chloro-phenyl)-7-oxo-7,8-dihydro-pyrido[2,3-d]pyrimidin-2-ylamino]-acetic acid ethyl ester The product of Example 47, and ethyl glycinate were reacted by the procedure of Example 60 to afford the title compound [4,8-bis-(2-chloro-phenyl)-7-oxo-7,8-dihydro-pyrido[2,3-d]pyrimidin-2-ylamino]-acetic acid ethyl ester. $^1$H-NMR (CDCl$_3$) δ 1.21 (m, 3H), 3.59 (m, 2H), 4.12 (m, 2H), 5.91 (br s, 1H), 6.41 (m, 2H), 7.25-7.62 (m, 9H). LC MS (m/e)=469 (MH+). Rt=2.12 min

Example 84

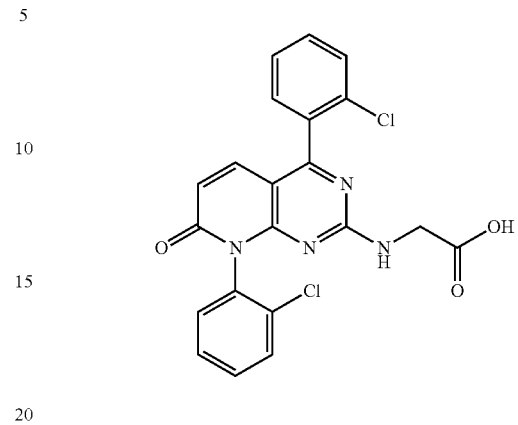

[4,8-Bis-(2-chloro-phenyl)-7-oxo-7,8-dihydro-pyrido[2,3-d]pyrimidin-2-ylamino]-acetic acid To a solution of the product of Example 83 (20 mg, 0.43 mmol) in THF (2 mL) was added LiOH (40 mg, 1.67 mmol) dissolved in H$_2$O (1 mL). The reaction mixture was stirred 1 h at 23° and then neutralized with 1 M HCl, extracted with EtOAc (5 mL) and the layers were separated. The organic layer was washed with H$_2$O, satd. aq NaCl, and dried (MgSO$_4$). The solution was filtered and evaporated to give the title compound [4,8-bis-(2-chloro-phenyl)-7-oxo-7,8-dihydro-pyrido[2,3-d]pyrimidin-2-ylamino]-acetic acid. LC MS (m/e)=441 (MH+). Rt=1.85 min

Example 85

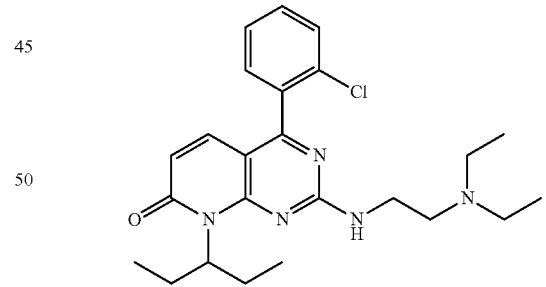

4-(2-Chloro-phenyl)-2-(2-diethylamino-ethylamino)-8-(1-ethyl-propyl)-8H-pyrido[2,3-d]pyrimidin-7-one The product of Example 44, and N,N-diethylethylenediamine were reacted by the procedure of Example 60 to afford 4-(2-chloro-phenyl)-2-(2-diethylamino-ethylamino)-8-(1-ethyl-propyl)-8H-pyrido[2,3-d]pyrimidin-7-one (371 mg, 80% yield. LC MS (m/e)=442 (MH+). Rt=1.77 min

Example 86

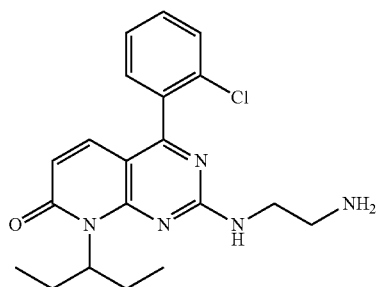

2-(2-Amino-ethylamino)-4-(2-chloro-phenyl)-8-(1-ethyl-propyl)-8H-pyrido[2,3-d]pyrimidin-7-one The product of Example 44, and 1,2-diaminoethane were reacted by the procedure of Example 60 to afford 2-(2-amino-ethylamino)-4-(2-chloro-phenyl)-8-(1-ethyl-propyl)-8H-pyrido[2,3-d]pyrimidin-7-one. LC MS (ride)=386 (MH-F). Rt=1.54 min

Example 87

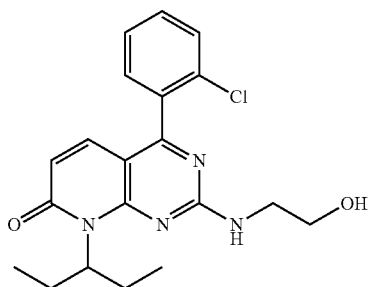

4-(2-Chloro-phenyl)-8-(1-ethyl-propyl)-2-(2-hydroxy-ethylamino)-8H-pyrido[2,3-d]pyrimidin-7-one The product of Example 44, and 2-aminoethanol were reacted by the procedure of Example 60 to afford the title compound 4-(2-chloro-phenyl)-8-(1-ethyl-propyl)-2-(2-hydroxy-ethylamino)-8H-pyrido[2,3-d]pyrimidin-7-one. LC MS (m/e)=387 (MH+). Rt =1.94 min

Example 88

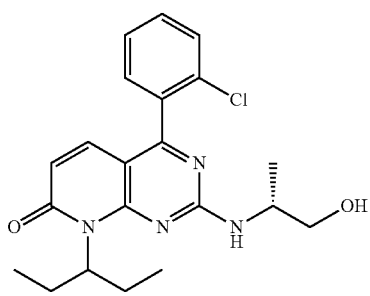

4-(2-Chloro-phenyl)-8-(1-ethyl-propyl)-2-((R)-2-hydroxy-1-methyl-ethylamino)-8H-pyrido[2,3-d]pyrimidin-7-one The product of Example 44, and (R)-2-aminopropan-1-ol were reacted by the procedure of Example 60 to afford the title compound 4-(2-chloro-phenyl)-8-(1-ethyl-propyl)-2-((R)-2-hydroxy-1-methyl-ethylamino)-8H-pyrido[2,3-d]pyrimidin-7-one. $^1$H-NMR: δ 0.81 (m, 6H), 1.30 (m, 2H), 1.96 (m, 2H), 2.36 (m, 2H), 3.71 (m, 2H), 4.25(m, 1H), 5.31 (m, 0.5H), 5.56 (m, 0.5H), 5.71 (br s, 1H), 6.26 (br d, 1H, J=9.6), 7.12 (d, 1H, J=9.6 Hz), 7.30-7.54 (m, 4H). LC MS (m/e)=401 (MH+). Rt=2.07 min

Example 89

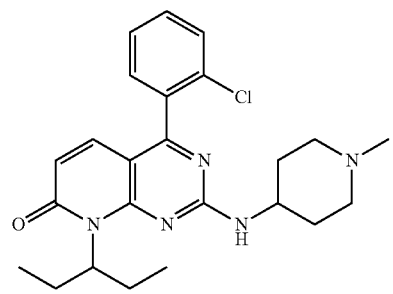

4-(2-Chloro-phenyl)-8-(1-ethyl-propyl)-2-(1-methyl-piperidin-4-ylamino)-8H-pyrido[2,3-d]pyrimidin-7-one The product of Example 44, and 1-methylpiperidin-4-ylamine were reacted by the procedure of Example 60 to afford the title compound 4-(2-chloro-phenyl)-8-(1-ethyl-propyl)-2-(1-methyl-piperidin-4-ylamino)-8H-pyrido[2,3-d]pyrimidin-7-one. LC MS (m/e)=440 (MH+). Rt=1.67 min

Example 90

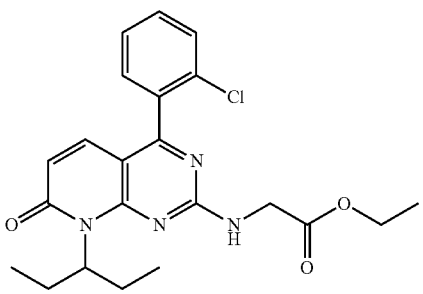

4-(2-Chloro-phenyl)-8-(1-ethyl-propyl)-7-oxo-7,8-dihydro-pyrido[2,3-d]pyrimidin-2-ylamino]-acetic acid ethyl ester The product of Example 44, and ethyl glycinate were reacted by the procedure of Example 60 to afford the title compound [4-(2-chloro-phenyl)-8-(1-ethyl-propyl)-7-oxo-7,8-dihydro-pyrido[2,3-d]pyrimidin-2-ylamino]-acetic acid ethyl ester. LC MS (m/e)=429 (MH+). Rt=2.49 min

Example 91

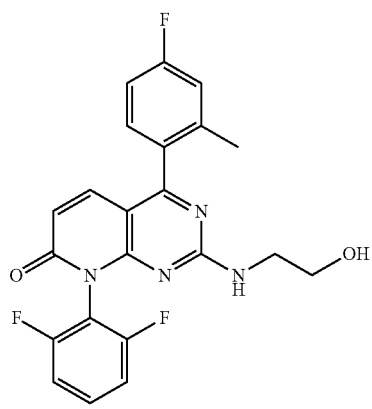

8-(2,6-Difluoro-phenyl)-4-(4-fluoro-2-methyl-phenyl)-2-(2-hydroxy-ethylamino)-8H-pyrido[2,3-d]pyrimidin-7-one The product of Example 48, and 2-aminoethanol were reacted by the procedure of Example 60 to afford the title compound 8-(2,6-difluoro-phenyl)-4-(4-fluoro-2-methyl-phenyl)-2-(2-hydroxy-ethylamino)-8H-pyrido[2,3-d]pyrimidin-7-one. $^1$H-NMR (CDCl$_3$) δ 2.26 (s, 3H), 3.18 (m, 2H), 3.53 (m, 2H), 3.70 (br s, 1H), 6.21 (br s, 1H), 6.40 (d, 1H, J=9.7 Hz), 7.09 (m, 4H), 7.21-7.65 (m, 3H). LC MS (m/e)= 427 (MH+). Rt=1.96 min

Example 92

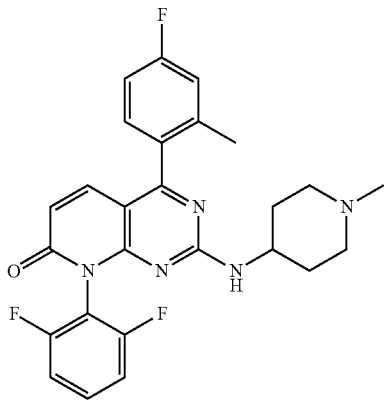

8-(2,6-Difluoro-phenyl)-4-(4-fluoro-2-methyl-phenyl)-2-(1-methyl-piperidin-4-ylamino)-8H-pyrido[2,3-d]pyrimidin-7-one The product of Example 48, and 1-methylpiperidin-4-ylamine were reacted by the procedure of Example 60 to afford the title compound 8-(2,6-difluoro-phenyl)-4-(4-fluoro-2-methyl-phenyl)-2-(1-methyl-piperidin-4-ylamino)-8H-pyrido[2,3-d]pyrimidin-7-one. $^1$H-NMR (CDCl$_3$) δ1.45 (m, 2H), 1.85 (m, 4H), 2.40 (s, 3H), 2.72 (m, 2H), 3.30 (m, 1H), 5.41 (m, 1H), 6.38 (d, 1H, J=9.7 Hz), 7.05 (m, 4H), 7.29 (m, 3H). LC MS (m/e)=480 (MH+). Rt=1.67 min

Example 93

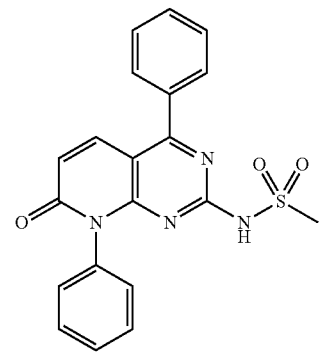

N-(7-Oxo-4,8-diphenyl-7,8-dihydro-pyrido[2,3-d]pyrimidin-2-yl)-methanesulfonamide To a solution of methylsulfonamide (200 mg, 2 mmol, 4 eq) in DMF (2 mL) was added NaH (80 mg, 2 mmol, 60% dispersion in mineral oil, 4 eq) and the reaction mixture was stirred for 30 min at 23°. To this solution was added a solution of 2-methanesulfonyl-4,8-diphenyl-8H-pyrido[2,3-d]pyrimidin-7-one (190 mg, 0.5 mmol) in DMF (1 mL) and the mixture was heated to 50°. After 1 h, H$_2$O (10 mL) was added and then Et$_2$O (10 mL), the layers were separated, and the organic layer was washed with satd aq NaCl, dried (MgSO$_4$), filtered and the solvent was evaporated. The yellow residue was then purified by Flash chromatography to afford N-(7-oxo-4,8-diphenyl-7,8-dihydro-pyrido[2,3-d]pyrimidin-2-yl)-methanesulfonamide (101 mg, 51% yield). $^1$H-NMR (CDCl$_3$) δ 2.82 (s, 3H), 6.69 (d, 1H, J=9.8 Hz), 7.31 (m, 2H), 7.59 (m, 8H), 7.91 (d, 1H, J=9.8 Hz), LC MS (m/e)=393 (MH+).

Example 94

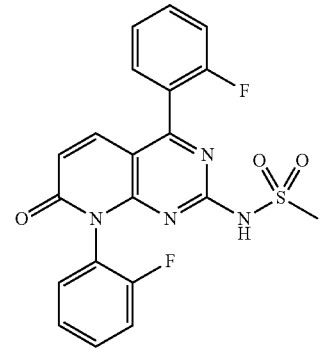

N-[4,8-Bis-(2-fluoro-phenyl)-7-oxo-7,8-dihydro-pyrido[2,3-d]pyrimidin-2-yl]-methanesulfonamide The product of Example 49, was reacted by the procedure of Example 93 to afford the title compound N-[4,8-bis-(2- fluoro-phenyl)-7-oxo-7,8-dihydro-pyrido[2,3-d]pyrimidin-2-yl]-methanesulfonamide. $^1$H-NMR (CDCl$_3$) δ 2.81 (s, 3H), 6.66 (d, 1H, J=9.6 Hz), 7.24 (m, 4H), 7.48 (m, 4H), 7.87 (d, 1H, J=9.8 Hz), LC MS (m/e)=429 (MH+). Rt=1.84 min Example 95

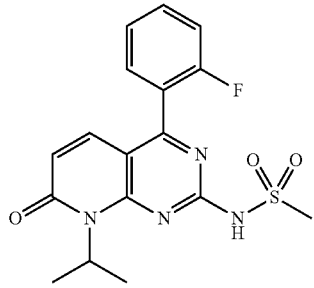

N-[4-(2-Fluoro-phenyl)-8-isopropyl-7-oxo-7,8-dihydro-pyrido[2,3-d]pyrimidin-2-yl]-methanesulfonamide The product of Example 52, was reacted by the procedure of Example 93 to afford the title compound N-[4-(2-fluoro-phenyl)-8-isopropyl-7-oxo-7,8-dihydro-pyrido[2,3-d]pyrimidin-2-yl]-methanesulfonamide. $^1$H-NMR (CDCl$_3$) δ1.68 (m, 6H), 3.52 (s, 3H), 5.82 (m, 1H), 6.68 (d, 1H, J=9.6 Hz), 7.21-7.61 (m, 5H). LC MS (m/e)=377 (MH+). Rt=1.83 min Example 96

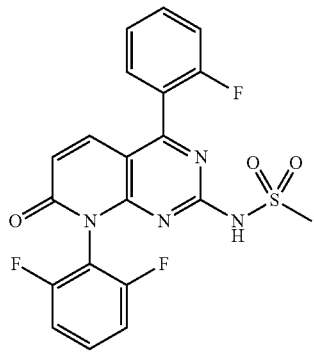

N-[8-(2,6-Difluoro-phenyl)-4-(2-fluoro-phenyl)-7-oxo-7,8-dihydro-pyrido[2,3-d]pyrimidin-2-yl]-methanesulfonamide The product of Example 56, was reacted by the procedure of Example 93 to afford the title compound N-[8-(2,6-difluoro-phenyl)-4-(2-fluoro-phenyl)-7-oxo-7,8-dihydro-pyrido[2,3-d]pyrimidin-2-yl]-methanesulfonamide. $^1$H-NMR (CDCl$_3$) δ 3.08 (s, 3H), 6.72 (d, 1H, J=9.6 Hz), 7.20 (m, 2H), 7.39 (m, 3H), 7.74 (m, 3H), LC MS (m/e)=447 (MH+). Rt=1.84 min Example 97

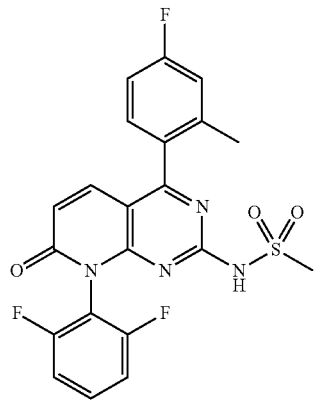

N-[8-(2,6-Difluoro-phenyl)-4-(4-fluoro-2-methyl-phenyl)-7-oxo-7,8-dihydro-pyrido[2,3-d]pyrimidin-2-yl]-methanesulfonamide The product of Example 48, was reacted by the procedure of Example 93 to afford the title compound N-[8-(2,6-difluoro-phenyl)-4-(4-fluoro-2-methyl-phenyl)-7-oxo-7,8-dihydro-pyrido[2,3-d]pyrimidin-2-yl]-methanesulfonamide. $^1$H-NMR (CDCl$_3$) δ 2.29 (s, 3H), 3.04 (s, 3H), 6.69 (d, 1H, J=9.6 Hz), 7.16 (m, 4H), 7.59 (m, 3H). LC MS (m/e)=461 (MH+). Rt=1.90 min Example 98

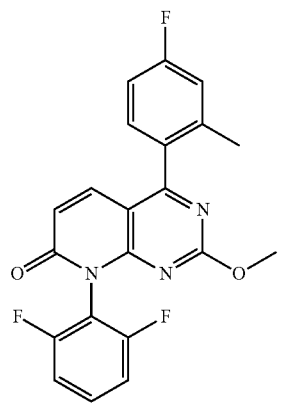

8-(2,6-Difluoro-phenyl)-4-(4-fluoro-2-methyl-phenyl)-2-methoxy-8H-pyrido[2,3-d]pyrimidin-7-one To a solution of the product of Example 30 (90 mg, 0.2 mmol) in methanol (5 mL) was added sodium methoxide (1 mL of 25% w/w solution in methanol, excess). The reaction mixture turned yellow and was heated under reflux for 2 h evaporated and H$_2$O (5 mL), then EtOAc (20 mL), was added. The layers were separated. The organic layer was washed with satd aq NaCl, dried (MgSO$_4$), filtered and evaporated. The yellow residue was then purified by Flash chromatography to afford 71 mg (83% yield) of 8-(2,6-difluoro-phenyl)-

4-(4-fluoro-2-methyl-phenyl)-2-methoxy-8H-pyrido[2,3-d]pyrimidin-7-one. ¹H-NMR (CDCl₃) δ 2.30 (s, 3H), 3.82 (s, 3H), 6.61 (d, 1H, J=9.7 Hz), 7.01-7.18 (m, 4H), 7.25 (m, 1H), 7.52 (m, 2H); LC MS (m/e)=398 (MH+).

Example 99

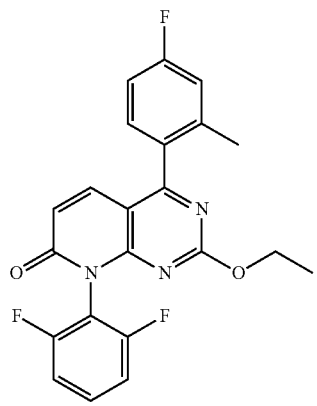

8-(2,6-Difluoro-phenyl)-2-ethoxy-4-(4-fluoro-2-methyl-phenyl)-8H-pyrido[2,3-d]pyrimidin-7-one Prepared by the procedure of Example 98 using sodium ethoxide to afford the title compound 8-(2,6-difluoro-phenyl)-2-ethoxy-4-(4-fluoro-2-methyl-phenyl)-8H-pyrido[2,3-d]pyrimidin-7-one. ¹H-NMR (CDCl₃) δ 1.26 (m, 3H), 2.30 (s, 3H), 4.22 (m, 2H), 6.60 (d, 1H, J=9.6 Hz), 6.98-7.20 (m, 4H), 7.25 (m, 1H), 7.51 (m, 2H), LC MS (m/e)=412 (MH+).

Example 100

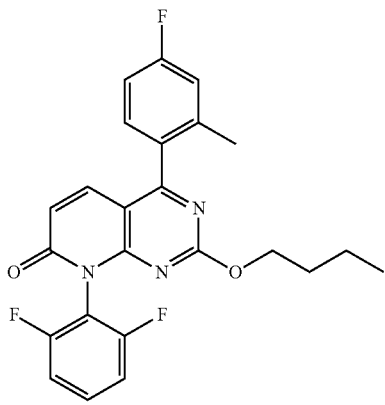

2-Butoxy-8-(2,6-difluoro-phenyl)-4-(4-fluoro-2-methyl-phenyl)-8H-pyrido[2,3-d]pyrimidin-7-one Prepared by the procedure of Example 98 using sodium butoxide to afford the title compound 2-butoxy-8-(2,6-difluoro-phenyl)-4-(4-fluoro-2-methyl-phenyl)-8H-pyrido[2,3-d]pyrimidin-7-one. ¹H-NMR (CDCl₃) δ 0.87 (m, 3H), 1.31 (m, 2H), 1.65 (m, 2H), 2.27 (s, 3H), 4.16 (m, 2H), 6.58 (d, 1H, J=9.6 Hz), 6.95-7.21 (m, 4H), 7.25 (m, 1H), 7.52 (m, 2H), LC MS (m/e)=440 (MH+).

Example 101

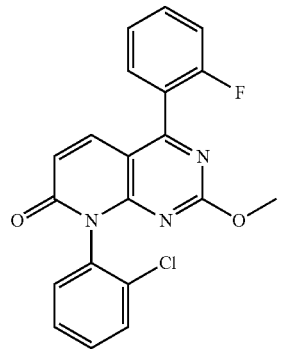

8-(2-Chloro-phenyl)-4-(2-fluoro-phenyl)-2-methoxy-8H-pyrido[2,3-d]pyrimidin-7-one Prepared as described above in Example 98 starting from (E)-3-[4-(2-chloro-phenylamino)-6-(2-fluoro-phenyl)-2-methylsulfanyl-pyrimidin-5-yl]-acrylic acid methyl ester and sodium methoxide to afford the title compound 8-(2-chloro-phenyl)-4-(2-fluoro-phenyl)-2-methoxy-8H-pyrido[2,3-d]pyrimidin-7-one. ¹H-NMR (CDCl₃) δ 3.70 (s, 3H), 6.59 (d, 1H, J=9.7 Hz), 7.01-7.20 (m, 3H), 7.40 (m, 2H), 7.56 (m, 4H); LC MS (m/e)=382 (MH+). Rt=2.24 min Example 102

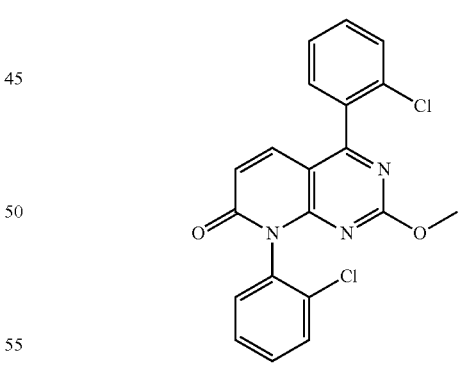

4,8-Bis-(2-chloro-phenyl)-2-methoxy-8H-pyrido[2,3-d]pyrimidin-7-one

Prepared as described above in Example 98 starting from (E)-3-[4-(2-chloro-phenylamino)-6-(2-chloro-phenyl)-2-methylsulfanyl-pyrimidin-5-yl]-acrylic acid methyl ester and sodium methoxide to afford the title compound 4,8-bis-(2-chloro-phenyl)-2-methoxy-8H-pyrido[2,3-d]pyrimidin-7- one. ¹H-NMR (CDCl₃) δ 3.71 (s, 3H), 6.55 (d, 1H, J=9.6 Hz), 7.24-7.60 (m, 9H). LC MS (m/e)=398 (MH+). Rt=2.27 min

Example 103

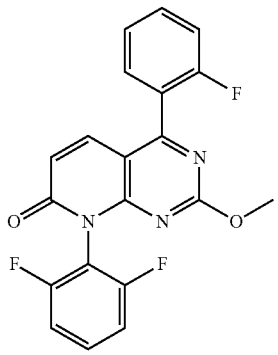

8-(2,6-Difluoro-phenyl)-4-(2-fluoro-phenyl)-2-methoxy-8H-pyrido[2,3-d]pyrimidin-7-one Prepared as described above in Example 98 starting from (E)-3-[4-(2,6-difluoro-phenyl amino)-6-(2-fluoro-phenyl)-2-methylsulfanyl-pyrimidin-5-yl]-acrylic acid methyl ester and sodium methoxide to afford the title compound 8-(2,6-difluoro-phenyl)-4-(2-fluoro-phenyl)-2-methoxy-8H-pyrido[2,3-d]pyrimidin-7-one. ¹H-NMR (CDCl₃) δ 3.82 (s, 3H), 6.56 (d, 1H, J=9.6 Hz), 7.08 (m, 2H), 7.26-7.59 (m, 6H). LC MS (m/e)=384 (MH+). Rt=2.22 min.

Example 104

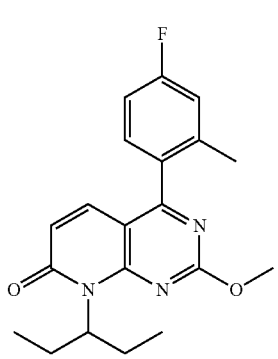

8-(1-Ethyl-propyl)-4-(4-fluoro-2-methyl-phenyl)-2-methoxy-8H-pyrido[2,3-d]pyrimidin-7-one Prepared as described above in Example 98 starting from (E)-3-[4-(1-ethyl-propylamino)-6-(4-fluoro-2-methyl-phenyl)-2-methylsulfanyl-pyrimidin-5-yl]-acrylic acid methyl ester and sodium methoxide to afford the title compound 8-(1-ethyl-propyl)-4-(4-fluoro-2-methyl-phenyl)-2-methoxy-8H-pyrido[2,3-d]pyrimidin-7-one. ¹H-NMR (CDCl₃) δ 0.89 (m, 6H), 2.02 (m, 2H), 2.22 (s, 3H), 2.33 (m, 2H), 3.39 (m, 2H), 4.09 (s, 3H), 5.35 (m, 0.5H), 5.62 (m, 0.5H), 6.41 (br d, 1H, J=9.6 Hz), 7.03 (m, 2H), 7.28 (m, 2H). LC MS (m/e)=356 (MH+). Rt=2.50 min.

Example 105

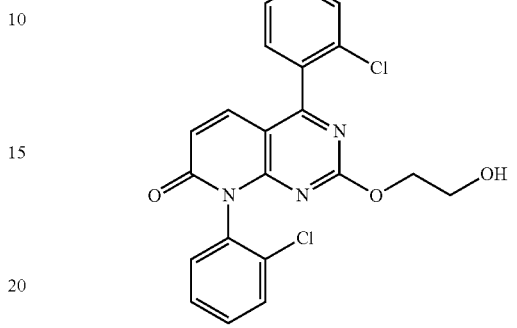

4,8-Bis-(2-chloro-phenyl)-2-(2-hydroxy-ethoxy)-8H-pyrido[2,3-d]pyrimidin-7-one

Prepared as described above in Example 98 starting from (E)-3-[4-(2-chloro-phenylamino)-6-(2-chloro-phenyl)-2-methylsulfanyl-pyrimidin-5-yl]-acrylic acid methyl ester and ethylene glycol sodium salt to afford the title compound 4,8-bis-(2-chloro-phenyl)-2-(2-hydroxy-ethoxy)-8H-pyrido[2,3-d]pyrimidin-7-one. ¹H-NMR (CDCl₃) δ 3.81 (m, 2H), 4.23 (m, 2H), 5.62 (m, 0.5 H), 6.65 (d, 1H, J=9.6 Hz), 7.29-7.58 (9H). LC MS (m/e)=428 (MH+). Rt=1.85 min

Example 106

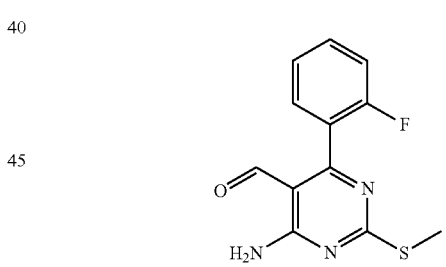

4-Amino-6-(2-fluoro-phenyl)-2-methylsulfanyl-pyrimidine-5-carbaldehyde

To a solution of the product of Example 17 (217 mg, 1.07 mmol) in dioxane (21 mL) and H₂O (7 mL) was added anhydrous K₂CO₃ (443 mg, 3.21 mmol, 3 eq) followed by 2-fluorophenylboronic acid (218 mg, 1.6 mmol, 1.5 eq). The reaction mixture was degassed and tetrakis(triphenylphophine) palladium (61 mg, 0.053 mmol, 0.05 eq) was added, and heated under reflux 24 h, cooled to 23°. The layers were separated. EtOAc (50 mL), followed by H₂O (10 mL), was added and the organic layer was separated, washed with satd aq NaCl, dried (MgSO₄), filtered, and the solvent was evaporated. The residue was purified by flash chromatography (1:20 EtOAc:hexane to afford 180 mg (72% yield) of pure 4-amino-6-(2-fluoro-phenyl)-2-methylsulfanyl-pyrimidine- 5-carbaldehyde. $^1$H-NMR δ 2.58 (s, 3H), 5.80 (br s, 1H), 7.16 (m, 1H), 7.28 (m, 1H), 7.59 (m, 2H), 8.68 (br s, 1H), 9.71 (s, 1H), LC MS (m/e)=264 (MH+). Rt=1.89 min Example 107

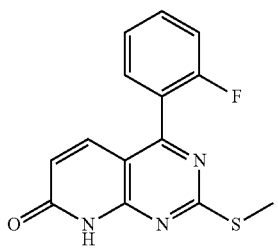

4-(2-Fluoro-phenyl)-2-methylsulfanyl-8H-pyrido[2,3-d]pyrimidin-7-one

A solution of 18-crown-6 (422 mg, 1.6 mmol, 5 eq) and bis(2,2,2-trifluoroethyl)(methoxycarbonylmethyl)phosphonate (81 uL, 0.38 mmol, 1.2 eq) in anhyd THF (20 mL) was cooled to −78°, potassium bis(trimethylsilyl)amide (0.96 mL, 0.48 mmol, 1.5 eq) as a 0.5 mol solution in toluene was added. This solution was stirred for additional 30 min at −78° and 4-amino-6-(2-fluoro-phenyl)-2-methylsulfanyl-pyrimidine-5-carbaldehyde (85 mg, 0.32 mmol) in dry THF (1 mL) was added dropwise. The reaction mixture was then stirred for 8 h at −78° and warmed to 23°, and stirred 16 h. Saturated aq NH$_4$Cl (5 mL), followed by Et$_2$O (20 mL), was added. The layers were separated. The organic layer was washed with satd aq NaCl, dried (MgSO$_4$), filtered and solvent was evaporated. The yellow residue was purified by Flash chromatography to afford 100 mg (91% yield) of 4-(2-fluoro-phenyl)-2-methylsulfanyl-8H-pyrido[2,3-d]pyrimidin-7-one. $^1$H-NMR δ 2.62 (s, 3H), 6.55 (d, 1H, J=9.9 Hz), 7.26 (m, 3H), 7.52 (m, 2H), 8.99 (br s, 1H). LC MS (m/e)=288 (MH+). Rt=1.75 min.

Example 108

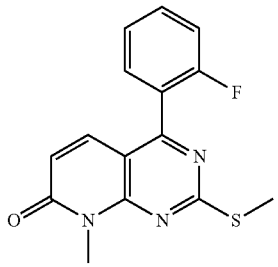

4-(2-Fluoro-phenyl)-8-methyl-2-methylsulfanyl-8H-pyrido[2,3-d]pyrimidin-7-one

To a solution of 4-(2-fluoro-phenyl)-2-methylsulfanyl-8H-pyrido[2,3-d]pyrimidin-7-one (120 mg, 0.42 mmol) in 20 mL of anhyd THF was added NaH (50 mg, 1.2 mmol, 60% dispersion in mineral oil, 3 eq) followed by iodomethane (74 µL, 1.2 mmol, 3 eq). The reaction mixture was stirred 1 h at 23°, quenched with saturated aq NH$_4$Cl. (20 mL), Et$_2$O (100 mL) was added and the layers were separated. The organic layer was washed with satd aq NaCl, dried (MgSO$_4$), filtered and evaporated. The yellow residue was then purified by Flash chromatography to afford 100 mg (92% yield) of 4-(2-Fluoro-phenyl)-8-methyl-2-methylsulfanyl-8H-pyrido[2,3-d]pyrimidin-7-one. $^1$H-NMR δ 2.68 (s, 3H), 3.81 (s, 3H), 6.61 (d, 1H, J=9.8 Hz), 7.22 (m, 3H), 7.50 (m, 3H). LC MS (m/e)=302 (MH+). Rt=2.17 min.

Example 109

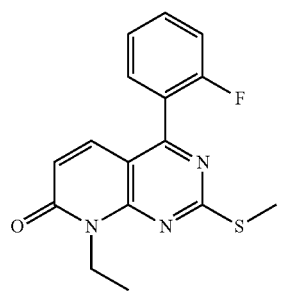

8-Ethyl-4-(2-fluoro-phenyl)-2-methylsulfanyl-8H-pyrido[2,3-d]pyrimidin-7-one

Prepared as described above in Example 108 starting from 4-(2-fluoro-phenyl)-2-methylsulfanyl-8H-pyrido[2,3-d]pyrimidin-7-one and iodoethane to afford the title compound 8-ethyl-4-(2-fluoro-phenyl)-2-methylsulfanyl-8H-pyrido[2,3-d]pyrimidin-7-one. LC MS (m/e)=316 (MH+). Rt=2.29 min Example 110

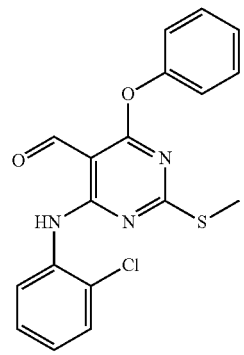

4-(2-Chloro-phenylamino)-2-methylsulfanyl-6-phenoxy-pyrimidine-5-carbaldehyde

To a solution of 4-chloro-6-(2-chloro-phenylamino)-2-methylsulfanyl-pyrimidine-5-carbaldehyde (315 mg, 1 mmol) in 10 mL of anhyd DMSO was added NaH (50 mg, 1.2 mmol, 60% dispersion in mineral oil, 1.2 eq) followed by phenol (112 mg, 1.2 mmol, 1.2 eq). The reaction mixture was stirred for 1 h 23°, quenched with H$_2$O (20 mL), Et$_2$O (100 mL) was added and the layers were separated. The organic layer was washed with satd aq NaCl, dried (MgSO$_4$) filtered and solvent was removed in vacuo. The yellow residue was then purified by Flash chromatography to afford 120 mg (45% yield) of 4-(2-chloro-phenylamino)-2-methylsulfanyl-6-phenoxy-pyrimidine-5-carbaldehyde. $^1$H-NMR δ 2.32 (s, 3H), 7.01-7.49 (m, 8H), 8.51 (d, 1H, J=7.2 Hz), 10.49 (s, 1H), 11.58 (br s, 1H). LC MS (m/e)=372 (MH+). Rt=2.94 min.

Example 111

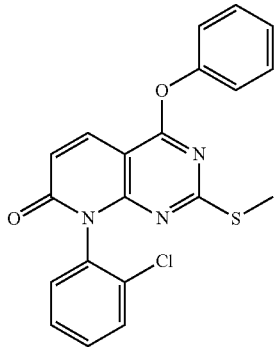

8-(2-Chloro-phenyl)-2-methylsulfanyl-4-phenoxy-8H-pyrido[2,3-d]pyrimidin-7-one

A solution of 18-crown-6 (422 mg, 1.6 mmol, 5 eq) and bis(2,2,2-trifluoroethyl)(methoxycarbonylmethyl)phosphonate (81 μL, 0.38 mmol, 1.2 eq) in anhyd THF (20 mL) was cooled to −78°. To this solution was added potassium bis(trimethylsilyl)amide (0.96 mL, 0.48 mmol, 1.5 eq) as a 0.5 mol solution in toluene. This solution was stirred for additional 30 min at −78° and 4-(2-chloro-phenylamino)-2-methylsulfanyl-6-phenoxy-pyrimidine-5-carbaldehyde (119 mg, 0.32 mmol) in dry THF (1 mL) was added dropwise. The reaction mixture was then stirred for 8 h at −78° and warmed to 23° and stirred 16 h. Saturated aq NH$_4$Cl (5 mL), followed by Et$_2$O (20 mL), was added. The layers were separated. The organic layer was washed with satd aq NaCl, dried (MgSO$_4$) filtered and solvent was removed in vacuo. The yellow residue was then purified by Flash chromatography to give 100 mg (91% yield) of pure 8-(2-chloro-phenyl)-2-methylsulfanyl-4-phenoxy-8H-pyrido[2,3-d]pyrimidin-7-one. $^1$H-NMR δ 1.89 (s, 3H), 6.55 (d, 1H, J=9.9 Hz), 7.18 (m, 4H), 7.28 (m, 4H), 7.44 (m, 1H), 7.98 (d, 1H, J=9.9 Hz). LC MS (m/e)=396 (MH+). Rt=2.68 min.

Example 112

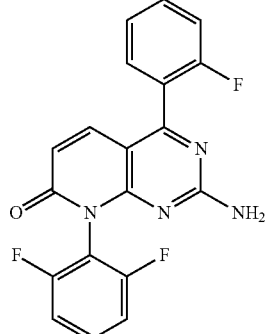

2-Amino-8-(2,6-difluoro-phenyl)-4-(2-fluoro-phenyl)-8H-pyrido[2,3-d]pyrimidin-7-one To a solution of 8-(2,6-difluoro-phenyl)-4-(2-fluoro-phenyl)-2-methanesulfonyl-8H-pyrido[2,3-d]pyrimidin-7-one (432 mg, 1 mmol) in 1-methyl-2-pyrrolidinone (5 mL) was added NaNH$_2$ (195 mg, 5 mmol, 5 eq) and the mixture was heated to 50°. After 1 h, H$_2$O (20 mL) was added then Et$_2$O (20 mL) The layers were separated. The organic layer was washed with satd aq NaCl, dried (MgSO$_4$), filtered and solvent was removed in vacuo. The yellow residue was then purified by Flash chromatography to afford 2-amino-8-(2,6-difluoro-phenyl)-4-(2-fluoro-phenyl)-8H-pyrido[2,3-d]pyrimidin-7-one (100 mg, 53% yield). $^1$H-NMR (CDCl$_3$) δ 5.51 (br s, 2H), 6.42 (d, 1H, J=9.8 Hz), 7.08 (m, 2H), 7.30 (m, 2H), 7.50 (m, 4H), LC MS (m/e)=369 (MH+). Rt=1.77 min Example 113

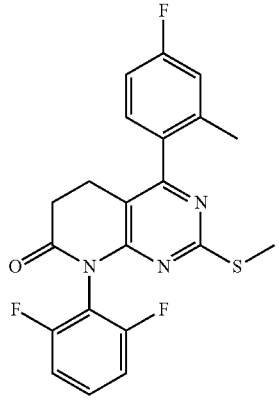

8-(2,6-Difluoro-phenyl)-4-(4-fluoro-2-methyl-phenyl)-2-methylsulfanyl-5,8-dihydro-6H-pyrido[2,3-d]pyrimidin-7-one a) 3-[4-(2,6-difluoro-phenylamino)-6-(4-fluoro-2-methyl-phenyl)-2-methylsulfanyl-pyrimidin-5-yl]-propionic acid methyl ester To a solution of SmI$_2$ in THF (0.1M) (Aldrich) (15 mL, 1 5 mmol) and MeOH (3 mL) was added the product of Example 30 (100 mg, 0.22 mmol) and the reaction mixture maintained its blue color. The presence of new product and the disappearance of starting material was indicated by hplc. After 30 min, the reaction was diluted with H$_2$O (10 mL), then 1 M HCl (3 mL), followed by EtOAc (20 mL), the layers were shaken together and separated. The aq phase was washed with EtOAc (20 mL) and the combined EtOAc was dried (MgSO$_4$) and the solvent was evaporated in vacuo and the residue was crystalized from i-PrOH/H$_2$O (1:1) to afford 3-[4-(2,6-difluoro-phenylamino)-6-(4-fluoro-2-methyl-phenyl)-2-methylsulfanyl-pyrimidin-5-yl]-propionic acid methyl ester. LC MS (m/e)= 448.2 (MH+), Rt=2.17 min.

b) 8-(2,6-Difluoro-phenyl)-4-(4-fluoro-2-methyl-phenyl)-2-methylsulfanyl-5,8-dihydro-6H-pyrido[2,3-d]pyrimidin-7-one To a solution of 3-[4-(2,6-difluoro-phenylamino)-6-(4-fluoro-2-methyl-phenyl)-2-methylsulfanyl-pyrimidin-5-yl]-propionic acid methyl ester (45 mg, 0.1 mmol) in methanol (5 mL) was added a solution of sodium methoxide (0.5 mL) and the reaction mixture was heated under reflux for 1 h. The reaction mixture was then evaporated, and EtOAc (20 mL) followed by H₂O (10 mL) were added. Layers were separated, organic washed with satd aq NaCl, dried (MgSO₄), filtered and the solvent was evaporated. Dichloromethane (5 mL) was added followed by 0.5 mL of oxalyl chloride and 0.1 mL of Et₃N. The reaction mixture was then stirred for 2 h at 23°, H₂O (5 mL) was then added followed by dichloromethane (15 mL). Layers were separated, organic layer was washed with sat'd aq. NaCl, dried (MgSO₄), filtered and solvent was evaporated. The yellow residue was purified by Flash chromatography to give 11.2 mg (21% yield) of pure 8-(2,6-difluoro-phenyl)-4-(4-fluoro-2-methyl-phenyl)-2-methylsulfanyl-5,8-dihydro-6H-pyrido[2,3-d]pyrimidin-7-one. ¹H-NMR (CDCl₃): δ 2.20 (s, 3H), 2.29 (s, 3H), 3.85 (m, 4H), 7.02 (m, 4H), 7.21 (m, 1H), 7.42 (m, 1H). LC MS (m/e)=416.2 (MH+). Rt=2.44 min.

Example 114

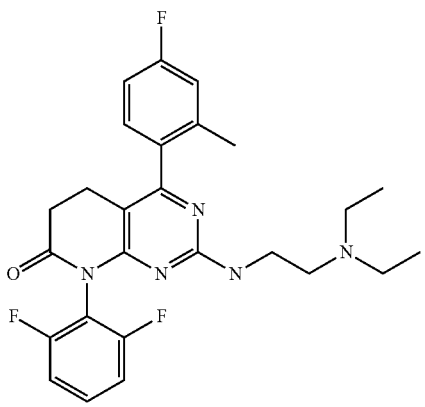

2-(2-Diethylamino-ethylamino)-8-(2,6-difluoro-phenyl)-4-(4-fluoro-2-methyl-phenyl)-5,8-dihydro-6H-pyrido[2,3-d]pyrimidin-7-one The product of Example 113(b), and N,N-diethylenediamine were reacted by the procedure of Example 60 to afford the title compound 2-(2-diethylamino-ethylamino)-8-(2,6-difluoro-phenyl)-4-(4-fluoro-2-methyl-phenyl)-5,8-dihydro-6H-pyrido[2,3-d]pyrimidin-7-one. ¹H-NMR (CDCl₃): δ 1.01 (m, 6H), 2.01-2.80 (m, 11H), 6.89-7.40 (m, 6H). LC MS (m/e)=484.2 (MH+). Rt=1.80 min Example 115

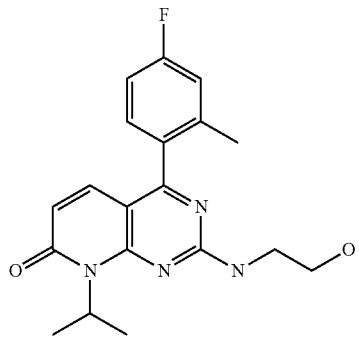

4-(4-Fluoro-2-methyl-phenyl)-2-(2-hydroxy-ethylamino)-8-isopropyl-8H-pyrido[2,3-d]pyrimidin-7-one The product of Example 56 and 2-aminoethanol were reacted by the procedure of Example 60 to afford the title compound 4-(4-fluoro-2-methyl-phenyl)-2-(2-hydroxy-ethylamino)-8-isopropyl-8H-pyrido[2,3-d]pyrimidin-7-one. ¹H-NMR (CDCl₃): δ 1.78 (m, 6H), 2.29 (s, 3H), 3.70 (br s, 2H), 3.89 (br s, 3H), 5.81 (m 1H), 6.02 (br s, 1H), 6.23 (d, 1H, J=9.7 Hz), 7.00 (m, 2H). 7.11 (d, 1H, J=9.7 Hz), 7.19 (m, 1H), LC MS (m/e)=357.2 (MH+). Rt=1.80 min.

Example 116

N-[8-(2,6-Difluoro-phenyl)-4-(4-fluoro-2-methyl-phenyl)-7-oxo-7,8-dihydro-pyrido[2,3-d]pyrimidin-2-yl]-N-methyl-methanesulfonamide To the solution of N-[8-(2,6-difluoro-phenyl)-4-(4-fluoro-2-methyl-phenyl)-7-oxo-7,8-dihydro-pyrido[2,3-d]pyrimidin-2-yl]-methanesulfonamide (92 mg, 0.2 mmol) in anhydrous DMF (2 mL) was added NaH (80 mg of 60% dispersion in mineral oil, 2 mmol, 10 eq) and the reaction mixture was stirred for 30 minutes at 23°. Iodomethane (280 mg, 2 mmol, 10 eq) was added and the reaction mixture was stirred 1 h at 23°. Saturated aq NH₄Cl (5 mL) was added and the reaction mixture was extracted with EtOAc (2×20 mL). Organic layers were combined, washed with satd aq NaCl, dried (MgSO₄), filtered and solvent was evaporated. The yellow residue was then purified by Flash chromatography to give 80 mg of pure N-[8-(2,6-difluoro-phenyl)-4-(4-fluoro-2-methyl-phenyl)-7-oxo-7,8-dihydro-pyrido[2,3-d]pyrimidin-2-yl]-N-methyl-methanesulfonamide. ¹H-NMR (CDCl₃): δ 2.22 (s, 3H), 2.96 (s, 3H), 3.30 (s, 3H), 6.68 (d, 1H, J=9.8 Hz), 7.02 (m, 4H). 7.213 (m, 1H), 7.42 (m, 2H), LC MS (m/e)=475.4 (MH+) Rt=2.25 min.

Example 117

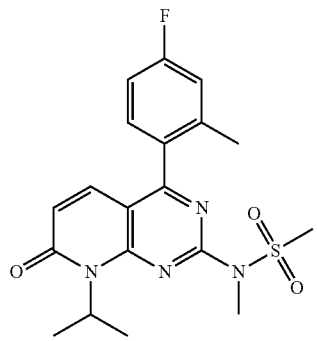

N-[4-(4-Fluoro-2-methylphenyl)-8-isopropyl-7-oxo-7,8-dihydro-pyrido[2,3-d]pyrimidin-2-yl]-N-methyl-methanesulfonamide Prepared as described above in Example 115 starting from N-[4-(4-fluoro-2-methyl-phenyl)-8-isopropyl-7-oxo-7,8-dihydro-pyrido[2,3-d]pyrimidin-2-yl]-methanesulfonamide to give the title compound N-[4-(4-fluoro-2-methyl-phenyl)-8-isopropyl-7-oxo-7,8-dihydro-pyrido[2,3-d]pyrimidin-2-yl]-N-methyl-methanesulfonamide. $^1$H-NMR (CDCl$_3$): δ 1.75 (d, 6H, J=6.9 Hz), 2.18 (s, 3H), 3.39 (s, 3H), 3.53 (s, 3 H), 5.81 (m 1H), 6.40 (d, 1H, J=9.7 Hz), 6.96 (m, 2H), 7.11 (m, 1H), 7.21 (d, 1H, J=9.7 Hz), LC MS (m/e)=405.4 (MH+). Rt=2.20 min

Example 118

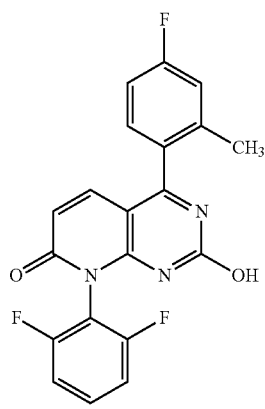

8-(2,6-Difluoro-phenyl)-4-(4-fluoro-2-methyl-phenyl)-2-hydroxy-8H-pyrido[2,3-d]pyrimidin-7-one To a solution of 8-(2,6-difluoro-phenyl)-4-(4-fluoro-2-methyl-phenyl)-2-methanesulfonyl-8H-pyrido[2,3-d]pyrimidin-7-one (223 mg, 0.5 mmol) in N-methylpyrollidine (5 mL) was added Et$_3$N (0.1 mL) followed by 2-aminoethanesulfonic acid (200 mg, 1.5 mmol, 3 eq) and the reaction mixture was heated to 50° for 12 h. 1 M aq HCl was then added dropwise till pH 3. The reaction mixture was then extracted with EtOAc (2×20 mL). Organic layers were combined, washed with satd aq NaCl, dried (MgSO$_4$), filtered and solvent was evaporated. The yellow residue was then purified by flash chromatography to give an oily product, which was then recrystalized from methanol:H$_2$O (3:1) to afford 51 mg of pure 8-(2,6-difluoro-phenyl)-4-(4-fluoro-2-methyl-phenyl)-2-hydroxy-8H-pyrido[2,3-d]pyrimidin-7-one. $^1$H-NMR (CDCl$_3$): δ 2.24 (s, 3H), 6.31 (d, 1H, J=9.8 Hz), 7.02 (m, 5H). 7.23 (m, 1H), 7.352 (m, 1H), LC MS (m/e)=384.2 (MH+). Rt=1.65 min

Example 119

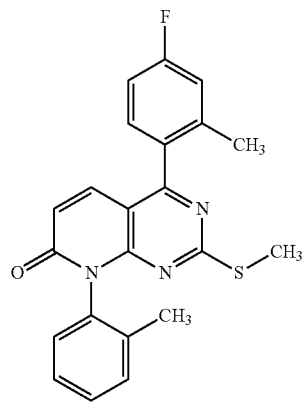

4-(4-Fluoro-2-methyl-phenyl)-2-methylsulfanyl-8-ortho-tolyl-8H-pyrido[2,3-d]pyrimidin-7-one Prepared as described above in Example 32 starting from 4-(4-Fluoro-2-methyl-phenyl)-2-methylsulfanyl-6-ortho-tolylamino-pyrimidine-5-carbaldehyde to give the title compound 4-(4-fluoro-2-methyl-phenyl)-2-methylsulfanyl-8-ortho-tolyl-8H-pyrido[2,3-d]pyrimidin-7-one. $^1$H-NMR (CDCl$_3$): δ 2.02 (s, 3H), 2.20 (s, 3H), 2.28 (s, 3H), 6.79 (d, 1H, J=9.7 Hz).7.02 (m, 2H), 7.17 (m, 1H), 7.22 (m, 2H), 7.40 (m, 2H). 7.53 (d, 1H, J=9.7 Hz). LC MS (m/e)=392.2 (MH+). Rt=2.40 min

Example 120

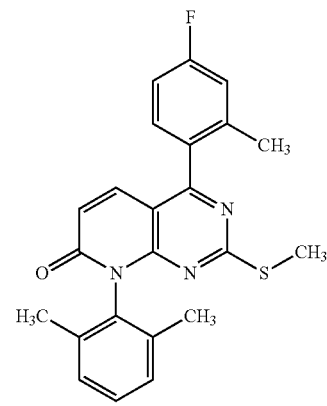

8-(2,6-Dimethyl-phenyl)-4-(4-fluoro-2-methyl-phenyl)-2-methylsulfanyl-8H-pyrido[2,3-d]pyrimidin-7-one Prepared as described above in Example 32 starting from 4-(2,6-dimethyl-phenylamino)-6-(4-fluoro-2-methyl-phenyl)-2-methylsulfanyl-pyrimidine-5-carbaldehyde to give the title compound 8-(2,6-dimethyl-phenyl)-4-(4-fluoro-2-methyl-phenyl)-2-methylsulfanyl-8H-pyrido[2,3-d]pyrimidin-7-one. ¹H-NMR (CDCl₃): δ 2.05 (s, 6H), 2.26 (s, 3H), 2.31 (s, 3H), 6.81 (d, 1H, J=9.7 Hz), 7.02 (m, 2H), 7.17 (m, 5H), 7.51 (d, 1H, J=9.7 Hz). LC MS (m/e)=406.4 (MH+). Rt=2.55 min Example 121

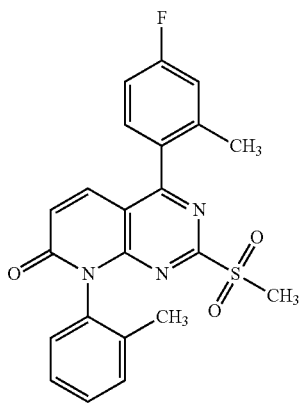

4-(4-Fluoro-2-methyl-phenyl)-2-methanesulfonyl-8-ortho-tolyl-8H-pyrido[2,3-d]pyrimidin-7-one Prepared as described above in Example 47 starting from 4-(4-fluoro-2-methyl-phenyl)-2-methylsulfanyl-8-ortho-tolyl-8H-pyrido[2,3-d]pyrimidin-7-one to give the title compound 4-(4-fluoro-2-methyl-phenyl)-2-methanesulfonyl-8-ortho-tolyl-8H-pyrido[2,3-d]pyrimidin-7-one. LC MS (m/e)= 424.2 (MH+). Rt=2.02 min Example 122

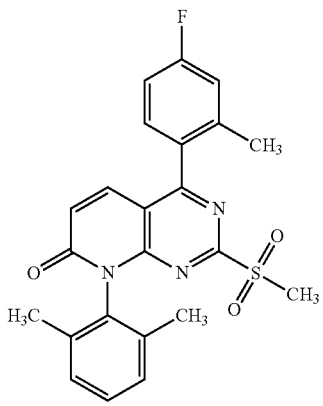

8-(2,6-Dimethyl-phenyl)-4-(4-fluoro-2-methyl-phenyl)-2-methanesulfonyl-8H-pyrido[2,3-d]pyrimidin-7-one Prepared as described above in Example 47 starting from 8-(2,6-dimethyl-phenyl)-4-(4-fluoro-2-methyl-phenyl)-2-methylsulfanyl-8H-pyrido[2,3-d]pyrimidin-7-one to give the title compound 8-(2,6-dimethyl-phenyl)-4-(4-fluoro-2-methyl-phenyl)-2-methanesulfonyl-8H-pyrido[2,3-d]pyrimidin-7-one. LC MS (m/e)=438.0 (MH+). Rt=2.07 min Example 123

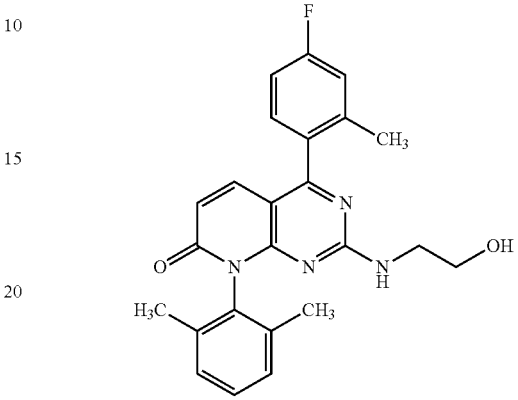

8-(2,6-Dimethyl-phenyl)-4-(4-fluoro-2-methyl-phenyl)-2-(2-hydroxy-ethylamino)-8H-pyrido[2,3-d]pyrimidin-7-one Prepared as described above in Example 60 starting from 8-(2,6-dimethyl-phenyl)-4-(4-fluoro-2-methyl-phenyl)-2-methanesulfonyl-8H-pyrido[2,3-d]pyrimidin-7-one and 2-aminoethanol to give the title compound 8-(2,6-dimethyl-phenyl)-4-(4-fluoro-2-methyl-phenyl)-2-(2-hydroxy-ethylamino)-8H-pyrido[2,3-d]pyrimidin-7-one. ¹H-NMR (CDCl₃): δ 1.92 (s, 6H), 2.12 (s, 3H), 2.95 (br s, 2H), 3.30 (br s, 2H), 3.45 (br s, 1H), 6.31 (d, 1H, J=9,7 Hz), 6.92 (m, 2H), 7.17 (m, 5H). LC MS (m/e)=419.4 (MH+). Rt=1.84 min Example 124

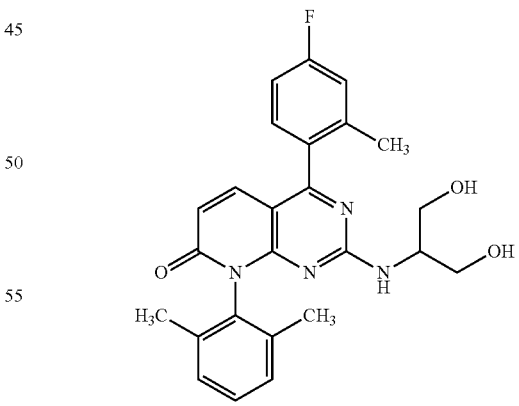

8-(2,6-Dimethyl-phenyl)-4-(4-fluoro-2-methyl-phenyl)-2-(2-hydroxy-1-hydroxymethyl-ethylamino)-8H-pyrido[2,3-d]pyrimidin-7-one The product of Example 122, and serinol were reacted by the procedure of Example 60 to afford the title compound 8-(2,6-dimethyl-phenyl)-4-(4-fluoro-2-methyl-phenyl)-2-(2-hydroxy-1-hydroxymethyl-ethylamino)-8H-pyrido[2,3-d]pyrimidin-7-one. ¹H-NMR (CDCl₃): δ 1.91 (s, 6H), 2.14 (s, 3H), 3.45 (br s, 4H), 3.93 (br s, 1H), 6.20 (br s, 1H), 6.31 (d, 1H, J=9.7 Hz), 6.93 (m, 2H), 7.11 (m, 5H). LC MS (m/e)= 449.0 (MH+). Rt=1.62 min Example 125

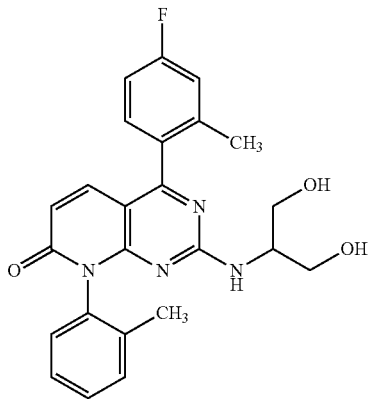

4-(4-Fluoro-2-methyl-phenyl)-2-(2-hydroxy-1-hydroxymethyl-ethylamino)-8-ortho-tolyl-8H-pyrido[2,3-d]pyrimidin-7-one The product of Example 121, and serinol were reacted by the procedure of Example 60 to afford the title compound 4-(4-fluoro-2-methyl-phenyl)-2-(2-hydroxy-1-hydroxymethyl-ethylamino)-8-ortho-tolyl-8H-pyrido[2,3-d]pyrimidin-7-one. ¹H-NMR (CDCl₃): δ 2.09 (s, 3H), 2.26 (s, 3H), 3.73 (br s, 4H), 4.02 (br s, 1H), 6.30 (br s, 1H), 6.41 (d, 1H, J=9.7 Hz), 7.05 (m, 2H), 7.24 (m, 6H). LC MS (m/e)=435.2 (MH+). Rt=1.60 min Example 126

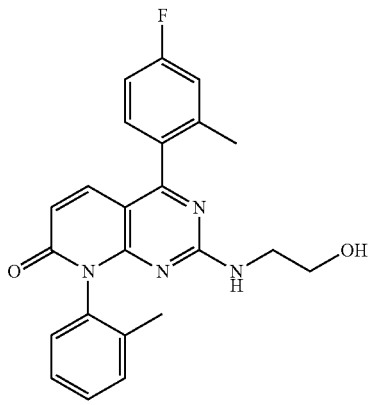

4-(4-Fluoro-2-methyl-phenyl)-2-(2-hydroxy-ethylamino)-8-o-tolyl-8H-pyrido[2,3-d]pyrimidin-7-one The product of Example 121 (400 mg, 0.95 mmol) and ethanolamine (0.29 mL, 4.73 mmol) in NMP (2 mL) was stirred at 23° for 1 h. The mixture was diluted with EtOAc, washed with H₂O, the organic phase was separated, EtOAc was removed in vacuo and the residue was purified by Flash chromatography on silica gel, eluting with EtOAc/hexane/triethylamine (50/50/2, v/v/v), followed by evaporation of solvent to afford a gummy residue. Trituration with H₂O, gave the title compound compound 4-(4-fluoro-2-methyl-phenyl)-2-(2-hydroxy-1-hydroxymethyl-ethylamino)-8-ortho-tolyl-8H-pyrido[2,3-d]pyrimidin-7-one as a white solid (340 mg, 88%). LC-MS: 405.4 (MH+, m/z), Rt=1.85 min Example 127

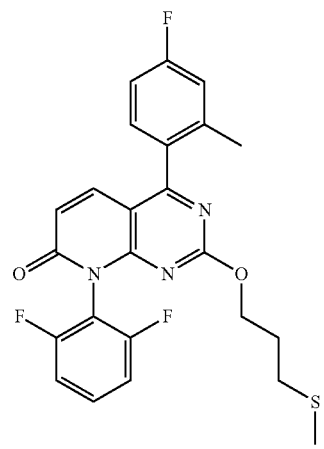

8-(2,6-Difluorophenyl)-4-(4-fluoro-2-methylphenyl)-2-(3-methylsulfanylpropoxy)-8H-pyrido[2,3-d]pyrimidin-7-one NaH (12 mg, 0.5 mmol) was added to 3-(methylthio)-1-propanol (0.5 mL) and the mixture was stirred under Ar at 23°. After 5 min, gas evolution ceased, and the product of Example 48 (223 mg, 0.5 mmol) was added in a single portion. The mixture was stirred for 30 minutes. Most of the excess 3-(methylthio)-1-propanol was removed in vacuo, and the residue partitioned between EtOAc and H₂O. The organic phase was washed with H₂O, satd aq NaCl, dried over anhyd Na₂SO₄, filtered and evaporated to give the crude product. Flash chromatography eluted with 10-30% EtOAc/hexane, followed by recrystallization from CH₂Cl₂/hexane gave the title compound as a white crystalline solid. mp 127-128°, LC MS m/z=472 (MH+) Retention time=2.47 min.

Example 128

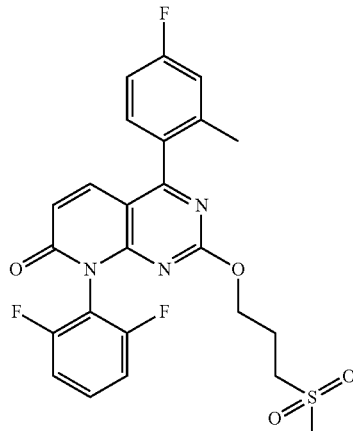

101

8-(2,6-Difluorophenyl)-4-(4-fluoro-2-methylphenyl)-
2-(3-methanesulfonylpropoxy)-8H-pyrido[2,3-d]
pyrimidin-7-one To the product of Example 127 (100 mg, 0.21 mmol) in chloroform (10 mL) was added 80% 3-chloroperoxybenzoic acid (135 mg, 0.63 mmol). The mixture was stirred under Ar at 23° for 2 h, after which time the solvent was removed in vacuo, and the residue was partitioned between EtOAc and 1 M Na₂CO₃. The organic phase was washed with H2O, satd aq NaCl, dried over anhyd Na₂SO₄, filtered and evaporated to give the crude product. Flash chromatography eluted with 0-20% EtOAc/CH₂Cl₂, followed by recrystallization from CH₂Cl₂/hexane gave the title compound as a white crystalline solid. mp 160-162°, LC MS m/z=504 (MH+) Retention time=2.02 min.

Example 129

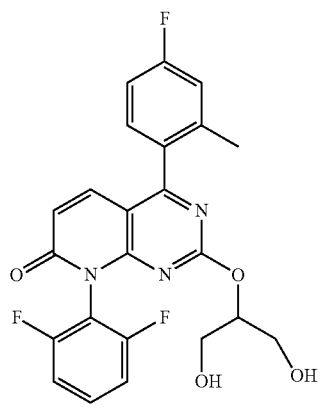

8-(2,6-Difluorophenyl)-4-(4-fluoro-2-methylphenyl)-
2-(2-hydroxy-1-hydroxymethylethoxy)-8H-pyrido[2,
3-d]pyrimidin-7-one 1,3-O-Benzylideneglycerol (100 mg, 0.55 mmol) was dissolved in dry THF (5 mL) and stirred under Ar at 23° C. NaH (14 mg, 0.55 mmol) was added and the mixture stirred for 15 minutes at 23° C., and then cooled to −78°. The product of Example 48 (222 mg, 0.5 mmol) was added, and the mixture was allowed to slowly warm to 23°. The solvent was removed in vacuo, and the residue was dissolved in acetic acid (2 mL), and H2O (0.5 mL) was added. The mixture was heated in an oil bath to 60° C. for three h, and then the solvents were removed in vacua to give the crude product. The crude product was flash chromatographed twice on silica gel eluted with 20-50% EtOAc/CH₂Cl₂ to give the product as a white-amorphous solid. 104-107° C., LC MS m/z=458 (MH+) Retention time=1.88 min.

102

Example 130

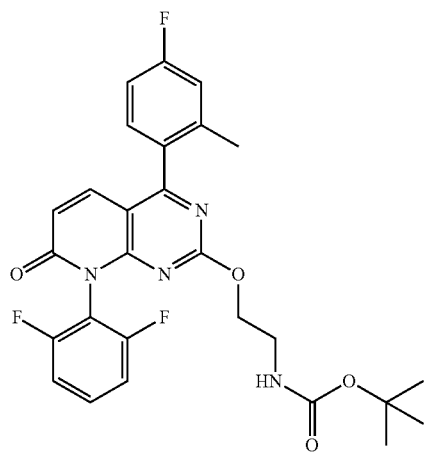

8-(2,6-Difluorophenyl)-4-(4-fluoro-2-methylphenyl)-
2-[2-(tert-butoxycarbonylamino)ethoxy]-8H-pyrido
[2,3-d]pyrimidin-7-one The product of Example 48 (445 mg, 1 mmol) and BOC-aminoethanol (177 mg, 1.1 mmol) was dissolved in THF (10 mL), and cooled to −78° while stirring under Ar.NaH (28 mg, 1.1 mmol) was added in a single portion. The mixture allowed to slowly warm to 23°, but the reaction did not go to completion. Additional NaH (10 mg, 0.4 mmol) was added, and the reaction went to completion. The solvent was removed in vacuo, and the residue was partitioned between EtOAc and H2O. The organic phase was washed with H2O, satd aq NaCl, dried over anhyd Na₂SO₄, filtered and evaporated to give the crude product. Flash chromatography eluted with 0-10% EtOAc/hexane gave the title compound as a white-amorphous solid. mp 103-105°, LC MS m/z=527(MH+) Retention time=2.44 min.

Example 131

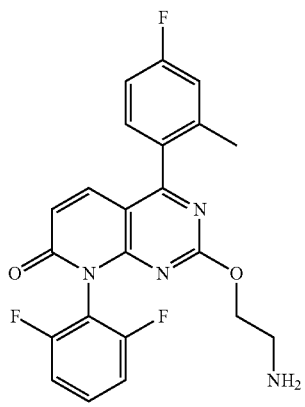

8-(2,6-Difluorophenyl)-4-(4-fluoro-2-methylphenyl)-
2-(2-aminoethoxy)-8H-pyrido[2,3-d]pyrimidin-7-one The product of Example 130 (1 g, 1.9 mmol) was dissolved in CH₂Cl₂ (8 mL) and stirred under Ar in an ice bath. A chilled solution of 25% TFA in CH$_2$Cl$_2$ (40 mL) was added, and the mixture was stirred for 45 min at 0° C. The solvents were removed in vacuo, and the residue was partitioned between EtOAc and a saturated NaHCO$_3$ solution. The organic phase was washed with H2O, satd aq NaCl, dried over anhyd Na$_2$SO$_4$, filtered and evaporated to give the crude product. Flash chromatography eluted with 0-10% MeOH/CH$_2$Cl$_2$ gave the title compound as a white-amorphous solid. mp 96-99°, LC MS in/z=427 (MH+) Retention time=1.52 min.

Example 132

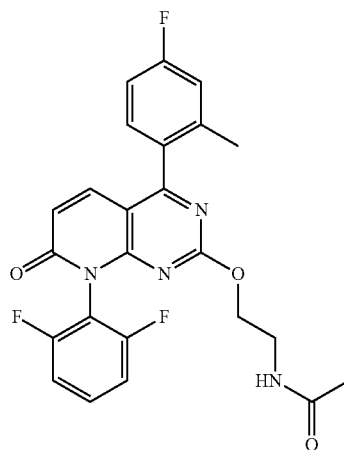

8-(2,6-Difluorophenyl)-4-(4-fluoro-2methylphenyl)-2-(2-acetylaminoethoxy)-8H-pyrido[2,3-d]pyrimidin-7-one The product of Example 131 (61 mg, 0.14 mmol)was dissolved in CH$_2$Cl$_2$ (2 mL) and stirred at 0° C. under Ar. Triethylamine (0.1 mL) was added followed by the addition of acetic anhydride (0.2 g, 2 mmol). The reaction was allowed to slowly warm to 23° and stir for 18 h. The solvents were removed in vacuo, and the residue was flash chromatographed eluted with 10-30% EtOAc/CH$_2$Cl$_2$ to give the title compound as a white-amorphous solid. mp 75-79°, LC MS m/z=469 (MH+) Retention time=1.95 min.

Example 133

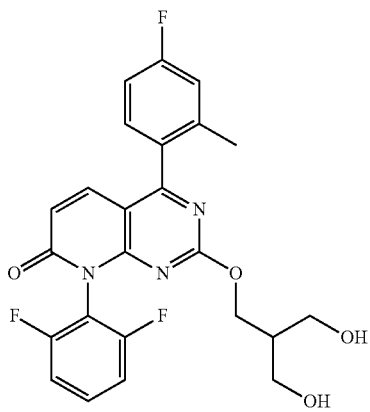

8-(2,6-Difluorophenyl)-4-(4-fluoro-2-methylphenyl)-2-(3-hydroxy-2-hydroxymethylpropoxy)-8H-pyrido[2,3-d]pyrimidin-7-one NaH (15 mg, 0.6 mmol) was added to 2-(hydroxymethyl)-1,3-propanediol in THF (5 mL). The mixture was allowed to stir at 23° under Ar for 10 min and was then cooled to −78°. The product of Example 48 (224 mg, 0.5 mmol) in THF (5 mL) was added at −78° and the mixture allowed to warm to 23° and stir for 2 h. The solvents were removed in vacuo, and the residue was partitioned between EtOAc and H$_2$O. The organic phase was washed with H$_2$O, satd aq NaCl, dried over anhyd Na$_2$SO$_4$, filtered and evaporated to give the crude product. Flash chromatography eluted with 70% EtOAc/CH$_2$Cl$_2$ the title compound as a white-amorphous solid. mp 77-81°, LC MS m/z=472 (MH+) Retention time=1.79 min.

Example 134

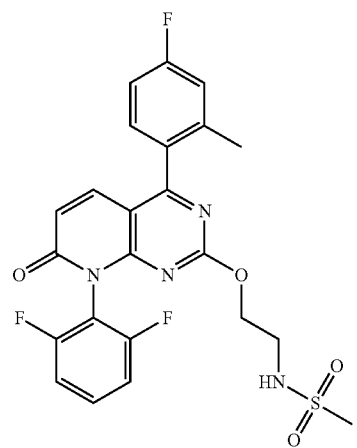

8-(2,6-Difluorophenyl)-4-(4-fluoro-2-methylphenyl)-2-(2-methanesulfonyl-aminoethoxy)-8H-pyrido[2,3-d]pyrimidin-7-one The product of Example 131 (100 mg, 0.23 mmol) in CH$_2$Cl$_2$ (4 mL) was stirred under Ar at 23°. Triethylamine (0.1 mL) was added followed by the addition of a solution of methanesulfonyl chloride (29 mg, 0.25 mmol) in CH$_2$Cl$_2$ (1 mL). The solvents were removed in vacuo, and the residue was partitioned between EtOAc and H$_2$O. The organic phase was washed with H2O, satd aq NaCl, dried over anhyd Na$_2$SO$_4$, filtered and evaporated to give the crude product. Flash chromatography eluted with 0-10% EtOAc/CH$_2$Cl$_2$ gave the title compound as a white-amorphous solid. mp 95-99°, LC MS m/z=505 (MH+) Retention time=2.02 min.

Example 135

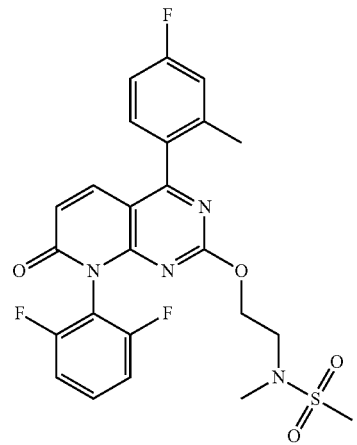

8-(2,6-Difluorophenyl)-4-(4-fluoro-2-methylphenyl)-2-(2-N-methanesulfonyl-N-methylaminoethoxy)-8H-pyrido[2,3-d]pyrimidin-7-one The product of Example 134 (20 mg, 0.04 mmol) was dissolved in acetone (2 mL) and stirred under Ar at 23°. Potassium carbonate (7 mg, 0.05 mmol) was added, followed by the addition of a solution of iodomethane (6.4 mg, 0.045 mmol) in acetone (1 mL). The mixture was allowed to stir for 18 h, the solvents were removed in vacuo, and the residue was partitioned between EtOAc and H$_2$O. The organic phase was washed with H2O, satd aq NaCl, dried over anhyd Na$_2$SO$_4$, filtered and evaporated to give the crude product. Flash chromatography eluted with 0-5% EtOAc/CH$_2$Cl$_2$ gave the title compound as a white-amorphous solid. mp 89-92°, LC MS m/z=519 (MH+) Retention time=2.2 min.

Example 136

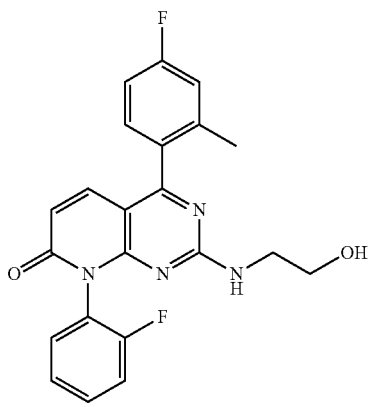

4-(4-fluoro-2-methylphenyl)-8-(2-fluorophenyl)-2-(2-hydroxylethylamino)-8H-pyrido[2,3-d]pyrimidin-7-one The product of Example 59 (200 mg, 0.47 mmol) was dissolved in THF (4 ml) and a solution of ethanolamine (115 mg, 1.87 mmol) in THF (1 mL) was added. The mixture was stirred under Ar at 23° for 18 h. The solvents were removed in vacuo, and the residue was partitioned between EtOAc and H$_2$O. The organic phase was washed with H$_2$O, satd aq NaCl, dried over anhyd Na$_2$SO$_4$, filtered and evaporated to give the crude product. Flash chromatography eluted with 0-15% EtOAc/CH$_2$Cl$_2$ gave the title compound as a light-yellow amorphous solid. mp 120-124°, LC MS m/z=409 (MH+) Retention time=1.84 min.

Example 137

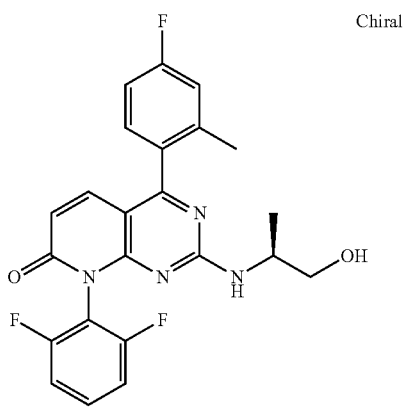

(S)-4-(4-fluoro-2-methylphenyl)-8-(2,6-difluorophenyl)-2-[(1-hydroxyprop-2-yl)amino]-8H-pyrido[2,3-d]pyrimidin-7-one The product of Example 48 (200 mg, 0.45 mmol) and (S)-2-amino-1-propanol (75 mg, 1 mmol) were dissolved in THF (10 ml) and stirred under Ar at 23° for 10 days. The solvents were removed in vacuo, and the residue was partitioned between EtOAc and H2O. The organic phase was washed with H2O, satd aq NaCl, dried over anhyd Na$_2$SO$_4$, filtered and evaporated to give the crude product. Flash chromatography eluted with 0-15% EtOAc/CH$_2$Cl$_2$ gave the title compound as an off-white amorphous solid. mp 96-101°, LC MS m/z=441 (MH+) Retention time=2.04 min.

Example 138

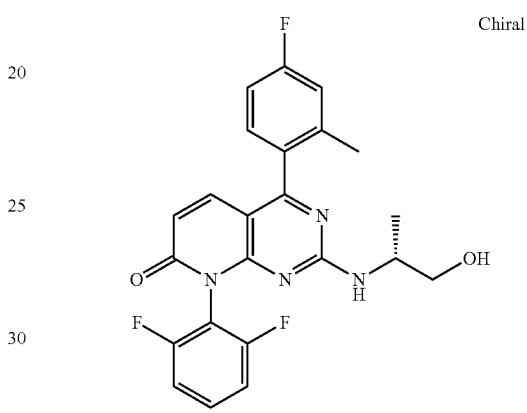

(R)-4-(4-fluoro-2-methylphenyl)-8-(2,6-difluorophenyl)-2-[(1-hydroxyprop-2-yl)amino]-8H-pyrido[2,3-d]pyrimidin-7-one The product of Example 48 (200 mg, 0.45 mmol) and (R)-2-amino-1-propanol (75 mg, 1 mmol) were dissolved in THF (10 ml) and stirred under Ar at 23° for 18 h. The solvents were removed in vacuo, and the residue was partitioned between EtOAc and H$_2$O. The organic phase was washed with H$_2$O, satd aq NaCl, dried over anhyd Na$_2$SO$_4$, filtered and evaporated to give the crude product. Flash chromatography eluted with 0-15% EtOAc/CH$_2$Cl$_2$ gave the title compound as a off-white amorphous solid. mp 90-95°, LC MS m/z=441 (MH+) Retention time=2.09 min.

Example 139

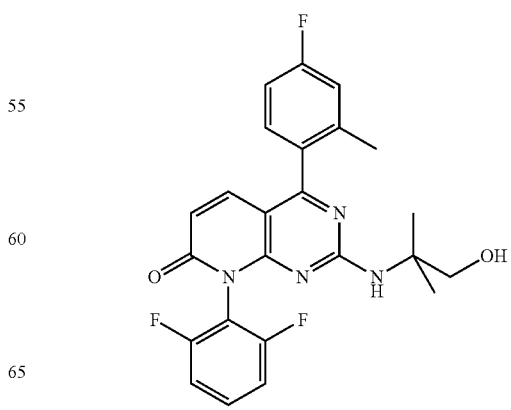

4-(4-fluoro-2-methylphenyl)-8-(2,6-difluorophenyl)-2-(1,1-dimethyl-2-hydroxyethylamino)-8H-pyrido[2,3-d]pyrimidin-7-one The product of Example 48 (200 mg, 0.45 mmol) and 95% 2-amino-2-methyl-1-propanol (94 mg, 1 mmol) were dissolved in THF (10 ml) and stirred under Ar at 50° for 3 days. The solvents were removed in vacuo, and the residue was partitioned between EtOAc and H$_2$O. The organic phase was washed with H$_2$O, satd aq NaCl, dried over anhyd Na$_2$SO$_4$, filtered and evaporated to give the crude product. Flash chromatography eluted with 0-15% EtOAc/CH$_2$Cl$_2$ gave the title compound as a off-white amorphous solid. mp 99-105° C., LC MS m/z=455 (MH+) Retention time=2.19 min.

Example 140

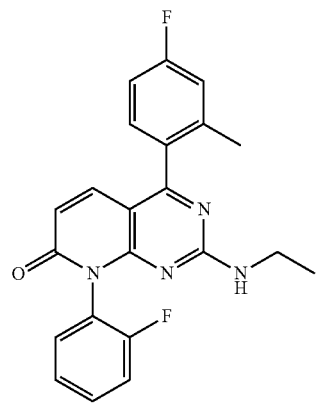

2-Ethylamino-4-(4-fluoro-2-methylphenyl)-8-(2-fluorophenyl)-8H-pyrido[2,3-d]pyrimidin-7-one The product of Example 59 (200 mg, 0.47 mmol) was combined and stirred with 5 mL of a 2M solution of ethylamine in THF. After 5 min the solvents were removed in vacuo, and the residue was partitioned between EtOAc and H$_2$O. The organic phase was washed with H$_2$O, satd aq NaCl, dried over anhyd Na$_2$SO$_4$, filtered and evaporated to give the crude product. Flash chromatography eluted with 0-2% EtOAc/CH$_2$Cl$_2$ followed by recrystallization from CH$_2$Cl$_2$/hexane gave the product as a light-yellow crystalline solid. mp 176-177°, LC MS m/z=393 (MH+) Retention time=2.38 min.

Example 141

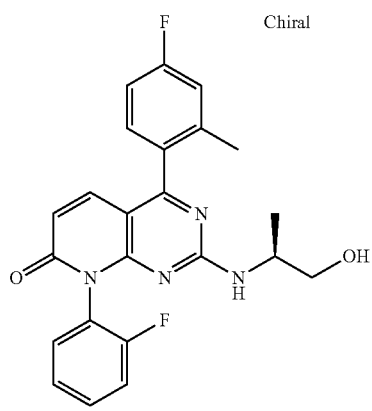

(S)-4-(4-fluoro-2-methylphenyl)-8-(2-fluorophenyl)-2-[(1-hydroxyprop-2-yl)amino]-8H-pyrido[2,3-d]pyrimidin-7-one The product of Example 59 (200 mg, 0.47 mmol) and (S)-2-amino-1-propanol (75 mg, 1 mmol) were dissolved in THF (10 ml) and stirred under Ar at 23° C. for 18 h. The solvents were removed in vacuo, and the residue was partitioned between EtOAc and H2O. The organic phase was washed with H$_2$O, satd aq NaCl, dried over anhyd Na$_2$SO$_4$, filtered and evaporated to give the crude product. Flash chromatography eluted with 0-20% EtOAc/CH$_2$Cl$_2$ gave the title compound as an off-white amorphous solid. mp 114-120°, LC MS m/z=423 (MH$_+$) Retention time=2.0 min.

Example 142

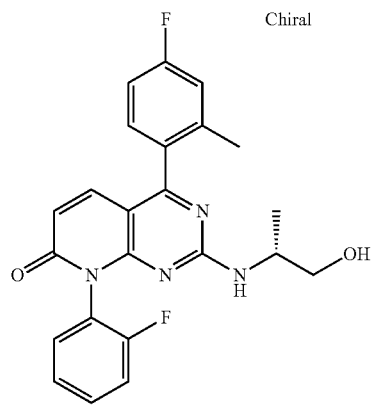

(R)-4-(4-fluoro-2-methylphenyl)-8-(2-fluorophenyl)-2-[(1-hydroxyprop-2-yl)amino]-8H-pyrido[2,3-d]pyrimidin-7-one The product of Example 59 (200 mg, 0.47 mmol) and (R)-2-amino-1-propanol (75 mg, 1 mmol) were dissolved in THF (10 ml) and stirred under Ar at 23° for 18 h. The solvents were removed in vacuo, and the residue was partitioned between EtOAc and H$_2$O. The organic phase was washed with H$_2$O, satd aq NaCl, dried over anhyd Na$_2$SO$_4$, filtered and evaporated to give the crude product. Flash chromatography eluted with 0-20% EtOAc/CH$_2$Cl$_2$ gave the title compound as a off-white amorphous solid. mp 116-122°, LC MS m/z=423 (MH+) Retention time=2.04 min.

Example 143

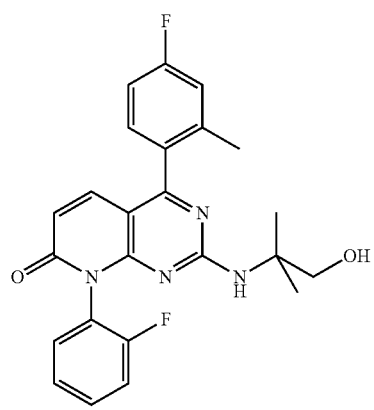

2-(1,1-dimethyl-2-hydroxyethylamino)-4-(4-fluoro-2-methylphenyl)-8-(2-fluorophenyl)-8H-pyrido[2,3-d]pyrimidin-7-one The product of Example 59 (200 mg, 0.47 mmol) and 2-amino-2-methyl-1-propanol (94 mg, 1 mmol) were dissolved in THF (10 ml) and stirred under Ar at 50° for 3 days. The solvents were removed in vacuo, and the residue was partitioned between EtOAc and H₂O. The organic phase was washed with H₂O, satd aq NaCl, dried over anhyd Na₂SO₄, filtered and evaporated to give the crude product. Flash chromatography eluted with 0-15% EtOAc/CH₂Cl₂ gave the title compound as a light-yellow amorphous solid. mp 106-112°, LC MS m/z=437 (MH+) Retention time=1.94 min.

Example 144

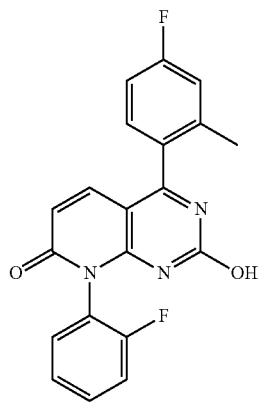

2-Hydroxy-4-(4-fluoro-2-methylphenyl)-8-(2-fluorophenyl)-8H-pyrido[2,3-d]pyrimidin-7-one A much more polar product formed in Example 143 was eluted from the flash column on silica gel with 5% MeOH/CH₂Cl₂. This was recrystallized from EtOAc to give the title compound as a white crystalline solid. This compound was presumably formed by reaction of the starting material sulfone with H₂O that contaminated the amine starting material. mp >280°, LC MS m/z=366 (MH+) Retention time=1.7 min Example 145

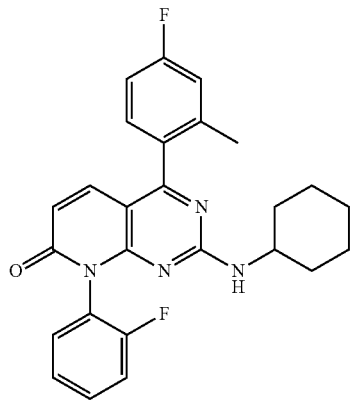

2-Cyclohexylamino-4-(4-fluoro-2-methylphenyl)-8-(2-fluorophenyl)-8H-pyrido[2,3-d]pyrimidin-7-one The product of Example 59 (200 mg, 0.47 mmol) and cyclohexylamine (100 mg, 1 mmol) were combined in THF (10 mL) and stirred under Ar at 23° for 18 h. The solvents were removed in vacuo, and the residue was flash chromatographed on silica gel eluted with 50-100% CH₂Cl₂/hexane. Recrystallization from CH₂Cl₂/hexane gave the title compound as a white-crystalline solid. mp 181-182°, LC MS m/z=447 (MH+) Retention time=2.71 min.

Example 146

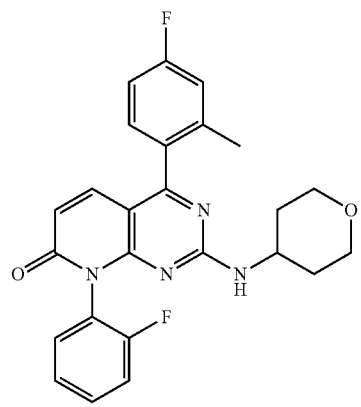

2-(Tetrahydropyran-4-ylamino)-4-(4-fluoro-2-methylphenyl)-8-(2-fluorophenyl)-8H-pyrido[2,3-d]pyrimidin-7-one The product of Example 59 (200 mg, 0.47 mmol) and 4-aminotetra-hydropyran (102 mg, 1 mmol) were combined in THF (10 mL) and stirred under Ar at 23° for 18 h. The solvents were removed in vacuo, and the residue was flash chromatographed with 0-15% EtOAc/CH₂Cl₂. Recrystallization from CH₂Cl₂/hexane gave the title compound as a light-yellow crystalline solid. mp 211-212°, LC MS m/z=449 (MH+) Retention time=2.21 min Example 147

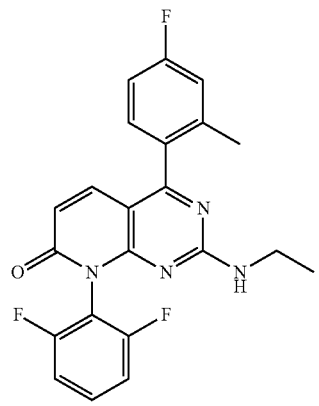

2-Ethylamino-4-(4-fluoro-2-methylphenyl)-8-(2,6-difluorophenyl)-8H-pyrido[2,3-d]pyrimidin-7-one The product of Example 48 (200 mg, 0.45 mmol) was combined and stirred with 5 mL of a 2M solution of ethylamine in THF. After 5 min the solvents were removed in vacuo, and the residue was partitioned between EtOAc and H₂O. The organic phase was washed with H₂O, satd aq NaCl, dried over anhyd Na₂SO₄, filtered and evaporated to give the crude product. Flash chromatography with 0-2% EtOAc/CH₂Cl₂ followed by recrystallization from CH₂Cl₂/hexane gave the product as a white-crystalline solid. mp 195-196°, LC MS m/z=411 (MH+) Retention time=2.4 min.

Example 148

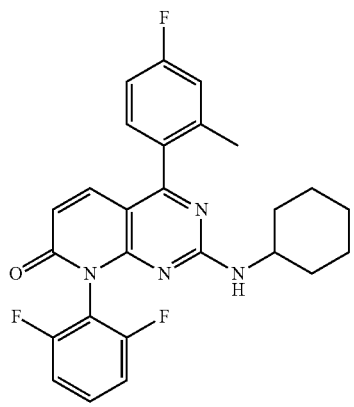

2-Cyclohexylamino-4-(4-fluoro-2-methylphenyl)-8-(2,6-difluorophenyl)-8H-pyrido[2,3-d]pyrimidin-7-one The product of Example 48 (200 mg, 0.45 mmol) and cyclohexylamine (100 mg, 1 mmol) were combined in THF (10 mL) and stirred under Ar at 23° for 18 h. The solvents were removed in vacuo, and the residue was flash chromatographed with 50-100% CH₂Cl₂/hexane. Recrystallization from CH₂Cl₂/hexane gave the title compound as a white-crystalline solid. mp 218-219° C., LC MS m/z=465 (MH+) Retention time=2.8 min.

Example 149

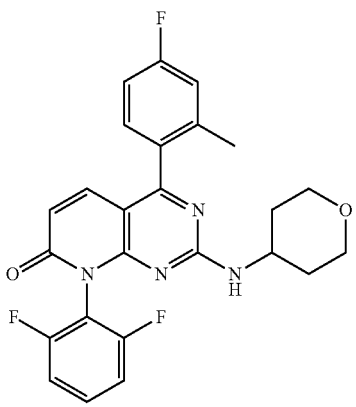

2-(Tetrahydropyran-4-ylamino)-4-(4-fluoro-2-methylphenyl)-8-(2,6-difluorophenyl)-8H-pyrido[2,3-d]pyrimidin-7-one The product of Example 48 (200 mg, 0.45 mmol) and 4-aminotetra-hydropyran (102 mg, 1 mmol) were combined in THF (10 mL) and stirred under Ar at 23° for 18 h. The solvents were removed in vacuo, and the residue was flash chromatographed with 0-15% EtOAc/CH₂Cl₂ Recrystallization from CH₂Cl₂/hexane gave the title compound as a light-yellow crystalline solid. mp 231-232°, LC MS m/z=467 (MH+) Retention time=2.27 min.

Example 150

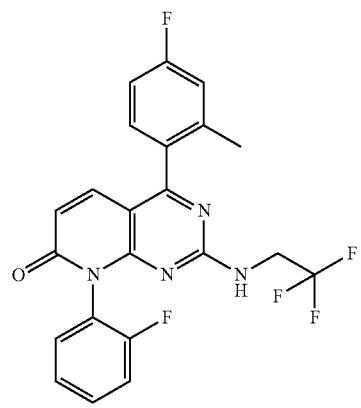

2-(2,2,2-Trifluoroethylamino)-4-(4-fluoro-2-methylphenyl)-8-(2-fluorophenyl)-8H-pyrido[2,3-d]pyrimidin-7-one The product of Example 59 (200 mg, 0.47 mmol) and trifluoroethylamine (200 mg, 2 mmol) were dissolved in THF (7 ml) and sealed in a vial under Ar. The mixture was heated in an oil bath to 60° for 4 days. The solvents were removed in vacuo, and the residue was flash chromatographed with 60-90% CH₂Cl₂/hexane. Recrystallization from CH₂Cl₂/hexane gave the title compound as a white crystalline solid. mp 187-188°, LC MS m/z=447(MH+) Retention time=2.27 min.

Example 151

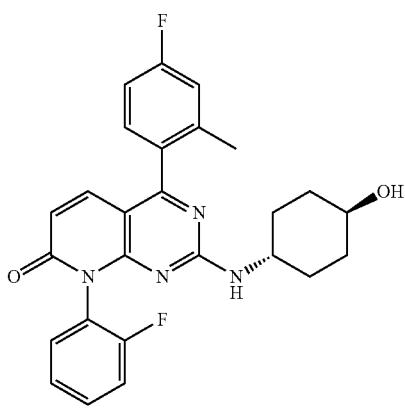

trans-2-(4-Hydroxycyclohexylamino)-4-(4-fluoro-2-methylphenyl)-8-(2-fluorophenyl)-8H-pyrido[2,3-d]pyrimidin-7-one The product of Example 59 (200 mg, 0.47 mmol), trans-4-aminocyclohexanol hydrochloride (151 mg, 1 mmol), and triethylamine (0.28 mL, 2 mmol) were combined in THF (10 mL) and stirred under Ar at 50° for 2 days. The solvents were removed in vacuo, and the residue was partitioned between EtOAc and H₂O. The organic phase was washed with H2O, satd aq NaCl, dried over anhyd Na₂SO₄, filtered and evaporated to give the crude product. Flash chromatography with 0-20% EtOAc/CH₂Cl₂ followed by recrystallization from CH₂Cl₂/hexane gave the product as a pale yellow crystalline solid. mp 148-151°, LC MS m/z=463 (MH+) Retention time=2.0 min.

Example 152

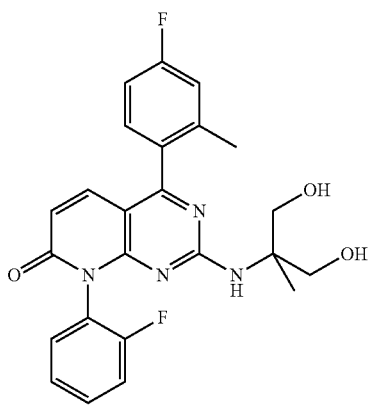

2-(1-hydroxymethyl-1-methyl-2-hydroxyethylamino)-4-(4-fluoro-2-methylphenyl)-8-(2-fluorophenyl)-8H-pyrido[2,3-d]pyrimidin-7-one The product of Example 59 (200 mg, 0.47 mmol) and 2-amino-2-methyl-1,3-propanediol (105 mg, 1 mmol) were combined in THF (10 mL) and stirred under Ar at 50° for 3 days. The solvents were removed in vacuo, and the residue was flash chromatographed with 0-25% EtOAc/CH₂Cl₂ Recrystallization from CH₂Cl₂/hexane gave the title compound as a white-crystalline solid. mp 160-162°, LC MS m/z=453 (MH+) Retention time=1.75 min Example 153

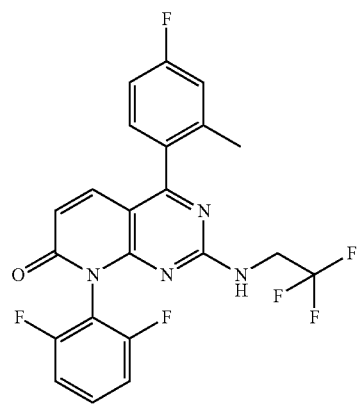

2-(2,2,2-Trifluoroethylamino)-4-(4-fluoro-2-methylphenyl)-8-(2,6-difluorophenyl)-8H-pyrido[2,3-d]pyrimidin-7-one The product of Example 48 (300 mg, 0.67 mmol) and trifluoroethylamine (300 mg, 3 mmol) were dissolved in THE (10 ml) and sealed in a vial under Ar. The mixture was heated in an oil bath to 60° for 4 days. The solvents were removed in vacuo, and the residue was flash chromatographed with 60-90% CH₂Cl₂/hexane. Recrystallization from CH₂Cl₂/hexane gave the title compound as a white crystalline solid. mp 195-196°, LC MS m/z=465(MH+) Retention time=2.38 min.

Example 154

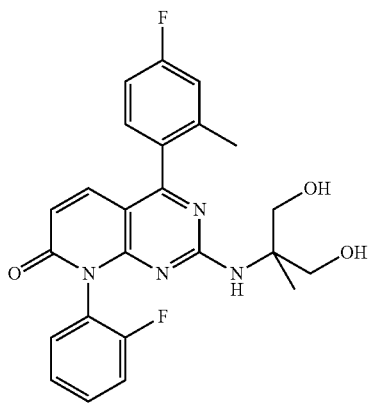

2-(1-hydroxymethyl-1-methyl-2-hydroxyethylamino)-4-(4-fluoro-2-methylphenyl)-8-(2,6-difluorophenyl)-8H-pyrido[2,3-d]pyrimidin-7-one The product of Example 48 (300 mg, 0.67 mmol) and 2-amino-2-methyl-1,3-propanediol (158 mg, 1.5 mmol) were combined in THF (10 mL) and stirred under Ar at 50° for 3 days. The solvents were removed in vacuo, and the residue was flash chromatographed with 0-25% EtOAc/CH₂Cl₂. Recrystallization from CH₂Cl₂/hexane gave the title compound as a white-crystalline solid. mp 158-160°, LC MS m/z=471 (MH+) Retention time=1.75 min.

Example 155

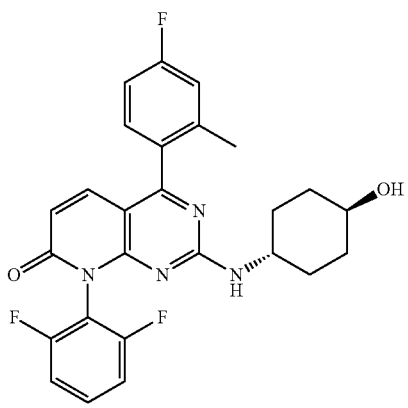

trans-2-(4-Hydroxycyclohexylamino)-4-(4-fluoro-2-methylphenyl)-8-(2,6-difluorophenyl)-8H-pyrido[2,3-d]pyrimidin-7-one The product of Example 48 (300 mg, 0.67 mmol), trans-4-aminocyclohexanol hydrochloride (226 mg, 1.5 mmol), and triethylamine (0.42 mL, 3 mmol) were combined in THF (15mL) and stirred under Ar at 50° for 2 days. The solvents were removed in vacuo, and the residue was partitioned between EtOAc and H$_2$O. The organic phase was washed with H$_2$O, satd aq NaCl, dried over anhyd Na$_2$SO$_4$, filtered and evaporated to give the crude product. Flash chromatography with 0-20% EtOAc/CH$_2$Cl$_2$ followed by recrystallization from CH$_2$Cl$_2$/hexane gave the product as a white-crystalline solid. mp 158-160°, LC MS m/z=481 (MH+) Retention time=2.08 min.

Example 156

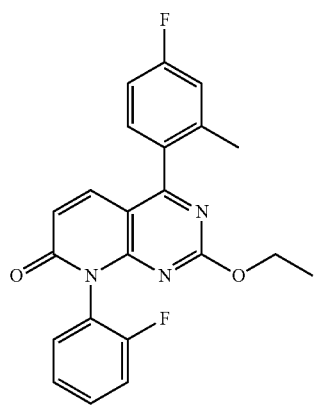

2-Ethoxy-4-(4-fluoro-2-methylphenyl)-8-(2-fluorophenyl)-8H-pyrido[2,3-d]pyrimidin-7-one The product of Example 59 (200 mg, 0.47 mmol) was placed in EtOH (10 mL) and the mixture stirred under Ar. Approximately 2 mL of the ethanol was distilled off to dry the mixture. When the mixture was cooled to 23°, some of the starting material sulfone crystallized out. NaH (11.5 mg, 0.46 mmol) was added. The reaction did not go to completion, so additional NaH (4 mg, 0.16 mmol) was added. The solvent was removed in vacuo, and the residue was flash chromatographed on silica gel eluted with 60-100% CH$_2$Cl$_2$/hexane. Recrystallization from CH$_2$Cl$_2$/hexane gave the title compound as a white crystalline solid. mp 137-139°, LC MS m/z=394(MH+) Retention time=2.32 min.

Example 157

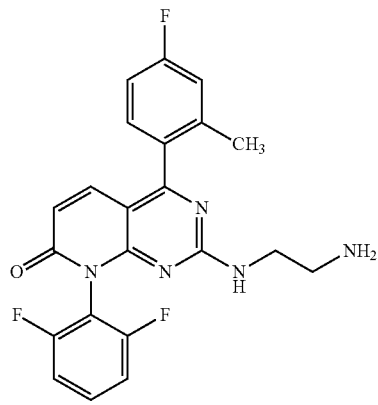

8-(2,6-Difluorophenyl)-4-(4-fluoro-2-methylphenyl)-2-[(2-aminoethyl)amino]-8H-pyrido[2,3-d]pyrimidin-7-one The title compound of Example 48 [8-(2,6-difluorophenyl)-4-(4-fluoro-2-methylphenyl)-2-methanesulfonyl-8H-pyrido[2,3-d]pyrimidin-7-one] (0.89 g, 0.002 mol) in dry THF, stirring at 23°, under Ar, was treated with ethylenediamine (668 uL, 0.01 mol). The color became orange. LC MS showed no starting material after 5 min. Reaction was stripped to dryness; the residue taken up in EtOAc-H2O. The layers were separated and the aq phase adjusted to pH 10.5 with 10% NaOH. Aq phase was extracted twice with EtOAc; combined organic layers were dried (Na$_2$SO$_4$), then evaporated to give 0.762 g (89%) of the title compound as a glass. LC MS (m/e)=426 (MH+). Rt=1.52 min.

Example 158

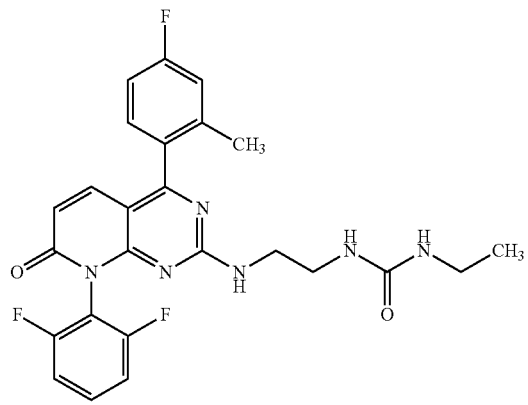

1-[2-[8-(2,6-Difluorophenyl)-4-(4-fluoro-2-methylphenyl)-7-oxo-7,8-dihydro-pyrido[2,3-d]pyrimidin-2-ylamino]ethyl]-3-ethylurea The product of Example 157 (42.5 mg., 0.0001 mol) stirring at 23° in dry THF (5 mL), under Ar, was treated with ethyl isocyanate (9.6 mg, 0.0001 mol) in one portion. After 30 min., the resulting red solution was stripped to dryness; taken up in methylene chloride (5 mL) and applied to a Chromatotron™ Rotor Plate (1000 u thickness); plate eluted with methylene chloride-methanol gradient (0% to 2% MeOH), to afford 30 mg (60.4%) of pure title compound. (m.p. 130°-133°). LC MS (m/e)=497 (MH+). Rt=2.04 min.

Example 159

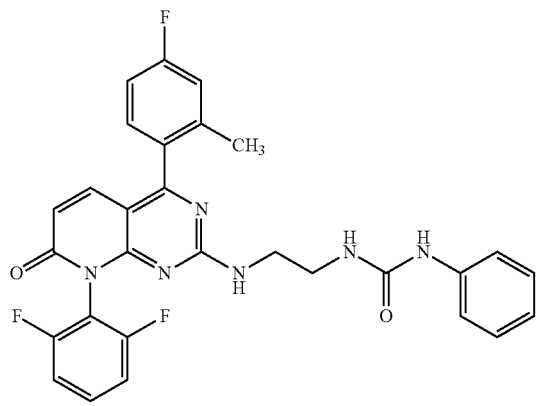

1-[2-[8-(2,6-Difluorophenyl)-4-(4-fluoro-2-methylphenyl)-7-oxo-7,8-dihydro-pyrido[2,3-d]pyrimidin-2-ylamino]ethyl]-3-phenylurea The title compound from Example 157 (42.3 mg, 0.0001 mol) was treated with phenylisocyanate (11.9 mg, 0.00011 mol) in the same manner as described in Example 158. Purification afforded 43 mg (79%) of the title compound as a red solid (m.p. 142°-148°) LC MS (m/e)=545 (MH+). Rt=2.34 min.

Example 160

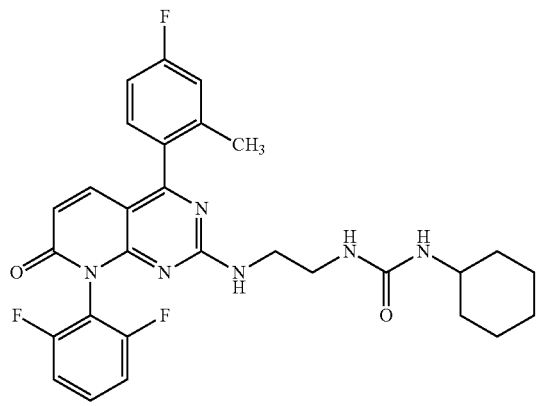

1-[2-[8-(2,6-Difluorophenyl)-4-(4-fluoro-2-methylphenyl)-7-oxo-7,8-dihydro-pyrido[2,3-d]pyrimidin-2-ylamino]ethyl]-3-cyclohexylurea The title compound from Example 157 (42.3 mg, 0.0001 mol) was treated with cyclohexylisocyanate (12.5 mg, 0.00011 mol) in the same manner as described in Example 158. Purification afforded 43 mg (78%) of the title compound as a red solid (m.p. 178°-183°) LC MS (m/e)=551 (MH+). Rt=2.38 min.

Example 161

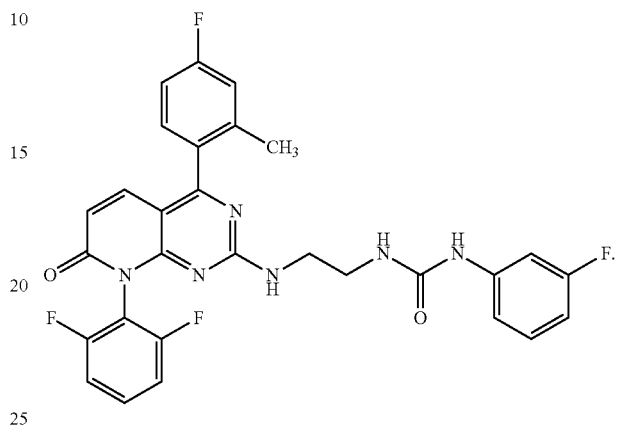

1-[2-[8-(2,6-Difluorophenyl)-4-(4-fluoro-2-methylphenyl)-7-oxo-7,8-dihydro-pyrido[2,3-d]pyrimidin-2-ylamino]ethyl]-3-[3-fluorophenyl]urea The title compound from Example 157 (42.3 mg, 0.0001 mol) was treated with 3-fluorophenylisocyanate (12 mg, 0.0001 mol) in the same manner as described in Example 158. Purification afforded 38 mg (67.6%) of the title compound as a light yellow solid (m.p. 131°-144°) LC MS (m/e)=563 (MH+). Rt=2.22 min.

Example 162

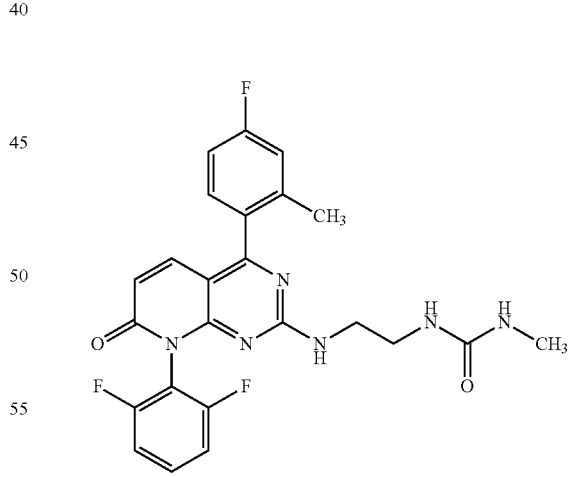

8-(2,6-Difluorophenyl)-4-(4-fluoro-2-methylphenyl)-2-[1-(2-aminoethyl)-3-methylureido]-8H-pyrido[2,3-d]pyrimidin-7-one The title compound from Example 157 (150 mg, 0.00035 mol) was treated with methylisocyanate (22 uL, 21.6 mg, 0.00035 mol) in the same manner as described in Example 158. Purification afforded 100.5 mg (59%) of the title compound as a light red solid (m.p. 124°-133°) LC MS (m/e)=452 (MH+). Rt=1.85 min.

Example 163

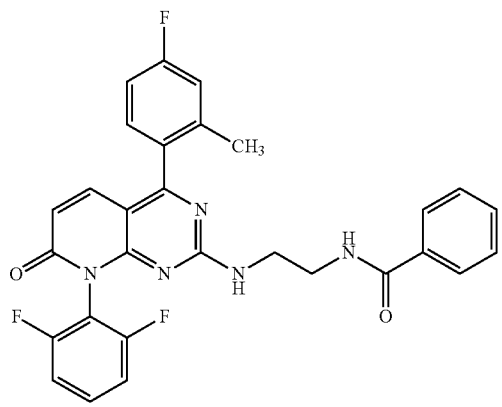

8-(2,6-Difluorophenyl)-4-(4-fluoro-2-methylphenyl)-2-[N-(2-aminoethyl)-3-benzamido]-8H-pyrido[2,3-d]pyrimidin-7-one The title compound from Example 157 (300 mg, 0.00071 mol) in dry THF (10 mL) was treated with stirring, under Ar, with triethylamine (78.8 mg, 109 uL, 0.00078 mol) followed by benzoyl chloride (119 mg, 99 uL, 0.00085 mol). The mixture was stirred for 18 h at 23°; stripped to dryness, then taken up in methylene chloride (5 mL) and applied to a Chromatotron™ Rotor Plate (2000 u thickness); plate eluted with methylene chloride-methanol gradient (0% to 2% MeOH). This afforded 141 mg (37.5%) of the title compound as a off white solid. (m.p. 246°-248°) LC MS (m/e)=530 (MH+). Rt=2.25 min.

Example 164

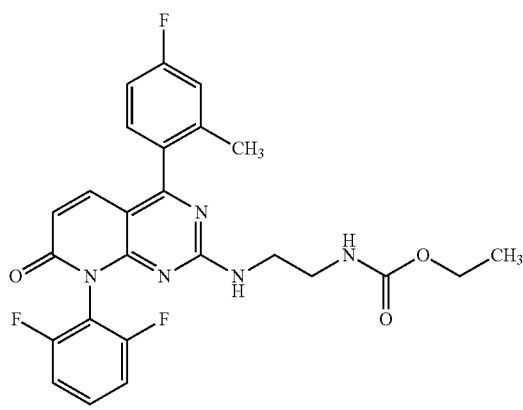

8-(2,6-Difluorophenyl)-4-(4-fluoro-2-methylphenyl)-2-[N-(2-aminoethyl)-carbamic acid ethyl ester)]-8H-pyrido[2,3-d]pyrimidin-7-one The title compound from Example 157 (300 mg, 0.00071 mol) was treated in the same manner as described in Example 163 using ethyl chloroformate (91.8 mg, 81.2 uL, 0.00085 mol) as the chlorocarbonyl reagent. Purification of the crude product afforded 64 mg (18%) of the title compound as a light brown solid.) (m.p. 91°-109°) LC MS (m/e)=4.98 (MH+). Rt=2.09 min.

Example 165

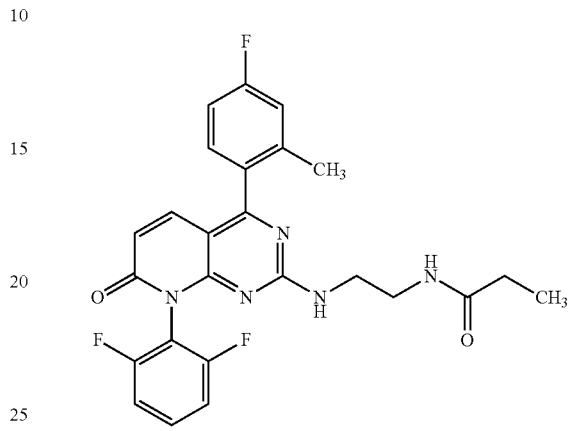

8-(2,6-Difluorophenyl)-4-(4-fluoro-2-methylphenyl)-2-[N-(2-aminoethyl)-propanamido)]-8H-pyrido[2,3-d]pyrimidin-7-one The title compound from Example 157 (300 mg, 0.00071 mol) was treated in the same manner as described in Example 163 using propanoic anhydride (110 mg, 110 uL, 0.00085 mol) as the acylating reagent. Purification of the crude product afforded 180 mg (53%) of the title compound as a off white solid. (m.p. 214°-16°) LC MS (m/e)=482 (MH+). Rt=1.95 min.

Example 166

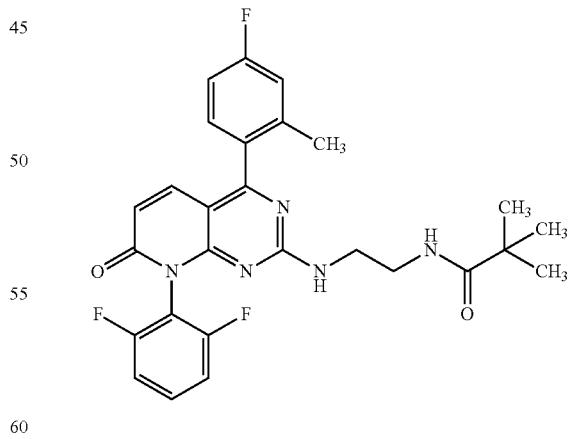

8-(2,6-Difluorophenyl)-4-(4-fluoro-2-methylphenyl)-2-[N-(2-aminoethyl)-2,2-dimethylpropanamido)]-8H-pyrido[2,3-d]pyrimidin-7-one The title compound from Example 157 (300 mg, 0.00071 mol) was treated in the same manner as described in Example 163 using 2,2-dimethylpropanoyl chloride (102 mg, 104 uL, 0.00085 mol) as the acylating reagent. Purification of the crude product afforded 149 mg (41%) of the title compound as a off white solid.) (m.p. 111°-133°) LC MS (m/e)=510 (MH+). Rt=2.14 min.

Example 167

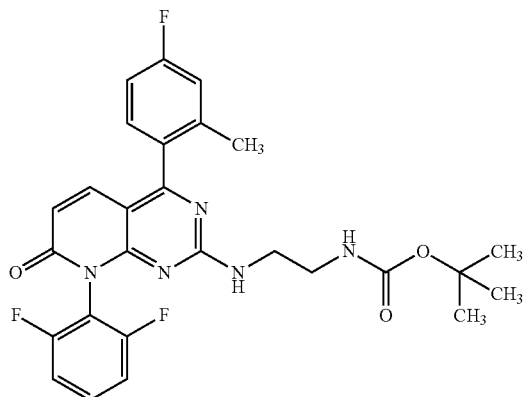

8-(2,6-Difluorophenyl)-4-(4-fluoro-2-methylphenyl)-2-[N-(2-aminoethyl)-carbamic acid tert-butyl ester)]-8H-pyrido[2,3-d]pyrimidin-7-one The title compound from Example 157 (300 mg, 0.00071 mol) was treated in the same manner as described in Example 163 using di-tert-butyl dicarbonate (185 mg, 0.00085 mol) as the reagent for carbamate formation; triethylamine was omitted from this reaction. Purification of the crude product afforded 210 mg (56%) of the title compound as a off white solid. (m.p.106°-119°) LC MS (m/e)=526 (MH+). Rt=2.30 min.

Example 168

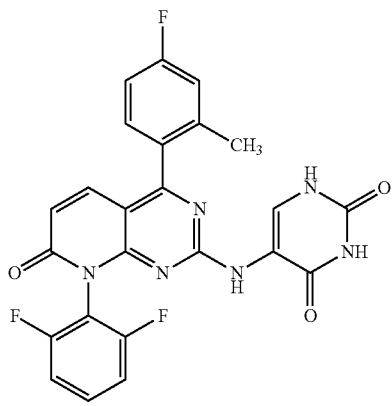

8-(2,6-Difluorophenyl)-4-(4-fluoro-2-methylphenyl)-2-(N-aminouracil-5-yl)-8H-pyrido[2,3-d]pyrimidin-7-one The title compound of Example 48 [8-(2,6-difluorophenyl)-4-(4-fluoro-2-methylphenyl)-2-methanesulfonyl-8H-pyrido[2,3-d]pyrimidin-7-one] (100 mg, 0.000225 mol) and 5-aminouracil (70 mg, 0.00055 mol) were taken up in dry DMSO (1.5 mL) and, with stirring under Ar, warmed to 65° for 6.5 h. Reaction was cooled to 23°, then diluted with EtOAc; solution was washed with H₂O; the aq phase was extracted with EtOAc; combined organic layers were dried (Na₂SO₄) then evaporated to an amber glass. This glass was crystallized from a small amount of MeOH, which crystals when dried afforded 15 mg (14%) of the title compound as a light yellow crystalline solid. (m.p. >300°) LC MS (m/e)=493 (MH+). Rt=1.82 min.

Example 169

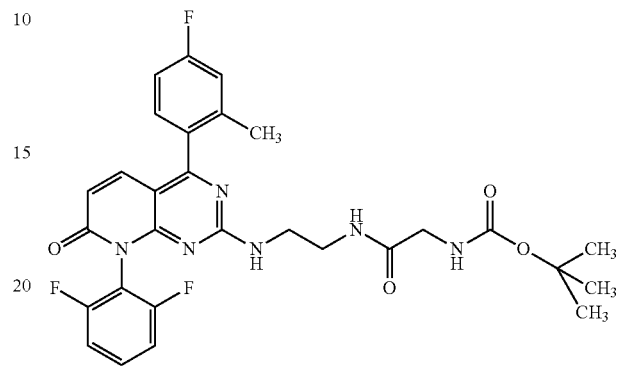

8-(2,6-Difluorophenyl)-4-(4-fluoro-2-methylphenyl)-2-N-(2-aminoethyl)-N'-(t-Butoxycarbonylglycyl-)-8H-pyrido[2,3-d]pyrimidin-7-one The title compound of Example 157 (168 mg, 0.0004 mol) in dry THF (2 mL) with tert-butoxycarbonylglycine (70 mg, 0.0004 mol) was treated with dicyclohexylcarbodiimide (82.4 mg, 0.0004 mol) in dry THF (2 mL). The solution was stirred 16h at 23°; filtered and stripped to dryness. The residue was taken up in methylene chloride (5 mL) and applied to a Chromatotron™ Rotor Plate (1000 u thickness); plate eluted with methylene chloride-methanol gradient (0% to 3% MeOH). This afforded 122 mg (52%) of the title compound as a light red solid. LC MS (m/e)=583(MH+). Rt=2.12 min.

Example 170

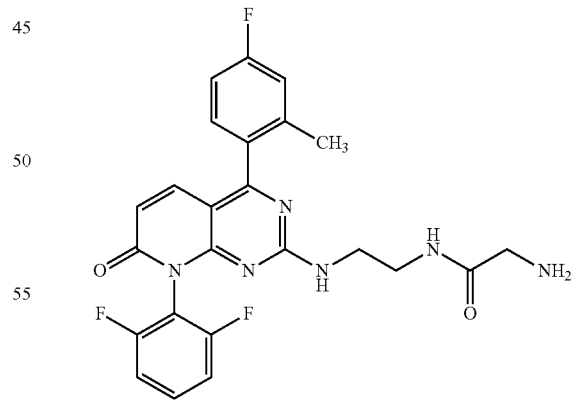

8-(2,6-Difluorophenyl)-4-(4-fluoro-2-methylphenyl)-2-[N-(2-aminoethyl)-N'-glycyl]-8H-pyrido[2,3-d]pyrimidin-7-one The title compound of Example 169 (80 mg, 0.000137 mol) was taken up in methylene chloride (2 mL); TFA (2 mL)

was added and the solution stirred for 0.5 hrs at 23° giving a pale amber solution. This was evaporated to an amber residue which was triturated with ethyl ether to give a solid. Solid was collected and dried in vacuo to afford the title compound as the ditrifluoroacetic acid salt, an off white solid 60 mg (62%). LC MS (mle)=483(MH+). Rt=1.55 min.

Example 171

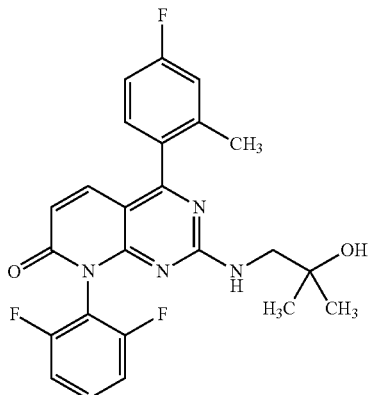

8-(2,6-Difluorophenyl)-4-(4-fluoro-2-methylphenyl)-2-[N-([2,2-dimethyl-2-hydroxy]ethylamino)]-8H-pyrido[2,3-d]pyrimidin-7-one The title compound of Example 48 (150 mg, 0.000337 mol) in dry THF (5 mL) was treated with 2,2-dimethylethanolamine (50 mg., 50 uL, 0.00067 mol) [Prepared by the method of Bijaya L. Rai et al., J. Med. Chem. 1998, 41, 3347]. stirred at 23°; reaction progress monitored by LC MS. Reaction was stripped to dryness; the residue was taken up in methylene chloride (5 mL) and applied to a Chromatotron™ Rotor Plate (2000 u thickness); plate eluted with methylene chloride-methanol gradient (0% to 1.5% MeOH). This afforded 116 mg (69%) of pure title compound as an off white solid. LC MS (m/e)=455 (MH+). Rt=1.99 min.

Example 172

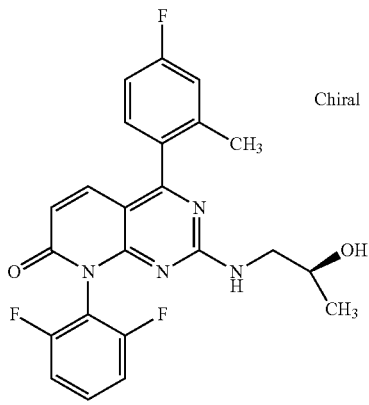

S-(+)-8-(2,6-Difluorophenyl)-4-(4-fluoro-2-methylphenyl)-2-[N-(1-Amino-2-propanol)]-8H-pyrido[2,3-d]pyrimidin-7-one The title compound of Example 48 (150 mg, 0.000337 mol) in dry THF (5 mL) was treated with S-(+)-1-amino-2-propanol (76 mg., 79 uL, 0.00098 mol) and stirred at 23°; reaction progress monitored by LC MS. Reaction was stripped to dryness; the residue was taken up in methylene chloride (5 mL) and applied to a Chromatotron™ Rotor Plate (2000 u thickness); plate eluted with methylene chloride-methanol gradient (0% to 1.5% MeOH). This afforded 76 mg (51%) of pure title compound as an off white solid. LC MS (m/e)=441 (MH+). Rt=1.94 min.

Example 173

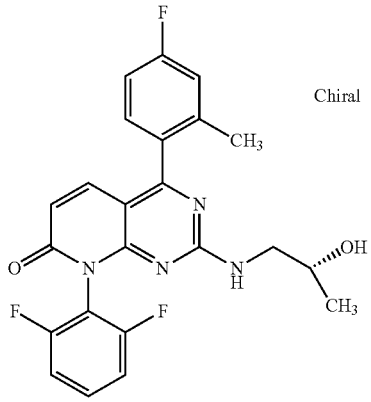

R-(−)-8-(2,6-Difluorophenyl)-4-(4-fluoro-2-methylphenyl)-2-[N-(1-Amino-2-propanol)]-8H-pyrido[2,3-d]pyrimidin-7-one The title compound of Example 48 (150 mg, 0.000337 mol) in dry THF (5 mL) was treated with R-(−)-1-amino-2-propanol (50.5 mg., 54 uL, 0.00067 mol) and stirred at 23°; reaction progress monitored by LC MS. Reaction was stripped to dryness; the residue was taken up in methylene chloride (5 mL) and applied to a Chromatotron™ Rotor Plate (2000 u thickness); plate eluted with methylene chloride-methanol gradient (0% to 1.5% MeOH). This afforded 89 mg (60%) of pure title compound as an off white solid. LC MS (m/e)=441 (MH+). Rt=1.94 min.

Example 174

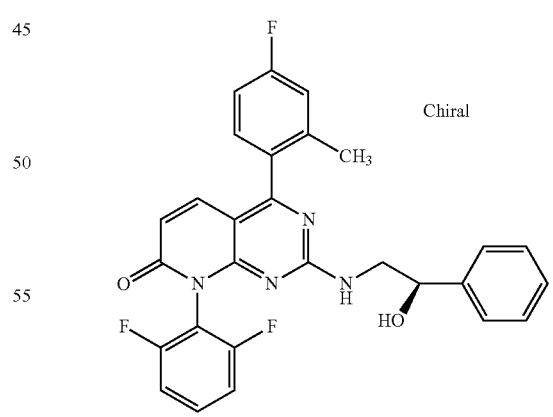

(R)-8-(2,6-Difluorophenyl)-4-(4-fluoro-2-methylphenyl)-2-[N-(1-amino-2-hydroxy-2-phenylethyl)]-8H-pyrido[2,3-d]pyrimidin-7-one The title compound of Example 48 (150 mg, 0.000337 mol) in dry THF (5 mL) was treated with R-2-Amino-1- phenylethanol (93 mg., 0.00067 mol) and stirred at 23°; reaction progress monitored by LC MS. Reaction was stripped to dryness; the residue was taken up in methylene chloride (5 mL) and applied to a Chromatotron™ Rotor Plate (2000 u thickness); plate eluted with methylene chloride-methanol gradient (0% to 1.5% MeOH). This afforded 108 mg (64%) of pure title compound as a light orange gum. LC MS (m/e)=503 (MH+). Rt=2.20 min.

Example 175

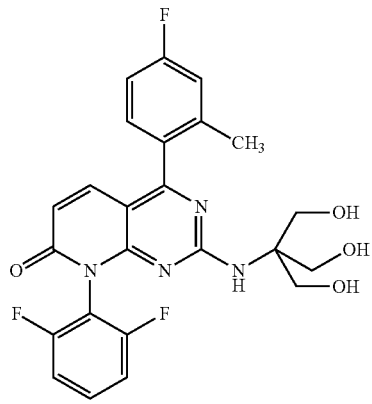

8-(2,6-Difluorophenyl)-4-(4-fluoro-2-methylphenyl)-2-[N-trihydroxy-methylaminomethyl]-8H-pyrido[2,3-d]pyrimidin-7-one The title compound of Example 48 (150 mg, 0.000337 mol) and TRIS (trihydroxymethylaminomethane) (121 mg, 0.0001 mol) in N-methylpyrrolidinone (1.5 mL) was microwaved at 180° for 2 min (with a 3 min ramp up) at 300 watts with a MARS 5™ Microwave (CEM Corporation). No starting material remained as monitored by LC MS. The solvent was stripped off at pump vacuum and the residue was taken up in methylene chloride (5 mL) and applied to a Chromatotron™ Rotor Plate (2000 u thickness); plate eluted with methylene chloride-methanol gradient (0% to 1.5% MeOH). This afforded 42 mg (26%) of pure title compound as a light brown solid. LC MS (m/e)=487 (MH+). Rt=1.55 min.

Example 176

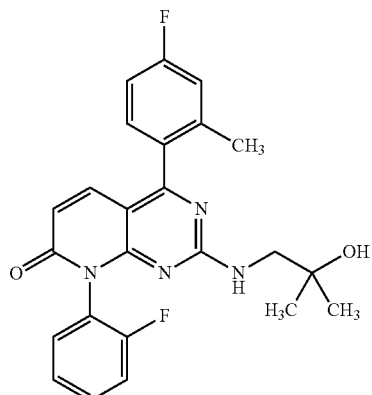

8-(2-Fluorophenyl)-4-(4-fluoro-2-methylphenyl)-2-[N-([2,2-dimethyl-2-hydroxy]ethylamino)]-8H-pyrido[2,3-d]pyrimidin-7-one The title compound of Example 59 (144 mg, 0.000337 mol) in dry THF (5 mL) was treated with 2,2-dimethylethanolamine (50 mg., 50 uL, 0.00067 mol) [Prepared by the method of Bijaya L. Rai et al., J. Med. Chem. 1998, 41, 3347] and stirred at 23°; reaction progress monitored by LC MS. Reaction was stripped to dryness; the residue was taken up in methylene chloride (5 mL) and applied to a Chromatotron™ Rotor Plate (2000 u thickness); plate eluted with methylene chloride-methanol gradient (0% to 1.5% MeOH). This afforded 106 mg (72%) of pure title compound as an off white solid. LC MS (m/e)=437 (MH+). Rt=1.92 min Example 177

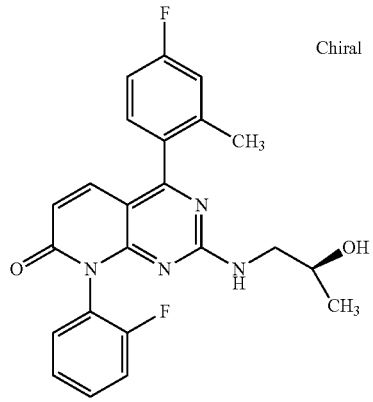

(S)-(+)-8-(2-Fluorophenyl)-4-(4-fluoro-2-methylphenyl)-2-[N-([2-methyl-2-hydroxy]ethylamino)]-8H-pyrido[2,3-d]pyrimidin-7-one The title compound of Example 59 (144 mg, 0.000337 mol) in dry THF (5 mL) was treated with S-(+)-1-amino-2-propanol (76 mg., 79 uL, 0.00098 mol) and stirred at 23°; reaction progress monitored by LC MS. Reaction was stripped to dryness; the residue was taken up in methylene chloride (5 mL) and applied to a Chromatotron™ Rotor Plate (2000 u thickness); plate eluted with methylene chloride-methanol gradient (0% to 1.5% MeOH). This afforded 132 mg (93%) of pure title compound as a pale yellow solid. LC MS (m/e)=423 (MH+). Rt=1.82 min Example 178

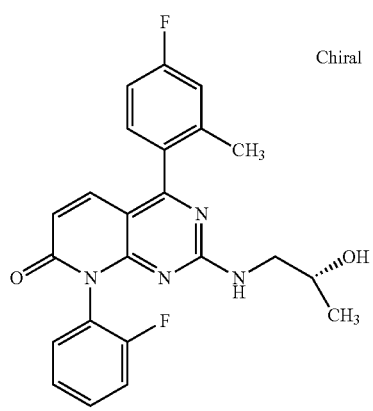

(R)-(−)-8-(2-Fluorophenyl)-4-(4-fluoro-2-methylphenyl)-2-[N-([2-methyl-2-hydroxy]ethylamino)]-8H-pyrido[2,3-d]pyrimidin-7-one The title compound of Example 59 (150 mg, 0.000337 mol) in dry THF (5 mL) was treated with R-(−)-1-amino-2-propanol (50.5 mg., 54 uL, 0.00067 mol) and stirred at 23°; reaction progress monitored by LC MS. Reaction was stripped to dryness; the residue was taken up in methylene chloride (5 mL) and applied to a Chromatotron™ Rotor Plate (2000 u thickness); plate eluted with methylene chloride-methanol gradient (0% to 1.5% MeOH). This afforded 151 mg (Quant.) of pure title compound as a pale yellow gum. LC MS (m/e)=423 (MH+). Rt=1.84 min.

Example 179

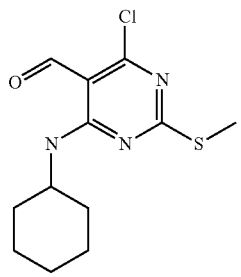

4-Chloro-2-methylsulfanyl-6-cyclohexylaminopyrimidine-5-carboxaldehyde 4,6-Dichloro-2-methylsulfanylpyrimidine-5-carboxaldehyde (4.0 g, 0.018 mol) in acetonitrile (65 mL) was treated with rapid stirring with cyclohexylamine (3.76 g, 4.3 mL, 0.038 mol) over 1 min. Reaction stirred 16 h then diluted with 3 volumes of $H_2O$. The precipitated solid was collected, washed with $H_2O$ and dried in vacuo to afford 5.1 g. (99%) of the title compound as a white solid. LC MS (m/e)=286 (MH+). Rt=2.85 min.

Example 180

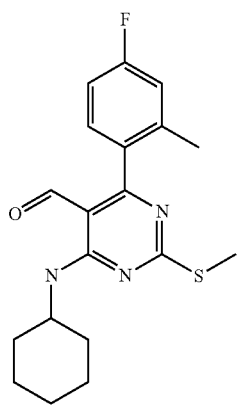

2-Methylsulfanyl-4-(2-methyl-4-fluorophenyl)-6-cyclohexylaminopyrimidine-5-carbaldehyde A mixture of the title compound from Example 180 (5.1 g., 0.018 mol), 2-methyl-4-fluoroboronic acid (5.54 g., 0.036 mol), $Na_2CO_3$ (3.82 g, 0.036 mol), tetrakis(triphenylphosphine)palladium (0), dioxane (100 mL) and $H_2O$ (50 mL), stirring under Ar, was warmed to 65° and stirred 16 h. Reaction was cooled to 23°; diluted with EtOAc, and the mixture washed in turn with $H_2O$, aq $NaHCO_3$, and satd aq NaCl. Organic phase was dried ($Na_2SO_4$), then stripped to a viscous syrup. The syrup was crystallized from a small amount of MeOH with sonication and gentle warming. This afforded 5.5 g (86%) of the title compound as a white solid. LC MS (m/e)=360 (MH+). Rt=3.00 min.

Example 181

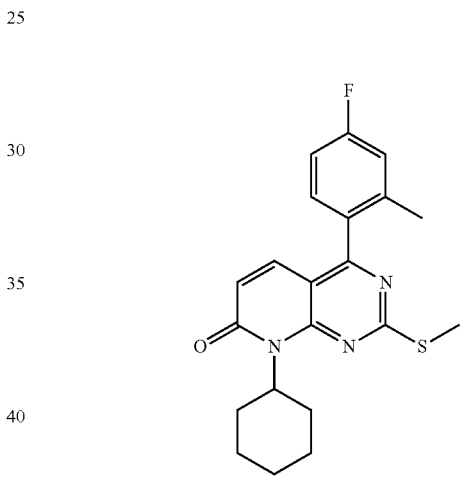

8-Cyclohexyl-4-(4-fluoro-2-methylphenyl)-2-methylthio-8H-pyrido[2,3-]pyrimidin-7-one Triethylphosphonoacetate (3.87 mL, 0.01953 mol) in dry THF (56 mL) was treated with NaH (60% in mineral oil) (967.5 mg, 0.0243 mol). The mixture was stirred for 30 min giving a clear solution. The title compound from Example 180 (4.5 g, 0.0125 mol) in dry THF (75 mL) was added in one portion and the solution gently refluxed for 72 h. After cooling to 23°, the reaction mixture was diluted with ethyl ether, then washed in turn with satd aq $NH_4Cl$ and $H_2O$. Organic layer was dried ($Na_2SO_4$), then evaporated to a viscous syrup which was flash chromatographed in methylene chloride-hexane gradient (20% to 0% hexane) to afford first 920 mg (19%) of the title compound as a white solid. LC MS (m/e)= 384 (MH+). Rt=2.79 min.

Example 182

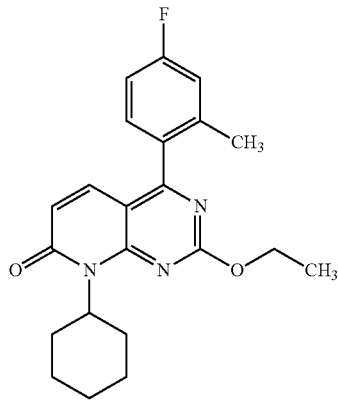

8-Cyclohexyl-4-(4-fluoro-2-methylphenyl)-2-ethoxy-8H-pyrido[2,3-d]pyrmidin-7-one The column of Example 181 was eluted with additional methylene chloride/hexane to afford 580 mg (12.2%) of the title compound of the present example as a white solid. LC MS (m/e)=382 (MH+). Rt=2.67 min Example 183

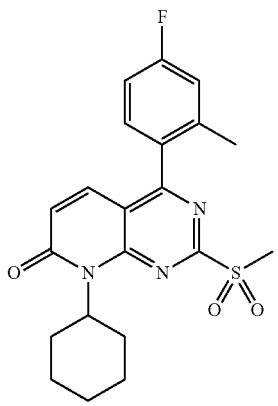

8-Cyclohexyl-4-(4-fluoro-2-methylphenyl)-2-methanesulfonyl-8H-pyrido[2,3-d]pyrimidin-7-one The title compound from Example 181 (850 mg, 0.0022 mol) stirring in methylene chloride (100 mL) was treated with m-chloroperbenzoic acid (77%) (992 mg, 0.0044 mol). Solution stirred overnight at 23°. LC MS showed about 90% conversion to the title compound, therefore, an additional 120 mg of m-chloroperbenzoic acid was added to the reaction. After 1 h, the reaction was washed in turn with 5% Na$_2$CO$_3$, then satd aq NaCl, dried (Na$_2$SO$_4$). Methyl sulfide (0.5 mL) was added to quench any excess peroxides. Solution was stripped to give 0.96 g, (quant.) of the title compound as a white solid. LC MS (m/e)=416 (MH+). Rt=2.24 min Example 184

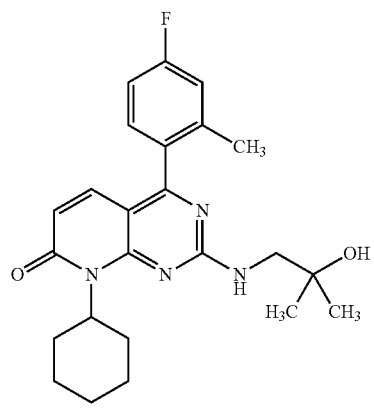

8-Cyclohexyl-4-(4-fluoro-2-methylphenyl)-2-[N-2,2-dimethylethanolamino]-8H-pyrido[2,3-d]pyrimidin-7-one The title compound of Example 183 (150 mg, 0.00036 mol) in dry THF (2.5 mL) was treated with 2,2-dimethylethanolamine (64 mg., 64 uL, 0.00072 mol). [Prepared by the method of Bijaya L. Rai et al., J. Med. Chem. 1998, 41, 3347] and stirred at 23°, 16 h; reaction progress monitored by LC MS. Reaction was stripped to dryness; the residue was taken up in methylene chloride (5 mL) and applied to a Chromatotron™ Rotor Plate (2000 u thickness); plate eluted with methylene chloride-methanol gradient (0% to 2% MeOH to afford 107 mg (70%) of pure title compound as a colorless glass. LC MS (m/e)=425 (MH+). Rt=2.22 min Example 185

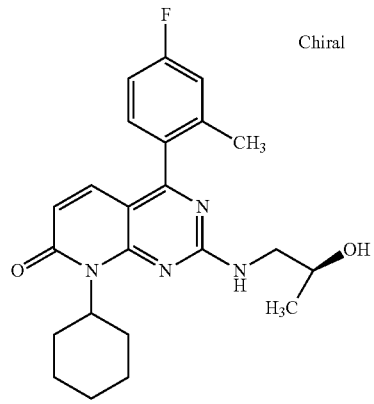

(S)-(+)-8-Cyclohexyl-4-(4-fluoro-2-methylphenyl)-2-[N-1-amino-2-hydroxypropanyl]-8H-pyrido[2,3-d]pyrimidin-7-one The title compound of Example 183 (150 mg, 0.00036 mol) in dry THF (2.5 mL) was treated with S-(+)-1-amino-2- propanol (76 mg., 79 uL, 0.00098 mol) and stirred at room temperature; reaction progress monitored by LC MS. Reaction warmed 15 h at 90° Reaction was stripped to dryness; the residue was taken up in methylene chloride (5 mL) and applied to a Chromatotron™ Rotor Plate (2000 u thickness); plate eluted with methylene chloride-methanol gradient (0% to 2% MeOH). This afforded 118 mg (80%) of pure title compound as a colorless gum. LC MS (m/e)=411 (MH+). Rt=2.10 min.

Example 186

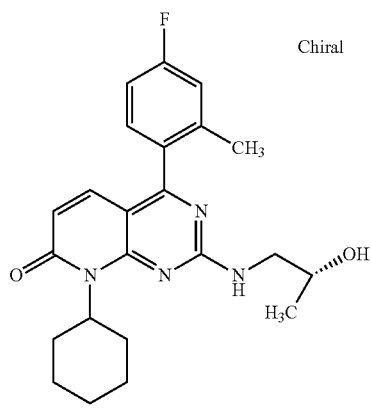

(R)-(−)-8-Cyclohexyl-4-(4-fluoro-2-methylphenyl)-2-[N-1-amino-2-hydroxypropanyl]-8H-pyrido[2,3-d]pyrimidin-7-one The title compound of Example 183 (150 mg, 0.00036 mol) in dry THF (2.5 mL) was treated with R-(−)-1-amino-2-propanol (54 mg., 58 uL, 0.00072 mol) and stirred at 23° 16 h; reaction progress monitored by LC MS. Reaction was stripped to dryness; the residue was taken up in methylene chloride (5 mL) and applied to a Chromatotron™ Rotor Plate (2000 u thickness); plate eluted with methylene chloride-methanol gradient (0% to 2% MeOH) to afford 158 mg (Quant.) of pure title compound as a colorless gum. LC MS (m/e)=411 (MH+). Rt=2.12 min Example 187

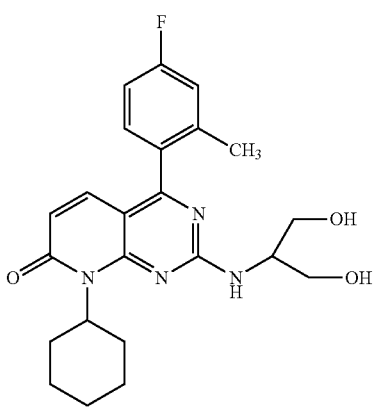

8-Cyclohexyl-4-(4-fluoro-2-methylphenyl)-2-[N-dihydroxymethylmethylamino]-8H-pyrido[2,3-d]pyrimidin-7-one The title compound of Example 183 (150 mg, 0.00036 mol) in dry THF (2.5 mL) was treated with serinol (62 mg., 0.000674 mol) and warmed at 90° 16 h; reaction progress monitored by LC MS. Reaction was stripped to dryness; the residue was taken up in methylene chloride (5 mL) and applied to a Chromatotron™ Rotor Plate (2000 u thickness); plate eluted with methylene chloride-methanol gradient (0% to 2% MeOH). This afforded 163 mg (Quant.) of pure title compound as a colorless gum. LC MS (m/e)=427 (MH+). Rt=1.75 min Example 188

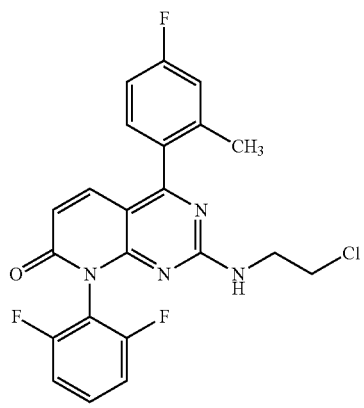

8-(2,6-Difluorophenyl)-4-(4-fluoro-2-methylphenyl)-2-[N-(2-chloroethylamino)]-8H-pyrido[2,3-d]pyrimidin-7-one The title compound from Example 48 (890 mg, 0.002 mol) in dry DMF (18 mL) was treated with stirring 2-chloroethylamine (345 mg, 0.003 mol) and $K_2CO_3$ (207 mg, 0.0015 mol). The mixture was stirred 16 h at 23°. The reaction was stripped to a residue; taken up in EtOAc; washed with $H_2O$ (2×); organic extract dried ($Na_2SO_4$), then evaporated to a brown gum. This residue was taken up in methylene chloride (5 mL) and applied to a Chromatotron™ Rotor Plate (2000 u thickness); plate eluted with methylene chloride. This afforded 510 mg of the title compound with improved purity. This compound was then taken up in acetonitrile (2 mL) and sonicated to give a white crystalline solid. Solid was collected and dried to give 280 mg (31.5%) of pure title compound. LC MS (m/e)=445 (MH+). Rt=2.44 min.

Example 189

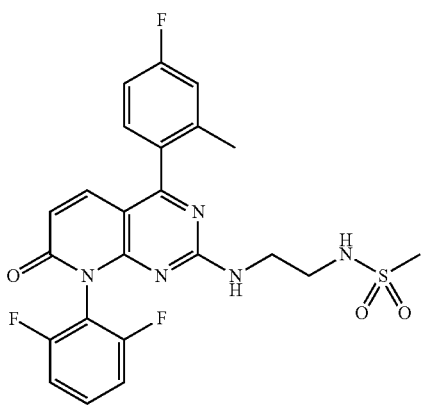

N-[2-[[8-(2,6-Difluorophenyl)-4-(4-fluoro-2-methylphenyl)-7,8-dihydro-7-oxopyrido[2,3-d]pyrimidin-2-yl]amino]ethyl]methanesulfonamide A solution of the product of Example 157 (250 mg, 0.58 mmol), di-isopropylethylamine (111 uL, 0.64 mmol) and CH$_2$Cl$_2$ (10 mL) was cooled to −5° and methanesulfonyl chloride (50 uL, 0.64 mmol) was added and the resulting soln was warmed to 23°, stirred 15 min, diluted with CH$_2$Cl$_2$ (75 mL) and washed with 10% aq NaOH (2×20 mL) and satd aq NaCl, dried (Na$_2$SO$_4$), and concentrated to afford a brown solid. Chromatotron chromatography (CH$_2$Cl$_2$/CH$_3$OH) and crystallization from Et$_2$O afforded a pink solid. mp=105-115° (dec); LC MS (m/e)=504.2 (MH+). Rt=1.94 min

Example 190

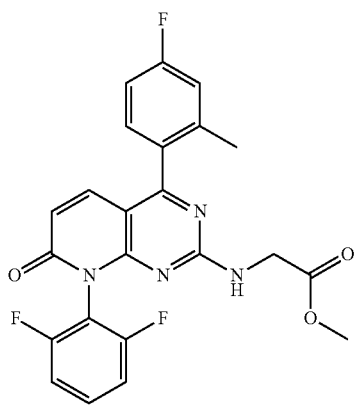

Methyl N-[8-(2,6-difluorophenyl)-4-(4-fluoro-2-methylphenyl)-7,8-dihydro-7-oxopyrido[2,3-d]pyrimidin-2-yl]glycinate The product of Example 48 (2.25 g mg, 5.0 mmol), methyl glycinate hydrochloride (3.13 g, 25.0 mmol), anhyd K$_2$CO$_3$ (3.45 g, 25.0 mmol) and NMP (25 mL) were stirred for 1 h at 60°. The reaction was diluted with EtOAc (200 mL), washed with 10% aq citric acid (2×25 mL), H$_2$O (25 mL) and satd aq NaCl (40 mL) dried (Na$_2$SO$_4$) and concentrated. The resulting brown residue was filtered through a plug of silica (350 mL) (dichloromethane/methanol) to afford a brown foam. Trituration with Et$_2$O afforded the title compound, methyl N-[8-(2,6-difluorophenyl)-4-(4-fluoro-2-methylphenyl)-7,8-dihydro-7-oxopyrido[2,3-d]pyrimidin-2-yl]glycinate as a white solid. mp=212-213°.

Example 191

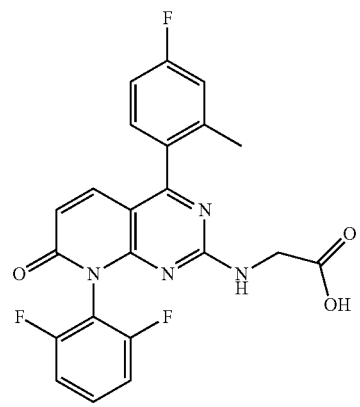

N-[8-(2,6-Difluorophenyl)-4-(4-fluoro-2-methylphenyl)-7,8-dihydro-7-oxopyrido[2,3-d]pyrimidin-2-yl] glycine The product of reaction 190 was reacted by the procedure of Example 84 to afford the title compound N-[8-(2,6-Difluorophenyl)-4-(4-fluoro-2-methylphenyl)-7,8-dihydro-7-oxopyrido[2,3-d]pyrimidin-2-yl]glycine as a white solid. mp=260-261.

Example 192

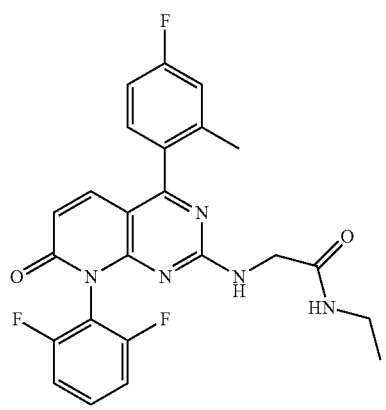

2-[[8-(2,6-Difluorophenyl)-4-(4-fluoro-2-methylphenyl)-7,8-dihydro-7-oxopyrido[2,3-d]pyrimidin-2-yl]amino]-N-ethylacetamide The product of Example 191 (50 mg, 0.11 mmol), n-hydroxybenzotriazole (21 mg, 0.34 mmol), 1-methylmorpholine (19 uL, 0.172 mmol), N-methylpyrrolidinone (2.5 mmol) were dissolved together, then 1-(3-dimethylaminopropyl)-3-ethylcarbodiimide hydrochloride (66 mg, 0.34 mmol) was added, stirred 1 h, and then ethylamine (2 M in THF) (1.0 mL, 2.0 mmol) was added and the reaction was stirred at 23° for 16 h, diluted with EtOAc (50 mL), and washed with 10% aq citric acid (2×20 mL), H$_2$O (20 mL), and satd aq NaCl (20 mL), dried (MgSO$_4$) concentrated and purified by chromatotron chromatography (CH$_2$Cl$_2$/CH$_3$OH) to afford 35 mg of the title compound 2-[[8-(2,6-difluorophenyl)-4-(4-fluoro-2-methylphenyl)-7,8-dihydro-7-oxopyrido[2,3-d]pyrimidin-2- yl]amino]-N-ethylacetamide as a white powder. mp=250-253 (dec). LC MS (m/e)=468.2 (MH+). Rt=1.87 min.

Example 193

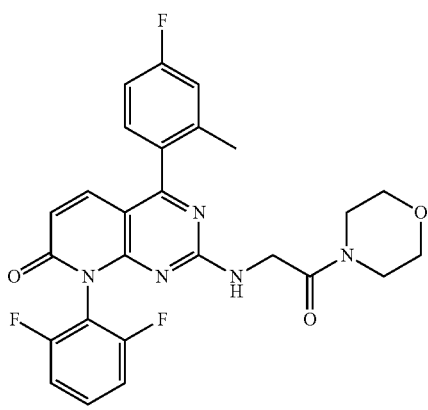

8-(2,6-Difluoro-phenyl)-4-(4-fluoro-2-methyl-phenyl)-2-(2-morpholin-4-yl-2-oxo-ethylamino)-8H-pyrido[2,3-d]pyrimidin-7-one Under Ar, a soln of morpholine (58 mg, 0.66 mmol) and trimethylaluminum (2M in toluene) (0.33 mL, 0.66 mmol) in dichloromethane was stirred for 10 min. A soln of the product of Example 190 (100 mg, 0.22 mmol) in dichloromethane (2 mL) was added. The resulting mixture was stirred for 16 h, diluted with EtOAc and washed with H$_2$O to give the crude material. Purification by Flash chromatography on silica gel, eluting with EtOAc/hexane/triethylamine (70/30/2, v/v/v), followed by recrystallization from dichloromethane and hexane, gave the desired product (35 mg, 31%). LC-MS: 510.10 (MH+, m/z), 1.96 (Rt, min).

Example 194

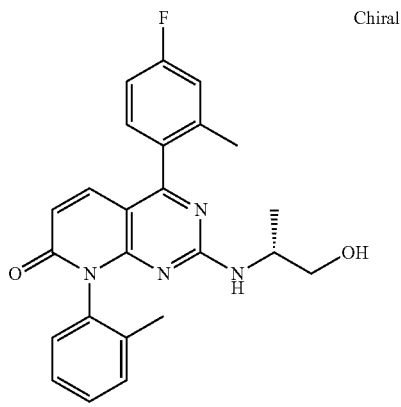

4-(4-Fluoro-2-methyl-phenyl)-2-((R)-2-hydroxy-1-methyl-ethylamino)-o-tolyl-8H-pyrido[2,3-d]pyrimidin-7-one Following the general procedure outlined in Example 126, the product of Example 121 (200 mg, 0.47 mmol) and (R)-

(−)-2-amino-1-propanol (0.18 mL, 2.36 mmol) afforded the title compound as a white solid. 170 mg (86%). LC-MS: 419.2 (MH+, m/z), 2.00 (Rt, min).

Example 195

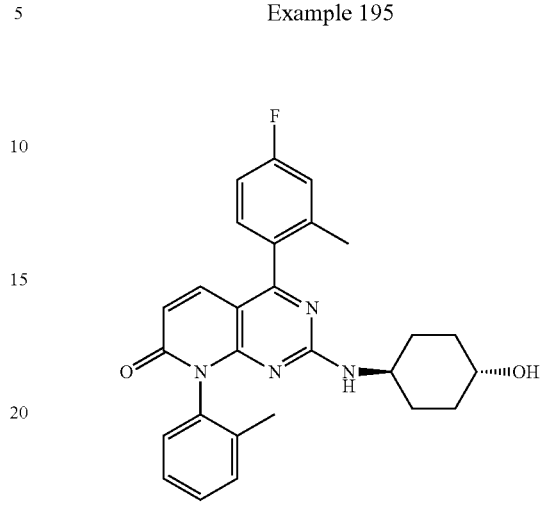

4-(4-Fluoro-2-methyl-phenyl)-2-(4-hydroxyl-cylclohexylamino)-8-o-tolyl-8H-pyrido[2,3-d]pyrimidin-7-one trans-4-Aminocyclohexanol hydrochloride (270 mg, 2.35 mmol), NMP (1 mL) and triethylamine (0.33 mL, 2.35 mmol) were stirred at 23° for 10 min. The product of Example 121 (200 mg, 0.47 mmol) was added and the mixture was stirred 2 h, diluted with EtOAc and washed with H$_2$O. Separation of the organic phase and evaporation of solvent afforded the crude material, which was purified as described in Example 126 to give the desired product 98 mg (46%). LC-MS: 459.4 (MH+, m/z), 2.12 (Rt, min).

Example 196

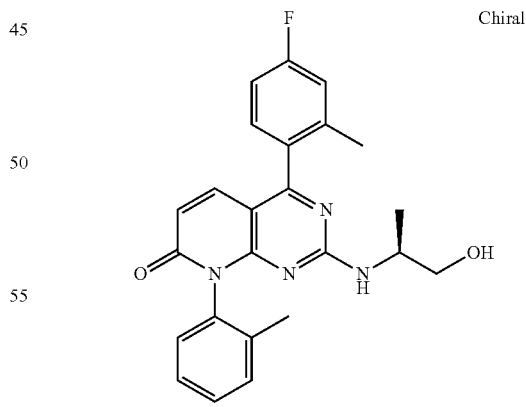

4-(4-Fluoro-2-methyl-phenyl)-2-((S)-2-hydroxy-1-methyl-ethylamino)-8-o-tolyl-8H-pyrido[2,3-d]pyrimidin-7-one Following the general procedure outlined in Example 126, the product of Example 121 (200 mg, 0.47 mmol) and (S)-

(+)-2-amino-1-propanol (0.18 mL, 2.36 mmol) afforded the desired product 185 mg (94%). LC-MS: 419.2 (MH+, m/z), 1.96 (Rt, min)

Example 197

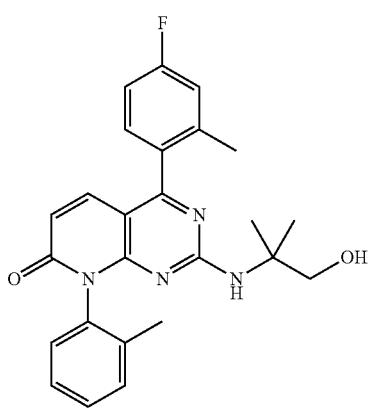

4-(4-Fluoro-2-methyl-phenyl)-2-(2-hydroxy-1,1-dimethyl-ethylamino)-8-o-tolyl-8H-pyrido[2,3-d]pyrimidin-7-one Following the general procedure outlined in Example 126, the product of Example 121 (222 mg, 0.52 mmol) and 2-amino-2-methyl-1-propanol (0.25 mL, 2.62 mmol) were reacted to give the crude material. Purification by Flash chromatography eluting with dichloromethane/ethanol/triethylamine (100/1/2, v/v/v), followed by preparative HPLC, eluting with acetonitrile/H$_2$O (10/90, v/v to 90/10, v/v, over 10 min), gave the desired product 25 mg (11%). LC-MS: 433.4 (MH+, m/z), 2.10 (Rt, min).

Example 198

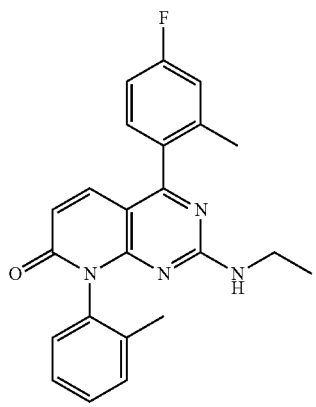

2-Ethylamino-4-(4-fluoro-2-methyl-phenyl)-8-o-tolyl-8H-pyrido[2,3-d]pyrimidin-7-one Following the general procedure outlined in Example 126, the product of Example 121 (200 mg, 0.47 mmol), and ethylamine (1.18 mL, 2.36 mmol) were reacted to give the crude material. Purification by flash chromatography eluting with EtOAc/hexane/triethylamine (30/70/2, v/v/v), followed by recrystallization from dichloromethane and hexane, gave the desired product 150 mg (82%). LC-MS: 389.2 (MH+, m/z), 2.39 (Rt, min).

Example 199

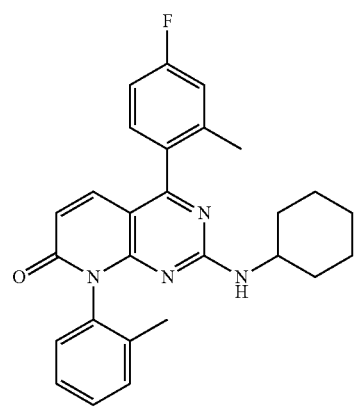

2-Cyclohexylamino-4-(4-fluoro-2-methyl-phenyl)-8-o-tolyl-8H-pyrido[2,3-d]pyrimidin-7-one Following the general procedure outlined in Example 126, the product of Example 121 (200 mg, 0.47 mmol), and cyclohexylamine (0.27 mL, 2.36 mmol) were reacted to give the crude material, which was purified as described in Example 198 to give the desired product 100 mg (48%). LC-MS: 443.4 (MH+, m/z), 2.79 (Rt, min).

Example 200

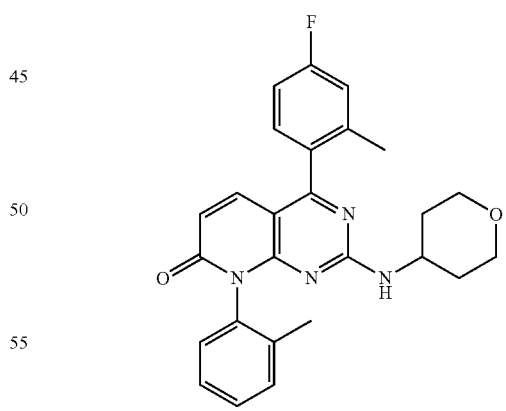

4-(4-Fluoro-2-methyl-phenyl)-2(tetrahydro-pyran-4-ylamino)-8-o-tolyl-8H-pyrido[2,3-d]pyrimidin-7-one Following the general procedure outlined in Example 126, the product of Example 121 (150 mg, 0.35 mmol), and 4-aminotetrahydropyran (179 mg, 1.77 mmol) were reacted to give the crude material, which was purified as described in Example 198 to give the desired product 140 mg (90%). LC-MS: 445.4 (MH+, m/z), 2.27 (Rt, min).

Example 201

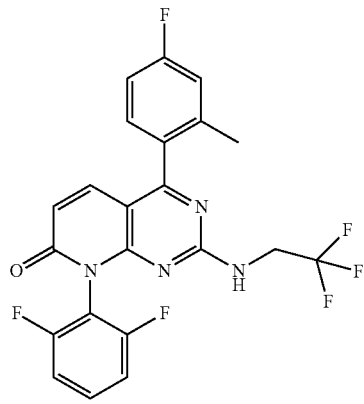

4-(4-Fluoro-2-methyl-phenyl)-8-o-tolyl-2-(2,2,2-trifluoro-ethylamino)-8H-pyrido[2,3-d]pyrimidin-7-one Following the general procedure outlined in Example 126, the product of Example 121 (150 mg, 0.35 mmol), 2,2,2-trifluoro-ethylamine (176 mg, 1.77 mmol) were reacted to give the crude material, which was purified as described in Example 198 to give the desired product 130 mg (84%). LC-MS: 443.0 (MH+, m/z), 2.27 (Rt, min).

Example 202

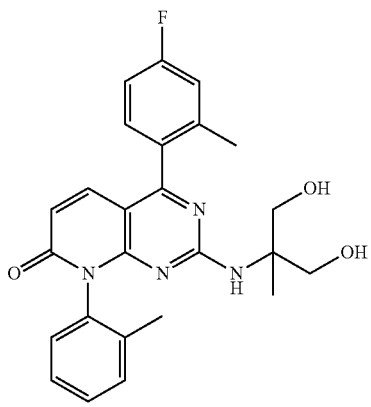

4-(4-Fluoro-2-methyl-phenyl)-2-(2-hydroxy-1-hydroxymethyl-1-methyl-ethylamino)-8-o-tolyl-8H-pyrido[2,3-d]pyrimidin-7-one Following the general procedure outlined in Example 60, the product of Example 121 (200 mg, 0.47 mmol) and 2-amino-2-methyl-1,3-propanediol (494 mg, 4.7 mmol) were reacted to give the crude material, which was purified as described in Example 126 to give the desired product 130 mg (62%). LC-MS: 449.0 (MH+, m/z), 1.67 (Rt, min)

Example 203

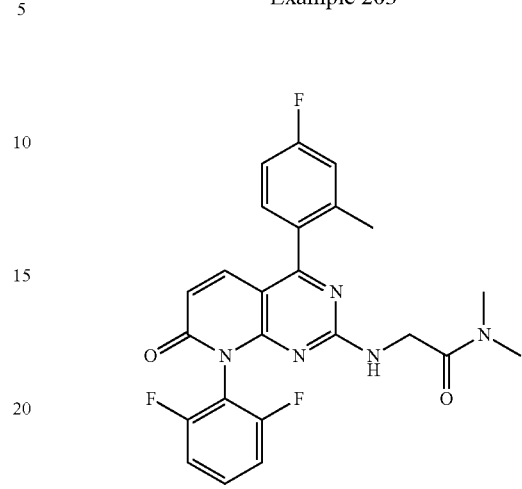

2-[8-(2,6-Difluoro-phenyl)-4-(4-fluoro-2-methyl-phenyl)-7-oxo-7,8-dihydro-pyrido[2,3-d]pyrimidine-2-ylamino]-N,N-dimethyl-acetamide Following the general procedure outlined in Example 193, dimethylamine (1.1 mL, 2.2 mmol), trimethylaluminum (1.1 mL, 2.2 mmol) and the product of Example 190 (100 mg, 0.22 mmol) were reacted to give the desired product 56 mg (54%). LC-MS: 468.2 (MH+, m/z), 2.00 (Rt, min).

Example 204

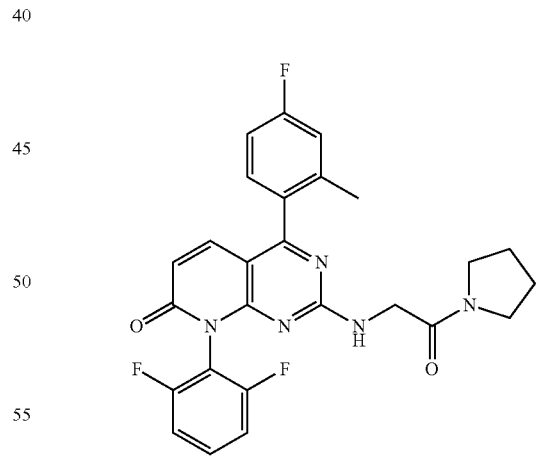

2-[8-(2,6-Difluoro-phenyl)-4-(4-fluoro-2-methyl-phenyl)-2-(2-oxo-2-pyrrolidin-1-yl-ethylamino)-8H-pyrido[2,3-d]pyrimidin-7-one Following the general procedure outlined in Example 193, pyrrolidine (0.18 mL, 2.2 mmol), trimethylaluminum (1.1 mL, 2.2 mmol) and the product of Example 190 (100 mg, 0.22 mmol) were reacted to give the desired product 52 mg (48%). LC-MS: 494.4 (MH+, m/z), 2.10 (Rt, min)

Example 205

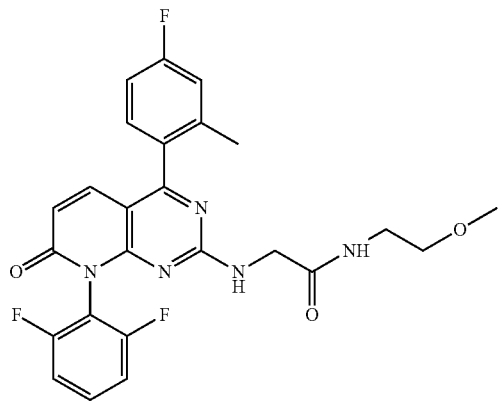

2-[8-(2,6-Difluoro-phenyl)-4-(4-fluoro-2-methyl-phenyl)-7-oxo-7,8-dihydro-pyrido[2,3-d]pyrimidin-2-ylamino]-N-(2-methoxy-ethyl)-acetamide Following the general procedure outlined in Example 193, 2-methoxy-ethylamine (0.17 mL, 2.2 mmol), trimethylaluminum (1.1 mL, 2.2 mmol) and the product of Example 190 (200 mg, 0.44 mmol) were reacted to give the desired product 145 mg (66%). LC-MS: 498.2 (MH+, m/z), 1.90 (Rt, min).

Example 206

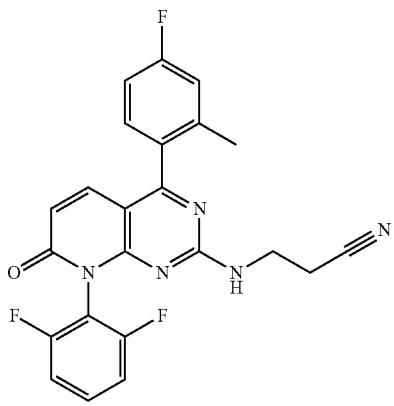

3-[8-(2,6-Difluoro-phenyl)-4-(4-fluoro-2-methyl-phenyl)-7-oxo-7,8-dihydro-pyrido[2,3-d]pyrimidin-2-ylamino]-propionitrile Following the general procedure outlined in Example 126, the product of Example 48 (500 mg, 1.12 mmol) and 3-aminopropionitrile (0.41 mL, 5.6 mmol) were reacted to give the desired product 270 mg (55%). LC-MS: 436.0 (MH+, m/z), 2.17 (Rt, min).

Example 207

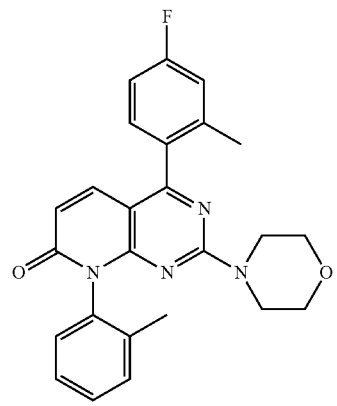

4-(4-Fluoro-2-methyl-phenyl)-2-morpholin-4-yl-8-o-tolyl-8H-pyrido[2,3-d]pyrimidin-7-one Following the general procedure outlined in Example 193, the product of Example 121 (100 mg, 0.22 mmol), morpholine (58 mg, 0.66 mmol) and trimethylaluminum (0.33 mL, 0.66 mmol) were reacted to give the desired product, 61 mg (64%). LC-MS: 431.2 (MH+, m/z), 2.46 (Rt, min).

Example 208

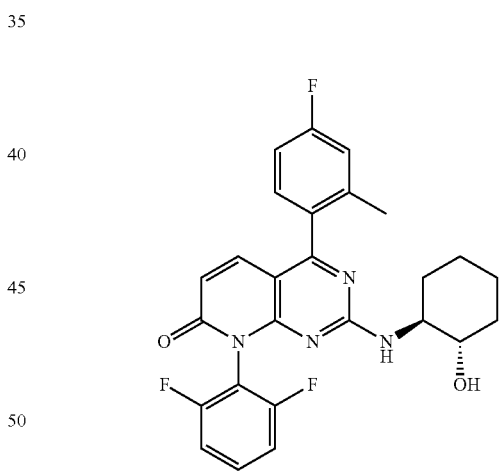

8-(2,6-Difluoro-phenyl)-4-(4-fluoro-2-methyl-phenyl)-2-(1SR,2SR)-2-hydroxy-cyclohexylamino)-8H-pyrido[2,3-d]pyrimidin-7-one Following the general procedure outlined in Example 195, the product of Example 48 (200 mg, 0.45 mmol), trans-2-hydroxy-1-cyclohexylamine hydrochloride (341 mg, 2.25 mmol) and triethylamine (0.31 mL, 2.25 mmol) were reacted to give the crude material, which was purified as described in Example 193 to give the desired product 100 mg (46%). LC-MS: 481.2 (MH+, m/z), 2.25 (Rt, min).

Example 209

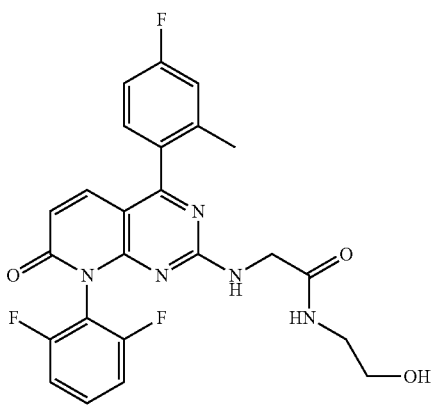

2-[8-(2,6-Difluoro-phenyl)-4-(4-fluoro-2-methyl-phenyl)-7-oxo-7,8-dihydro-pyrido[2,3-d]pyrimidin-2-ylamino]-N-(2-hydroxy-ethyl)-acetamide To a soln of the product of Example 205 (50 mg, 0.1 mmol), in dichloromethane (2 mL) was added 1 M boron tribromide in dichloromethane (0.5 mL, 0.5 mmol). The mixture was stirred at 23° for 2 h, H$_2$O was added, extracted with EtOAc. The organic layer was dried (Na$_2$SO$_4$) and concentrated to give the crude material. Recrystallization from dichloromethane and hexane afforded the title product (30 mg, 62%). LC-MS: 484.2 (MH+, m/z), 1.59 (Rt, min).

Example 210

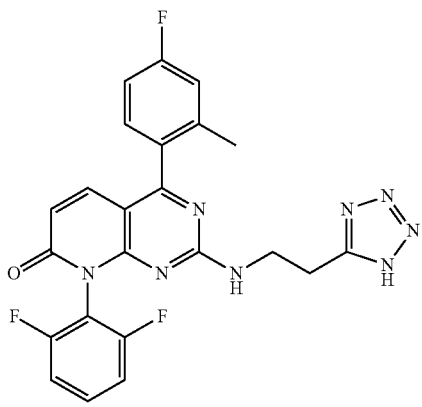

8-(2,6-Difluoro-phenyl)-4-(4-fluoro-2-methyl-phenyl)-2-[2-(1H-tetrazol-5-yl)-ethylamino]-8H-pyrido[2,3-d]pyrimidin-7-one A suspension of the product of Example 206 (200 mg, 0.46 mmol), triethylamine hydrochloride (630 mg, 4.6 mmol) and NaN$_3$ (299 mg, 4.6 mmol) in toluene (20 mL) was heated to toluene reflux for 60 h. Preparative HPLC afforded the title compound 100 mg (45%). LC-MS: 479.0 (WM+, m/z), 1.82 (Rt, min).

Example 211

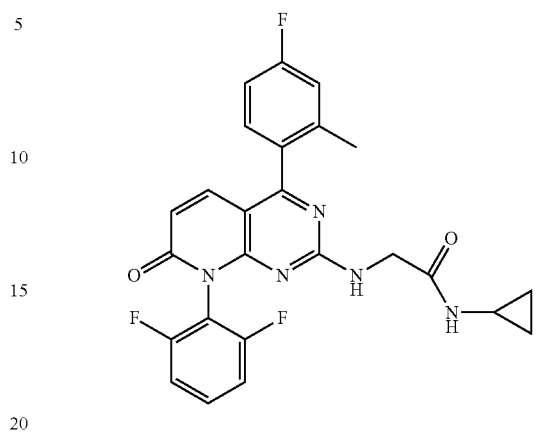

N-Cyclopropyl-2-[8-(2,6-difluoro-phenyl)-4-(4-fluoro-2-methyl-phenyl)-7-oxo-7,8-dihydro-pyrido[2,3-d]pyrimidin-2-ylamino]-acetamide Following the procedure outlined in Example 193, cyclopropylamine (0.23 mL, 3.3 mmol), trimethylaluminum (1.7 mL, 3.3 mmol) and the product of Example 190 (150 mg, 0.33 mmol) were reacted to give the desired product, 20 mg (13%). LC-MS: 480.0 (MH+, m/z), 1.89 (Rt, min).

Example 212

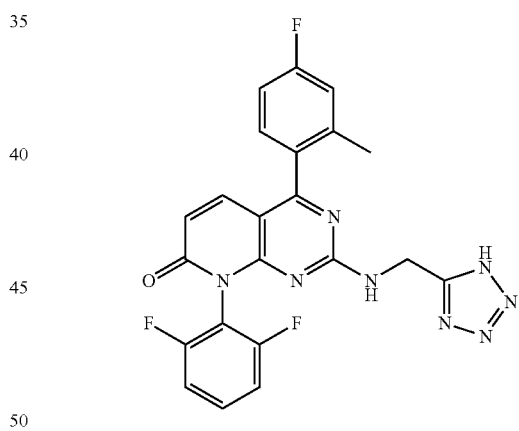

2-[8-(2,6-Difluoro-phenyl)-4-(4-fluoro-2-methyl-phenyl)-2-((1H-tetrazol-5-ylmethyl)amino)-8H-pyrido[2,3-d]pyrimidin-7-one a) [8-(2,6-difluoro-phenyl)-4-(4-fluoro-2-methyl-phenyl)-7-oxo-7,8-dihydro-pyrido[2,3-d]pyrimidin-2-ylamino]-acetonitrile Following the general procedure outlined in Example 195, the product of Example 48 (500 mg, 1.12 mmol), aminoacetonitrile hydrogen sulfate (1.16 g, 5.6 mmol) and triethylamine (0.78 mL, 5.6 mmol) were reacted at 65° for 2 h to give the crude material 460 mg. LC-MS: 421.8 (MH+, m/z), 2.08 (Rt, min).

b) 2-[8-(2,6-Difluoro-phenyl)-4-(4-fluoro-2-methyl-phenyl)-2-((1H-tetrazol-5-ylmethyl)amino)-8H-pyrido[2,3-d]pyrimidin-7-one Following the procedure outlined in Example 210, the crude product of Example 212(a), [8-(2,6-difluoro-phenyl)-4-(4-fluoro-2-methyl-phenyl)-7-oxo-7,8-dihydro-pyrido[2,3-d]pyrimidin-2-ylamino]-acetonitrile (460 mg), triethylaminehydrochloride (1.54 g, 11.2 mmol) and NaN₃ (728 mg, 11.2 mmol) were reacted to give the desired product 50 mg (9.6%). LC-MS: 465.2 (MH+, m/z), 1.79 (Rt, min).

Example 213

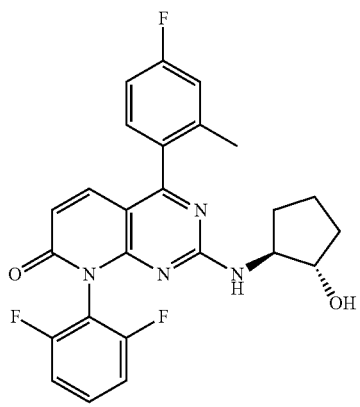

2-[8-(2,6-Difluoro-phenyl)-4-(4-fluoro-2-methyl-phenyl)-2-(1SR,2SR)-2-hydroxy-cyclopentylamino)-8H-pyrido[2,3-d]pyrimidin-7-one a) trans-2-azido-cyclopentanol To a soln of cyclopenteneoxide (2.0 g, 23.8 mmol) in CH₃OH and H₂O (40 mL) (4/1, v/v), were added NaN₃ (7.73 g, 119 mmol) and NH₄Cl (3.17 g, 59.2 mmol). The resulting mixture was heated to solvent reflux for 18 h then cooled to 23°. The mixture was concentrated and the residue was diluted with EtOAc, washed with H₂O, the organic layer was dried over Na₂SO₄, concentrated to give the desired product (2.8 g, 93%). ¹H NMR (CDCl₃): δ 4.10 (m, 1H), 3.72 (m, 1H), 2.10 (m, 2H), 1.72-1.60 (m, 4H).

b) trans-2-amino-cyclopentanol hydrochloride

To a solution of trans-2-azido-cyclopentanol (1.0 g, 7.87 mmol) in EtOAc, was added 10% Pd/C (0.5 g). The mixture was flushed with Ar, and then stirred on Parr apparatus at 40 psi for 2 h at 23°. The mixture was filtered through celite and the celite was washed with EtOAc. The filtrate was acidified with 3 mL of 4N HCl in 1,4-dioxane, and a white solid was precipitated. The mixture was filtered and the solid was collected to give the desired product (0.76 g, 99%). ¹H NMR (MeOD-d₄): δ 4.09-4.04 (m, 1H), 3.29-3.25 (m, 1H), 2.18 (m, 1H), 2.03 (m, 1H), 1.83-1.80 (m, 2H), 1.65-1.58 (m, 2H).

c) 2-[8-(2,6-Difluoro-phenyl)-4-(4-fluoro-2-methyl-phenyl)-2-(1SR,2SR)-2-hydroxy-cyclopentylamino)-8H-pyrido[2,3-d]pyrimidin-7-one Following the general procedure outlined in Example 195, the product of Example 48 (200 mg, 0.45 mmol), trans-2-amino-cyclopentanol hydrochloride (227 mg, 2.25 mmol) and triethylamine (0.31 mL, 2.25 mmol) were reacted for 2 h to give the desired product 63 mg (30%). LC-MS: 467.0 (MH+, m/z), 2.09 (Rt, min).

Example 214

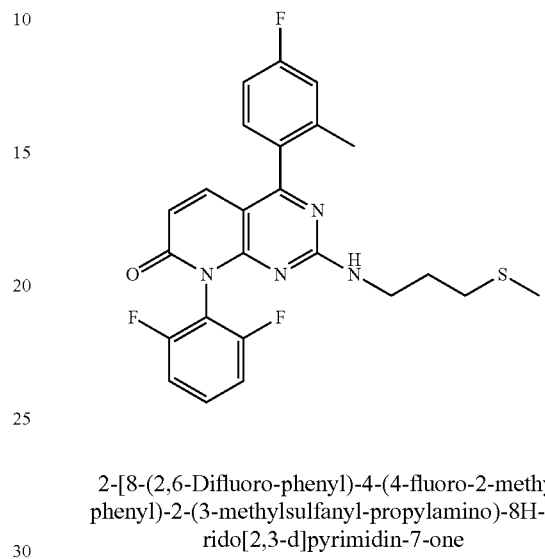

2-[8-(2,6-Difluoro-phenyl)-4-(4-fluoro-2-methyl-phenyl)-2-(3-methylsulfanyl-propylamino)-8H-pyrido[2,3-d]pyrimidin-7-one Following the general procedure outlined in Example 126, the product of Example 48 (200 mg, 0.44 mmol) and 3-(methylthio)propylamine (231 mg, 2.2 mmol) were reacted to afford the title compound 108 mg (52%). LC-MS: 471.2 (MH+, m/z), 2.37 (Rt, min).

Example 215

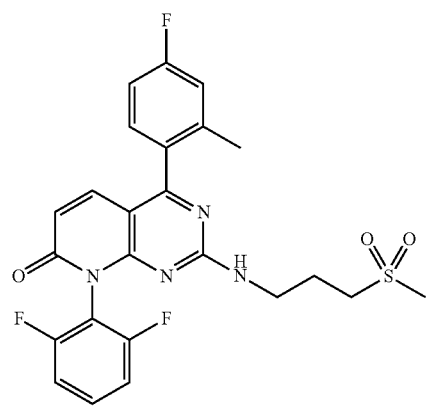

2-[8-(2,6-Difluoro-phenyl)-4-(4-fluoro-2-methyl-phenyl)-2-(3-methanesulfonyl-propylamino)-8H-pyrido[2,3-d]pyrimidin-7-one To a soln of the product of Example 214 (120 mg, 0.26 mmol) in dichloromethane (5 mL), was added m-chloroperbenzoic acid (130 mg, 0.52 mmol). The mixture was stirred for 1.5 h at 23°. The mixture was diluted with EtOAc and washed with H₂O to give the crude material. Purification by column chromatography eluting with EtOAc/triethylamine (100/2, v/v), followed by recrystallization from dichloromethane and hexane, gave the desired product (80 mg, 61%). LC-MS: 503.2 (MH+, m/z), 1.94 (Rt, min).

Example 216

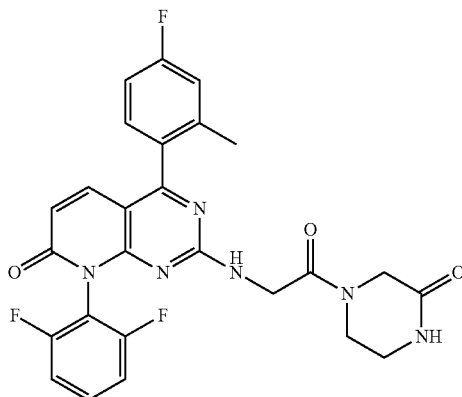

2-[8-(2,6-Difluoro-phenyl)-4-(4-fluoro-2-methyl-phenyl)-2-(2-oxo-2-(3-oxo-piperazin-1-yl)-ethylamino)-8H-pyrido[2,3-d]pyrimidin-7-one Following the general procedure outlined in Example 193, piperazine-2-one (165 mg, 1.65 mmol), trimethylaluminum (0.83 mL, 1.65 mmol) and the product of Example 190 (150 mg, 0.33 mmol) were reacted to give the crude material. Preparative HPLC, eluting with acetonitrile/H₂O (10/90, v/v to 90/10, v/v, over 10 min), followed by recrystallization from dichloromethane and hexane, gave the desired product 50 mg (29%). LC-MS: 523.2 (MH+, m/z), 1.68 (Rt, min).

Example 217

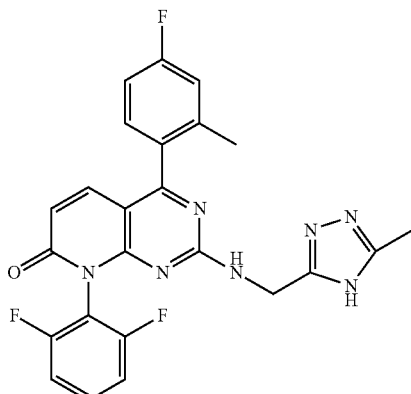

2-[8-(2,6-Difluoro-phenyl)-4-(4-fluoro-2-methyl-phenyl)-2-[(5-methyl-4H-[1,2,4]triazol-3-ylmethyl)-amino]-8H-pyrido[2,3-d]pyrimidin-7-one A solution of the product of Example 48 (150 mg, 0.34 mmol) and (5-methyl-4H-[1,2,4]triazol-3-yl)-methylamine (190 mg, 1.7 mmol) in NMP (2 mL) was stirred at 100° for 16 h to give the crude material. Preparative HPLC, eluting with acetonitrile/H₂O (10/90, v/v to 90/10, v/v, over 10 min), gave the desired product 23 mg (14%). LC-MS: 478.2 (MH+, m/z), 1.70 (Rt, min).

Alternatively, the desired product can be purified by flash chromatography eluting with EtOAc/triethylamine (100/2, v/v), followed by recrystallization as hydrochloride salt from EtOAc and methanol.

Example 218

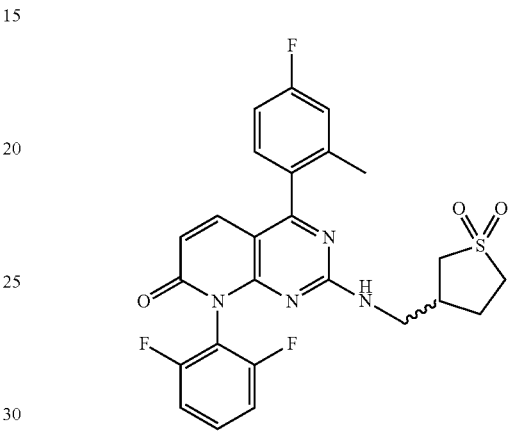

2-[8-(2,6-Difluoro-phenyl)-4-(4-fluoro-2-methyl-phenyl)-2-((1,1-dioxo-tetrahydro-1-thiophen-3-ylmethyl)-amino)-8H-pyrido[2,3-d]pyrimidin-7-one Following the general procedure outlined in Example 217, the product of Example 48 (100 mg, 0.22 mmol) and 3-aminomethylsulfolane (328 mg, 2.2 mmol) were reacted to give the crude material. Purification by Flash chromatography eluting with EtOAc/hexane/triethylamine (65/35/2, v/v/v), gave the desired product 25 mg (22%). LC-MS: 515.4 (MH+, m/z), 1.97 (Rt, min).

Example 219

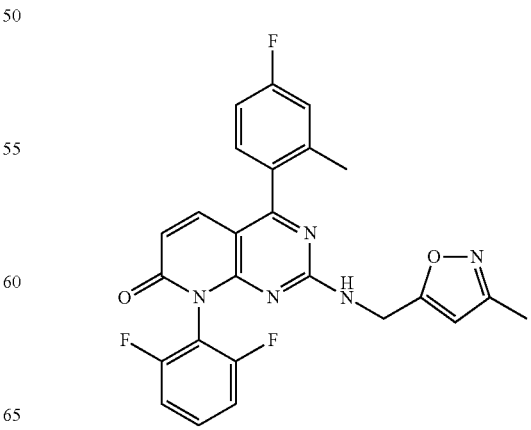

2-[8-(2,6-Difluoro-phenyl)-4-(4-fluoro-2-methyl-phenyl)-2-((3-methyl-isoxazol-5-ylmethyl)amino)-8H-pyrido[2,3-d]pyrimidin-7-one Following the general procedure outlined in Example 217, the product of Example 48 (100 mg, 0.22 mmol) and (3-methyl-isoxazol-5-yl)-methylamine (125 mg, 1.12 mmol) were reacted to give the desired product 50 mg (44%). LC-MS: 478.2 (MH+, m/z), 2.20 (Rt, min).

Example 220

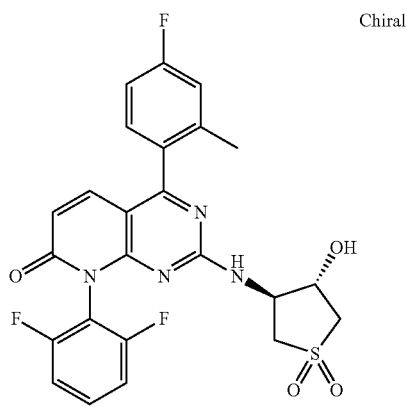

2-[8-(2,6-Difluoro-phenyl)-4-(4-fluoro-2-methyl-phenyl)-2-((3S,4S)-4-hydroxy-1,1-dioxo-tetrahydro-1-amino)-8H-pyrido[2,3-d]pyrimidin-7-one Following the general procedure outlined in Example 217, the product of Example 48 (100 mg, 0.22 mmol) and 3(S)-amino-4(S)-hydroxysulfolane (169 mg, 1.12 mmol) were reacted to give the desired product 50 mg (44%). LC-MS: 517.0 (MH+, m/z), 1.87 (Rt, min).

Example 221

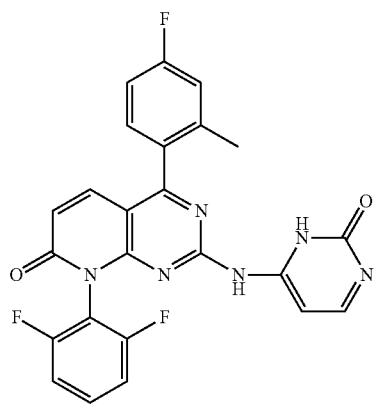

2-[8-(2,6-Difluoro-phenyl)-4-(4-fluoro-2-methyl-phenyl)-2-(2-oxo-2,3-dyhydro-pyrimidin-4-ylamino)-8H-pyrido[2,3-d]pyrimidin-7-one Following the general procedure outlined in Example 217, the product of Example 48 (100 mg, 0.22 mmol) and cytosine (124 mg, 1.12 mmol) were reacted to give the crude material. Preparative HPLC afforded the title compound, 27 mg (20%). LC-MS: 477.2 (MH+, m/z), 1.77 (Rt, min).

Example 222

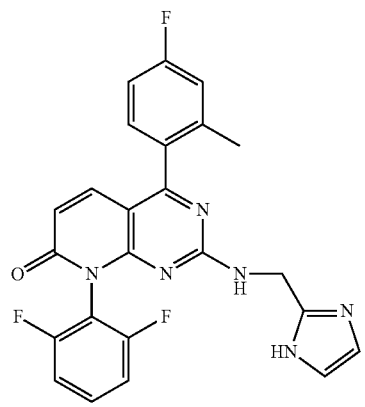

2-[8-(2,6-Difluoro-phenyl)-4-(4-fluoro-2-methyl-phenyl)-2-((1H-imidazol-2-ylmethyl)amino)-8H-pyrido[2,3-d]pyrimidin-7-one (1H-Imidazol-2-yl)-methylamine dihydrochloride (184 mg, 1.1 mmol), NMP (1 mL), and triethylamine (0.31 mL, 2.2 mmol) were stirred at 23° 10 min. The product of Example 48 (100 mg, 0.22 mmol) was added and the mixture was reacted at 100° for 16 h to give the crude material. Preparative hplc afforded the title compound, 36 mg (29%). LC-MS: 463.2 (MH+, m/z), 1.42 (Rt, min).

Example 223

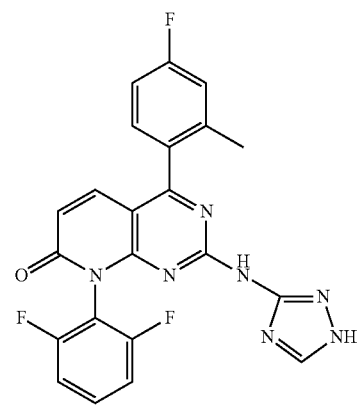

2-[8-(2,6-Difluoro-phenyl)-4-(4-fluoro-2-methyl-phenyl)-2-(1H-[1,2,4]triazol-3-ylamino)-8H-pyrido[2,3-d]pyrimidin-7-one Following the general procedure outlined in Example 217, the product of Example 48 (150 mg, 0.33 mmol) and 3-amino-1,2,4-triazole (141 mg, 1.68 mmol) were reacted to give the crude material. Preparative hplc afforded the title compound 28 mg (15%). LC-MS: 450.2 (MR+, m/z), 1.79 (Rt, min).

Example 224

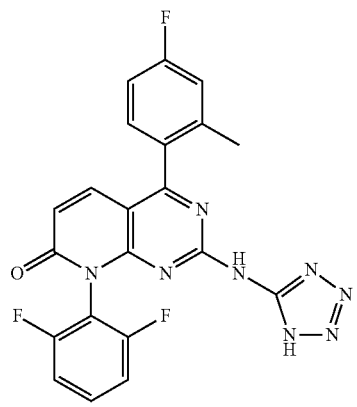

2-[8-(2,6-Difluoro-phenyl)-4-(4-fluoro-2-methyl-phenyl)-2-(1H-tetrazol-5-ylamino)-8H-pyrido[2,3-d]pyrimidin-7-one Following the general procedure outlined in Example 217, the product of Example 48 (150 mg, 0.33 mmol) and 5-amino-1H-tetrazole (143 mg, 1.68 mmol) were reacted to give the crude material, which was purified preparative hplc to afford the title compound, 17 mg (9%). LC-MS: 451.0 (MH+, m/z), 2.04 (Rt, min).

Example 225

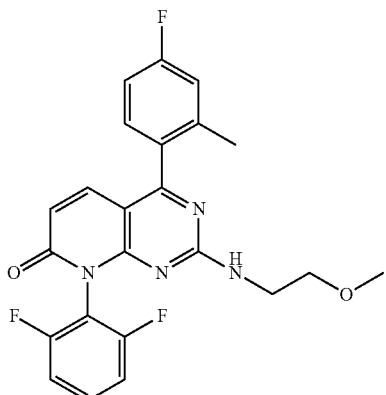

2-[8-(2,6-Difluoro-phenyl)-4-(4-fluoro-2-methyl-phenyl)-2-(2-methoxy-ethylamino)-8H-pyrido[2,3-d]pyrimidin-7-one A solution of the product of Example 48 (150 mg, 0.34 mmol) and 2-methoxy-ethylamine (0.09 mL, 1.01 mmol) in DMF (2 mL) was stirred 23° for 16 h. The mixture was diluted with EtOAc and washed with H$_2$O to give the crude material, which was purified as described in Example 198 to give the desired product 70 mg (47%). LC-MS: 441.2 (MH+, m/z), 2.10 (Rt, min)

Example 226

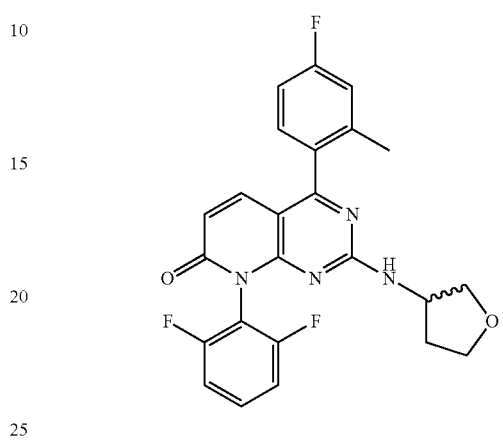

8-(2,6-Difluoro-phenyl)-4-(4-fluoro-2-methyl-phenyl)-2-(tetrahydro-furan-3-ylamino)-8H-pyrido[2,3-d]pyrimidin-7-one a) (Tetrahydro-furan-3-yl)-carbamic acid tert-butyl ester Under Ar, to a soln of (+/−)-tetrahydro-3-furoic acid (500 mg, 4.30 mmol) in DMF (2 mL) was added triethylamine (0.66 mL, 4.74 mmol), followed by diphenylphosphoryl azide (1.02 mL, 4.74 mmol). The mixture was heated to 80° for 3 h and cooled to 23°, tert-butanol (3 mL) was then added and the resulting mixture was stirred at 23° for 16 h. The mixture was diluted with EtOAc and washed with H$_2$O. The organic layer was dried over Na$_2$SO$_4$, and concentrated to give the crude intermediate 670 mg.

b) Tetrahydro-furan-3-ylamine hydrochloride

To a soln of the crude (tetrahydro-furan-3-yl)-carbamic acid tert-butyl ester (460 mg) in EtOAc (10 mL) was added 2 mL of 4N HCl in 1,4-dioxane. The mixture was stirred at 23° for 16 h, then concentrated to give crude material 240 mg.

c) 8-(2,6-Difluoro-phenyl)-4-(4-fluoro-2-methyl-phenyl)-2-(tetrahydro-furan-3-ylamino)-8H-pyrido[2,3-d]pyrimidin-7-one Following the general procedure outlined in Example 195, the product of Example 48 (125 mg, 0.28 mmol), the crude tetrahydro-furan-3-ylamine hydrochloride (240 mg) and triethylamine (0.27 mL, 1.9 mmol) were reacted to give the crude material. Purification by flash chromatography, eluting with EtOAc/hexane/triethylamine (50/50/2, v/v/v), gave the desired product (38 mg, 30%). LC-MS: 453.2 (MH+, m/z), 2.20 (Rt, min).

Example 227

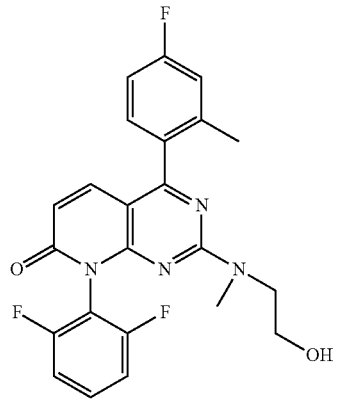

8-(2,6-Difluoro-phenyl)-4-(4-fluoro-2-methyl-phenyl)-2-[(2-hydroxy-ethyl)-methyl-amino]-8H-pyrido[2,3-d]pyrimidin-7-one Following the general procedure outlined in Example 126, the product of Example 48 (100 mg, 0.22 mmol), N-methylethanolamine (0.05 mL, 0.66 mmol) were reacted for 2 h to give the crude material, which was purified by preparative hplc to afforded the title compound, 26 mg (27%). LC-MS: 441.2 (MH+, m/z), 2.19 (Rt, min).

Example 228

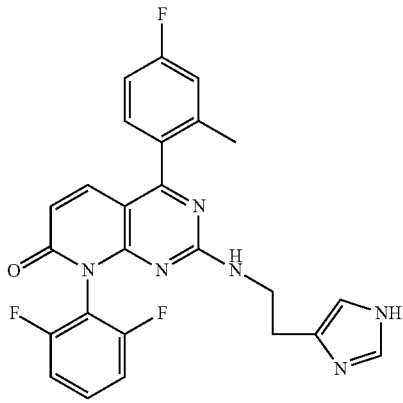

8-(2,6-Difluoro-phenyl)-4-(4-fluoro-2-methyl-phenyl)-2-[2-(1H-imidazol-4-yl)-ethylamino]-8H-pyrido[2,3-d]pyrimidin-7-one Following the general procedure outlined in Example 217, the product of Example 48 (150 mg, 0.34 mmol) and histamine (187 mg, 1.68 mmol) were reacted to give the desired product 50 mg (31%). LC-MS: 477.0 (MH+, m/z), 1.59 (Rt, min).

Example 229

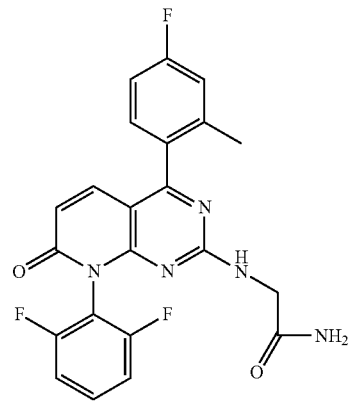

[8-(2,6-Difluoro-phenyl)-4-(4-fluoro-2-methyl-phenyl)-7-oxo-7,8-dihydro-pyrido[2,3-d]pyrimidine-2-ylamino]-acetamide To a soln of trimethylaluminum (3.3 mL, 6.6 mmol) in dichloromethane was bubbled $NH_3$ gas for 30 min, the product of Example 190 (500 mg, 1.1 mmol) was then added. The resulting mixture was stirred for 16 h. The mixture was diluted with EtOAc and washed with $H_2O$ to give the crude material. Purification by flash chromatography, eluting with EtOAc/triethylamine (100/2, v/v), gave the desired product (263 mg, 54%). LC-MS: 440.0 (MH+, m/z), 1.75 (Rt, min).

Example 230

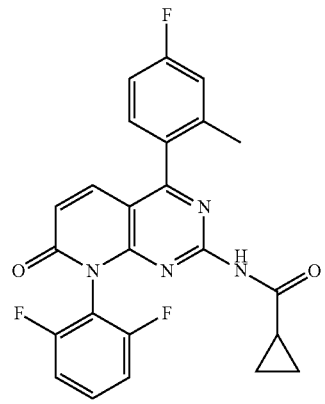

Cyclopropanecarboxylic acid [8-(2,6-difluoro-phenyl)-4-(4-fluoro-2-methyl-phenyl)-7-oxo-7,8-dihydro-pyrido[2,3-d]pyrimidine-2-yl]-amide a) 2-Amino-8-(2,6-difluoro-phenyl)-4-(4-fluoro-2-methyl-phenyl)-8H-pyrido[2,3-d]pyrimidin-7-one To a solution of the product of Example 48 (1.0 g, 2.2 mmol) and triethylamine (1 mL) in 2 mL of NMP was bubbled $NH_3$ gas at 23° for 30 min. The mixture was diluted with EtOAc and washed with $H_2O$ to give the crude material. Purification by flash chromatography eluting with EtOAc/hexane/triethylamine (50/50/2, v/v/v), followed by recrystallization from dichloromethane and hexane, gave the title compound, (360 mg, 43%). LC-MS: 383.0 (MH+, m/z), 1.95 (Rt, min).

b) Cyclopropanecarboxylic acid[8-(2,6-difluoro-phenyl)-4-(4-fluoro-2-methyl-phenyl)-7-oxo-7,8-dihydro-pyrido[2,3-d]pyrimidine-2-yl]-amide To a solution of the product of Example 230(a), 2-amino-8-(2,6-difluoro-phenyl)-4-(4-fluoro-2-methyl-phenyl)-8H-pyrido[2,3-d]pyrimidin-7-one (100 mg, 0.26 mmol) in 3 mL of tetrahydrofuran was added NaH (19 mg, 0.78 mmol). The mixture was stirred for 20 min at 23°, a soln of cyclopropanecarbonyl chloride (27 mg, 0.26 mmol) in tetrahydrofuran (1 mL) was added. The resulting mixture was heated to solvent reflux for 16 h to give the crude material, which was purified by preparative hplc to afford 25 mg (21%). LC-MS: 451.2 (MH+, m/z), 2.14 (Rt, min).

Example 231

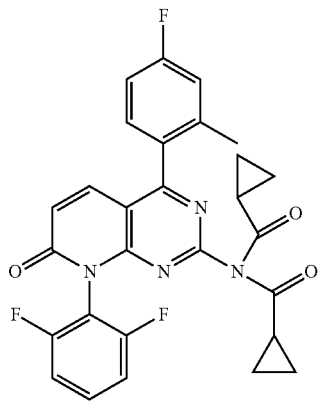

Cyclopropanecarboxylic acid(1-cyclopropyl-methanoyl)-[8-(2,6-difluoro-phenyl)-4-(4-fluoro-2-methyl-phenyl)-7-oxo-7,8-dihydro-pyrido[2,3-d]pyrimidin-2-yl]-amide A second compound from the reaction of Example 230 after hplc purification was the purified tile compound, 33 mg (24%). LC-MS: 519.0 m/z), 2.37 (Rt, min).

Example 232

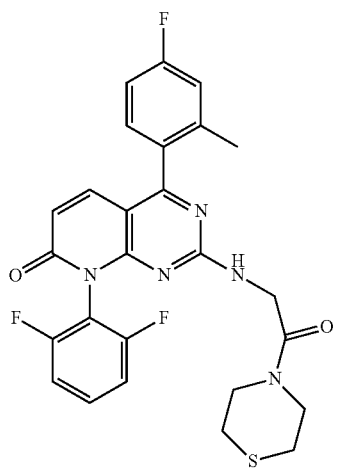

8-(2,6-Difluoro-phenyl)-4-(4-fluoro-2-methyl-phenyl)-2-(2-oxo-2-thiomorpholin-4-yl-ethylamino)-8H-pyrido[2,3-d]pyrimidin-7-one Following the general procedure outlined in Example 193, thiomorpholine (0.22 mL, 2.2 mmol), trimethylaluminum (1.1 mL, 2.2 mmol) and the product of Example 190 (200 mg, 0.44 mmol) were reacted to give the desired product 200 mg (86%). LC-MS: 526.0 (MH+, m/z), 2.07 (Rt, min).

Example 233

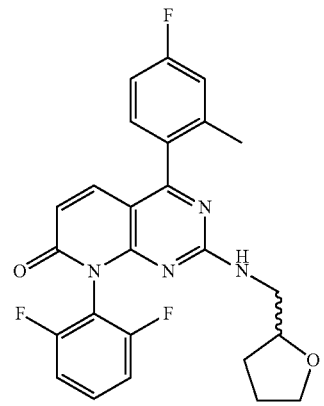

8-(2,6-Difluoro-phenyl)-4-(4-fluoro-2-methyl-phenyl)-2-[(tetrahydro-furan-2-ylmethyl)-amino]-8H-pyrido[2,3-d]pyrimidin-7-one Following the general procedure outlined in Example 225, the product of Example 48 (100 mg, 0.22 mmol) and tetrahydrofurfurylamine (0.07 mL, 0.66 mmol) afforded the title compound, 50 mg (49%). LC-MS: 467.0 (MH+, m/z), 2.22 (Rt, min)

Example 234

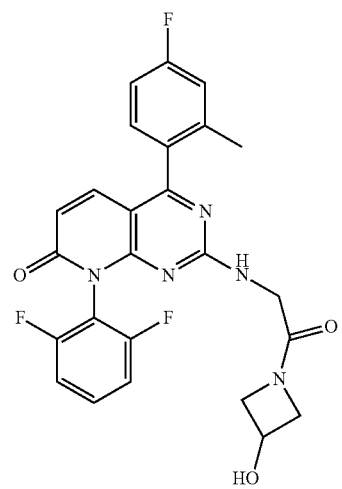

8-(2,6-Difluoro-phenyl)-4-(4-fluoro-2-methyl-phenyl)-2-[2-(3-hydroxy-azetidin-1-yl)-2-oxo-ethylamino]-8H-pyrido[2,3-d]pyrimidin-7-one a) Azetidin-3-ol hydrochloride

To a soln of 1-benzhydrylazetan-3-ol (1.0 g, 4.16 mmol) in methanol (20 mL) were added 10% Pd/C (1.0 g) and 4N HCl in 1,4-dioxane (2 mL). The mixture was flushed with Ar, and then stirred on Parr apparatus at 40 psi H₂ for 6 h at 60°. The mixture was cooled to room temperature and filtered through celite. The filtrate was concentrated and the resulting solid was washed with diethyl ether to give the desired product 0.31 g (68%). ¹H NMR (MeOD-d₄): δ 4.17 (m, 1H), 4.22 (m, 2H), 3.91 (m, 2H).

b) 8-(2,6-Difluoro-phenyl)-4-(4-fluoro-2-methyl-phenyl)-2-[2-(3-hydroxy-azetidin-1-yl)-2-oxo-ethylamino]-8H-pyrido[2,3-d]pyrimidin-7-one A mixture of [8-(2,6-difluoro-phenyl)-4-(4-fluoro-2-methyl-phenyl)-7-oxo-7,8-dihydro-pyrido[2,3-d]pyrimidin-2-ylamino]-acetic acid (100 mg, 0.23 mmol), azetidin-3-ol hydrochloride (37 mg, 0.34), o-benzotriazol-1-yl-N,N,N',N'-tetramethyluronium hexafluorophosphate (129 mg, 0.34 mmol) and N-methyl-morpholine (0.12 mL, 1.13 mmol) in DMF (2 mL) was stirred at 23° for 16 h to give the crude material, which was purified by preparative hplc to afford the title compound 56 mg (49%). LC-MS: 496.2 (MH+, m/z), 1.69 (Rt, min).

Example 235

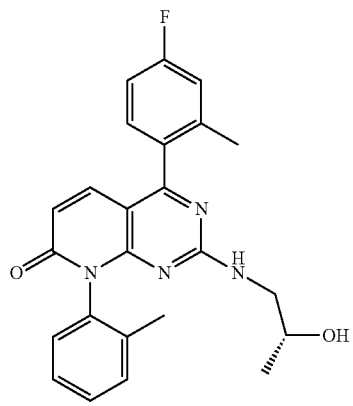

4-(4-Fluoro-2-methyl-phenyl)-2-((R)-2-hydroxy-propylamino)-8-o-tolyl-8H-pyrido[2,3-d]pyrimidin-7-one Following the general procedure outlined in Example 225, the product of 121 (120 mg, 0.28 mmol) and R(−)-1-amino-2-propanol (0.064 mL, 0.85 mmol) were reacted to give the crude material. Purification by flash chromatography eluting with EtOAc/hexane/triethylamine (50/50/2, v/v/v), followed by recrystallization from dichloromethane and hexane, afforded the desired product 110 mg (94%). LC-MS: 419.0 (MH+, m/z), 1.83 (Rt, min).

Example 236

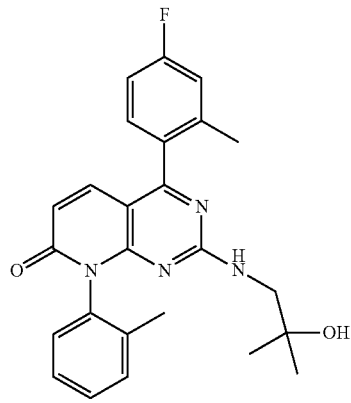

4-(4-Fluoro-2-methyl-phenyl)-2-(2-hydroxy-2-methyl-propylamino)-8-o-tolyl-8H-pyrido[2,3-d]pyrimidin-7-one Following the general procedure outlined in Example 225, the product of Example 121 (120 mg, 0.28 mmol) and 1-amino-2-methyl-2-propanol (76 mg, 0.85 mmol) were reacted to give the crude material. Purification by flash chromatography eluting with EtOAc/hexane/triethylamine (50/50/2, v/v/v), followed by recrystallization from dichloromethane and hexane, afforded the desired product 96 mg (79%). LC-MS: 433.4 (MH+, m/z), 1.87 (Rt, min).

Example 237

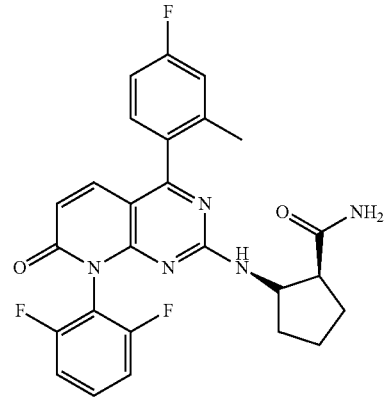

(1SR,2RS)-2-[8-(2,6-Difluoro-phenyl)-4-(4-fluoro-2-methyl-phenyl)-7-oxo-7,8-dihydro-pyrido[2,3-d]pyrimidin-2-ylamino]-cyclopentanecarboxylic acid amide Following the general procedure outlined in Example 225, the product of Example 48 (150 mg, 0.34 mmol) and cis-2-amino-1-cyclopentanecarboxamide (139 mg, 1.02 mmol) were reacted to give the crude material. Purification by flash chromatography eluting with EtOAc/hexane/triethylamine (50/50/2, v/v/v), followed by recrystallization from dichloromethane and hexane, afforded the desired product, 87 mg (52%). LC-MS: 494.0 (MEI+, m/z), 2.00 (Rt, min).

Example 238

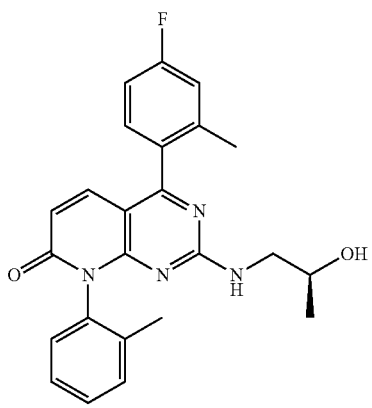

4-(4-Fluoro-2-methyl-phenyl)-2-((S)-2-hydroxy-propylamino)-8-o-tolyl-8H-pyrido[2,3-d]pyrimidin-7-one Following the general procedure outlined in Example 225, the product of 121 (220 mg, 0.52 mmol) and (S)-(+)-1-amino-2-propanol (0.12 mL, 1.56 mmol) were reacted to give the crude material. Purification by Flash chromatography eluting with EtOAc/hexane/triethylamine (50/50/2, v/v/v), followed by recrystallization from dichloromethane and hexane, afforded the desired product, the desired product 135 mg (62%). LC-MS: 419.2 (MH+, m/z), 1.79 (Rt, min).

Example 239

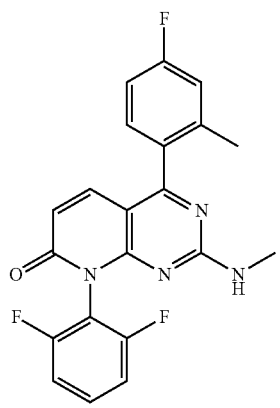

2-[8-(2,6-Difluoro-phenyl)-4-(4-fluoro-2-methyl-phenyl)-2-methyl amino-8H-pyrido[2,3-d]pyrimidin-7-one Following the general procedure outlined in Example 225, the product of Example 48 (1.0 g, 2.24 mmol) and methylamine (5.6 mL, 11.2 mmol) were reacted to give the crude material. Purification by flash chromatography eluting with EtOAc/hexane/triethylamine (30/70/2, v/v/v), followed by recrystallization from dichloromethane and hexane, gave the desired product 430 mg (48%). LC-MS: 397.2 (MH+, m/z), 2.14 (Rt, min).

Example 240

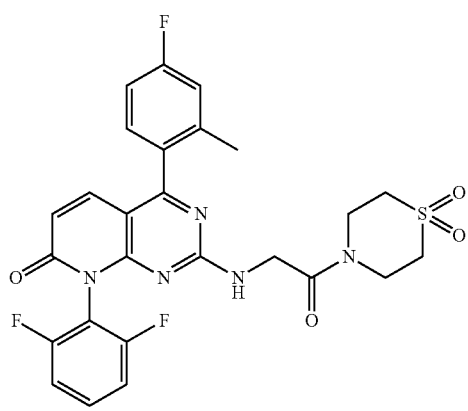

8-(2,6-Difluoro-phenyl)-2-[2-(1,1-dioxo-1 $1^6$-thiomorpholin-4-yl)-2-oxo-ethylamino]-4-(4-fluoro-2-methyl-phenyl)-8H-pyrido[2,3-d]pyrimidin-7-one Following the procedure outlined in Example 215, the product of Example 232, 8-(2,6-difluoro-phenyl)-4-(4-fluoro-2-methyl-phenyl)-2-(2-oxo-2-thiomorpholin-4-yl-ethylamino)-8H-pyrido[2,3-d]pyrimidin-7-one (164 mg, 0.31 mmol) and m-chloroperbenzoic acid (156 mg, 0.62 mmol) were reacted to give the desired product 165 mg (95%). LC-MS: 558.2 (MH+, m/z), 1.77 (Rt, min).

Example 241

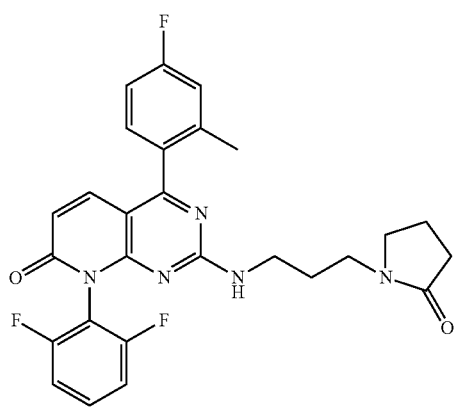

2-[8-(2,6-Difluoro-phenyl)-4-(4-fluoro-2-methyl-phenyl)-2-(3-(2-oxo-pyrrolidin-1-yl)-propylamino)-8H-pyrido[2,3-d]pyrimidin-7-one Following the general procedure outlined in Example 225, the product of Example 48 (100 mg, 0.22 mmol) and N-(3'-aminopropyl)-2-pyrrolidinone (96 mg, 0.67 mmol) were reacted to give the crude material. Purification by flash chromatography eluting with EtOAc/hexane/triethylamine (70/30/2, v/v/v), followed by recrystallization from ethanol and hexane, gave the desired product 95 mg (85%). LC-MS: 508.2 (MH+, m/z), 2.02 (Rt, min).

Example 242

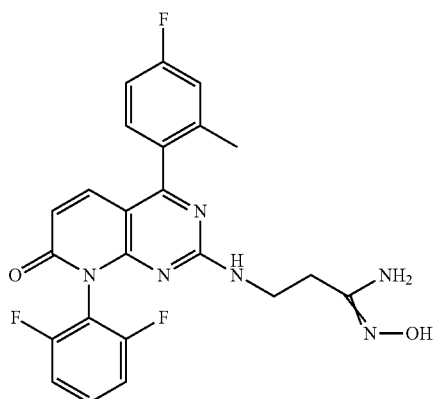

3-[8-(2,6-Difluoro-phenyl)-4-(4-fluoro-2-methyl-phenyl)-7-oxo-7,8-dihydro-pyrido[2,3-d]pyrimidin-2-ylamino]-N-hydroxy-propionamidine Under Ar, a soln of hydroxylamine hydrochloride (119 mg, 1.72 mmol) and triethylamine (0.26 mL, 1.89 mmol) in 5 mL of DMSO was stirred at room temperature for 5 min, the product of Example 206, 3-[8-(2,6-difluoro-phenyl)-4-(4-fluoro-2-methyl-phenyl)-7-oxo-7,8-dihydro-pyrido[2,3-d]pyrimidin-2-ylamino]-propionitrile (150 mg, 0.34 mmol) was added. The resulting mixture was heated to 80° for 16 h. Preparative hplc, followed by recrystallization from ethanol and hexane, gave the desired product 80 mg (45%). LC-MS: 469.2 (MH+, m/z), 1.52 (Rt, min).

Example 243

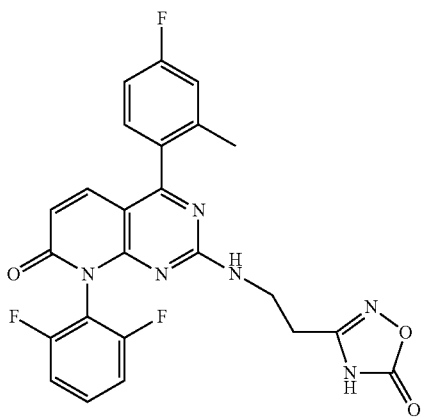

8-(2,6-Difluoro-phenyl)-4-(4-fluoro-2-methyl-phenyl)-2-[2-(5-oxo-4,5-dihydro-[1,2,4]-oxadiazol-3-yl)-ethylamino)-8H-pyrido[2,3-d]pyrimidin-7-one Under Ar, to a soln of the product of Example 242, 3-[8-(2,6-difluoro-phenyl)-4-(4-fluoro-2-methyl-phenyl)-7-oxo-7,8-dihydro-pyrido[2,3-d]pyrimidin-2-ylamino]-N-hydroxy-propionamidine (100 mg, 0.20 mmol), and pyridine (0.048 mL, 0.6 mmol), was added 2-ethylhexyl chloroformate (0.039 mL, 0.2 mmol). The mixture was stirred at room temperature for 2 h, then diluted with $H_2O$ and extracted with EtOAc. The organic layer was dried over sodium sulfate, filtered and concentrated. The resulting residue was diluted with xylene (10 mL) and heated to reflux for 18 h to give the crude material, which was purified by preparative hplc to give the desired product 28 mg (28%). LC-MS: 495.0 (MH+, m/z), 1.96 (Rt, min).

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

What is claimed is:

1. A compound of the formula:

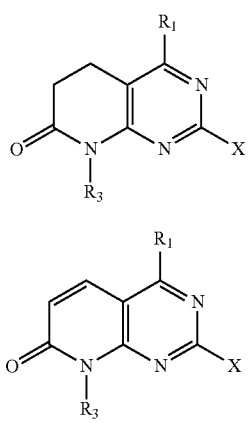

wherein $R_1$ is an optionally substituted aryl or an optionally substituted heteroaryl ring;

$R_2$ is hydrogen, $C_{1-10}$ alkyl, $C_{3-7}$ cycloalkyl, $C_{3-7}$ cycloalkylalkyl, aryl, aryl$C_{1-10}$ alkyl, heteroaryl, heteroaryl$C_{1-10}$ alkyl, heterocyclic, or a heterocyclyl$C_{1-10}$ alkyl moiety, which moieties are all optionally substituted, or $R_2$ is the moiety $X_1$ $(CR_{10}R_{20})_q C(A_1)(A_2)(A_3)$, or $C(A_1)(A_2)(A_3)$;

$A_1$ is an optionally substituted $C_{1-10}$ alkyl;

$A_2$ is an optionally substituted $C_{1-10}$ alkyl;

$A_3$ is hydrogen or is an optionally substituted $C_{1-10}$ alkyl;

$R_3$ is an $C_{1-10}$ alkyl, $C_{3-7}$ cycloalkyl, $C_{3-7}$ cycloalkyl$C_{1-4}$ alkyl, aryl, aryl$C_{1-10}$ alkyl, heteroaryl, heteroaryl$C_{1-10}$ alkyl, heterocyclic, or a heterocyclyl$C_{1-10}$ alkyl moiety, which moieties are optionally substituted;

$R_4$ and $R_{14}$ are each independently selected from hydrogen, optionally substituted $C_{1-4}$ alkyl, optionally substituted $C_{3-7}$ cycloalkyl, $C_{3-7}$ cycloalkyl$C_{1-4}$alkyl, optionally substituted aryl, or optionally substituted aryl-$C_{1-4}$ alkyl, or $R_4$ and $R_{14}$ together with the nitrogen which they are attached form an optionally substituted heterocyclic ring of 4 to 7 members, which ring optionally contains an additional heteroatom selected from oxygen, sulfur or $NR_9$;

$R_6$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl, wherein each of these moieties may be optionally substituted;

$R_9$ is hydrogen, $C(Z)R_6$ or optionally substituted $C_{1-10}$ alkyl, optionally substituted aryl or optionally substituted aryl-$C_{1-4}$ alkyl;

$R_{10}$ and $R_{20}$ are independently selected from hydrogen or $C_{1-4}$alkyl;

X is $R_2$, $OR_2$, $S(O)_m R_2$, $(CH_2)_n N(R_{10})S(O)_m R_2$, $(CH_2)_n N(R_{10})C(O)R_2$, $(CH_2)_n NR_4 R_{14}$, or $(CH_2)_n N(R_2)_2$;

$X_1$ is $N(R_{10})$, O, $S(O)_m$, or $CR_{10}R_{20}$;

n is 0 or an integer having a value of 1 to 10;

m is 0 or an integer having a value of 1 or 2;

q is 0 or an integer having a value of 1 to 10;

Z is oxygen or sulfur;

or a pharmaceutically acceptable salt thereof.

2. The compound according to claim 1 which is Formula (I), or a pharmaceutically acceptable salt thereof.

3. The compound according to claim 1 which is Formula (Ia), or a pharmaceutically acceptable salt thereof.

4. The compound according to claim 1 wherein $R_1$ is an optionally substituted phenyl or napthyl.

5. The compound according to claim 2 wherein $R_1$ is an optionally substituted phenyl or napthyl.

6. The compound according to claim 3 wherein $R_1$ is an optionally substituted phenyl or napthyl.

7. The compound according to claim 4 wherein $R_1$ is a phenyl substituted one or more times independently by halogen, alkyl, hydroxy, alkoxy, amino, or halosubstituted alkyl.

8. The compound according to claim 5 wherein $R_1$ is a phenyl substituted one or more times independently by halogen, alkyl, hydroxy, alkoxy, amino, or halosubstituted alkyl.

9. The compound according to claim 6 wherein $R_1$ is a phenyl substituted one or more times independently by halogen, alkyl, hydroxy, alkoxy, amino, or halosubstituted alkyl.

10. The compound according to claim 7 wherein the substituents are independently fluorine, $C_{1-4}$ alkyl, or $CF_3$.

11. The compound according to claim 8 wherein the substituents are independently fluorine, $C_{1-4}$ alkyl, or $CF_3$.

12. The compound according to claim 9 wherein the substituents are independently fluorine, $C_{1-4}$ alkyl, or $CF_3$.

13. The compound according to claim 5 wherein $R_1$ is a phenyl ring substituted in the 2, 4, or 6-position, di-substituted in the 2,4-position, or tri-substituted in the 2,4,6-position.

14. The compound according to claim 1 wherein X is $OR_2$, or $S(O)_m R_2$.

15. The compound according to claim 2 wherein X is $OR_2$, or $S(O)_m R_2$.

16. The compound according to claim 3 wherein X is $OR_2$, or $S(O)_m R_2$.

17. The compound according to claim 1 wherein X is $(CH_2)_n NR_4 R_{14}$, or $(CH_2)_n N(R_2)_2$.

18. The compound according to claim 2 wherein X is $(CH_2)_n NR_4 R_{14}$ or $(CH_2)_n N(R_2)_2$.

19. The compound according to claim 3 wherein X is $(CH_2)_n NR_4 R_{14}$, or $(CH_2)_n N(R_2)_2$.

20. The compound according to claim 1 wherein X is $R_2$ or $(CH_2)_n N(R_{10})S(O)_m R_2$, or $(CH_2)_n N(R_{10})C(O)R_2$.

21. The compound according to claim 1 wherein $R_2$ is optionally substituted independently one or more times with $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$alkyl, $C_{5-7}$cycloalkenyl, $C_{5-7}$ cycloalkenyl $C_{1-10}$ alkyl, halogen, —CH(O), cyano, nitro, $(CR_{10}R_{20})_n OR_6$, $(CR_{10}R_{20})_n SH$, $(CR_{10}R_{20})_n S$ $(O)_mR_7$, $(CR_{10}R_{20})_nNR_{10}S(O)_2R_7$, $(CR_{10}R_{20})_nNR_4R_{14}$, $(CR_{10}R_{20})_nCN$, $(CR_{10}R_{20})_nS(O)_2NR_4R_{14}$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_nC(Z)NR_4R_{14}$, $(CR_{10}R_{20})_nNR_{10}C(Z)R_6$, $(CR_{10}R_{20})_nNR_{10}C(=NR_{10})NR_4R_{14}$, $(CR_{10}R_{20})_nC(=NOR_6)NR_4R_{14}$, $(CR_{10}R_{20})_nOC(Z)NR_4R_{14}$, $(CR_{10}R_{20})_nNR_{10}C(Z)NR_4R_{14}$, or $(CR_{10}R_{20})_nNR_{10}C(Z)OR_7$ and wherein $R_7$ is a $C_{1-6}$alkyl, aryl, aryl$C_{1-6}$alkyl, heterocyclic, heterocyclyl$C_{1-6}$ alkyl, heteroaryl, or heteroaryl$C_{1-6}$ alkyl moiety; and wherein each of these moieties may be optionally substituted.

22. The compound according to claim 21 wherein $R_2$ is an optionally substituted alkyl.

23. The compound according to claim 22 wherein the alkyl is an optionally substituted by $(CR_{10}R_{20})_nC(Z)OR_6$, $(CR_{10}R_{20})_nOR_6$, or $(CR_{10}R_{20})_nNR_4R_{14}$.

24. The compound according to claim 1 wherein $R_2$ is $X_1(CR_{10}R_{20})_qC(A_1)(A_2)(A_3)$, or $C(A_1)(A_2)(A_3)$.

25. The compound according to claim 2 wherein $R_2$ is $X_1(CR_{10}R_{20})_qC(A_1)(A_2)(A_3)$, or $C(A_1)(A_2)(A_3)$.

26. The compound according to claim 3 wherein $R_2$ is $X_1(CR_{10}R_{20})_qC(A_1)(A_2)(A_3)$, or $C(A_1)(A_2)(A_3)$.

27. The compound according to claim 24 wherein $X_1$ is oxygen or $N(R_{10})$.

28. The compound according to claim 27 wherein at least one of $A_1$, $A_2$ or $A_3$ is substituted by $(CR_{10}R_{20})_nOR_6$.

29. The compound according to claim 28 wherein q is 0 or 1.

30. The compound according to claim 1 wherein $R_3$ is an optionally substituted $C_{1-10}$ alkyl, $C_{3-7}$ cycloalkyl, $C_{3-7}$ cycloalkyl$C_{1-4}$alkyl or aryl.

31. The compound according to claim 30 wherein $R_3$ is optionally substituted one or more times independently with $C_{1-10}$ alkyl, halo-substituted $C_{1-10}$ alkyl, $C_{2-10}$ alkenyl, $C_{2-10}$alkynyl, $C_{3-7}$ cycloalkyl, $C_{3-7}$cycloalkyl$C_{1-10}$ alkyl, $C_{5-7}$cycloalkenyl, $C_{5-7}$cycloalkenyl$C_{1-10}$ alkyl, halogen, cyano, nitro, $(CR_{10}R_{20})_nOR_6$, $(CR_{10}R_{20})_nSH$, $(CR_{10}R_{20})_nS(O)_mR_7$, $(CR_{10}R_{20})_nNR_{10}S(O)_2R_7$, $(CR_{10}R_{20})_nNR_4R_{14}$, $(CR_{10}R_{20})_nCN$, $(CR_{10}R_{20})_nS(O)_2NR_4R_{14}$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_nC(Z)NR_4R_{14}$, $(CR_{10}R_{20})_nNR_{10}C(Z)R_6$, $(CR_{10}R_{20})_nNR_{10}C(=NR_{10})NR_4R_{14}$, $(CR_{10}R_{20})_nOC(Z)NR_4R_{14}$, $(CR_{10}R_{20})_nNR_{10}C(Z)NR_4R_{14}$, or $(CR_{10}R_{20})_nNR_{10}C(Z)OR_7$ and wherein $R_7$ is a $C_{1-6}$alkyl, aryl, aryl$C_{1-6}$alkyl, heterocyclic, heterocyclyl$C_{1-6}$ alkyl, heteroaryl, or heteroaryl$C_{1-6}$ alkyl moiety; and wherein each of these moieties may be optionally substituted.

32. The compound according to claim 31 wherein the $R_3$ optional substituent is halogen, alkyl, hydroxy, alkoxy, amino, or halosubstituted alkyl.

33. The compound according to claim 31 wherein $R_3$ is optionally substituted aryl.

34. The compound according to claim 33 wherein $R_3$ is optionally substituted phenyl.

35. A pharmaceutical composition comprising an effective amount of a compound according to claim 1 and a pharmaceutically acceptable carrier or diluent.

* * * * *

SEQUENCE LISTING

```
<160> NUMBER OF SEQ ID NOS: 1

<210> SEQ ID NO 1
<211> LENGTH: 21
<212> TYPE: PRT
<213> ORGANISM: Artificial Sequence
<220> FEATURE:
<223> OTHER INFORMATION: Epidermal Growth Factor Receptor-Derived
      Peptide
```

```
<400> SEQUENCE: 1

Lys Arg Glu Leu Val Glu Pro Leu Thr Pro Ser Gly Glu Ala Pro Asn
1               5                   10                  15

Gln Ala Leu Leu Arg
            20
```